(12) United States Patent
Kumar et al.

(10) Patent No.: US 11,123,430 B2
(45) Date of Patent: Sep. 21, 2021

(54) METHODS FOR INCREASING RED BLOOD CELL LEVELS AND TREATING INEFFECTIVE ERYTHROPOIESIS

(71) Applicant: Acceleron Pharma Inc., Cambridge, MA (US)

(72) Inventors: Ravindra Kumar, Acton, MA (US); Pedro Martinez, Cambridge, MA (US); Naga Venkata Sai Rajasekhar Suragani, Wrentham, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 15/343,757

(22) Filed: Nov. 4, 2016

(65) Prior Publication Data

US 2017/0274077 A1    Sep. 28, 2017

Related U.S. Application Data

(60) Provisional application No. 62/251,024, filed on Nov. 4, 2015.

(51) Int. Cl.

| | | |
|---|---|---|
| A61K 38/18 | (2006.01) | |
| A61K 38/17 | (2006.01) | |
| C07K 14/71 | (2006.01) | |
| C07K 14/705 | (2006.01) | |
| A61P 7/06 | (2006.01) | |
| A61K 45/06 | (2006.01) | |
| A61K 31/192 | (2006.01) | |
| A61K 31/565 | (2006.01) | |
| A61K 31/136 | (2006.01) | |
| A61K 31/365 | (2006.01) | |
| A61K 31/138 | (2006.01) | |
| A61K 31/704 | (2006.01) | |
| A61K 31/4155 | (2006.01) | |
| A61K 31/46 | (2006.01) | |
| A61K 31/395 | (2006.01) | |
| A61K 38/00 | (2006.01) | |
| A61K 39/395 | (2006.01) | |
| C07K 16/22 | (2006.01) | |

(52) U.S. Cl.
CPC ............ *A61K 45/06* (2013.01); *A61K 31/136* (2013.01); *A61K 31/138* (2013.01); *A61K 31/192* (2013.01); *A61K 31/365* (2013.01); *A61K 31/395* (2013.01); *A61K 31/4155* (2013.01); *A61K 31/46* (2013.01); *A61K 31/565* (2013.01); *A61K 31/704* (2013.01); *A61K 38/00* (2013.01); *A61K 38/1709* (2013.01); *A61K 38/179* (2013.01); *A61K 38/18* (2013.01); *A61K 39/395* (2013.01); *A61P 7/06* (2018.01); *C07K 14/705* (2013.01); *C07K 14/71* (2013.01); *C07K 16/22* (2013.01); *C07K 2317/70* (2013.01); *C07K 2317/76* (2013.01); *C07K 2319/30* (2013.01)

(58) Field of Classification Search
CPC ........ A61K 38/18; A61K 38/17; C07K 14/71; C07K 14/705; A61P 7/06
See application file for complete search history.

(56) References Cited

U.S. PATENT DOCUMENTS

| | | | |
|---|---|---|---|
| 7,709,605 B2 | 5/2010 | Knopf et al. | |
| 7,842,663 B2 | 11/2010 | Knopf et al. | |
| 7,988,973 B2 | 8/2011 | Sherman et al. | |
| 8,058,229 B2 | 11/2011 | Seehra et al. | |
| 8,216,997 B2 | 7/2012 | Seehra et al. | |
| 8,895,016 B2 | 11/2014 | Sherman et al. | |
| 9,809,636 B2 | 11/2017 | Kumar et al. | |
| 9,850,298 B2 | 12/2017 | Attie | |
| 10,189,882 B2 | 1/2019 | Attie et al. | |
| 2010/0008918 A1 | 1/2010 | Sherman et al. | |
| 2010/0015144 A1 | 1/2010 | Sherman et al. | |
| 2010/0028332 A1 | 2/2010 | Sherman et al. | |
| 2012/0270780 A1 | 10/2012 | Lee | |
| 2013/0243743 A1* | 9/2013 | Seehra ................... | A61K 38/45 424/93.73 |
| 2015/0361163 A1 | 12/2015 | Kumar et al. | |
| 2017/0291935 A1 | 10/2017 | Sherman et al. | |
| 2017/0360887 A1 | 12/2017 | Attie et al. | |
| 2018/0125928 A1 | 5/2018 | Attie et al. | |
| 2018/0207236 A1 | 7/2018 | Kumar et al. | |

FOREIGN PATENT DOCUMENTS

| | | |
|---|---|---|
| WO | WO-2011/020045 A1 | 2/2011 |
| WO | WO-2012/027065 A2 | 3/2012 |
| WO | WO-2013/059347 A1 | 4/2013 |
| WO | WO-2013/104909 A1 | 7/2013 |
| WO | WO-2014/066486 A2 | 5/2014 |
| WO | WO-2014/066487 A2 | 5/2014 |
| WO | WO-2015/161220 A1 | 10/2015 |
| WO | WO-2016/183280 A1 | 11/2016 |
| WO | WO-2016/187378 A1 | 11/2016 |

OTHER PUBLICATIONS

Sako et al., J. Biol. Chem., 2010, vol. 285(27):21037-21048.*
Freson et al., Blood, 2008, 112:1243.*
Maratheftis et al., "GATA—a transcription factor is up-regulated in bone marrow hematopoietic progenitor CD34+ and erythroid CD71+ cells in myelodysplastic syndromes," American Journal of Hematology; Interscience: vol. 82:887-892 (2007).
Guerra et al., "Lack of GDF11 Does Not Ameliorate Erythropoiesis in β-Thalassemia and Does Not Prevent the Activity of the Trap-Ligand RAP—536," Blood, vol. 132:165 (6 pages) 2018.

(Continued)

*Primary Examiner* — Xiaozhen Xie
(74) *Attorney, Agent, or Firm* — White & Case LLP

(57) ABSTRACT

In certain aspects, the present disclosure provides compositions and methods for increasing red blood cell and/or hemoglobin levels in a subject in need thereof. Subjects in need include, for example, subjects having anemia and/or ineffective erythropoiesis as a result of having reduced GATA-1, heat shock factor and/or NFE2 levels as compared to the levels in a reference population.

20 Claims, 22 Drawing Sheets
(14 of 22 Drawing Sheet(s) Filed in Color)
Specification includes a Sequence Listing.

(56) References Cited

OTHER PUBLICATIONS

Amrolia, et al., "The activation domain of the enhancer binding protein p45NF-E2 interacts with TAFII130 abd mediates long-range activation of the α- and β-globin gene loci in an erythroid cell line," Proceedings of the National Academy of Sciences, vol. 94: 10051-10056 (1997).
Bottomley, et al., "Sideroblastic Anemia Diagnosis and Management," Hematology/Oncology Clinics of North America, vol. 28: 653-670 (2014).
Bron, et al., "Biological Basis of Anemia," Seminars in Oncology, vol. 28(2)Suppl 8: 1-6 (2001).
Bunn, "Drug-induced autoimmune red-cell aplasia," The New England Journal of Medicine, vol. 346(7): 522-523 (2002).
Cao et al., "Recent advances in β-thalassemias," Pediatric Reports, vol. 3(e17): 65-78 (2011).
Delanty, et al., "Erythropoietin-associated hyptertensive posterior leukoencephalopathy," Neurology, vol. 49: 686-689 (1997).
Demetri, et al., "Quality-of-life Benefit in Chemotherapy Patients Treated With Epoetin Alfa Is Independent of Disease Response or Tumor Type: Results From a Prospective Community Oncology Study," Journal of Clinical Oncology, vol. 16(10): 3412-3425 (1998).
Dussiot et al., "An activin receptor IIA ligand trap corrects ineffective erythropoiesis in B-thalassemia," Nature Medicine, vol. 20: 398-407 (2014).
Estey, "Current challenges in therapy of myelodysplastic syndromes," Current Opinion in Hematology, vol. 10: 60-67 (2003).
Gafter et al., "Anemia of uremia is associated with reduced in vitro cytokine secretion: Immunopotentiating activity of red blood cells," Kidney International, vol. 45: 224-231 (1994).
Ganz, "Molecular Control of Iron Transport," Journal of the American Society of Nephrology, vol. 18: 394-400 (2007).
Gardenghi, et al., "Hepcidin as a therapeutic tool to limit iron overload and improve anemia in β-thalassemic mice," The Journal of Clinical Investigation, vol. 120(12): 4466-4477 (2010).
Glaspy et al., "Erythropoietin in Cancer Patients," Annual Reviews in Medicine, vol. 60: 181-192 (2009).
Glaspy et al., "Impact of Therapy With Epoetin Alfa on Clinical Outcomes in Patients With Nonmyeloid Malignancies During Cancer Chemotherapy in Community Oncology Practice," Journal of Clinical Oncology, vol. 15(3): 1218-1234 (1997).
Groopman et al., "Chemotherapy-Induced Anemia in Adults: Incidence and Treatment," Journal of the National Cancer Institute, vol. 91(19): 1616-1634 (1999).
Hopfer et al., "Epigenetic dysregulation of GATA1 is involved in myelodysplastic syndromes dyserythropoesis," European Journal of Haematology, vol. 88: 144-153 (2012).
Horl et al., "European Best Practice Guidelines 14-16 Inadequate response to epoetin," Nephrology Dialysis Transplantation, vol. 15(Suppl 4): 43-50 (2000).
Horl et al., "European Best Practice Guidelines 17-18 Adverse effects," *Nephrol Dial Transplant*, vol. 15 (suppl. 4), 51-56 (2000).
International Search Report PCT/US2016/060574, dated Aug. 11, 2017.
Je, et al., "Mutational analysis of splicing machinery genes SF3B1, U2AF1 and SRSF2 in myelodysplasia and other common tumors," International Journal of Cancer, vol. 133: 260-266 (2013).
Jelkmann et al., "The erythropoietin receptor in normal and cancer tissues," Critical Reviews in Oncology/Hematology, vol. 67: 39-61 (2008).
Kabat, et al., "Sequences of Proteins of Immunological Interest," Fifth Edition, Public Health Service National Institutes of Health, NIH Publication No. 91-3242: 688-696 (1991).
Kalinowski and Richardson, "The Evolution of Iron Chelators for the Treatment of Iron Overload Disease and Cancer," Pharmacological Reviews, vol. 57(4): 547-583 (2005).

Koury, et al., "Erythropoietin Retards DNA Breakdown and Prevents Programmed Death in Erythroid Progenitor Cells," Science, vol. 248: 378-381 (1990).
Krapf et al., "Arterial Hypertension Induced by Erythropoietin and Erythropoiesis-Stimulating Agents (ESA)," Clinical Journal of the American Society of Nephrology, vol. 4: 470-480 (2009).
Leppa et al., "Overexpression of HSF2-beta Inhibits Hemin-induced Heat Shock Gene Expression and Erythroid Differentiation in K562 Cells," The Journal of Biological Chemistry, vol. 272(24): 15293-15298 (1997).
Levin, "Prevalent Left Ventricular Hypertrophy in the Predialysis Population: Identifying Opportunities for Intervention," American Journal of Kidney Diseases, vol. 27(3): 347-354 (1996).
Liboi, et al., "Erythropoietin receptor signals both proliferation and erythroid-specific differentiation," Proceedings of the National Academy of Sciences, vol. 90: 11351-11355 (1993).
Massagué, "How Cells Read TGF-β Signals," Nature Reviews Molecular Cell Biology, vol. 1(3): 169-178 (2000).
Mutschler, et al., "NF-E2 Overexpression Delays Erythroid Maturation and Increases Erythrocyte Productions," British Journal of Haematology, vol. 146(2): 203-217 (2009).
Nemeth, "Targeting the Hepcidin-Ferroportin Axis in the Diagnosis and Treatment of Anemias," Advances in Hematology, vol. 2010: 1-9.
Nissenson, "Epotin and Cognitive Function," American Journal of Kidney Diseases, vol. 20(1) Suppl 1:21-24 (1992).
Rajasekhar et al., "Modified activin receptor IIB ligand trap mitigates ineffective erythropoiesis and disease complications in murine beta-thalassemia," Blood, vol. 123(25): 3864-3872 (2014).
Revicki et al., "Health-Related Quality of Life Associated With Recombinant Human Erythropoietin Therapy for Predialysis Chronic Renal Disease Patients," American Journal of Kidney Diseases, vol. 25(4): 548-554 (1995).
Shivdasani et al., "Erthropoesis and globin gene expression in mice lacking the transcription factor NF-E2," Proc. Natl. Acadamy Sci., vol. 92: 8690-8694 (1995).
Singbartl, "Adverse events of erythropoietin in long-term and in acute/short-term treatment," The Clinical Investigator, vol. 72(6): S36-S43 (1994).
Suragani, et al., "Transforming Growth Factor-β Superfamily Ligand Trap ACE-536 Corrects Anemia by Promoting Late-Stage Erythropoiesis," Nature Medicine, vol. 20(4): 408-417 (2014).
The Cancer Genome Atlas Network, "Comprehensive molecular portraits of human breast tumours," Nature, vol. 490: 61-70 (2012).
Thotakura, et al., "Enzymatic Deglycosylation Glycoproteins," Methods in Enzymology, vol. 138: 350-359 (1987).
Tothova, et al., "New Strategies in Myelodysplastic Syndromes: Application of molecular diagnostics to clinical practice," Clinical Cancer Research, vol. 19(7): 1637-1643 (2013).
Weatherall et al., "Red Cells I: inherited anaemias," The Lancet, vol. 355: 1169-1175 (2000).
Blobel et al., "Ligand-dependent repression of the erythroid transcription factor GATA-1 by the estrogen receptor", Molecular and Cellular Biology, vol. 15(6): 3147-3153 (1995).
Grzasko et al., "Thalidomide can promote erythropoiesis by induction of STAT5 and repression of external pathway of apoptosis resulting in increased expression of GATA-1 transcription factor", Pharmacological Reports, vol. 67(6): 1193-1200 (2015).
Ludwig et al., "Altered translation of GATA1 in Diamond-Blackfan anemia", Nature Medicine, vol. 20(7): 748-753 (2014).
Ludwig et al., "Supplementary material for Altered translation of GATA1 in Diamond-Blackfan anemia", Nature Medicine, vol. 20(7): 748-753 (2014).
Ferreira, R. et al., "GATA1 Function, a Paradigm for Transcription Factors in Hematopoiesis," Molecular and Cellular Biology, vol. 25(4): 1215-1227 (2005).

* cited by examiner

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

FIGURE 1

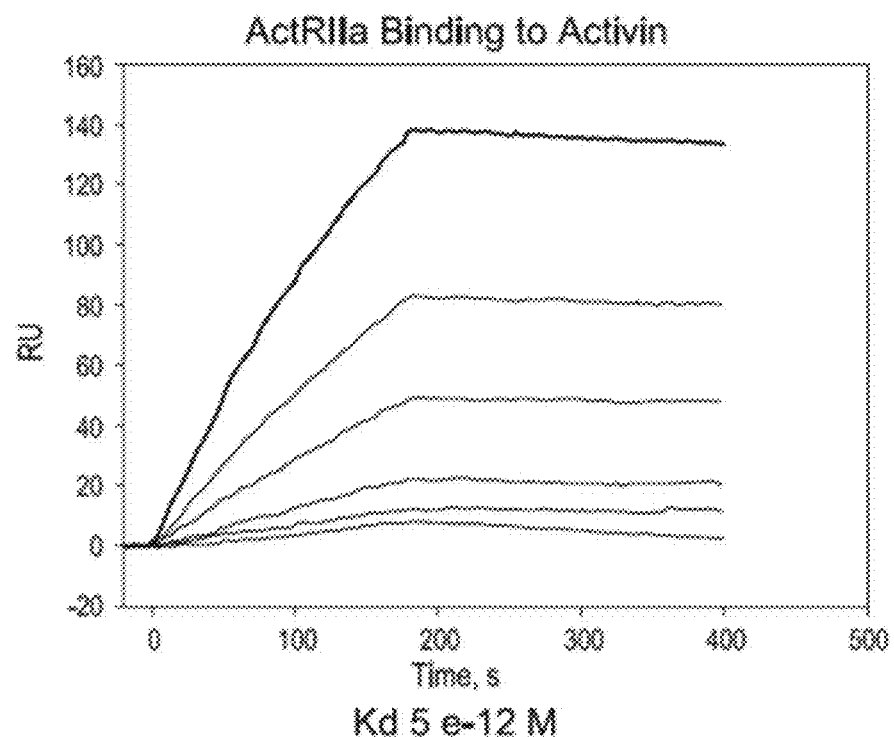
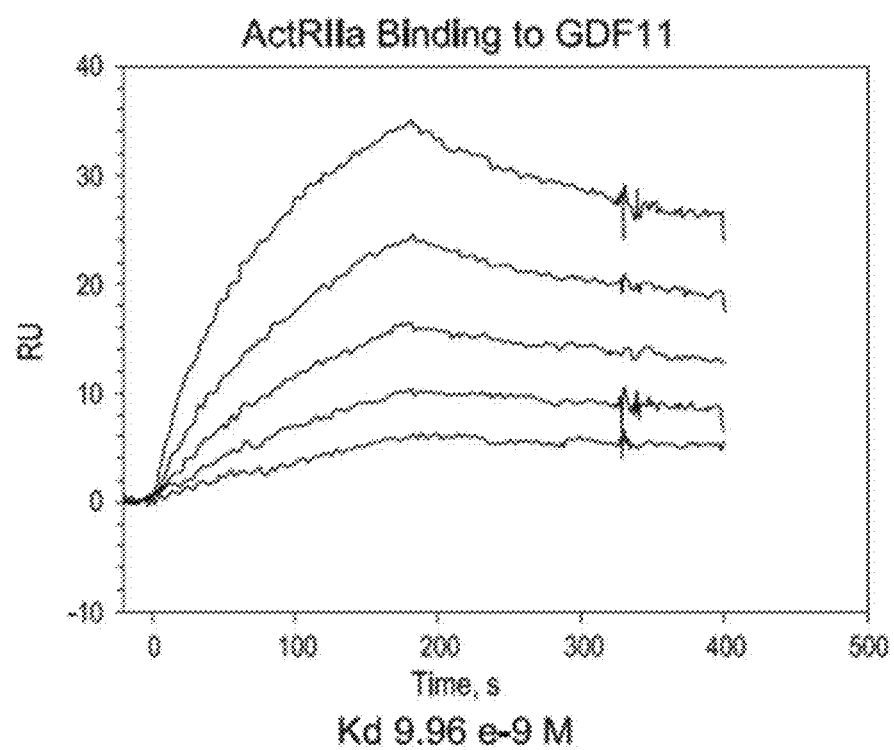
FIGURE 4

```
  1  MDAMKRGLCC VLLLCGAVFV SPGASXRGEA ETRECIYYNA NWELERTNQS

51  GLERCEGEQD KRLHCYASWR NSSGTIELVK KGCWXDDFNC YDRQECVATE

101  ENPQVYFCCC EGNFCNERFT HLPEAGGPEV TYEPPPTAPT GGGTHTCPPC

151  PAPELLGGPS VFLFPPKPKD TLMISRTPEV TCVVVDVSHE DPEVKFNWYV

201  DGVEVHNAKT KPREEQYNST YRVVSVLTVL HQDWLNGKEY KCKVSNKALP

251  APIEKTISKA KGQPREPQVY TLPPSREEMT KNQVSLTCLV KGFYPSDIAV

301  EWESNGQPEN NYKTTPPVLD SDGSFFLYSK LTVDKSRWQQ GNVFSCSVMH

351  EALHNHYTQK SLSLSPGK (SEQ ID NO:46)
```

FIGURE 5

```
  1   ATGGATGCAA TGAAGAGAGG GCTCTGCTGT GTGCTGCTGC TGTGTGGAGC
      TACCTACGTT ACTTCTCTCC CGAGACGACA CACGACGACG ACACACCTCG

51   AGTCTTCGTT TCGCCCGGCG CCTCTGGGCG TGGGGAGGCT GAGACACGGG
      TCAGAAGCAA AGCGGGCCGC GGAGACCCGC ACCCCTCCGA CTCTGTGCCC

101   AGTGCATCTA CTACAACGCC AACTGGGAGC TGGAGCGCAC CAACCAGAGC
      TCACGTAGAT GATGTTGCGG TTGACCCTCG ACCTCGCGTG GTTGGTCTCG

151   GGCCTGGAGC GCTGCGAAGG CGAGCAGGAC AAGCGGCTGC ACTGCTACGC
      CCGGACCTCG CGACGCTTCC GCTCGTCCTG TTCGCCGACG TGACGATGCG

201   CTCCTGGCGC AACAGCTCTG GCACCATCGA GCTCGTGAAG AAGGGCTGCT
      GAGGACCGCG TTGTCGAGAC CGTGGTAGCT CGAGCACTTC TTCCCGACGA

251   GGGATGATGA CTTCAACTGC TACGATAGGC AGGAGTGTGT GGCCACTGAG
      CCCTACTACT GAAGTTGACG ATGCTATCCG TCCTCACACA CCGGTGACTC

301   GAGAACCCCC AGGTGTACTT CTGCTGCTGT GAAGGCAACT TCTGCAACGA
      CTCTTGGGGG TCCACATGAA GACGACGACA CTTCCGTTGA AGACGTTGCT

351   GCGCTTCACT CATTTGCCAG AGGCTGGGGG CCCGGAAGTC ACGTACGAGC
      CGCGAAGTGA GTAAACGGTC TCCGACCCCC GGGCCTTCAG TGCATGCTCG

401   CACCCCCGAC AGCCCCCACC GGTGGTGGAA CTCACACATG CCCACCGTGC
      GTGGGGGCTG TCGGGGGTGG CCACCACCTT GAGTGTGTAC GGGTGGCACG

451   CCAGCACCTG AACTCCTGGG GGGACCGTCA GTCTTCCTCT TCCCCCCAAA
      GGTCGTGGAC TTGAGGACCC CCCTGGCAGT CAGAAGGAGA AGGGGGGTTT

501   ACCCAAGGAC ACCCTCATGA TCTCCCGGAC CCCTGAGGTC ACATGCGTGG
      TGGGTTCCTG TGGGAGTACT AGAGGGCCTG GGGACTCCAG TGTACGCACC

551   TGGTGGACGT GAGCCACGAA GACCCTGAGG TCAAGTTCAA CTGGTACGTG
      ACCACCTGCA CTCGGTGCTT CTGGGACTCC AGTTCAAGTT GACCATGCAC

601   GACGGCGTGG AGGTGCATAA TGCCAAGACA AAGCCGCGGG AGGAGCAGTA
      CTGCCGCACC TCCACGTATT ACGGTTCTGT TTCGGCGCCC TCCTCGTCAT

651   CAACAGCACG TACCGTGTGG TCAGCGTCCT CACCGTCCTG CACCAGGACT
      GTTGTCGTGC ATGGCACACC AGTCGCAGGA GTGGCAGGAC GTGGTCCTGA

701   GGCTGAATGG CAAGGAGTAC AAGTGCAAGG TCTCCAACAA AGCCCTCCCA
      CCGACTTACC GTTCCTCATG TTCACGTTCC AGAGGTTGTT TCGGGAGGGT

751   GCCCCCATCG AGAAAACCAT CTCCAAAGCC AAGGGCAGC  CCCGAGAACC
      CGGGGGTAGC TCTTTTGGTA GAGGTTTCGG TTCCCGTCG  GGGCTCTTGG
```

FIGURE 6A

```
 801   ACAGGTGTAC ACCCTGCCCC CATCCCGGGA GGAGATGACC AAGAACCAGG
       TGTCCACATG TGGGACGGGG GTAGGGCCCT CCTCTACTGG TTCTTGGTCC

851   TCAGCCTGAC CTGCCTGGTC AAAGGCTTCT ATCCCAGCGA CATCGCCGTG
       AGTCGGACTG GACGGACCAG TTTCCGAAGA TAGGGTCGCT GTAGCGGCAC

901   GAGTGGGAGA GCAATGGGCA GCCGGAGAAC AACTACAAGA CCACGCCTCC
       CTCACCCTCT CGTTACCCGT CGGCCTCTTG TTGATGTTCT GGTGCGGAGG

951   CGTGCTGGAC TCCGACGGCT CCTTCTTCCT CTATAGCAAG CTCACCGTGG
       GCACGACCTG AGGCTGCCGA GGAAGAAGGA GATATCGTTC GAGTGGCACC

1001   ACAAGAGCAG GTGGCAGCAG GGGAACGTCT TCTCATGCTC CGTGATGCAT
       TGTTCTCGTC CACCGTCGTC CCCTTGCAGA AGAGTACGAG GCACTACGTA

1051   GAGGCTCTGC ACAACCACTA CACGCAGAAG AGCCTCTCCC TGTCCCCGGG
       CTCCGAGACG TGTTGGTGAT GTGCGTCTTC TCGGAGAGGG ACAGGGGCCC

1101   TAAATGA (SEQ ID NO:90)
       ATTTACT (SEQ ID NO:60)
```

FIGURE 6B

```
  1  MDAMKRGLCC VLLLCGAVFV SPGAA TREC IYYNANWELE RTNQSGLERC
 51  EGEQDKRLHC YASWRNSSGT IELVKKGCW  DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 61)
```

FIGURE 7

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

E  T  R  E  C  I  Y  Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N  A  N  W  E  L  E  R  T  N  Q  S  G  L  E  R  C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E  G  E  Q  D  K  R  L  H  C  Y  A  S  W  R  N  S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S  G  T  I  E  L  V  K  G  C  W  D  D  D  F
201  CTCTGGCACC ATCGAGCTCG TGAAGAAGGG CTGCTGGGAC GATGACTTCA
     GAGACCGTGG TAGCTCGAGC ACTTCTTCCC GACGACCCTG CTACTGAAGT

N  C  Y  D  R  Q  E  C  V  A  T  E  N  P  Q  V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y  F  C  C  C  E  G  N  F  C  N  E  R  F  T  H  L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P  E  A  G  G  P  E  V  T  Y  E  P  P  P  T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG
```

FIGURE 8A

```
 601  AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG

801  CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851  GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901  GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951  CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 62)
      GTCTTCTCGG AGAGGGACAG GGGCCCATTT ACT (SEQ ID NO: 63)
```

FIGURE 8B

```
  1  ¤TRECIYYNA NWELERTNQS GLERCEGEQD KRLHCYASWR NSSGTIELVK

51  KGCW¤DDFNC YDRQECVATE ENPQVYFCCC EGNFCNERFT HLPEAGGPEV

101  TYEPPPTGGG THTCPPCPAP ELLGGPSVFL FPPKPKDTLM ISRTPEVTCV

151  VVDVSHEDPE VKFNWYVDGV EVHNAKTKPR EEQYNSTYRV VSVLTVLHQD

201  WLNGKEYKCK VSNKALPAPI EKTISKAKGQ PREPQVYTLP PSREEMTKNQ

251  VSLTCLVKGF YPSDIAVEWE SNGQPENNYK TTPPVLDSDG SFFLYSKLTV

301  DKSRWQQGNV FSCSVMHEAL HNHYTQKSLS LSPGK (SEQ ID NO: 64)
```

FIGURE 9

```
  1    STRECIYYNA NWELERTNQS GLERCEGEQD KRLHCYASWR NSSGTIELVK

51    KGCWLDDFNC YDRQECVATE ENPQVYFCCC EGNFCNERFT HLPEAGGPEV

101    TYEPPPT   (SEQ ID NO: 65)
```

FIGURE 10

```
                                                         E   T   R   E   C   I   Y   Y
  1  ATGGATGCAA TGAAGAGAGG GCTCTGCTGT GTGCTGCTGC TGTGTGGAGC
 51  AGTCTTCGTT TCGCCCGGCG CCGCCGAAAC CCGGGAATGC ATTTATTACA

N  A  N  W  E  L  E  R  T  N  Q  S  G  L  E  R  C
101  AGCCAATG GGACTGAA CGACAACC AACGGCT GAACGTG

E  G  E  Q  D  K  R  L  H  C  Y  A  S  W  R  N  S
151  GAGGGGAAC AGGAAAACG CTCATGC TATGCTCT GGAGGAACT

S  G  T  I  E  L  V  K  K  C  W  D  D  F
201  CTCGGGACC ATGAACTGG TAAGAAGG CTGCTGGGAC GAAGATTCA

N  C  Y  D  R  Q  E  C  V  A  T  E  N  P  Q  V
251  ATGCTATGA CCGCAGGAA TGTGTTGCCA CCGAAGAGAA ACCCCAGGTC

Y  F  C  C  E  G  N  F  C  N  E  R  F  T  H  L
301  TATTTCTGT GCTGCGAGGG GAATTTCTGC AATGAACGGT TTACCCACCT

P  E  A  G  G  P  E  V  T  Y  E  P  P  T
351  CCCGAAGCA GGGGGCCCG AAGTAACTA TGAACCCCC CCCACGGGTG

401  GTGGAACTCA CACATGCCCA CCGTGCCCAG CACCTGAACT CCTGGGGGGA

451  CCGTCAGTCT TCCTCTTCCC CCCAAAACCC AAGGACACCC TCATGATCTC

501  CCGGACCCCT GAGGTCACAT GCGTGGTGGT GGACGTGAGC CACGAAGACC

551  CTGAGGTCAA GTTCAACTGG TACGTGGACG GCGTGGAGGT GCATAATGCC

601  AAGACAAAGC CGCGGGAGGA GCAGTACAAC AGCACGTACC GTGTGGTCAG

651  CGTCCTCACC GTCCTGCACC AGGACTGGCT GAATGGCAAG GAGTACAAGT
```

FIGURE 11A

```
 701   GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA (SEQ ID NO: 66)
       GTCTTCTCGG AGAGGGACAG GGGCCCATTT ACT (SEQ ID NO: 67)
```

FIGURE 11B

```
GAAAC CCGCGAATGT ATTTATTACA AAGCTAATTG GGAACTCGAA CGGACAACC
AATCCGGCCT TGAACGTTGT GAGGGGGAAC AGGATAAACG CCTCCATTGC TAGCTTCTT
GGAGCAACTT CTCCGGCACC ATTGAACTCG TCAAGAAGGG CTGCTGGGAC GACGATTCA
ATTGTTATGA CCGTCAGGAA TGTGTCGCAA CCGAAGAGAA TCCCCAGGTC TATTTCTGTT
GTTGCGAGGG CAATTTCTGT AATGAACGCT TTACCCACCT TCCCGAAGCC GGGGGCCCG
ACGTAACTTA TGAACCCCCT CCAACC      (SEQ ID NO: 68)
```

```
IgG1   --------THTCPPCPAPELLGGPSVFLFPPKPKDTLMISRTPEVTCVVVDVSHEDPEVKF  53
IgG4   ----ESKYGPPCPSCPAPEFLGGPSVFLFPPKPKDTLMISRTPEVTCVVVDVSQEDPEVQF  57
IgG2   --------VECPPCPAPPVAG-PSVFLFPPKPKDTLMISRTPEVTCVVVDVSHEDPEVQF  51
IgG3   EPKSCDTPPPCPRCPAPELLGGPSVFLFPPKPKDTLMISRTPEVTCVVVDVSHEDPEVQF  60
                 ** ****   *  ******************************.****.*

IgG1   NWYVDGVEVHNAKTKPREEQYNSTYRVVSVLTVLHQDWLNGKEYKCKVSNKALPAPIEKT  113
IgG4   NWYVDGVEVHNAKTKPREEQFNSTYRVVSVLTVLHQDWLNGKEYKCKVSNKGLPSSIEKT  117
IgG2   NWYVDGVEVHNAKTKPREEQFNSTFRVVSVLTVVHQDWLNGKEYKCKVSNKGLPAPIEKT  111
IgG3   KWYVDGVEVHNAKTKPREEQYNSTFRVVSVLTVLHQDWLNGKEYKCKVSNKALPAPIEKT  120
       :***************** :***:*******:*******************.**:.****

IgG1   ISKAKGQPREPQVYTLPPSREEMTKNQVSLTCLVKGFYPSDIAVEWESNGQPENNYKTTP  173
IgG4   ISKAKGQPREPQVYTLPPSQEEMTKNQVSLTCLVKGFYPSDIAVEWESNGQPENNYKTTP  177
IgG2   ISKTKGQPREPQVYTLPPSREEMTKNQVSLTCLVKGFYPSDIAVEWESNGQPENNYKTTP  171
IgG3   ISKTKGQPREPQVYTLPPSREEMTKNQVSLTCLVKGFYPSDIAVEWESSGQPENNYNTTP  180
       ***.***************:****************************.******.****

IgG1   PVLDSDGSFFLYSKLTVDKSRWQQGNVFSCSVMHEALHNHYTQKSLSLSPGK  225
IgG4   PVLDSDGSFFLYSRLTVDKSRWQEGNVFSCSVMHEALHNHYTQKSLSLSLGK  229
IgG2   PMLDSDGSFFLYSKLTVDKSRWQQGNVFSCSVMHEALHNHYTQKSLSLSPGK  223
IgG3   PMLDSDGSFFLYSKLTVDKSRWQQGNIFSCSVMHEALHNRFTQKSLSLSPGK  232
       *:***********:*********:**:***********: ********** **
```

FIGURE 14

1    MDAMKRGLCC VLLLCGAVFV SPGAA▓TREC IYYNANWELE RTNQSGLERC
51   EGEQDKRLHC YASWRNSSGT IELVKKGCWL DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 79)

FIGURE 15

```
  1   ATGGATGCAA TGAAGAGAGG GCTCTGCTGT GTGCTGCTGC TGTGTGGAGC
      TACCTACGTT ACTTCTCTCC CGAGACGACA CACGACGACG ACACACCTCG

A  E  T  R  E  C  I  Y  Y
 51   AGTCTTCGTT TCGCCCGGCG CCGCTGAGAC ACGGGAGTGC ATCTACTACA
      TCAGAAGCAA AGCGGGCCGC GGCGACTCTG TGCCCTCACG TAGATGATGT

N  A  N  W  E  L  E  R  T  N  Q  S  G  L  E  R  C
101   ACGCCAACTG GGAGCTGGAG CGCACCAACC AGAGCGGCCT GGAGCGCTGC
      TGCGGTTGAC CCTCGACCTC GCGTGGTTGG TCTCGCCGGA CCTCGCGACG

E  G  E  Q  D  K  R  L  C  Y  A  S  W  R  N  S
151   GAAGGCGAGC AGGACAAGCG GCTGTGCTAC GCCTCCTGG CGCAACAG
      CTTCCGCTCG TCCTGTTCGC CGACGTGACG ATGCGGAGGA CCGCGTTGTC

S  G  T  I  E  L  V  K  K  G  C  W  L  D  D  F
201   CTCTGGCACC ATCGAGCTCG TGAAGAAGGG CTGCTGGCTA GATGACTTCA
      GAGACCGTGG TAGCTCGAGC ACTTCTTCCC GACGACCGAT CTACTGAAGT

N  C  Y  D  R  Q  E  C  V  A  T  E  E  N  P  Q  V
251   ACTGCTACGA TAGGCAGGAG TGTGTGGCCA CTGAGGAGAA CCCCCAGGTG
      TGACGATGCT ATCCGTCCTC ACACACCGGT GACTCCTCTT GGGGGTCCAC

Y  F  C  C  E  G  N  F  C  N  E  R  F  T  H  L
301   TACTTCTGCT GCTGTGAAGG CAACTTCTGC AACGAGCGCT TCACTCATTT
      ATGAAGACGA CGACACTTCC GTTGAAGACG TTGCTCGCGA AGTGAGTAAA

P  E  A  G  G  P  E  V  T  Y  E  P  P  T
351   GCCAGAGGCT GGGGGCCCGG AAGTCACGTA CGAGCCACCC CCGACAGGTG
      CGGTCTCCGA CCCCCGGGCC TTCAGTGCAT GCTCGGTGGG GGCTGTCCAC

401   GTGGAACTCA CACATGCCCA CCGTGCCCAG CACCTGAACT CCTGGGGGGA
      CACCTTGAGT GTGTACGGGT GGCACGGGTC GTGGACTTGA GGACCCCCCT

451   CCGTCAGTCT TCCTCTTCCC CCCAAAACCC AAGGACACCC TCATGATCTC
      GGCAGTCAGA AGGAGAAGGG GGGTTTTGGG TTCCTGTGGG AGTACTAGAG

501   CCGGACCCCT GAGGTCACAT GCGTGGTGGT GGACGTGAGC CACGAAGACC
      GGCCTGGGGA CTCCAGTGTA CGCACCACCA CCTGCACTCG GTGCTTCTGG

551   CTGAGGTCAA GTTCAACTGG TACGTGGACG GCGTGGAGGT GCATAATGCC
      GACTCCAGTT CAAGTTGACC ATGCACCTGC CGCACCTCCA CGTATTACGG

601   AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA

701   GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG
```

FIGURE 16A

```
801   CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 80)
      GTCTTCTCGG AGAGGGACAG GGGCCCATTT ACT (SEQ ID NO: 81)
```

FIGURE 16B

```
                                                        A   E   T   R   E   C   I   Y   Y
  1   ATGGATGCAA TGAAGAGAGG GCTCTGCTGT GTGCTGCTGC TGTGTGGAGC
      TACCTACGTT ACTTCTCTCC CGAGACGACA CACGACGACG ACACACCTCG

A   E   T   R   E   C   I   Y   Y
 51   AGTCTTCGTT TCGCCCGGCG CCGCCGAAAC CCGCGAATGC ATCTACTACA
      TCAGAAGCAA AGCGGGCCGC GGCGGCTTTG GGCGCTTACG TAGATGATGT

N   A   N   W   E   L   E   R   T   N   Q   S   G   L   E   R   C
101   ATGCTAATTG GGAACTCGAA CGGACCAACC AGTCCGGGCT CGAACGGTGC
      TACGATTAAC CCTTGAGCTT GCCTGGTTGG TCAGGCCCGA GCTTGCCACG

E   G   E   Q   D   K   R   L   H   C   Y   A   S   W   R   N   S
151   GAGGGCGAAC AGGATAAACG GCTCCATTGC TACGCCTCGT GGAGGAACTC
      CTCCCGCTTG TCCTATTTGC CGAGGTAACG ATGCGGAGCA CCTCCTTGAG

S   G   T   I   E   L   V   K   G   C   W   L   D   D   F
201   CTCCGGAACC ATCGAACTCG TCAAGAAGGG CTGCTGGCTC GACGATTTCA
      GAGGCCCTGC TAGCTTGACC AGTTCTTCCC CACGACCGAC CTGCTAAAGT

N   C   Y   D   R   Q   E   C   V   A   T   E   E   N   P   Q   V
251   ACTGTTATGA CCGCCAGGAA TGTGTTGCCA CCGAAGAGAA CCCCCAGGTC
      TGACAATACT GGCGGTCCTT ACACAACGGT GGCTTCTCTT GGGGGTCCAG

Y   F   C   C   E   G   N   F   C   N   E   R   F   T   H   L
301   TATTTCTGTT GTTGCGAGGG CAATTTCTGC AATGAGCGTT TCACCCATCT
      ATAAAGACAA CAACGCTCCC GTTAAAGACG TTACTCGCAA AGTGGGTAGA

P   E   A   G   G   P   E   V   T   Y   E   P   P   T
351   CCCGGAGGCC GGCGGGCCGG AGGTGACCTA TGAGCCGCCG CCGACGGGTG
      GGGGCTCCGG CCGCCCGGCC TCCACTGGAT ACTCGGCGGC GGCTGCCCAC

401   GTGGAACTCA CACATGCCCA CCGTGCCCAG CACCTGAACT CCTGGGGGGA
      CACCTTGAGT GTGTACGGGT GGCACGGGTC GTGGACTTGA GGACCCCCCT

451   CCGTCAGTCT TCCTCTTCCC CCCAAAACCC AAGGACACCC TCATGATCTC
      GGCAGTCAGA AGGAGAAGGG GGGTTTTGGG TTCCTGTGGG AGTACTAGAG

501   CCGGACCCCT GAGGTCACAT GCGTGGTGGT GGACGTGAGC CACGAAGACC
      GGCCTGGGGA CTCCAGTGTA CGCACCACCA CCTGCACTCG GTGCTTCTGG

551   CTGAGGTCAA GTTCAACTGG TACGTGGACG GCGTGGAGGT GCATAATGCC
      GACTCCAGTT CAAGTTGACC ATGCACCTGC CGCACCTCCA CGTATTACGG

601   AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA

701   GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG
```

FIGURE 17A

```
 801   CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA  (SEQ ID NO: 82)
       GTCTTCTCGG AGAGGGACAG GGGCCCATTT ACT  (SEQ ID NO: 83)
```

FIGURE 17B

METHODS FOR INCREASING RED BLOOD CELL LEVELS AND TREATING INEFFECTIVE ERYTHROPOIESIS

RELATED APPLICATION

This application claims the benefit of priority from U.S. Provisional Application No. 62/251,024, filed Nov. 4, 2015. The specification of the foregoing application is incorporated herein by reference in its entirety.

SEQUENCE LISTING

The instant application contains a Sequence Listing which has been submitted electronically in ASCII format and is hereby incorporated by reference in its entirety. Said ASCII copy, created on May 19, 2017, is named PHPH-093-101 SL.txt and is 156,917 bytes in size.

BACKGROUND OF THE INVENTION

The mature red blood cell, or erythrocyte, is responsible for oxygen transport in the circulatory systems of vertebrates. Red blood cells contain high concentrations of hemoglobin, a protein that binds to oxygen in the lungs at relatively high partial pressure of oxygen ($pO_2$) and delivers oxygen to areas of the body with a relatively low $pO_2$. Mature red blood cells are produced from pluripotent hematopoietic stem cells in a process termed erythropoiesis. Postnatal erythropoiesis occurs primarily in the bone marrow and in the red pulp of the spleen. The coordinated action of various signaling pathways controls the balance of cell proliferation, differentiation, survival, and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

Erythropoietin (EPO) is widely recognized as the most significant positive regulator of postnatal erythropoiesis in vertebrates. EPO regulates the compensatory erythropoietic response to reduced tissue oxygen tension (hypoxia) and low red blood cell levels or low hemoglobin levels. In humans, elevated EPO levels promote red blood cell formation by stimulating the generation of erythroid progenitors in the bone marrow and spleen. In the mouse, EPO enhances erythropoiesis primarily in the spleen.

Effects of EPO are mediated by a cell-surface receptor belonging to the cytokine receptor superfamily. The human EPO receptor gene encodes a 483 amino acid transmembrane protein; however, the active EPO receptor is thought to exist as a multimeric complex even in the absence of ligand [see, e.g., U.S. Pat. No. 6,319,499]. The cloned full-length EPO receptor expressed in mammalian cells binds EPO with an affinity similar to that of the native receptor on erythroid progenitor cells. Binding of EPO to its receptor causes a conformational change resulting in receptor activation and biological effects including increased proliferation of immature erythroblasts, increased differentiation of immature erythroblasts, and decreased apoptosis in erythroid progenitor cells [see, e.g., Liboi et al. (1993) Proc Natl Acad Sci USA 90:11351-11355 and Koury et al. (1990) Science 248:378-381].

Various forms of recombinant EPO are used by physicians to increase red blood cell levels in a variety of clinical settings, particularly in the treatment of anemia. Anemia is a broadly-defined condition characterized by lower than normal levels of hemoglobin or red blood cells in the blood. In some instances, anemia is caused by a primary disorder in the production or survival of red blood cells (e.g., a thalassemia disorder or sickle cell anemia). More commonly, anemia is secondary to diseases of other systems [see, e.g., Weatherall & Provan (2000) Lancet 355, 1169-1175]. Anemia may result from a reduced rate of production or increased rate of destruction of red blood cells or by loss of red blood cells due to bleeding. Anemia may result from a variety of disorders that include, for example, acute or chronic renal failure or end stage renal disease, chemotherapy treatment, a myelodysplastic syndrome, rheumatoid arthritis, and bone marrow transplantation.

Treatment with EPO typically causes a rise in hemoglobin by about 1-3 g/dL in healthy humans over a period of weeks. When administered to anemic individuals, this treatment regimen often provides substantial increases in hemoglobin and red blood cell levels and leads to improvements in quality of life and prolonged survival. However, EPO is not uniformly effective, and many individuals are refractory to even high doses [see, e.g., Horl et al. (2000) Nephrol Dial Transplant 15, 43-50]. For example, over 50% of patients with cancer have an inadequate response to EPO, approximately 10% with end-stage renal disease are hyporesponsive to EPO [see, e.g., Glaspy et al. (1997) J Clin Oncol 15, 1218-1234 and Demetri et al. (1998) J Clin Oncol 16, 3412-3425], and less than 10% with myelodysplastic syndrome respond favorably to EPO [see Estey (2003) Curr Opin Hematol 10, 60-670]. Several factors, including inflammation, iron and vitamin deficiency, inadequate dialysis, aluminum toxicity, and hyperparathyroidism may predict a poor therapeutic response. The molecular mechanisms of resistance to EPO are as yet unclear. Recent evidence suggests that higher doses of EPO may be associated with an increased risk of cardiovascular morbidity, tumor growth, and mortality in some patient populations [see, e.g., Krapf et al. (2009) Clin J Am Soc Nephrol 4:470-480 and Glaspy (2009) Annu Rev Med 60:181-192]. It has been therefore recommended that EPO-based therapeutic compounds (e.g., erythropoietin-stimulating agents, ESAs) be administered at the lowest dose required to avoid red blood cell transfusions [see, e.g., Jelkmann et al. (2008) Crit Rev Oncol. Hematol 67:3

Ineffective erythropoiesis is a term used to describe a group of erythroid disorders in which erythrocyte production is decreased despite increased numbers of earlier-stage erythroid cells [see, e.g., Tanno (2010) Adv Hematol 2010: 358283]. Ineffective erythropoiesis often gives rise to anemia, elevated erythropoietin levels, formation of excessive numbers of red blood cell precursors, and iron overload. If they persist, these conditions can lead to splenomegaly, liver and heart disorders, and bone damage as well as other complications. As endogenous erythropoietin levels are commonly very high in patients with ineffective erythropoiesis, EPO-based therapeutics often will not treat the anemia in these patients and/or may cause an aggravation of other aspects of the disease, such as splenomegaly and iron overload.

It has previously been demonstrated that Smad2/3 signaling (of the TGFβ superfamily) is elevated in several diseases and disorders associated with ineffective erythropoiesis, e.g., myelodysplastic syndromes and β-thalassemia (Suragani et al., 2014, Nat Med, 20(4):408-14). In addition, it has been shown that inhibition of Smad 2/3 signaling using a modified activin receptor type IIB ligand trap (a GDF trap polypeptide) decreased ineffective erythropoiesis and alleviated disease pathology in a murine model of β-thalassemia (Suragani et al., 2014). However, the exact mechanism by which the GDF trap induces its beneficial effects in treating ineffective erythropoiesis was not known. Elucidating gene regulation in response to Smad inhibitors such as this GDF trap would be useful for identifying genes and proteins that could serve as useful therapeutic targets for increasing red blood cell levels, treating or preventing an anemia, and/or treating or preventing ineffective erythropoiesis in a subject.

Thus, it is an object of the present disclosure to provide alternative methods for increasing red blood cell levels and/or addressing other disorders in the context of ineffective erythropoiesis.

SUMMARY OF THE INVENTION

It has been reported that Smad signaling (of the TGFβ superfamily) is elevated in myelodysplastic syndromes (MDS) and thalassemia, diseases that are characterized by ineffective erythropoiesis (Suragani et al., 2014, Nat Med, 20(4):408-14). Smad pathway inhibition [e.g., using an ActRII antagonist (inhibitor)] decreases ineffective erythropoiesis and alleviates disease pathology in thalassemia patients. As described herein, transcriptome analysis of thalassemic erythroblasts reveales various differentially expressed genes in response to treatment with a Smad signaling antagonist. In particular, it was observed that target genes of multiple transcriptional regulators including GATA-1 (erythroid differentiation), NFE2, and heat shock factor (involved in globin expression and protein quality-control) are upregulated. In particular, the data indicate that ActRII antagonist treatment results in transcriptional upregulation of genes known to promote erythroid differentiation and processing of unpaired α-globins. Therefore, these data provide a potential mechanistic role for Smad antagonists in the treatment of disorders associated with ineffective erythropoiesis including, for example, thalassemia. By inhibiting Smad signaling, an ActRII antagonist may relieve the block of terminal erythroid maturation and decreases ineffective erythropoiesis in patients in need thereof including, for example, thalassemia patients.

Furthermore, the data suggest that other agents which agonize (activate), reduce inhibition of, and/or supplement the activity of, for example, any one of, or combination of, GATA-1, heat shock factor, and/or NFE2, or one or more downstream factors of any one of GATA-1, heat shock factor, and/or NFE2, may be useful in the treatment of ineffective erythropoiesis associated with a variety of disorders including, for example, thalassemia. Moreover, the data indicate ineffective erythropoiesis patients that may particularly benefit from treatment with one or more Smad inhibitors disclosed herein [e.g., ActRII inhibitors such as ActRIIB(L79D 25-131)-Fc] are patients that have low levels and/or activity of one or more GATA-1, heat shock factor, and/or NFE2. In such ineffective erythropoiesis patients with low levels and/or activity of one or more GATA-1, heat shock factor, and/or NFE2, these biomarkers may be useful for determining the therapeutically effectiveness of an agent, or combination of agents, and thus be useful in managing dosing of a patient (e.g., dose amount administered and/or interval of dosing) particularly when administering one or more Smad antagonists as described herein [e.g., ActRIIB (L79D 25-131)-Fc].

In certain aspects, the disclosure provides methods for increasing red blood cell levels, treating or preventing an anemia, and/or treating or preventing ineffective erythropoiesis in a subject comprising administering to a subject in need thereof an effective amount of an agent, or combination of agents, that agonizes (activates), reduces inhibition of, and/or supplements the activity of any one of, or combination of, GATA-1, heat shock factor, and/or NFE2.

In some embodiments, the disclosure provides a method for treating or preventing ineffective erythropoiesis in a subject comprising administering to a subject in need thereof a pharmaceutically effective amount of an agent, or combination of agents, that agonizes, reduces inhibition of, supplements the activity of, increases the levels of, and/or increases the activity of GATA-1 in the subject. In some embodiments, prior to said administration the subject has a decreased level of GATA-1 compared to levels of GATA-1 in a reference population. In some embodiments, the disclosure provides a method for treating or preventing ineffective erythropoiesis in a subject in whom it has been determined has a decreased level of GATA-1 as compared to a reference population, comprising administering to said subject a pharmaceutically effective amount of an agent, or combination of agents, that agonizes, reduces inhibition of, supplements the activity of, increases the levels of, and/or increases the activity of GATA-1 in the subject. In some embodiments, the subject has a decreased level of one or more heme biosynthesis genes selected from the group consisting of: Ppox, Fech, Alas2, and Abcb10l, compared to levels of Ppox, Fech, Alas2, and Abcb10l in a reference population. In some embodiments, the subject has a decreased level of one or more erythroid differentiation factors selected from the group consisting of: KLF1, NFE2, GYPA, Bcl21, Bnip31, Bach1, and ANK1, compared to levels of KLF1, NFE2, GYPA, Bcl21, Bnip31, Bach1, and ANK1 in a reference population. In some embodiments, the subject is a human. In some embodiments, the reference population consists of one or more humans. In some embodiments, the reference population consists of subjects not having MDS, a hemoglobinopathy, sickle-cell disease, and/or beta-thalassemia. In some embodiments, the reference population consists of 1, 2, 3, 5, 10, 20, 25, 30, 50, 70, 75, 80, 90, 100, 200, 250, 500, or 1000 individuals. In some embodiments, the reference population consists of healthy individuals. In some embodiments, the reference population consists of people of the same gender, age, and/or weight as the subject. In some embodiments, the reference population consists of people without ineffective erythropoiesis. In some embodiments, the decreased level of GATA-1 is about 10%, 20%, 25%, 30%, 40%, 50%, 60%, 70%, 75%, 80%, 90%, 100%, 200%, or 500% lower than the levels of GATA-1 in the reference population. In some embodiments, the decreased level of Ppox, Fech, Alas2, and Abcb10l is about 10%, 20%, 25%, 30%, 40%, 50%, 60%, 70%, 75%, 80%, 90%, 100%, 200%, or 500% lower than the levels of Ppox, Fech, Alas2, and/or Abcb10l in the reference population. In some embodiments, the decreased level of KLF1, NFE2, GYPA, Bcl21, Bnip31, Bach1, and/or ANK1 is about 10%, 20%, 25%, 30%, 40%, 50%, 60%, 70%, 75%, 80%, 90%, 100%, 200%, or 500% lower than the levels of KLF1, NFE2, GYPA, Bcl21, Bnip31, Bach1, and/or ANK1 in the reference population. In some embodiments, the decreased level of GATA-1 is about 10%, 20%, 25%, 30%, 40%, 50%, 60%, 70%, 75%, 80%, 90%, 100%, 200%, or 500% lower than the levels of GATA-1 in the bottom 10%, bottom 5%, bottom 4%, bottom 3%, bottom 2%, or bottom 1% of the reference population. In some embodiments, the decreased level of Ppox, Fech, Alas2, and/or Abcb10l is about 10%, 20%, 25%, 30%, 40%, 50%, 60%, 70%, 75%, 80%, 90%, 100%, 200%, or 500% lower than the levels of Ppox, Fech, Alas2, and/or Abcb10l in the bottom 10%, bottom 5%, bottom 4%, bottom 3%, bottom 2%, or bottom 1% of the reference population. In some embodiments, the decreased level of KLF1, NFE2, GYPA, Bcl21, Bnip31, Bach1, and/or ANK1 is about 10%, 20%, 25%, 30%, 40%, 50%, 60%, 70%, 75%, 80%, 90%, 100%, 200%, or 500% lower than the levels of KLF1, NFE2, GYPA, Bcl21, Bnip31, Bach1, and/or ANK1 in the bottom 10%, bottom 5%, bottom 4%, bottom 3%, bottom 2%, or bottom 1% of the reference population. In some embodiments, the agent increases GATA-1 levels and/or activity in erythroblasts in the subject. In some embodiments, the agent is an estrogen receptor antagonist. In some embodiments, the agent is an estrogen receptor inhibitor. In some embodiments, the agent inhibits the binding of ErbB2/HER2 to the estrogen receptor. In some embodiments, the agent inhibits the binding of endogenous estrogen to the estrogen receptor. In some embodiments, the agent is tamoxifen. In some embodiments, the agent is an estrogen receptor agonist. In some embodiments, the agent is an estrogen receptor activator. In some embodiments, the agent is an agonist of estrogen receptor alpha (ERα) and estrogen receptor beta (ERβ). In some embodiments, the agent is an agonist of membrane estrogen receptors (mER). In some embodiments, the agent is an estrogen sex hormone. In some embodiements, the agent is estriol or estrone. In some embodiments, the agent is oestradiol. In some embodiments, the agent is chemotherapeutic. In some embodiments, the agent inhibits the synthesis of DNA or RNA. In some embodiments, the agent inhibits the topoisomerase II enzyme. In some embodiments, the agent results in iron-mediated generation of free oxygen radicals. In some embodiments, the agent induces histone eviction from chromatin. In some embodiments, the agent is an anthracycline. In some embodiments, the anthracycline is selected from the group consisting of: aclacinomycin A, daunorubicin, doxorubicin, epirubicin, idarubicin, valrubicin, mitoxantrone, and any analogs thereof. In some embodiments, the agent is a vector comprising a polynucleotide encoding recombinant GATA-1 protein. In some embodiments, the agent is erythroid transcription factor. In some embodiments, the agent is recombinant GATA-1 protein. In some embodiments, the agent is recombinant erythroid transcription factor. In some embodiments, the agent agonizes, reduces the inhibition of, supplements the activity of, increases the levels of and/or increases the activity of one or more heme biosynthesis genes selected from the group consisting of: Ppox, Fech, Alas2, and Abcb10l. In some embodiments, the agent agonizes, reduces the inhibition of, supplements the activity of, increases the levels, and/or increases the activity of one or more erythroid differentiation factors selected from the group consisting of: KLF1, NFE2, GYPA, Bcl21, Bnip31, Bach1, and ANK1.

In some embodiments, the disclosure provides a method for treating or preventing ineffective erythropoiesis in a subject comprising: a) taking a first measurement of GATA-1 level in the subject, b) administering to the subject an initial dose of an ActRII antagonist, c) taking a second measurement of GATA-1 level in the subject, d) administering to the subject an additional dose of the ActRII antagonist that is the same as the initial dose or an adjusted dose of the ActRII antagonist. In some embodiments, the disclosure provides a method for treating or preventing ineffective erythropoiesis in a subject comprising: a) administering to the subject an initial dose of an ActRII antagonist, b) taking a measurement of GATA-1 level in the subject, c) administering to the subject an additional dose of the ActRII antagonist that is the same as the initial dose or an adjusted dose of the ActRII antagonist. In some embodiments, the level of GATA-1 in the subject is compared to GATA-1 levels in a reference population. In some embodiments, the initial dose and/or adjusted dose of the ActRII antagonist is about 0.1 mg/kg, about 0.3 mg/kg, about 0.5 mg/kg, about 0.7 mg/kg, about 0.8 mg/kg, about 0.9 mg/kg, about 1.0 mg/kg, about 2.0 mg/kg, about 3 mg/kg, about 5 mg/kg, about 10 mg/kg. In some embodiments, the initial and/or adjusted dose is administered about twice a week, about once a week, about once every two weeks, about once a month, about once every two months, about once every three months, about once every six months, about once every five weeks, about once every six weeks, about once every seven weeks, about every 5 days, about every 10 days, about every 15 days, about every 20 days, about every 25 days, about every 30 days, about every 35 days, or about every 40 days. In some embodiments, the adjusted dose of the ActRII antagonist is greater than the initial dose if the level of GATA-1 is decreased compared to levels of GATA-1 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg greater than the initial dose. In some embodiments, the adjusted dose is administered more frequently than the initial dose. In some embodiments, the additional dose of the ActRII antagonist is the same as the initial dose, and wherein the additional dose is administered more frequently than the initial dose if the level of GATA-1 is decreased compared to levels of GATA-1 in a reference population. In some embodiments, the first measurement of the levels of GATA-1 in the subject is compared to the second measurement of the levels of GATA-1 in the subject.

In some embodiments, the adjusted dose of the ActRII antagonist is greater than the initial dose if the level of GATA-1 in the second measurement is about the same as or lower than the level of GATA-1 in the first measurement. In some embodiments, the additional dose is administered more frequently than the initial dose if the level of GATA-1 in the second measurement is about the same as or lower than the level of GATA-1 in the first measurement. In some embodiments, the additional dose is the same as the initial dose. In some embodiments, the adjusted dose of the ActRII antagonist is less than the initial dose if levels of GATA-1 is elevated compared to the level of GATA-1 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg less than the initial dose. In some embodiments, the adjusted dose is administered less frequently than the initial dose. In some embodiments, the additional dose is the same as the initial dose, and wherein the additional dose is administered less frequently than the initial dose if the level of GATA-1 is elevated compared to levels of GATA-1 in a reference population. In some embodiments, the adjusted dose is administered continuously. In some embodiments, the first measurement or measurement is taken prior to commencement of the treatment. In some embodiments, the first measurement or measurement is taken immediately after commencement of the treatment. In some embodiments, the first measurement or measurement is taken within about 1 day, about 2 days, about 3 days, about 4 days, about 5 days, about 6 days, about 7 days, about 10 days, about 14 days, about 21 days, about 28 days, about 30 days, or about 60 days after commencement of treatment. In some embodiments, the second measurement is taken immediately after commencement of the treatment. In some embodiments, the second measurement is taken within about 1 day, about 2 days, about 3 days, about 4 days, about 5 days, about 6 days, about 7 days, about 10 days, about 14 days, about 21 days, about 28 days, about 30 days, about two months, about three months, about four months, about five months, about six months, about eight months, about 10 months, or about 12 months after commencement of treatment. In some embodiments, the decreased level of GATA-1 is about 10%, 20%, 25%, 30%, 40%, 50%, 60%, 70%, 75%, 80%, 90%, 100%, 200%, or 500% lower than the levels of GATA-1 in the reference population. In some embodiments, the decreased level of GATA-1 is about 10%, 20%, 25%, 30%, 40%, 50%, 60%, 70%, 75%, 80%, 90%, 100%, 200%, or 500% lower than the levels of GATA-1 in the bottom 10%, bottom 5%, bottom 4%, bottom 3%, bottom 2%, or bottom 1% of the reference population. In some embodiments, the elevated level of GATA-1 is about 10%, 20%, 25%, 30%, 40%, 50%, 60%, 70%, 75%, 80%, 90%, 100%, 200%, or 500% higher than the levels of GATA-1 in the reference population. In some embodiments, the elevated level of GATA-1 is about 10%, 20%, 25%, 30%, 40%, 50%, 60%, 70%, 75%, 80%, 90%, 100%, 200%, or 500% higher than the levels of GATA-1 in the bottom 10%, bottom 5%, bottom 4%, bottom 3%, bottom 2%, or bottom 1% of the reference population. In some embodiments, the level of GATA-1 is the protein level of GATA-1. In some embodiments, the protein level of GATA-1 is determined by ELISA. In some embodiments, the level of GATA-1 is the mRNA level of GATA-1. In some embodiments, the mRNA level of GATA-1 is determined by qRT-PCR. In some embodiments, the level of GATA-1 is measured in a tissue. In some embodiments, the level of GATA-1 is measured in erythroblasts. In some embodiments, the level of GATA-1 is measured in serum. In some embodiments, the level of GATA-1 is measured in bone marrow.

In some embodiments, the disclosure provides a method for treating or preventing ineffective erythropoiesis in a subject comprising administering to a subject in need thereof a pharmaceutically effective amount of an agent or combination of agents, that agonizes, reduces inhibition of, supplements the activity of, increases the levels of, and/or increases the activity of heat shock factor in the subject. In some embodiments, the subject has a decreased level of heat shock factor compared to levels of heat shock factor in a reference population. In some embodiments, the disclosure provides a method for treating or preventing ineffective erythropoiesis in a subject in whom it has been determined has a decreased level of heat shock factor as compared to a reference population, comprising administering to said subject a pharmaceutically effective amount of an agent, or combination of agents, that agonizes, reduces inhibition of, supplements the activity of, increases the levels of, and/or increases the activity of that increases heat shock factor in the subject. In some embodiments, the subject is a human. In some embodiments, the reference population consists of one or more humans. In some embodiments, the reference population consists of subjects not having MDS, a hemoglobinopathy, sickle-cell disease, and/or beta-thalassemia. In some embodiments, the reference population consists of 1, 2, 3, 5, 10, 20, 25, 30, 50, 70, 75, 80, 90, 100, 200, 250, 500, or 100 individuals. In some embodiments, the reference population consists of healthy individuals. In some embodiments, the reference population consists of people of the same gender, age, and/or weight as the subject. In some embodiments, the reference population consists of people without ineffective erythropoiesis. In some embodiments, the decreased level of heat shock factor is about 10%, 20%, 25%, 30%, 40%, 50%, 60%, 70%, 75%, 80%, 90%, 100%, 200%, or 500% lower than the levels of heat shock factor in the reference population. In some embodiments, the decreased level of heat shock factor is about 10%, 20%, 25%, 30%, 40%, 50%, 60%, 70%, 75%, 80%, 90%, 100%, 200%, or 500% lower than the levels of heat shock factor in the bottom 10%, bottom 5%, bottom 4%, bottom 3%, bottom 2%, or bottom 1% of the reference population. In some embodiments, the agent is selected from the group consisting of: a pentacyclic triterpenoid, tricyclic bis(cyanoenone), celastrol, HSF1A, gedunin, sappanone A, and/or derivatives thereof. In some embodiments, the agent is an antibiotic. In some embodiments, the agent inhibits the function of Hsp90. In some embodiments, the agent is an antitumor antibiotic. In some embodiments, the agent is selected from the group consisting of: geldanamycin, radicicol, 17-AAG, 17-DMAG, IPI-493, OCH3, NHCH2CH=CH2, NHCH2CH2N(CH3)2, NH2, NVP-AUY922, KW-2478, AT13387, BIIB021, PU-H71, SNX-5422, NVP-BEP800, CUDC-305, XL888, and/or derivatives thereof. In some embodiments, the agent is a transcription factor. In some embodiments, the agent binds to Heat Shock sequence Elements (HSE). In some embodiments, the agent is a vector comprising a polynucleotide encoding recombinant heat shock factor protein. In some embodiments, the agent is a recombinant heat shock factor protein. In some embodiments, the agent increases heat shock factor levels and/or activity in erythroblasts in the subject. In some embodiments, the agent increases levels and/or activity of one or more heme biosynthesis genes selected from the group consisting of: Ppox, Fech, Alas2, and Abcb10l. In some embodiments, the agent increases levels and/or activity of one or more erythroid differentiation factors selected from the group consisting of: KLF1, NFE2, GYPA, Bcl21, Bnip31, Bach1, and ANK1.

In some embodiments, the disclosure provides a method for treating or preventing ineffective erythropoiesis in a subject comprising: a) taking a first measurement of heat shock factor level in the subject, b) administering to the subject an initial dose of an ActRII antagonist, c) taking a second measurement of heat shock factor level in the subject, d) administering to the subject an additional dose of the ActRII antagonist that is the same as the initial dose or an adjusted dose of the ActRII antagonist. In some embodiments, the disclosure provides a method for treating or preventing ineffective erythropoiesis in a subject comprising: a) administering to the subject an initial dose of an ActRII antagonist, b) taking a measurement of heat shock factor level in the subject, c) administering to the subject an additional dose of the ActRII antagonist that is the same as the initial dose or an adjusted dose of the ActRII antagonist. In some embodiments, the level of heat shock factor in the subject is compared to heat shock factor levels in a reference population. In some embodiments, the initial dose and/or adjusted dose of the ActRII antagonist is about 0.1 mg/kg, about 0.3 mg/kg, about 0.5 mg/kg, about 0.7 mg/kg, about 0.8 mg/kg, about 0.9 mg/kg, about 1.0 mg/kg, about 2.0 mg/kg, about 3 mg/kg, about 5 mg/kg, about 10 mg/kg. In some embodiments, the initial and/or adjusted dose is administered about twice a week, about once a week, about once every two weeks, about once a month, about once every two months, about once every three months, about once every six months, about once every five weeks, about once every six weeks, about once every seven weeks, about every 5 days, about every 10 days, about every 15 days, about every 20 days, about every 25 days, about every 30 days, about every 35 days, or about ever 40 days. In some embodiments, the adjusted dose of the ActRII antagonist is greater than the initial dose if the level of heat shock factor is decreased compared to levels of heat shock factor in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg greater than the initial dose. In some embodiments, the adjusted dose is administered more frequently than the initial dose. In some embodiments, the additional dose of the ActRII antagonist is the same as the initial dose, and wherein the additional dose is administered more frequently than the initial dose if the level of heat shock factor is decreased compared to levels of heat shock factor in a reference population. In some embodiments, the first measurement of the levels of heat shock factor in the subject is compared to the second measurement of the levels of heat shock factor in the subject. In some embodiments, the adjusted dose of the ActRII antagonist is greater than the initial dose if the level of heat shock factor in the second measurement is about the same as or lower than the level of heat shock factor in the first measurement. In some embodiments, the additional dose is administered more frequently than the initial dose if the level of heat shock factor in the second measurement is about the same as or lower than the level of heat shock factor in the first measurement. In some embodiments, the additional dose is the same as the initial dose. In some embodiments, the adjusted dose of the ActRII antagonist is less than the initial dose if the level of heat shock factor is elevated compared to levels of heat shock factor in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg less than the initial dose. In some embodiments, the adjusted dose is administered less frequently than the initial dose. In some embodiments, the adjusted dose is administered continuously. In some embodiments, the additional dose is the same as the initial dose, and wherein the additional dose is administered less frequently than the initial dose if the level of heat shock factor is elevated compared to levels of heat shock factor in a reference population. In some embodiments, the first measurement or measurement is taken prior to commencement of the treatment. In some embodiments, the first measurement or measurement is taken immediately after commencement of the treatment. In some embodiments, the first measurement or measurement is taken within about 1 day, about 2 days, about 3 days, about 4 days, about 5 days, about 6 days, about 7 days, about 10 days, about 14 days, about 21 days, about 28 days, about 30 days, or about 60 days after commencement of treatment. In some embodiments, the second measurement is take immediately after commencement of the treatment. In some embodiments, the second measurement is taken within about 1 day, about 2 days, about 3 days, about 4 days, about 5 days, about 6 days, about 7 days, about 10 days, about 14 days, about 21 days, about 28 days, about 30 days, about two months, about three months, about four months, about five months, about six months, about eight months, about 10 months, or about 12 months after commencement of treatment. In some embodiments, the decreased level of heat shock factor is about 10%, 20%, 25%, 30%, 40%, 50%, 60%, 70%, 75%, 80%, 90%, 100%, 200%, or 500% lower than the levels of heat shock factor in the reference population. In some embodiments, the decreased levels of heat shock factor is about 10%, 20%, 25%, 30%, 40%, 50%, 60%, 70%, 75%, 80%, 90%, 100%, 200%, or 500% lower than the levels of heat shock factor in the bottom 10%, bottom 5%, bottom 4%, bottom 3%, bottom 2%, or bottom 1% of the reference population. In some embodiments, the elevated level of heat shock factor is about 10%, 20%, 25%, 30%, 40%, 50%, 60%, 70%, 75%, 80%, 90%, 100%, 200%, or 500% higher than the levels of heat shock factor in the reference population. In some embodiments, the elevated level of heat shock factor is about 10%, 20%, 25%, 30%, 40%, 50%, 60%, 70%, 75%, 80%, 90%, 100%, 200%, or 500% higher than the levels of heat shock factor in the bottom 10%, bottom 5%, bottom 4%, bottom 3%, bottom 2%, or bottom 1% of the reference population. In some embodiments, the level of heat shock factor is the protein level of heat shock factor. In some embodiments, the protein level of heat shock factor is determined by ELISA. In some embodiments, the level of heat shock factor is the mRNA level of heat shock factor. In some embodiments, the mRNA level of heat shock factor is determined by qRT-PCR. In some embodiments, the level of heat shock factor is measured in a tissue. In some embodiments, the level of heat shock factor is measured in erythroblasts. In some embodiments, the level of heat shock factor is measured in serum. In some embodiments, the level of heat shock factor is measured in bone marrow.

In some embodiments, the disclosure provides a method for treating or preventing ineffective erythropoiesis in a subject comprising administering to a subject in need thereof a pharmaceutically effective amount of an agent, or combination of agents, that agonizes, reduces inhibition of, supplements the activity of, increases the levels of, and/or increases the activity of NFE2 in the subject. In some embodiments, the subject has a decreased level of NFE2 compared to levels of NFE2 in a reference population. In some embodiments, the disclosure provides a method for treating or preventing ineffective erythropoiesis in a subject in whom it has been determined has a decreased level of NFE2 as compared to a reference population, comprising administering to said subject a pharmaceutically effective amount of an agent, or combination of agents, that agonizes, reduces inhibition of, supplements the activity of, increases the levels of, and/or increases the activity of NFE2 in the subject. In some embodiments, the subject is a human. In some embodiments, the reference population consists of one or more humans. In some embodiments, the reference population consists of subjects not having MDS, a hemoglobinopathy, sickle-cell disease, and/or beta-thalassemia. In some embodiments, the reference population consists of 1, 2, 3, 5, 10, 20, 25, 30, 50, 70, 75, 80, 90, 100, 200, 250, 500, or 100 individuals. In some embodiments, the reference population consists of healthy individuals. In some embodiments, the reference population consists of people of the same gender, age, and/or weight as the subject. In some embodiments, the reference population consists of people without ineffective erythropoiesis. In some embodiments, the decreased level of NFE2 is about 10%, 20%, 25%, 30%, 40%, 50%, 60%, 70%, 75%, 80%, 90%, 100%, 200%, or 500% lower than the levels of NFE2 in the reference population. In some embodiments, the decreased level of NFE2 is about 10%, 20%, 25%, 30%, 40%, 50%, 60%, 70%, 75%, 80%, 90%, 100%, 200%, or 500% lower than the levels of NFE2 in the bottom 10%, bottom 5%, bottom 4%, bottom 3%, bottom 2%, or bottom 1% of the reference population. In some embodiments, the agent is a vector comprising a polynucleotide encoding recombinant NFE2 protein. In some embodiments, the agent is recombinant NFE2 protein.

In some embodiments, the disclosure provides a method for treating or preventing ineffective erythropoiesis in a subject comprising: a) taking a first measurement of NFE2 level in the subject, b) administering to the subject an initial dose of an ActRII antagonist, c) taking a second measurement of NFE2 level in the subject, d) administering to the subject an additional dose of the ActRII antagonist that is the same as the initial dose or an adjusted dose of the ActRII antagonist. In some embodiments, the disclosure provides a method for treating or preventing ineffective erythropoiesis in a subject comprising: a) administering to the subject an initial dose of an ActRII antagonist, b) taking a measurement of NFE2 level in the subject, c) administering to the subject an additional dose of the ActRII antagonist that is the same as the initial dose or an adjusted dose of the ActRII antagonist. In some embodiments, the level of NFE2 in the subject is compared to NFE2 levels in a reference population. In some embodiments, the initial dose and/or adjusted dose of the ActRII antagonist is about 0.1 mg/kg, about 0.3 mg/kg, about 0.5 mg/kg, about 0.7 mg/kg, about 0.8 mg/kg, about 0.9 mg/kg, about 1.0 mg/kg, about 2.0 mg/kg, about 3 mg/kg, about 5 mg/kg, about 10 mg/kg. In some embodiments, the initial and/or adjusted dose is administered about twice a week, about once a week, about once every two weeks, about once a month, about once every two months, about once every three months, about once every six months, about once every five weeks, about once every six weeks, about once every seven weeks, about every 5 days, about every 10 days, about every 15 days, about every 20 days, about every 25 days, about every 30 days, about every 35 days, or about every 40 days. In some embodiments, the adjusted dose of the ActRII antagonist is greater than the initial dose if the level of NFE2 is decreased compared to levels of NFE2 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg greater than the initial dose. In some embodiments, the adjusted dose is administered more frequently than the initial dose. In some embodiments, the additional dose of the ActRII antagonist is the same as the initial dose, and wherein the additional dose is administered more frequently than the initial dose if the level of NFE2 is decreased compared to levels of NFE2 in a reference population. In some embodiments, the first measurement of the level of NFE2 in the subject is compared to the second measurement of the level of NFE2 in the subject. In some embodiments, the adjusted dose of the ActRII antagonist is greater than the initial dose if the level of NFE2 in the second measurement is about the same as or lower than the level of NFE2 in the first measurement. In some embodiments, the additional dose is administered more frequently than the initial dose if the level of NFE2 in the second measurement is about the same as or lower than the level of NFE2 in the first measurement. In some embodiments, the additional dose is the same as the initial dose. In some embodiments, the adjusted dose of the ActRII antagonist is less than the initial dose if the level of NFE2 is elevated compared to levels of NFE2 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg less than the initial dose. In some embodiments, the adjusted dose is administered less frequently than the initial dose. In some embodiments, the adjusted dose is administered continuously. In some embodiments, the additional dose is the same as the initial dose, and wherein the additional dose is administered less frequently than the initial dose if the level of NFE2 is elevated compared to levels of NFE2 in a reference population. In some embodiments, the first measurement or measurement is taken prior to commencement of the treatment. In some embodiments, the first measurement or measurement is taken immediately after commencement of the treatment. In some embodiments, the first measurement or measurement is taken within about 1 day, about 2 days, about 3 days, about 4 days, about 5 days, about 6 days, about 7 days, about 10 days, about 14 days, about 21 days, about 28 days, about 30 days, or about 60 days after commencement of treatment. In some embodiments, the second measurement is take immediately after commencement of the treatment. In some embodiments, the second measurement is taken within about 1 day, about 2 days, about 3 days, about 4 days, about 5 days, about 6 days, about 7 days, about 10 days, about 14 days, about 21 days, about 28 days, about 30 days, about two months, about three months, about four months, about five months, about six months, about eight months, about 10 months, or about 12 months after commencement of treatment. In some embodiments, the decreased level of NFE2 is about 10%, 20%, 25%, 30%, 40%, 50%, 60%, 70%, 75%, 80%, 90%, 100%, 200%, or 500% lower than the levels of NFE2 in the reference population. In some embodiments, the decreased level of NFE2 is about 10%, 20%, 25%, 30%, 40%, 50%, 60%, 70%, 75%, 80%, 90%, 100%, 200%, or 500% lower than the levels of NFE2 in the bottom 10%, bottom 5%, bottom 4%, bottom 3%, bottom 2%, or bottom 1% of the reference population. In some embodiments, the elevated level of NFE2 is about 10%, 20%, 25%, 30%, 40%, 50%, 60%, 70%, 75%, 80%, 90%, 100%, 200%, or 500% higher than the levels of NFE2 in the reference population. In some embodiments, the elevated level of NFE2 is about 10%, 20%, 25%, 30%, 40%, 50%, 60%, 70%, 75%, 80%, 90%, 100%, 200%, or 500% higher than the levels of NFE2 in the bottom 10%, bottom 5%, bottom 4%, bottom 3%, bottom 2%, or bottom 1% of the reference population. In some embodiments, the level of NFE2 is the protein level of NFE2. In some embodiments, the protein level of NFE2 is determined by ELISA. In some embodiments, the level of NFE2 is the mRNA level of NFE2. In some embodiments, the mRNA level of NFE2 is determined by qRT-PCR. In some embodiments, the level of NFE2 is measured in a tissue. In some embodiments, the level of NFE2 is measured in erythroblasts. In some embodiments, the level of NFE2 is measured in serum. In some embodiments, the level of NFE2 is measured in bone marrow.

In some embodiments, the agent for use in any of the methods disclosed herein is not a polypeptide comprising an amino acid sequence that is identical to SEQ ID NO: 64 or a variant thereof comprising an acidic amino acid at the position corresponding to position 79 of SEQ ID NO: 1. In some embodiments, the agent is an ActRII antagonist. In some embodiments, the agent is an ActRIIA antagonist. In some embodiments, the agent is an ActRIIB antagonist. In some embodiments, the ActRII antagonist is an ActRIIA polypeptide. In some embodiments, the ActRIIA polypeptide is selected from: a) a polypeptide comprising the amino acid sequence of SEQ ID NO: 10 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 10; b) a polypeptide comprising the amino acid sequence of SEQ ID NO: 11 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 11; and c) a polypeptide comprising an amino acid sequence that is identical to amino acids 30-110 of SEQ ID NO:9 or comprising an amino acid sequence that is at least 70%, 75% 80%, 85%, 90%, 91%, 92%, 93%, 94%, 95%, 96%, 97%, 98%, or 99% identical to the sequence of amino acid 30-110 of SEQ ID NO: 9. In some embodiments, the ActRII antagonist is an ActRIIB polypeptide. In some embodiments, the ActRIIB polypeptide selected from: a) a polypeptide comprising an amino acid sequence that is identical to amino acids 29-109 of SEQ ID NO: 1 or comprising an amino acid sequence that is at least 70%, 75% 80%, 85%, 90%, 91%, 92%, 93%, 94%, 95%, 96%, 97%, 98%, or 99% identical to the sequence of amino acids 29-109 of SEQ ID NO: 1; b) a polypeptide comprising an amino acid sequence that is identical to amino acids 25-131 of SEQ ID NO: 1 or comprising an amino acid sequence that is at least 70%, 75% 80%, 85%, 90%, 91%, 92%, 93%, 94%, 95%, 96%, 97%, 98%, or 99% identical to the sequence of amino acids 25-131 of SEQ ID NO: 1; c) a polypeptide comprising the amino acid sequence of SEQ ID NO: 2 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 2; d) a polypeptide comprising the amino acid sequence of SEQ ID NO: 3 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 3; e) a polypeptide comprising the amino acid sequence of SEQ ID NO: 5 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 5; f) a polypeptide comprising the amino acid sequence of SEQ ID NO: 6 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 6; g) a polypeptide comprising the amino acid sequence of SEQ ID NO: 45 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 45; h) a polypeptide comprising the amino acid sequence of SEQ ID NO: 48 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 48; i) a polypeptide comprising the amino acid sequence of SEQ ID NO: 49 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 49; and a polypeptide comprising the amino acid sequence of SEQ ID NO: 65 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 65. In some embodiments, the polypeptide comprises an acidic amino acid at position 79 with respect to SEQ ID NO: 1. In some embodiments, the polypeptide comprises a D or E at position 79 with respect to SEQ ID NO: 1. In some embodiments, the ActRII antagonist is a GDF trap polypeptide. In some embodiments, the polypeptide is a fusion protein comprising, in addition to an ActRIIA or ActRIIB polypeptide domain, one or more heterologous polypeptide domains that enhance one or more of: in vivo half-life, in vitro half-life, administration, tissue localization or distribution, formation of protein complexes, and purification. In some embodiments, the fusion protein comprises a heterologous polypeptide domain selected from: an immunoglobulin Fc domain and a serum albumin. In some embodiments, the immunoglobulin Fc domain is an IgG1 Fc domain. In some embodiments, the immunoglobulin Fc domain comprises an amino acid sequence that is at least 70%, 75% 80%, 85%, 90%, 91%, 92%, 93%, 94%, 95%, 96%, 97%, 98%, 99%, or 100% identical to any one of SEQ ID NOs: 14-18. In some embodiments, the fusion protein further comprises a linker domain positioned between the ActRIIA or ActRIIB domain and the immunoglobulin Fc domain. In some embodiments, the linker domain comprises the amino acid sequence of any one of SEQ ID NOs: 19-25. In some embodiments, the polypeptide is an ActRIIA-Fc fusion protein comprising a polypeptide selected from: a) a polypeptide comprising the amino acid sequence of SEQ ID NO: 32 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 32; b) a polypeptide comprising the amino acid sequence of SEQ ID NO: 36 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 36; and c) a polypeptide comprising the amino acid sequence of SEQ ID NO: 39 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 39. In some embodiments, the polypeptide is an ActRIIB-Fc fusion protein comprising a polypeptide selected from: a) a polypeptide comprising the amino acid sequence of SEQ ID NO: 40 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 40; b) a polypeptide comprising the amino acid sequence of SEQ ID NO: 41 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 41; c) a polypeptide comprising the amino acid sequence of SEQ ID NO: 44 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 44; d) a polypeptide comprising the amino acid sequence of SEQ ID NO: 46 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 46; e) a polypeptide comprising the amino acid sequence of SEQ ID NO: 50 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 50; f) a polypeptide comprising the amino acid sequence of SEQ ID NO: 78 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 78; g) a polypeptide comprising the amino acid sequence of SEQ ID NO: 71 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 61; h) a polypeptide comprising the amino acid sequence of SEQ ID NO: 64 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 64; and i) a polypeptide comprising the amino acid sequence of SEQ ID NO: 79 or comprising an amino acid sequence that is at least 70%, 75% 80%, 85%, 90%, 91%, 92%, 93%, 94%, 95%, 96%, 97%, 98%, or 99% identical to the amino acid sequence of SEQ ID NO: 79. In some embodiments, the polypeptide comprises an acidic amino acid at position 79 with respect to SEQ ID NO: 1. In some embodiments, the polypeptide comprises a D or E at position 79 with respect to SEQ ID NO: 1. In some embodiments, the polypeptide comprises one or more amino acid modifications selected from: a glycosylated amino acid, a PEGylated amino acid, a farnesylated amino acid, an acetylated amino acid, a biotinylated amino acid, an amino acid conjugated to a lipid moiety, and amino acid conjugated to an organic derivatizing agent. In some embodiments, the polypeptide is glycosylated and has a mammalian glycosylation pattern. In some embodiments, the polypeptide is glycosylated and has a glycosylation pattern obtainable from a Chinese hamster ovary cell line. In some embodiments, the polypeptide binds to GDF11. In some embodiments, the polypeptide binds to GDF8. In some embodiments, the polypeptide binds to activin. In some embodiments, the polypeptide binds to activin A. In some embodiments, the polypeptide binds to activin B. In some embodiments, the ActRII antagonist is an anti-GDF11 antibody. In some embodiments, the ActRII antagonist is an anti-GDF8 antibody. In some embodiments, the ActRII antagonist is a multispecific antibody that binds to at least GDF11. In some embodiments, the multispecific antibody further binds to GDF8. In some embodiments, the multispecific antibody further binds to one or more of: activin A, activin B, activin C, activin E, or BMP6. In some embodiments, the antibody is a bispecific antibody. In some embodiments, the bispecific antibody binds to GDF11 and GDF8. In some embodiments, the antibody is a chimeric antibody, a humanized antibody, or a human antibody. In some embodiments, the antibody is a single-chain antibody, an F(ab')2 fragment, a single-chain diabody, a tandem single-chain Fv fragment, a tandem single-chain diabody, a or a fusion protein comprising a single-chain diabody and at least a portion of an immunoglobulin heavy-chain constant region. In some embodiments, the agent is an inhibitor of SMAD signaling. In some embodiments, the agent is selected from the group consisting of: Lerdelimumab, Metelimumab, Fresolimumab, 2G7, LY2382770, IMC-TR1, PF-03446962, Stromedix, Ad.sTβRII-Fc, Disitertide, LSKL, Trabedersen, AP11014, AP15012, Belagenpu-matucel-L, LY550410, SB-431542, SB-505124, Ki26894, LY364937, SD-208, LY2157299, Trx-SARA, pyrrole-imidazole polyamides, SMAD7, and Avotermin. In some embodiments, the agent inhibits GDF11, GDF8, activin B, BMP6, and/or BMP10 binding to and/or activating of an ActRII receptor. In some embodiments, the agent is an agent that inhibits transcription, translation, and/or cellular secretion of an ActRII ligand and/or an ActRII receptor.

In some embodiments, the disclosure provides a method in which a subject is administered a pharmaceutically effective amount of any of the ActRII antagonists disclosed herein as well as a pharmaceutically effective amount of an additional agent. In some embodiments, the subject is administered a pharmaceutically effective amount of an additional agent. In some embodiments, the additional agent is an estrogen receptor antagonist. In some embodiments, the additional agent is an estrogen receptor inhibitor. In some embodiments, the additional agent inhibits the binding of ErbB2/HER2 to the estrogen receptor. In some embodiments, the additional agent inhibits the binding of endogenous estrogen to the estrogen receptor. In some embodiments, the additional agent is tamoxifen. In some embodiments, the additional agent is an estrogen receptor agonist. In some embodiments, the additional agent is an estrogen receptor activator. In some embodiments, the additional agent is an agonist of estrogen receptor alpha (ERα) and estrogen receptor beta (ERβ). In some embodiments, the additional agent is an agonist of membrane estrogen receptors (mER). In some embodiments, the additional agent is an estrogen sex hormone. In some embodiements, the additional agent is estriol or estrone. In some embodiments, the additional agent is oestradiol. In some embodiments, the additional agent is a chemotherapeutic agent. In some embodiments, the additional agent inhibits the synthesis of DNA or RNA. In some embodiments, the additional agent inhibits the topoisomerase II enzyme. In some embodiments, the additional agent results in iron-mediated generation of free oxygen radicals. In some embodiments, the additional agent induces histone eviction from chromatin. In some embodiments, the additional agent is an anthracycline. In some embodiments, the anthracycline is selected from the group consisting of: aclacinomycin A, daunorubicin, doxorubicin, epirubicin, idarubicin, valrubicin, mitoxantrone, and any analogs thereof. In some embodiments, the additional agent is a vector comprising a polynucleotide encoding recombinant GATA-1 protein. In some embodiments, the additional agent is recombinant GATA-1 protein. In some embodiments, the additional agent is selected from the group consisting of: a pentacyclic triterpenoid, tricyclic bis(cyanoenone), celastrol, HSF1A, gedunin, sappanone A, and/or derivatives thereof. In some embodiments, the additional agent is selected from the group consisting of: geldanamycin, radicicol, 17-AAG, 17-DMAG, IPI-493, OCH3, NHCH2CH=CH2, NHCH2CH2N(CH3)2, NH2, NVP-AUY922, KW-2478, AT13387, BIIB021, PU-H71, SNX-5422, NVP-BEP800, CUDC-305, XL888, and/or derivatives thereof. In some embodiments, the additional agent is a vector comprising a polynucleotide encoding recombinant heat shock factor protein. In some embodiments, the additional agent is a recombinant heat shock factor protein. In some embodiments, the additional agent is a vector comprising a polynucleotide encoding recombinant NFE2 protein. In some embodiments, the additional agent is recombinant NFE2 protein.

In some embodiments, the ineffective erythropoiesis to be treated or prevented in any of the methods disclosed herein is associated with a hemoglobinopathy. In some embodiments, the hemoglobinopathy is a thalassemia. In some embodiments, the thalassemia is alpha-thalassemia. In some embodiments, the alpha-thalassemia is alpha-thalassemia minima. In some embodiments, the alpha-thalassemia is alpha-thalassemia-minor. In some embodiments, the alpha-thalassemia is Hemoglobin H disease. In some embodiments, the alpha-thalassemia is alpha-thalassemia-major. In some embodiments, the thalassemia is beta-thalassemia. In some embodiments, the beta-thalassemia is beta-thalassemia minor. In some embodiments, the beta-thalassemia is beta-thalassemia intermedia. In some embodiments, the beta-thalassemia is beta-thalassemia major. In some embodiments, the beta-thalassemia is Hemoglobin E disease. In some embodiments, the thalassemia is delta-beta-thalassemia. In some embodiments, the hemoglobinopathy is sickle-cell anemia. In some embodiments, the hemoglobinopathy is Hemoglobin C disease. In some embodiments, the hemoglobinopathy is hemoglobin S-C disease. In some embodiments, the subject has myelodysplastic syndrome (MDS). In some embodiments, the subject has sideroblastic anemia. In some embodiments, the subject has congenital sideroblastic anemia. In some embodiments, the subject has acquired clonal sideroblastic anemia. In some embodiments, the subject has acquired reversible sideroblastic anemia. In some embodiments, the subject has X-linked sideroblastic anemia. In some embodiments, the subject has sideroblastic anemia with spinocerebellar ataxia. In some embodiments, the subject has pyridoxine-refractory autosomal recessive sideroblastic anemia. In some embodiments, the subject has pyridoxine-responsive sideroblastic anemia.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows an alignment of extracellular domains of human ActRIIA (SEQ ID NO: 51) and human ActRIIB (SEQ ID NO: 2) with the residues that are deduced herein, based on composite analysis of multiple ActRIIB and ActRIIA crystal structures, to directly contact ligand indicated with boxes.

FIG. 4 shows the binding of ActRIIA-hFc to activin (top panel) and GDF-11 (bottom panel), as measured by Biacore™ assay.

FIG. 5 shows the full amino acid sequence for the GDF trap ActRIIB(L79D 20-134)-hFc (SEQ ID NO: 46), including the TPA leader sequence (doubleunderline), ActRIIB extracellular domain (residues 20-134 in SEQ ID NO: 1; singleunderline), and hFc domain. The aspartate substituted at position 79 in the native sequence is doubleunderlined and highlighted, as is the glycine revealed by sequencing to be the N-terminal residue in the mature fusion protein.

FIGS. 6A and 6B show a nucleotide sequence encoding ActRIIB(L79D 20-134)-hFc. SEQ ID NO: 90 corresponds to the sense strand, and SEQ ID NO: 60 corresponds to the antisense strand. The TPA leader (nucleotides 1-66) is double underlined, and the ActRIIB extracellular domain (nucleotides 76-420) is single underlined.

FIG. 7 shows the full amino acid sequence for the truncated GDF trap ActRIIB(L79D 25-131)-hFc (SEQ ID NO: 61), including the TPA leader (doubleunderline), truncated ActRIIB extracellular domain (residues 25-131 in SEQ ID NO:1; singleunderline), and hFc domain. The aspartate substituted at position 79 in the native sequence is doubleunderlined and highlighted, as is the glutamate revealed by sequencing to be the N-terminal residue in the mature fusion protein.

FIGS. 8A and 8B show a nucleotide sequence encoding ActRIIB(L79D 25-131)-hFc. SEQ ID NO: 62 corresponds to the sense strand, and SEQ ID NO: 63 corresponds to the antisense strand. The TPA leader (nucleotides 1-66) is double underlined, and the truncated ActRIIB extracellular domain (nucleotides 76-396) is single underlined. The amino acid sequence for the ActRIIB extracellular domain is also shown (SEQ ID NO: 65).

FIG. 9 shows the amino acid sequence for the truncated GDF trap ActRIIB(L79D 25 131) hFc without a leader (SEQ ID NO: 64). The truncated ActRIIB extracellular domain is underlined (SEQ ID NO: 65). The aspartate substituted at position 79 in the native sequence is double underlined and highlighted, as is the glutamate revealed by sequencing to be the N-terminal residue in the mature fusion protein.

FIG. 10 shows the amino acid sequence for the truncated GDF trap ActRIIB(L79D 25-131) without the leader, hFc domain, and linker (SEQ ID NO: 65). The aspartate substituted at position 79 in the native sequence is underlined and highlighted, as is the glutamate revealed by sequencing to be the N-terminal residue in the mature fusion protein.

FIGS. 11A and 11B show an alternative nucleotide sequence encoding ActRIIB(L79D 25-131)-hFc. SEQ ID NO: 66 corresponds to the sense strand, and SEQ ID NO: 67 corresponds to the antisense strand. The TPA leader (nucleotides 1-66) is double underlined, the truncated ActRIIB extracellular domain (nucleotides 76-396) is underlined, and substitutions in the wild-type nucleotide sequence of the extracellular domain are double underlined and highlighted (compare with SEQ ID NO: 62, FIG. 8). The amino acid sequence for the ActRIIB extracellular domain is also shown (SEQ ID NO: 65).

FIG. 12 shows nucleotides 76-396 (SEQ ID NO: 68) of the alternative nucleotide sequence shown in FIGS. 11A and 11B (SEQ ID NO: 66). The same nucleotide substitutions indicated in FIGS. 11A and B are also underlined and highlighted here. SEQ ID NO: 68 encodes only the truncated ActRIIB extracellular domain (corresponding to residues 25-131 in SEQ ID NO: 1) with a L79D substitution, e.g., ActRIIB(L79D 25-131).

FIG. 13 shows a multiple sequence alignment of various vertebrate ActRIIA proteins and human ActRIIA (SEQ ID NOs: 69-76).

FIG. 14 shows multiple sequence alignment of Fc domains from human IgG isotypes using Clustal 2.1 (SEQ ID Nos: 14, 18, 15 and 16, respectively, in order of appearance). Hinge regions are indicated by dotted underline.

FIG. 15 shows the full, unprocessed amino acid sequence for ActRIIB(25-131)-hFc (SEQ ID NO: 79). The TPA leader (residues 1-22) and double-truncated ActRIIB extracellular domain (residues 24-131, using numbering based on the native sequence in SEQ ID NO: 1) are each underlined. Highlighted is the glutamate revealed by sequencing to be the N-terminal amino acid of the mature fusion protein, which is at position 25 relative to SEQ ID NO: 1.

FIGS. 16A and 16B show a nucleotide sequence encoding ActRIIB(25-131)-hFc (the coding strand is shown at top, SEQ ID NO: 80, and the complement shown at bottom 3'-5', SEQ ID NO: 81). Sequences encoding the TPA leader (nucleotides 1-66) and ActRIIB extracellular domain (nucleotides 73-396) are underlined. The corresponding amino acid sequence for ActRIIB(25-131) is also shown (SEQ ID NO: 89).

FIGS. 17A and 17B show an alternative nucleotide sequence encoding ActRIIB(25-131)-hFc (the coding strand is shown at top, SEQ ID NO: 82, and the complement shown at bottom 3'-5', SEQ ID NO: 83). This sequence confers a greater level of protein expression in initial transformants, making cell line development a more rapid process. Sequences encoding the TPA leader (nucleotides 1-66) and ActRIIB extracellular domain (nucleotides 73-396) are underlined, and substitutions in the wild type nucleotide sequence of the ECD (see FIG. 16) are highlighted. The corresponding amino acid sequence for ActRIIB(25-131) is also shown (SEQ ID NO: 89).

DETAILED DESCRIPTION OF THE INVENTION

1. Overview

Figure 2:
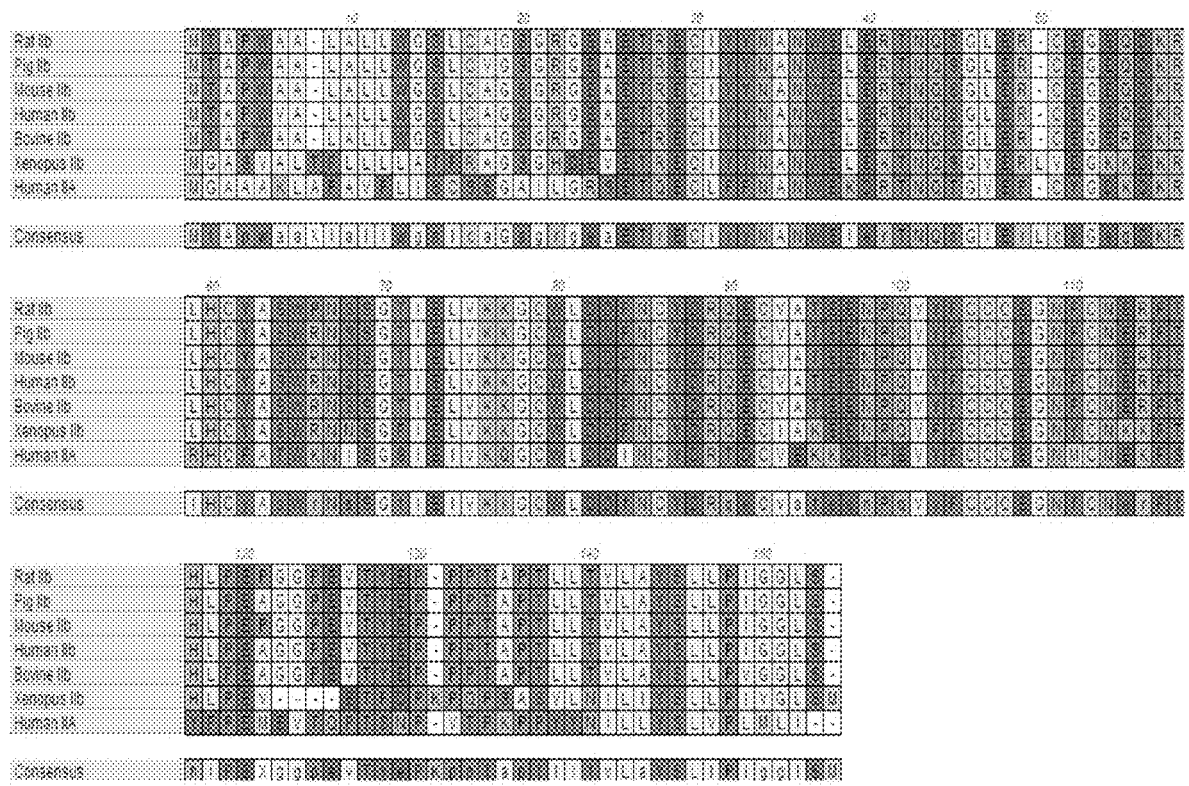
FIG. 2 shows a multiple sequence alignment of various vertebrate ActRIIB proteins and human ActRIIA (SEQ ID NOs: 52-58) as well as a consensus ActRII sequence derived from the alignment (SEQ ID NO: 59).

The transforming growth factor-beta (TGF-β) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-β family, it is often possible to cause significant physiological changes in an organism. For example, the Piedmontese and Belgian Blue cattle breeds carry a loss-of-function mutation in the GDF8 (also called myostatin) gene that causes a marked increase in muscle mass [see, e.g., Grobet et al. (1997) Nat Genet. 17(1):71-4]. Furthermore, in humans, inactive alleles of GDF8 are associated with increased muscle mass and, reportedly, exceptional strength [see, e.g., Schuelke et al. (2004) N Engl J Med, 350:2682-8.

TGF-β signals are mediated by heteromeric complexes of type I and type II serine/threonine kinase receptors, which phosphorylate and activate downstream Smad proteins (e.g., Smad proteins 1, 2, 3, 5, and 8) upon ligand stimulation [see, e.g., Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling. Type II receptors are required for binding ligands and for expression of type I receptors. Type I and II activin receptors form a stable complex after ligand binding, resulting in phosphorylation of type I receptors by type II receptors.

Two related type II receptors (ActRII), ActRIIA and ActRIIB, have been identified as the type II receptors for activins [see, e.g., Mathews and Vale (1991) Cell 65:973-982; and Attisano et al. (1992) Cell 68: 97-108]. Besides activins, ActRIIA and ActRIIB can biochemically interact with several other TGF-β family proteins including, for example, BMP6, BMP7, Nodal, GDF8, and GDF11 [see, e.g., Yamashita et al. (1995) J. Cell Biol. 130:217-226; Lee and McPherron (2001) Proc. Natl. Acad. Sci. USA 98:9306-9311; Yeo and Whitman (2001) Mol. Cell 7: 949-957; and Oh et al. (2002) Genes Dev. 16:2749-54]. ALK4 is the primary type I receptor for activins, particularly for activin A, and ALK-7 may serve as a receptor for other activins as well, particularly for activin B. In certain embodiments, the present disclosure relates to antagonizing a ligand of an ActRII receptor (also referred to as an ActRII ligand) with one or more inhibitor agents disclosed herein, particularly inhibitor agents that can antagonize one or more of activin A, activin B, activin C, activin E, GDF11 and/or GDF8.

Activins are dimeric polypeptide growth factors that belong to the TGF-β superfamily. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing $β_C$ or $β_E$ are also known.

In the TGF-β superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al. (1991) Proc Soc Ep Biol Med. 198:500-512; Dyson et al. (1997) Curr Biol. 7:81-84; and Woodruff (1998) Biochem Pharmacol. 55:953-963]. Moreover, an erythroid differentiation factor (EDF) isolated from the stimulated human monocytic leukemic cells was found to be identical to activin A [Murata et al. (1988) PNAS, 85:2434]. It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP, also known as FLRG or FSTL3), and $α_2$-macroglobulin.

As described herein, agents that bind to "activin A" are agents that specifically bind to the $β_A$ subunit, whether in the context of an isolated $β_A$ subunit or as a dimeric complex (e.g., a $β_Aβ_A$ homodimer or a PAN heterodimer). In the case of a heterodimer complex (e.g., a $β_Aβ_B$ heterodimer), agents that bind to "activin A" are specific for epitopes present within the $β_A$ subunit, but do not bind to epitopes present within the non-$β_A$ subunit of the complex (e.g., the $β_B$ subunit of the complex). Similarly, agents disclosed herein that antagonize (inhibit) "activin A" are agents that inhibit one or more activities as mediated by a $β_A$ subunit, whether in the context of an isolated $β_A$ subunit or as a dimeric complex (e.g., a $β_Aβ_A$ homodimer or a $β_Aβ_B$ heterodimer). In the case of PAN heterodimers, agents that inhibit "activin A" are agents that specifically inhibit one or more activities of the $β_A$ subunit, but do not inhibit the activity of the non-$β_A$ subunit of the complex (e.g., the $β_B$ subunit of the complex). This principle applies also to agents that bind to and/or inhibit "activin B", "activin C", and "activin E". Agents disclosed herein that antagonize "activin AB" are agents that inhibit one or more activities as mediated by the $β_A$ subunit and one or more activities as mediated by the $β_B$ subunit.

Growth and differentiation factor-8 (GDF8) is also known as myostatin. GDF8 is a negative regulator of skeletal muscle mass. GDF8 is highly expressed in developing and adult skeletal muscle. The GDF8 null mutation in transgenic mice is characterized by a marked hypertrophy and hyperplasia of the skeletal muscle [McPherron et al., Nature (1997) 387:83-90]. Similar increases in skeletal muscle mass are evident in naturally occurring mutations of GDF8 in cattle [see, e.g., Ashmore et al. (1974) Growth, 38:501-

507; Swatland and Kieffer (1994) J. Anim. Sci. 38:752-757; McPherron and Lee (1997) Proc. Natl. Acad. Sci. USA 94:12457-12461; and Kambadur et al. (1997) Genome Res. 7:910-915] and, strikingly, in humans [see, e.g., Schuelke et al. (2004) N Engl J Med 350:2682-8]. Studies have also shown that muscle wasting associated with HIV-infection in humans is accompanied by increases in GDF8 protein expression [see, e.g., Gonzalez-Cadavid et al. (1998) PNAS 95:14938-43]. In addition, GDF8 can modulate the production of muscle-specific enzymes (e.g., creatine kinase) and modulate myoblast cell proliferation [see, e.g. international patent application publication no. WO 00/43781]. The GDF8 propeptide can noncovalently bind to the mature GDF8 domain dimer, inactivating its biological activity [see, e.g., Miyazono et al. (1988) J. Biol. Chem., 263: 6407-6415; Wakefield et al. (1988) J. Biol. Chem., 263: 7646-7654; and Brown et al. (1990) Growth Factors, 3: 35-43]. Other proteins which bind to GDF8 or structurally related proteins and inhibit their biological activity include follistatin, and potentially, follistatin-related proteins [see, e.g., Gamer et al. (1999) Dev. Biol., 208: 222-232].

Growth and differentiation factor-11 (GDF11), also known as bone morphogenetic protein-11 (BMP11), is a secreted protein [McPherron et al. (1999) Nat. Genet. 22: 260-264]. GDF11 is expressed in the tail bud, limb bud, maxillary and mandibular arches, and dorsal root ganglia during mouse development [see, e.g., Nakashima et al. (1999) Mech. Dev. 80: 185-189]. GDF11 plays a unique role in patterning both mesodermal and neural tissues [see, e.g., Gamer et al. (1999) Dev Biol., 208:222-32]. GDF11 was shown to be a negative regulator of chondrogenesis and myogenesis in developing chick limb [see, e.g., Gamer et al. (2001) Dev Biol. 229:407-20]. The expression of GDF11 in muscle also suggests a role for this ligand in regulating muscle growth in a manner similar to that of GDF8. In addition, the expression of GDF11 in brain suggests that GDF11 may also possess activities that relate to the function of the nervous system. Interestingly, GDF11 was found to inhibit neurogenesis in the olfactory epithelium [see, e.g., Wu et al. (2003) Neuron. 37:197-207].

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. BMP7 also plays a role in calcium regulation and bone homeostasis. Like activin, BMP7 binds to ActRIIA and ActRIIB. However, BMP7 and activin recruit distinct type I receptors into heteromeric receptor complexes. Whereas BMP7 signals preferentially through ALK2, activin signals through ALK4. This difference allows BMP7 and activin to activate different Smad pathways and elicit distinct biological responses [see, e.g., Macias-Silva et al. (1998) J Biol Chem. 273:25628-36].

It has been demonstrated that ActRII polypeptides (e.g., ActRIIA and ActRIIB polypeptides as well as variants thereof such as GDF traps) can be used to increase red blood cell levels in vivo (see, e.g., WO 2008/046437 and WO 2010/019261)). For example, it recently has been shown that GDF trap polypeptides [e.g., an ActRIIB(L79D 25-131)-Fc fusion protein as described herein] are more potent stimulators of erythropoiesis compared to corresponding, non-variant ActRIIB polypeptides and can be used to increase red blood cell levels in a variety of anemia models. As described previously, an ActRIIB(L79D 25-131)-Fc GDF trap is characterized, in part, by unique ligand-binding properties. In particular, it has been shown that ActRIIB (L79D 25-131)-Fc, as well as additional ActRIIB variants comprising an acidic amino acid at position L79 with respect to the ActRIIB precursor protein (e.g., SEQ ID NO: 1), has dramatically reduced ability to bind to, and therefore diminished capacity to inhibit, activin A compared to a corresponding, non-variant ActRIIB polypeptide (an ActRIIB polypeptide comprising the native leucine at position 79). However, ActRIIB(L79D 25-131)-Fc still binds to other native ActRIIB ligands including, for example, GDF11, GDF8 (also known as myostatin), and activin B. Therefore, these findings demonstrate that the observed biological activity of an ActRII polypeptide, with respect to red blood cell levels, is not dependent on activin A inhibition. However, it is to be noted that the unmodified ActRII polypeptide, which retains activin A binding, still demonstrates the capacity to increase red blood cells in vivo. Furthermore, an ActRII polypeptide that retains activin A inhibition may be more desirable in some applications, in comparison to a GDF trap having diminished binding affinity for activin A, where more modest gains in red blood cell levels are desirable and/or where some level of off-target activity is acceptable (or even desirable).

Further studies have shown how multiple ActRII ligands (e.g., activin B, GDF11, and GDF8) appear to be regulators of erythropoiesis. For example, WO 2015/143403 describes there is a trend toward increased levels of various blood parameters (e.g., hematocrit, hemoglobin, and red blood cell levels) as more of these ligands are inhibited. Indeed, it has been shown that administration of an agent that inhibits GDF8 and GDF11 activity has a more substantial effect on increasing red blood cell levels in vivo compared to an agent that only antagonizes GDF8. Furthermore, it was demonstrated that combination therapy using agents that inhibit activin B, GDF8, and GDF11 have even a greater effect on increasing red blood cells compared to treatment with a GDF8/GDF11 antagonist.

It should be noted that hematopoiesis is a complex process, regulated by a variety of factors, including erythropoietin, G-CSF, and iron homeostasis. The terms "increase red blood cell levels" and "promote red blood cell formation" refer to clinically observable metrics, such as hematocrit, red blood cell counts, and hemoglobin measurements, and are intended to be neutral as to the mechanism by which such changes occur.

As demonstrated herein, multiple genes, e.g., GATA-1, NFE2 and heat shock factor, were surprisingly found to be upregulated in a murine model of β-thalassemia treated with a modified activin receptor Type IIB ligand trap, ActRIIB (L79D 25-131)-hFc GATA-1 is a transcription factor that activates nearly all erythroid-specific genes while silencing genes associated with immature proliferative red blood cell precursor cells (erythroblasts). As described herein, GATA-1 upregulation as a result of Smad inhibition was associated with a corresponding upregulation of several genes involved in heme biosynthesis (e.g., Ppox, Fech, Alas2 and Abcb10) and erythroid differentiation (Klf1, NFE2, Gypa, BcL2, Bnip31, Bach1 and Ank1).

NFE2 expression is regulated, in part, by the GATA-1 transcription Factor. NFE2 is ahematopoietic transcription factor that is essential for platelet formation, but that also plays a role in erythropoiesis. It has previously been shown that NFE2 overexpression delays early phase of erythroid maturation, resulting in an expansion of erythroid progenitors, thereby increasing the number of erythrocytes from CD34$^+$ cells (Mutschler M et al., 2009, Br J Haemotol, 164(2):203-217).

Heat shock factors (HSFs) are transcriptional regulators of heat shock protein (HSP) gene expression. HSFs bind to Heat Shock Element (HSE) sequences found throughout the genome to regulate HSP gene expression. Specific HSPs regulated by HSFs include HSP60, HSP70 and HSP90

Accordingly, the present disclosure provides, in part, methods for increasing red blood cell levels, treating or preventing anemia, and/or treating or preventing ineffective erythropoiesis in a subject in need thereof with an agent, or combination of agents, that agonizes (activates), reduces inhibition of, and/or supplements the activity of any one of, or combination of, GATA-1, heat shock factor, and/or NFE2. In some embodiments, such agents may be antagonists (inhibitors) of Smad signaling. Agents that antagonize Smad signaling (e.g., antagonists of GDF11, activin B, GDF8, BMP6, activin C, activin E, activin A, GDF15, Nodal, GDF3, BMP3, BMP3B, BMP9, and/or BMP10) may be combined with one or more agents that act downstream of Smad inhibition to agonize (activate), reduce inhibition of, and/or supplement the activity of any one of, or combination of, GATA-1, heat shock factor, and/or NFE2.

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope or meaning of any use of a term will be apparent from the specific context in which they are used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Wash. D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

A "reference population," as used herein, is a population of subjects against which a test subject is compared. In some embodiments, the reference patient or population is the test subject prior to diagnosis. In some embodiments, the reference patient or population is the test subject prior to treatment with any of the agents disclosed herein. In some embodiments, the test subject is a subject to whom any of the agents described herein (e.g., any of the soluble ActRIIb polypeptides described herein) is administered, and the reference population is a population of subjects to whom the agent(s) is/are not administered. In some embodiments, the test subject is a subject to whom any of the agents described herein (e.g., any of the soluble ActRIIb receptors described herein) is administered at one dose (e.g., a high dose), and the reference population is a population of subjects to whom the agent(s) is administered at a different dose (e.g., a low dose). In some embodiments, the test subject is a subject to whom a first agent (e.g., any of the soluble ActRIIb receptors described herein) is administered in combination with an additional agent (e.g., tamoxifen, oestradiol, anthracycline and/or geldanamycin), and the reference population is a population of subjects to whom the first agent is administered without the administration of an additional agent. In some embodiments, the subjects in the reference population are selected to be of a similar or identical age, sex, diet, body type, genetic background, and/or health status as the test subject. In some embodiments, the subjects in the reference population and the test subject have the same disease or disorder, e.g., anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II); hereditary spherocytosis; pyruvate kinase deficiency; megaloblastic anemias; myelophthisic anemias including, for example, myelofibrosis (myeloid metaplasia) and myelophthisis, congenital erythropoietic porphyria, and/or lead poisoning.

As used herein, unless otherwise stated, "does not substantially bind to X" is intended to mean that an agent has a $K_D$ that is greater than about $10^{-6}$, $10^{-5}$, $10^{-4}$, or greater (e.g., no detectable binding by the assay used to determine the $K_D$) for "X".

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. Modifiers of GATA-1, NFE2 and Heat Shock Protein Expression and/or Activity

The data presented herein demonstrates that GATA-1, NFE2 and heat shock protein are surprisingly upregulated in a mouse model of β-thalassemia treated with the representative Smad inhibitor, ActRIIB(L79D 25-131)-mFc. It is contemplated that agents that agonize (activate), reduce inhibition of, and/or supplement the activity of any one of, or combination of, GATA-1, heat shock factor, and/or NFE2 would be useful for increasing red blood cell levels, treating or preventing an anemia, and/or treating or preventing ineffective erythropoiesis in a subject. In some embodiments, any of the agents disclosed herein increase GATA-1, heat shock factor and/or NFE2 levels and/or activity in erythroblasts in the subject. In some embodiments, the agent increases GATA-1, heat shock factor and/or NFE2 gene expression. In some embodiments, the agent increases GATA-1, heat shock factor and/or NFE2 protein activity. In some embodiments, the agent prevents degradation of GATA-1, heat shock factor and/or NFE2. In some embodiments, the agent antagonizes an inhibitor of GATA-1, heat shock factor and/or NFE2 protein activity. In some embodiments, the agent antagonizes a repressor of GATA-1, heat shock factor and/or NFE2 gene expression. In some embodiments, the agent increases levels and/or activity of one or more heme biosynthesis genes selected from the group consisting of: Ppox, Fech, Alas2, and Abcb10l. In some embodiments, the agent increase levels and/or activity of one or more erythroid differentiation factors selected from the group consisting of: KLF1, NFE2, GYPA, Bcl21, Bnip31, Bach1, and ANK1.

It is understood that agents, or combinations of agents, that agonize (activate), reduce inhibition of, and/or supplement the activity of any one of GATA-1, heat shock factor, and/or NFE2 may, as a result, indirectly agonize (activate), reduce inhibition of, and/or supplement the activity of another of GATA-1, heat shock factor, and/or NFE2. For example, an agent that agonizes (activates), reduces inhibition of, and/or supplements the activity of heat shock factor may, as a result, agonize (activate), reduce inhibition of, and/or supplement GATA-1, as heat shock factors may control expression of HSPs such as HSP70. Similarly, an agent that agonizes (activates), reduces inhibition of, and/or supplements the activity of GATA-1 may, as a result, agonize (activate), reduce inhibition of, and/or supplement NFE2, as NFE2 gene expression is regulated by GATA-1.

GATA-1 and NFE2 are transcription factors. As such, in some embodiments, the agents for use in the methods disclosed herein are agonists for the gene products regulated by GATA-1 and/or NFE2. For example, in some embodiments, the agent is an agent that agonizes (activates), reduces inhibition of, and/or supplements the activity of any one or more Ppox, Fech, Alas2, Abcb10, Klf1, NFE2, Gypa, BcL2, Bnip31, Bach1, Ank1, HSF1 and/or HSP70.

In some embodiments, any of the agents disclosed herein agonize (activate), reduce inhibition of, and/or supplement the activity of another of GATA-1, heat shock factor, and/or NFE2 act at the level of Smad (e.g., Smad 1, 2, 3, 5 and/or 8) inhibition. In some embodiments, any of the agents disclosed herein agonize (activate), reduce inhibition of, and/or supplement the activity of another of GATA-1, heat shock factor, and/or NFE2 act downstream of Smad inhibition.

A. Agents Acting Downstream of Smad Inhibition
  i. GATA-1

In some embodiments, the methods disclosed herein utilize one or more agents that agonize (activate), reduce inhibition of, and/or supplement the activity of, GATA-1. In some embodiments, the agent is a small molecule, a protein, and/or a nucleic acid.

In some embodiments, the agent is an estrogen receptor antagonist. In some embodiments, the agent is an estrogen receptor inhibitor. In some embodiments, the agent inhibits the binding of ErbB2/HER2 to the estrogen receptor. In some embodiments, the agent inhibits the binding of endogenous estrogen to the estrogen receptor.

In some embodiments, the agent is an estrogen receptor agonist. In some embodiments, the agent is an estrogen receptor activator. In some embodiments, the agent is an agonist of estrogen receptor alpha (ERα) and estrogen receptor beta (ERβ). In some embodiments, the agent is an agonist of membrane estrogen receptors (mER). In some embodiments, the agent is an estrogen sex hormone. In some embodiements, the agent is estriol or estrone.

In some embodiments, the agent is chemotherapeutic. In some embodiments, the agent inhibits the synthesis of DNA or RNA. In some embodiments, the agent inhibits the topoisomerase II enzyme. In some embodiments, the agent results in iron-mediated generation of free oxygen radicals. In some embodiments, the agent induces histone eviction from chromatin. In some embodiments, the agent is an anthracycline.

In some embodiments, the agent is selected from the group consisting of: erythropoietin, tamoxifen, oestradiol, or an anthracycline. In some embodiments, the anthracycline is any one or more of: aclacinomycin A, daunorubicin, doxorubicin, epirubicin, idarubicin, valrubicin, mitoxantrone, and any analogs thereof.

In some embodiments, the agent is a vector comprising a polynucleotide encoding recombinant GATA-1 protein, or a functional fragment thereof.

In some embodiments, the agent is recombinant GATA-1, or a functional fragment thereof. In some embodiments, the recombinant GATA-1 protein or functional fragment thereof is conjugated to a cellular internalization moiety.

In some embodiments, the recombinant GATA-1 protein comprises a sequence that comprises, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of SEQ ID NO: 84, or functional fragments thereof. In some embodiments, the recombinant GATA-1 protein or functional fragment thereof comprises a C-finger and/or N-finger domain. In some embodiments, the recombinant GATA-1 protein or functional fragment thereof activates expression of any one or more of Ppox, Fech, Alas2, Abcb10, Klf1, NFE2, Gypa, BcL2, Bnip31, Bach1 and/or Ank1.

The sequence of SEQ ID NO: 84 corresponds to the wildtype human GATA-1 amino acid sequence as follows:

(SEQ ID NO: 84; GenBank Accession Number:
NP_002040.1)
MEFPGLGSLGTSEPLPQFVDPALVSSTPESGVFFPSGPEGLDAAASSTAP

STATAAAAALAYYRDAEAYRHSPVFQVYPLLNCMEGIPGGSPYAGWAYGK

TGLYPASTVCPTREDSPPQAVEDLDGKGSTSFLETLKTERLSPDLLTLGP

ALPSSLPVPNSAYGGPDFSSTFFSPTGSPLNSAAYSSPKLRGTLPLPPCE

ARECVNCGATATPLWRRDRTGHYLCNACGLYHKMNGQNRPLIRPKKRLIV

SKRAGTQCTNCQTTTTTLWRRNASGDPVCNACGLYYKLHQVNRPLTMRKD

GIQTRNRKASGKGKKKRGSSLGGTGAAEGPAGGFMVVAGGSGSGNCGEVA

SGLTLGPPGTAHLYQGLGPVVLSGPVSHLMPFPGPLLGSPTGSFPTGPMP

PTTSTTVVAPLSS

GATA-1 is a transcription factor. As such, in some embodiments, the agents for use in the methods disclosed herein are agonists for the gene products regulated by GATA-1. For example, in some embodiments, the agent is an agent that agonizes (activates), reduces inhibition of, and/or supplements the activity of any one or more Ppox, Fech, Alas2, Abcb10, Klf1, NFE2, Gypa, BcL2, Bnip31, Bach1 and/or Ank1.

ii. NFE2

In some embodiments, the methods disclosed herein utilize one or more agents that agonize (activate), reduce inhibition of, and/or supplement the activity of NFE2. In some embodiments, the agent is a small molecule, a protein, and/or a nucleic acid.

In some embodiments, the agent is a vector comprising a polynucleotide encoding recombinant NFE2 protein, or a functional fragment thereof.

In some embodiments, the agent is a recombinant NFE2, or a functional fragment thereof. In some embodiments, the recombinant NFE2 protein or functional fragment thereof is conjugated to a cellular internalization moiety.

In some embodiments, the recombinant NFE2 protein comprises a sequence that comprises, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of SEQ ID NO: 85, or functional fragments thereof. In some embodiments, the recombinant NFE2 protein or functional thereof comprises the transcriptional activator domain (Amrolia et al., 1997, PNAS, 94:10051-56). In some embodiments, the recombinant NFE2 protein or functional thereof binds to locus control regions (LCRs).

The sequence of SEQ ID NO: 85 corresponds to the wildtype human NFE2 amino acid sequence as follows:

(SEQ ID NO: 85; GenBank Accession Number:
NP_001129495.1)
MSPCPPQQSRNRVIQLSTSELGEMELTWQEIMSITELQGLNAPSEPSFEP

QAPAPYLGPPPPTTYCPCSIHPDSGFPLPPPPYELPASTSHVPDPPYSYG

NMAIPVSKPLSLSGLLSEPLQDPLALLDIGLPAGPPKPQEDPESDSGLSL

NYSDAESLELEGTEAGRRRSEYVEMYPVEYPYSLMPNSLAHSNYTLPAAE

TPLALEPSSGPVRAKPTARGEAGSRDERRALAMKIPFPTDKIVNLPVDDF

NELLARYPLTESQLALVRDIRRRGKNKVAAQNCRKRKLETIVQLERELER

LTNERERLLRARGEADRTLEVMRQQLTELYRDIFQHLRDESGNSYSPEEY

ALQQAADGTIFLVPRGTKMEATD iii. Heat Shock Factor

In some embodiments, the methods disclosed herein utilize one or more agents that agonize (activate), reduce inhibition of, and/or supplement the activity of heat shock factor. In some embodiments, the agent is a small molecule, a protein, and/or a nucleic acid.

In some embodiments, the agent is a vector comprising a polynucleotide encoding recombinant heat shock factor protein, or a functional fragment thereof. In some embodiments, the recombinant heat shock factor protein is HSF1.

In some embodiments, the agent is recombinant heat shock factor, or a functional fragment thereof. In some embodiments, the recombinant heat shock factor protein, or a functional fragment thereof is conjugated to a cellular internalization moiety. In some embodiments, the recombinant heat shock factor protein is HSF1.

HSF1 positively regulates expression of certain HSPs, including HSP70. In some embodiments, the agent is an inducer of HSF1 activity. In some embodiments, the agent is selected from the group consisting of: a pentacyclic triterpenoid, tricyclic bis(cyanoenone), celastrol, HSF1A, gedunin, sappanone A, and/or derivatives thereof.

In some embodiments, the recombinant HSF1 protein comprises a sequence that comprises, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of SEQ ID NO: 86, or functional fragments thereof. In some embodiments, the HSF1 protein or functional fragment thereof comprises a transcriptional activation domain. In some embodiments, the HSF1 protein or functional fragment thereof activates expression of HSP70.

The sequence of SEQ ID NO: 86 corresponds to the wildtype human HSF1 amino acid sequence as follows:

(SEQ ID NO: 86; GenBank Accession Number:
NP_005517.1)
MDLPVGPGAAGPSNVPAFLTKLWTLVSDPDTDALICWSPSGNSFHVFDQG

QFAKEVLPKYFKHNNMASFVRQLNMYGFRKVVHIEQGGLVKPERDDTEFQ

HPCFLRGQEQLLENIKRKVTSVSTLKSEDIKIRQDSVTKLLTDVQLMKGK

QECMDSKLLAMKHENEALWREVASLRQKHAQQQKVVNKLIQFLISLVQSN

RILGVKRKIPLMLNDSGSAHSMPKYSRQFSLEHVHGSGPYSAPSPAYSSS

SLYAPDAVASSGPIISDITELAPASPMASPGGSIDERPLSSSPLVRVKEE

```
PPSPPQSPRVEEASPGRPSSVDTLLSPTALIDSILRESEPAPASVTALTD

ARGHTDTEGRPPSPPPTSTPEKCLSVACLDKNELSDHLDAMDSNLDNLQT

MLSSHGFSVDTSALLDLFSPSVTVPDMSLPDLDSSLASIQELLSPQEPPR

PPEAENSSPDSGKQLVHYTAQPLFLLDPGSVDTGSNDLPVLFELGEGSYF

SEGDGFAEDPTISLLTGSEPPKAKDPTVS
```

HSP90 is a negative regulator of HSF1. In some embodiments, the agent is an antibiotic. In some embodiments, the agent inhibits the function of Hsp90. In some embodiments, the agent is an antitumor antibiotic. In some embodiments, the agent is an inhibitor of HSP90. In some embodiments, the agent is geldanamycin, radicicol, 17-AAG, 17-DMAG, IPI-493, OCH$_3$, NHCH$_2$CH=CH$_2$, NHCH$_2$CH$_2$N(CH$_3$)$_2$, NH$_2$, NVP-AUY922, KW-2478, AT13387, BIIB021, PU-H71, SNX-5422, NVP-BEP800, CUDC-305, XL888, and/or derivatives thereof.

HSP70 is upregulated in response to activation of the heat shock factor HSF1. In some embodiments, the agent is an agonist of HSP70. In some embodiments, the agent is 115-7c and/or Compound A, or derivatives thereof. In some embodiments, the agent is a vector comprising a polynucleotide encoding recombinant HSP70 or a functional fragment thereof. In some embodiments, the agent is recombinant HSP70 or a functional fragment thereof. In some embodiments, the recombinant HSP70 protein is conjugated to a cellular internalization moiety. In some embodiments, the recombinant HSP70 protein comprises a sequence that comprises, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of SEQ ID NO: 87, or functional fragments thereof. In some embodiments, the recombinant HSP70 or functional fragment thereof comprises an ATPase domain, a substrate binding domain, and/or a C-terminal domain.

The sequence of SEQ ID NO: 87 corresponds to the wildtype human HSF1 amino acid sequence as follows:

```
(SEQ ID NO: 87; GenBank Accession Number:
NP_002145.3)

MSVVGIDLGFQSCYVAVARAGGIETIANEYSDRCTPACISFGPKNRSIGA

AAKSQVISNAKNTVQGFKRFHGRAFSDPFVEAEKSNLAYDIVQLPTGLTG

IKVTYMEEERNFTTEQVTAMLLSKLKETAESVLKKPVVDCVVSVPCFYTD

AERRSVMDATQIAGLNCLRLMNETTAVALAYGIYKQDLPALEEKPRNVVF

VDMGHSAYQVSVCAFNRGKLKVLATAFDTTLGGRKFDEVLVNHFCEEFGK

KYKLDIKSKIRALLRLSQECEKLKKLMSANASDLPLSIECFMNDVDVSGT

MNRGKFLEMCNDLLARVEPPLRSVLEQTKLKKEDIYAVEIVGGATRIPAV

KEKISKFFGKELSTTLNADEAVTRGCALQCAILSPAFKVREFSITDVVPY

PISLRWNSPAEEGSSDCEVFSKNHAAPFSKVLTFYRKEPFTLEAYYSSPQ

DLPYPDPAIAQFSVQKVTPQSDGSSSKVKVKVRVNVHGIFSVSSASLVEV

HKSEENEEPMETDQNAKEEEKMQVDQEEPHVEEQQQQTPAENKAESEEME

TSQAGSKDKKMDQPPQAKKAKVKTSTVDLPIENQLLWQIDREMLNLYIEN

EGKMIMQDKLEKERNDAKNAVEEYVYEMRDKLSGEYEKFVSEDDRNSFTL

KLEDTENWLYEDGEDQPKQVYVDKLAELKNLGQPIKIRFQESEERPKLFE

ELGKQIQQYMKIISSFKNKEDQYDHLDAADMTKVEKSTNEAMEWMNNKLN

LQNKQSLTMDPVVKSKEIEAKIKELTSTCSPIISKPKPKVEPPKEEQKNA

EQNGPVDGQGDNPGPQAAEQGTDTAVPSDSDKKLPEMDID
```

B. Smad Antagonists

The present disclosure demonstrates that Smad inhibition results in an increase in GATA-1, NFE2 and heat shock factor expression in a model of β-thalassemia. In some embodiments, the methods disclosed herein utilize agents that antagonize (inhibit) Smad (e.g., Smad 1, 2, 3, 5, and/or 8) signaling ("a Smad antagonist"). In some embodiments, the Smad antagonist agonizes (activate), reduces inhibition of, and/or supplements the activity of any one of, or combination of, GATA-1, NFE2 and/or heat shock factor. In some embodiments, the additional agent is a small molecule, a protein, and/or a nucleic acid.

In some embodiments, agent is not a polypeptide comprising an amino acid sequence that is identical to SEQ ID NO: 64 or a variant thereof comprising an acidic amino acid at the position corresponding to position 79 of SEQ ID NO: 1. In some embodiments, the agent is not a polypeptide comprising an amino acid sequence that is identical to amino acids 25-131 of SEQ ID NO: 1 or 4, comprising an acidic amino acid at the position corresponding to position 79 of SEQ ID NO: 1 or 4, or a functional fragment thereof. In some embodiments, the agent is not ActRIIB(L79D 25-131)-hFc (SEQ ID NO: 61 with TPA leader sequence; or SEQ ID NO: 64 as the processed form), or an ActRIIB (L79D 25-131)-hFc polypeptide comprising an acidic amino acid at the position corresponding to position 79 of SEQ ID NO: 1, or an ActRIIB(L79D 25-131)-hFc polypeptide comprising an alanine at the position corresponding to position 64 of SEQ ID NO: 1, or a functional fragment thereof. In some embodiments, the Smad antagonist is selected from the group consisting of Lerdelimumab, Metelimumab, Fresolimumab, 2G7, LY2382770, IMC-TR1, PF-03446962, Stromedix, Ad.sTβRII-Fc, Disitertide, LSKL, Trabedersen, AP11014, AP15012, Belagenpu-matucel-L, LY550410, SB-431542, SB-505124, Ki26894, LY364937, SD-208, LY2157299, Trx-SARA, pyrrole-imidazole polyamides, SMAD7, and Avotermin. In some embodiments, the Smad antagonist is an ActRII antagonist, an ActRII polypeptide, an antibody antagonist, a small molecule antagonist, an antagonist polynucleotide, a follistatin antagonist and/or an FLRG antagonist, as described in greater detail below.

i. ActRII Antagonists

In certain aspects, ActRII antagonists to be used in accordance with the methods disclosed herein are ActRII polypeptides (ActRIIA or ActRIIB polypeptides) including truncations and variants thereof. In some embodiments, preferred ActRII antagonists to be used in accordance with the methods disclosed herein are variant ActRII polypeptides that retain strong to intermediate binding affinity to GDF11 and/or GDF8 but have reduced binding to activin A compared to a corresponding, non-variant ActRII polypeptide. Such variant ActRII polypeptides are generally referred to herein as "GDF traps" or "GDF trap polypeptides".

Although soluble ActRII polypeptides and GDF traps of the disclosure may affect red blood cell levels and/or ineffective erythropoiesis through a mechanism other than GDF (e.g. GDF11 and/or GDF8) antagonism [e.g., GDF11 and/or GDF8 inhibition may be an indicator of the tendency of an agent to inhibit the activities of a spectrum of additional agents, including, perhaps, other members of the TGF-beta superfamily (e.g., activin B, activin C, activin E, BMP6, BMP7, and/or Nodal) and such collective inhibition may lead to the desired effect on, for example, erythropoiesis], other types of GDF-ActRII antagonists are expected to be useful in accordance with the methods of disclosure including, for example, anti-GDF11 antibodies; anti-GDF8 antibodies; anti-ActRIIA antibodies; anti-ActRIIB antibodies; anti-ActRIIA/IIB antibodies; nucleic acids that inhibit the expression (e.g., transcription, translation, secretion from a cell, or combinations thereof) of one or more of GDF11, GDF8, ActRIIA, and/or ActRIIB; as well as small molecule inhibitors of one or more of GDF11, GDF8, ActRIIA, and/or ActRIIB. Optionally, a GDF-ActRII antagonist, or combination of antagonists, of the present disclosure may inhibit the activity (or expression) of other ActRII ligands including, for example, activin (e.g., activin A, activin AB, activin B, activin C, activin E), BMP6, and BMP10. In some embodiments, ActRII antagonists to be used in accordance with the methods disclosed herein do not substantially bind to and/or inhibit activity of activin A. In other embodiments, ActRII antagonists to be used in accordance with the methods disclosed herein do not substantially bind to and/or inhibit activity of BMP10. In still other embodiments, ActRII antagonists to be used in accordance with the methods disclosed herein do not substantially bind to and/or inhibit activity of activin A and BMP10.

ii. ActRII Polypeptides

In certain aspects, the present disclosure relates to ActRII polypeptides. In particular, the disclosure provides methods of using ActRII polypeptides, alone or in combination with one or more additional supportive therapies, for increasing red blood cell levels, treating or preventing an anemia, and/or treating or preventing ineffective erythropoiesis, e.g., erythropoiesis associated with any of the following: anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficiency, megaloblastic anemias, myelophthisic anemias including, for example, myelofibrosis (myeloid metaplasia) and myelophthisis, congenital erythropoietic porphyria, and/or lead poisoning. In certain aspects, the present disclosure relates to ActRII polypeptides for use in any of the methods disclosed herein. As used herein the term "ActRII" refers to the family of type II activin receptors. This family includes the activin receptor type IIA (ActRIIA) and the activin receptor type IIB (ActRIIB).

As used herein, the term "ActRIIB" refers to a family of activin receptor type JIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

(SEQ ID NO: 1)

```
  1 MTAPWVALAL LWGSLCAGSG RGEAETRECI YYNANWELER TNQSGLERCE

51 GEQDKRLHCY ASWRNSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated with a singleunderline; the extracellular domain is indicated in bold font; and the potential, endogenous N-linked glycosylation sites are indicated with a doubleunderline.

The processed (mature) extracellular ActRIIB polypeptide sequence is as follows:

```
                                         (SEQ ID NO: 2)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT.
```

In some embodiments, the protein may be produced with an "SGR . . . " sequence at the N-terminus. The C-terminal "tail" of the extracellular domain is indicated by a singleunderline. The sequence with the "tail" deleted (a Δ15 sequence) is as follows:

```
                                         (SEQ ID NO: 3)
GRGEAETRECIYYNANWELERTNQSGLERCEGEQDKRLHCYASWRNSSG

TIELVKKGCWLDDFNCYDRQECVATEENPQVYFCCCEGNFCNERFTHLP

EA.
```

A form of ActRIIB with an alanine at position 64 of SEQ ID NO: 1 (A64) is also reported in the literature [Hilden et al. (1994) Blood, 83(8): 2163-2170]. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

The signal peptide is indicated by a singleunderline and the extracellular domain is indicated by bold font.

The processed (mature) extracellular ActRIIB polypeptide sequence of the alternative A64 form is as follows:

```
                                         (SEQ ID NO: 5)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

GGPEVTYEPPPTAPT
```

In some embodiments, the protein may be produced with an "SGR . . . " sequence at the N-terminus. The C-terminal "tail" of the extracellular domain is indicated by singleunderline. The sequence with the "tail" deleted (a Δ15 sequence) is as follows:

```
                                         (SEQ ID NO: 6)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA
```

A nucleic acid sequence encoding human ActRIIB precursor protein is shown below (SEQ ID NO: 7), consisting of nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

```
                                                  (SEQ ID NO: 4)
  1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

(SEQ ID NO: 7)
```
   1 ATGACGGCGC CCTGGGTGGC CCTCGCCCTC CTCTGGGGAT CGCTGTGCGC

51 CGGCTCTGGG CGTGGGGAGG CTGAGACACG GGAGTGCATC TACTACAACG

101 CCAACTGGGA GCTGGAGCGC ACCAACCAGA GCGGCCTGGA GCGCTGCGAA

151 GGCGAGCAGG ACAAGCGGCT GCACTGCTAC GCCTCCTGGC GCAACAGCTC

201 TGGCACCATC GAGCTCGTGA AGAAGGGCTG CTGGCTAGAT GACTTCAACT

251 GCTACGATAG GCAGGAGTGT GTGGCCACTG AGGAGAACCC CCAGGTGTAC

301 TTCTGCTGCT GTGAAGGCAA CTTCTGCAAC GAACGCTTCA CTCATTTGCC

351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC

751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT

851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC
```

A nucleic acid sequence encoding the processed extracellular human ActRIIB polypeptide is as follows (SEQ ID NO: 8):

(SEQ ID NO: 8)
```
  1    GGGCGTGGGG AGGCTGAGAC ACGGGAGTGC ATCTACTACA ACGCCAACTG

51    GGAGCTGGAG CGCACCAACC AGAGCGGCCT GGAGCGCTGC GAAGGCGAGC

101    AGGACAAGCG GCTGCACTGC TACGCCTCCT GGCGCAACAG CTCTGGCACC

151    ATCGAGCTCG TGAAGAAGGG CTGCTGGCTA GATGACTTCA ACTGCTACGA

201    TAGGCAGGAG TGTGTGGCCA CTGAGGAGAA CCCCCAGGTG TACTTCTGCT
```

```
251   GCTGTGAAGG CAACTTCTGC AACGAACGCT TCACTCATTT GCCAGAGGCT

301   GGGGGCCCGG AAGTCACGTA CGAGCCACCC CCGACAGCCC
```

The sequence as shown provides an arginine at position 64, and may be modified to provide an alanine instead.

An alignment of the amino acid sequences of human ActRIIB extracellular domain and human ActRIIA extracellular domain are illustrated in FIG. 1. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

In addition, ActRIIB is generally well-conserved among vertebrates, with large stretches of the extracellular domain completely conserved. For example, FIG. 2 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant to substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences.

Without meaning to be limiting, the following examples illustrate this approach to defining an active ActRIIB variant. L46 in the human extracellular domain (SEQ ID NO: 2) is a valine in *Xenopus* ActRIIB (SEQ ID NO: 57), and so this position may be altered, and optionally may be altered to another hydrophobic residue, such as V, I or F, or a non-polar residue such as A. E52 in the human extracellular domain is a K in *Xenopus*, indicating that this site may be tolerant of a wide variety of changes, including polar residues, such as E, D, K, R, H, S, T, P, G, Y and probably A. T93 in the human extracellular domain is a K in *Xenopus*, indicating that a wide structural variation is tolerated at this position, with polar residues favored, such as S, K, R, E, D, H, G, P, G and Y. F108 in the human extracellular domain is a Y in *Xenopus*, and therefore Y or other hydrophobic group, such as I, V or L should be tolerated. E111 in the human extracellular domain is K in *Xenopus*, indicating that charged residues will be tolerated at this position, including D, R, K and H, as well as Q and N. R112 in the human extracellular domain is K in *Xenopus*, indicating that basic residues are tolerated at this position, including R and H. A at position 119 in the human extracellular domain is relatively poorly conserved, and appears as P in rodents (SEQ ID NOs: 52 and 54) and V in *Xenopus*, thus essentially any amino acid should be tolerated at this position.

Moreover, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709, 605, 7,612,041, and 7,842,663]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 residues without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted. Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO: 1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, and zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

It has been previously demonstrated that the addition of a further N-linked glycosylation site (N—X—S/T) into the ActRIIB extracellular domain is well-tolerated (see, e.g., U.S. Pat. No. 7,842,663). Therefore, N—X—S/T sequences may be generally introduced at positions outside the ligand binding pocket defined in FIG. 1 in ActRIIB polypeptide of the present disclosure. Particularly suitable sites for the introduction of non-endogenous N—X—S/T sequences include amino acids 20-29, 20-24, 22-25, 109-134, 120-134 or 129-134 (with respect to SEQ ID NO: 1). N—X—S/T sequences may also be introduced into the linker between the ActRIIB sequence and an Fc domain or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E105N, R112N, G120N, E123N, P129N, A132N, R112S and R112T (with respect to SEQ ID NO: 1). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T (with respect to SEQ ID NO: 1) are contemplated. Likewise, in an A24N variant, an S26T alteration may be used. Accordingly, an ActRIIB polypeptide of the present disclosure may be a variant having one or more additional, non-endogenous N-linked glycosylation consensus sequences as described above.

In certain embodiments, the disclosure relates to ActRII antagonists that comprise at least one ActRIIB polypeptide, which includes fragments, functional variants, and modified forms thereof. Preferably, ActRIIB polypeptides for use in accordance with the disclosure are soluble (e.g., an extracellular domain of ActRIIB). In some embodiments, ActRIIB polypeptides for use in accordance with the disclosure inhibit (antagonize) activity (e.g., induction of Smad 1, 2, 3, 5, or 8 signaling) of one or more TGF-beta superfamily ligands (e.g., GDF11, GDF8, activin B, and BMP6). In some embodiments, ActRIIB polypeptides for use in accordance with the disclosure bind to one or more TGF-beta superfamily ligands (e.g., GDF11, GDF8, activin B, and BMP6). In some embodiments, ActRIIB polypeptide of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In some embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1. In some embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1, wherein the position corresponding to L79 of SEQ ID NO: 1 is an acidic amino acid (naturally occurring acidic amino acids D and E or an artificial acidic amino acid). In certain preferred embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1. In certain preferred embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1, wherein the position corresponding to L79 of SEQ ID NO: 1 is an acidic amino acid. In some embodiments, ActRIIB polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 40, 41, 44, 45, 46, 48, 49, 50, 61, 64, 65, 78 and 79. In some embodiments, ActRIIB polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 40, 41, 44, 45, 46, 48, 49, 50, 61, 64, 65, 78 and 79, wherein the position corresponding to L79 of SEQ ID NO: 1 is an acidic amino acid. In some embodiments, ActRIIB polypeptides of the disclosure consist, or consist essentially of, at least one ActRIIB polypeptide wherein the position corresponding to L79 of SEQ ID NO: 1 is not an acidic amino acid (i.e., is not a naturally occurring acid amino acids D or E or an artificial acidic amino acid residue).

In certain embodiments, the present disclosure relates to ActRIIA polypeptides. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Numbering of amino acids for all ActRIIA-related polypeptides described herein is based on the numbering of the human ActRIIA precursor protein sequence provided below (SEQ ID NO: 9), unless specifically designated otherwise.

The canonical human ActRIIA precursor protein sequence is as follows:

```
                                                           (SEQ ID NO: 9)
  1    MGAAAKLAFA VFLISCSSGA ILGRSETQEC LFFNANWEED RTNQTGVEPC

51    YGDKDKRRHC FATWKNISGS IEIVKQGCWL DDINCYDRTD CVEKKDSPEV

101    YFCCCEGNMC NEKFSYFPEM EVTQPTSNPV TPKPPYYNIL LYSLVPLMLI

151    AGIVICAFWV YRHHKMAYPP VLVPTQDPGP PPPSPLLGLK PLQLLEVKAR

201    GRFGCVWKAQ LLNEYVAVKI FPIQDKQSWQ NEYEVYSLPG MKHENILQFI

251    GAEKRGTSVD VDLWLITAFH EKGSLSDFLK ANVVSWNELC HIAETMARGL

301    AYLHEDIPGL KDGHKPAISH RDIKSKNVLL KNNLTACIAD FGLALKFEAG

351    KSAGDTHGQV GTRRYMAPEV LEGAINFQRD AFLRIDMYAM GLVLWELASR

401    CTAADGPVDE YMLPFEEEIG QHPSLEDMQE VVVHKKKRPV LRDYWQKHAG

451    MAMLCETIEE CWDHDAEARL SAGCVGERIT QMQRLTNIIT TEDIVVVIM

501    VTNVDFPPKE SSL
```

The signal peptide is indicated by a singleunderline; the extracellular domain is indicated in bold font; and the potential, endogenous N-linked glycosylation sites are indicated by a doubleunderline.

The processed (mature) extracellular human ActRIIA polypeptide sequence is as follows:

(SEQ ID NO: 10)
ILGRSETQECLFFNANWEKDRTNQTGVEPCYGDKDKRRHCFATWKNIS

GSIEIVKQGCWLDDINCYDRTDCVEKKDSPEVYFCCCEGNMCNEKFSY

FPEMEVTQPTSNPVTPKPP

The C-terminal "tail" of the extracellular domain is indicated by singleunderline. The sequence with the "tail" deleted (a Δ15 sequence) is as follows:

(SEQ ID NO: 11)
ILGRSETQECLFFNANWEKDRINQTGVEPCYGDKDKRRHCFATWKNIS

GSIEIVKQGCWLDDINCYDRTDCVEKKDSPEVYFCCCEGNMCNEKFSY

FPEM

The nucleic acid sequence encoding human ActRIIA precursor protein is shown below (SEQ ID NO: 12), as follows nucleotides 159-1700 of Genbank Reference Sequence NM_001616.4. The signal sequence is underlined.

(SEQ ID NO: 12)
```
   1 ATGGGAGCTG CTGCAAAGTT GGCGTTTGCC GTCTTTCTTA TCTCCTGTTC
  51 TTCAGGTGCT ATACTTGGTA GATCAGAAAC TCAGGAGTGT CTTTTCTTTA
 101 ATGCTAATTG GGAAAAAGAC AGAACCAATC AAACTGGTGT TGAACCGTGT
 151 TATGGTGACA AAGATAAACG GCGGCATTGT TTTGCTACCT GGAAGAATAT
 201 TTCTGGTTCC ATTGAAATAG TGAAACAAGG TTGTTGGCTG GATGATATCA
 251 ACTGCTATGA CAGGACTGAT TGTGTAGAAA AAAAAGACAG CCCTGAAGTA
 301 TATTTTTGTT GCTGTGAGGG CAATATGTGT AATGAAAAGT TTTCTTATTT
 351 TCCGGAGATG GAAGTCACAC AGCCCACTTC AAATCCAGTT ACACCTAAGC
 401 CACCCTATTA CAACATCCTG CTCTATTCCT TGGTGCCACT TATGTTAATT
 451 GCGGGGATTG TCATTTGTGC ATTTTGGGTG TACAGGCATC ACAAGATGGC
 501 CTACCCTCCT GTACTTGTTC CAACTCAAGA CCCAGGACCA CCCCCACCTT
 551 CTCCATTACT AGGTTTGAAA CCACTGCAGT TATTAGAAGT GAAAGCAAGG
 601 GGAAGATTTG GTTGTGTCTG GAAAGCCCAG TTGCTTAACG AATATGTGGC
 651 TGTCAAAATA TTTCCAATAC AGGACAAACA GTCATGGCAA AATGAATACG
 701 AAGTCTACAG TTTGCCTGGA ATGAAGCATG AGAACATATT ACAGTTCATT
 751 GGTGCAGAAA AACGAGGCAC CAGTGTTGAT GTGGATCTTT GGCTGATCAC
 801 AGCATTTCAT GAAAAGGGTT CACTATCAGA CTTTCTTAAG CTAATGTGG
 851 TCTCTTGGAA TGAACTGTGT CATATTCAG AAACCATGGC TAGAGGATTG
 901 GCATATTTAC ATGAGGATAT ACCTGGCCTA AAAGATGGCC ACAAACCTGC
 951 CATATCTCAC AGGGACATCA AAAGTAAAAA TGTGCTGTTG AAAAACAACC
1001 TGACAGCTTG CATTGCTGAC TTTGGGTTGG CCTTAAAATT TGAGGCTGGC
1051 AAGTCTGCAG GCGATACCCA TGGACAGGTT GGTACCCGGA GGTACATGGC
1101 TCCAGAGGTA TTAGAGGGTG CTATAAACTT CCAAAGGGAT GCATTTTTGA
1151 GGATAGATAT GTATGCCATG GGATTAGTCC TATGGGAACT GGCTTCTCGC
1201 TGTACTGCTG CAGATGGACC TGTAGATGAA TACATGTTGC CATTTGAGGA
1251 GGAAATTGGC CAGCATCCAT CTCTTGAAGA CATGCAGGAA GTTGTTGTGC
1301 ATAAAAAAA GAGGCCTGTT TTAAGAGATT ATTGGCAGAA ACATGCTGGA
1351 ATGGCAATGC TCTGTGAAAC CATTGAAGAA TGTTGGGATC ACGACGCAGA
1401 AGCCAGGTTA TCAGCTGGAT GTGTAGGTGA AAGAATTACC CAGATGCAGA
1451 GACTAACAAA TATTATTACC ACAGAGGACA TTGTAACAGT GGTCACAATG
1501 GTGACAAATG TTGACTTTCC TCCCAAAGAA TCTAGTCTA
```

The nucleic acid sequence encoding processed soluble (extracellular) human ActRIIA polypeptide is as follows:

```
                                              (SEQ ID NO: 13)
  1    ATACTTGGTA GATCAGAAAC TCAGGAGTGT CTTTTCTTTA ATGCTAATTG

51    GGAAAAAGAC AGAACCAATC AAACTGGTGT TGAACCGTGT TATGGTGACA

101    AAGATAAACG GCGGCATTGT TTTGCTACCT GGAAGAATAT TTCTGGTTCC

151    ATTGAAATAG TGAAACAAGG TTGTTGGCTG GATGATATCA ACTGCTATGA

201    CAGGACTGAT TGTGTAGAAA AAAAAGACAG CCCTGAAGTA TATTTTGTT

251    GCTGTGAGGG CAATATGTGT AATGAAAAGT TTTCTTATTT TCCGGAGATG

301    GAAGTCACAC AGCCCACTTC AAATCCAGTT ACACCTAAGC CACCC
```

Figure 13:
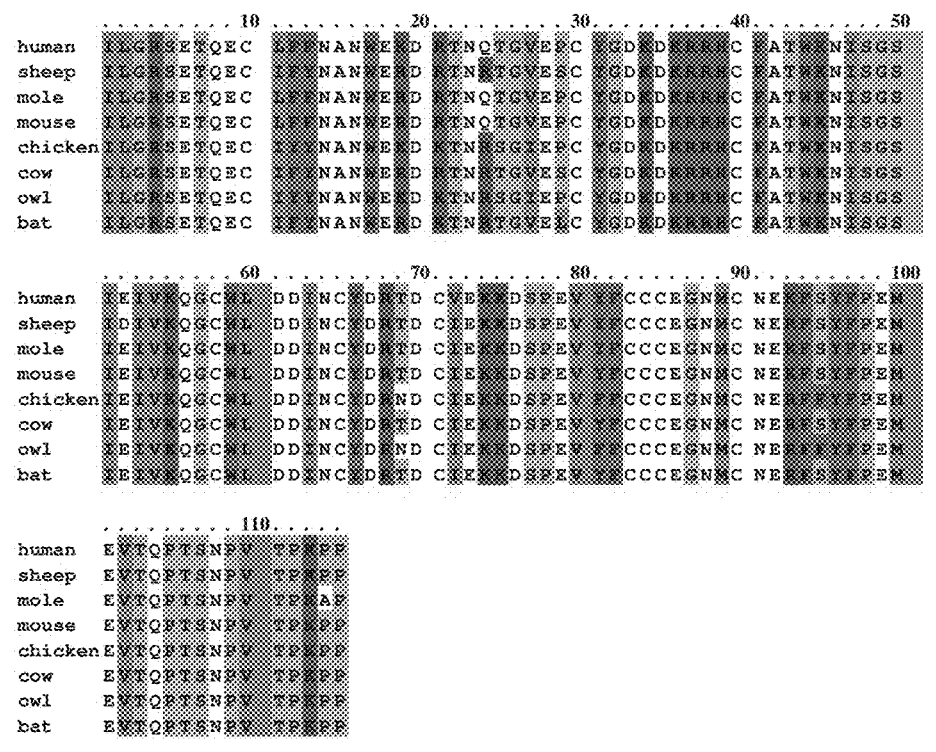

ActRIIA is well-conserved among vertebrates, with large stretches of the extracellular domain completely conserved. For example, FIG. 13 depicts a multi-sequence alignment of a human ActRIIA extracellular domain compared to various ActRIIA orthologs. Many of the ligands that bind to ActRIIA are also highly conserved. Accordingly, from these alignments, it is possible to predict key amino acid positions within the ligand-binding domain that are important for normal ActRIIA-ligand binding activities as well as to predict amino acid positions that are likely to be tolerant to substitution without significantly altering normal ActRIIA-ligand binding activities. Therefore, an active, human ActRIIA variant polypeptide useful in accordance with the presently disclosed methods may include one or more amino acids at corresponding positions from the sequence of another vertebrate ActRIIA, or may include a residue that is similar to that in the human or other vertebrate sequences.

Without meaning to be limiting, the following examples illustrate this approach to defining an active ActRIIA variant. F13 in the human extracellular domain is Y in *Ovis aries* (SEQ ID NO: 70), *Gallus gallus* (SEQ ID NO: 73), *Bos Taurus* (SEQ ID NO: 74), *Tyto alba* (SEQ ID NO: 75), and *Myotis davidii* (SEQ ID NO: 76) ActRIIA, indicating that aromatic residues are tolerated at this position, including F, W, and Y. Q24 in the human extracellular domain is R in *Bos Taurus* ActRIIA, indicating that charged residues will be tolerated at this position, including D, R, K, H, and E. S95 in the human extracellular domain is F in *Gallus gallus* and *Tyto alba* ActRIIA, indicating that this site may be tolerant of a wide variety of changes, including polar residues, such as E, D, K, R, H, S, T, P, G, Y, and probably hydrophobic residue such as L, I, or F. E52 in the human extracellular domain is D in *Ovis aries* ActRIIA, indicating that acidic residues are tolerated at this position, including D and E. P29 in the human extracellular domain is relatively poorly conserved, appearing as S in *Ovis aries* ActRIIA and L in *Myotis davidii* ActRIIA, thus essentially any amino acid should be tolerated at this position.

Moreover, as discussed above, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIA, as demarcated by the outermost of these conserved cysteines, corresponds to positions 30-110 of SEQ ID NO: 9 (ActRIIA precursor). Therefore, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, 28, or 29 residues at the N-terminus and by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIA extracellular domains truncations include SEQ ID NOs: 10 and 11.

Accordingly, a general formula for an active portion (e.g., ligand binding) of ActRIIA is a polypeptide that comprises, consists essentially of, or consists of amino acids 30-110 of SEQ ID NO:9. Therefore ActRIIA polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to any one of amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 135) of SEQ ID NO: 9. Other examples include constructs that begin at a position selected from 21-30 (e.g., beginning at any one of amino acids 21, 22, 23, 24, 25, 26, 27, 28, 29, or 30), 22-30 (e.g., beginning at any one of amino acids 22, 23, 24, 25, 26, 27, 28, 29, or 30), 23-30 (e.g., beginning at any one of amino acids 23, 24, 25, 26, 27, 28, 29, or 30), 24-30 (e.g., beginning at any one of amino acids 24, 25, 26, 27, 28, 29, or 30) of SEQ ID NO: 9, and end at a position selected from 111-135 (e.g., ending at any one of amino acids 111, 112, 113, 114, 115, 116, 117, 118, 119, 120, 121, 122, 123, 124, 125, 126, 127, 128, 129, 130, 131, 132, 133, 134 or 135), 112-135 (e.g., ending at any one of amino acids 112, 113, 114, 115, 116, 117, 118, 119, 120, 121, 122, 123, 124, 125, 126, 127, 128, 129, 130, 131, 132, 133, 134 or 135), 113-135 (e.g., ending at any one of amino acids 113, 114, 115, 116, 117, 118, 119, 120, 121, 122, 123, 124, 125, 126, 127, 128, 129, 130, 131, 132, 133, 134 or 135), 120-135 (e.g., ending at any one of amino acids 120, 121, 122, 123, 124, 125, 126, 127, 128, 129, 130, 131, 132, 133, 134 or 135), 130-135 (e.g., ending at any one of amino acids 130, 131, 132, 133, 134 or 135), 111-134 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 134), 111-133 (e.g., ending at any one of amino acids 110, 111, 112, 113, 114, 115, 116, 117, 118, 119, 120, 121, 122, 123, 124, 125, 126, 127, 128, 129, 130, 131, 132, or 133), 111-132 (e.g., ending at any one of amino acids 110, 111, 112, 113, 114, 115, 116, 117, 118, 119, 120, 121, 122, 123, 124, 125, 126, 127, 128, 129, 130, 131, or 132), or 111-131 (e.g., ending at any one of amino acids 110, 111, 112, 113, 114, 115, 116, 117, 118, 119, 120, 121, 122, 123, 124, 125, 126, 127, 128, 129, 130, or 131) of SEQ ID NO: 9. Thus, ActRIIA of the present disclosure may comprise, consists essentially of, or consist of a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9. Optionally, ActRIIA polypeptides of the present disclosure comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 9.

In certain embodiments, the disclosure relates to ActRII antagonists that comprise at least one ActRIIA polypeptide, which includes fragments, functional variants, and modified forms thereof. Preferably, ActRIIA polypeptides for use in accordance with the disclosure are soluble (e.g., an extracellular domain of ActRIIA). In some embodiments, ActRIIA polypeptides for use in accordance with the disclosure inhibit (antagonize) activity (e.g., induction of Smad 1, 2, 3, 5, or 8 signaling) of one or more TGF-beta superfamily ligands (e.g., GDF11, GDF8, activin A, activin B, and BMP6). In some embodiments, ActRIIA polypeptides for use in accordance with the disclosure bind to one or more TGF-beta superfamily ligands (e.g., GDF11, GDF8, activin, BMP10, and BMP6). In some embodiments, ActRIIA polypeptide of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 135) of SEQ ID NO: 9. In some embodiments, ActRIIA polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 30-110 of SEQ ID NO: 9. In certain embodiments, ActRIIA polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 21-135 of SEQ ID NO: 9. In some embodiments, ActRIIA polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 9, 10, 11, 32, 36, and 39.

In certain aspects, the present disclosure relates to GDF trap polypeptides (also referred to as "GDF traps"). In some embodiments, GDF traps of the present disclosure are variant ActRII polypeptides (e.g., ActRIIA and ActRIIB polypeptides) that comprise one or more mutations (e.g., amino acid additions, deletions, substitutions, and combinations thereof) in the extracellular domain (also referred to as the ligand-binding domain) of an ActRII polypeptide (e.g., a "wild-type" or unmodified ActRII polypeptide) such that the variant ActRII polypeptide has one or more altered ligand-binding activities than the corresponding wild-type ActRII polypeptide. In preferred embodiments, GDF trap polypeptides of the present disclosure retain at least one similar activity as a corresponding wild-type ActRII polypeptide. For example, preferable GDF traps bind to and inhibit (e.g. antagonize) the function of GDF11 and/or GDF8. In some embodiments, GDF traps of the present disclosure further bind to and inhibit one or more of ligand of the TGF-beta superfamily. Accordingly, the present disclosure provides GDF trap polypeptides that have an altered binding specificity for one or more ActRII ligands.

To illustrate, one or more mutations may be selected that increase the selectivity of the altered ligand-binding domain for GDF11 and/or GDF8 over one or more activins (activin A, activin B, activin AB, activin C, and/or activin E), particularly activin A. Optionally, the altered ligand-binding domain has a ratio of $K_d$ for activin binding to $K_d$ for GDF11 and/or GDF8 binding that is at least 2-, 5-, 10-, 20-, 50-, 100- or even 1000-fold greater relative to the ratio for the wild-type ligand-binding domain. Optionally, the altered ligand-binding domain has a ratio of $IC_{50}$ for inhibiting activin to $IC_{50}$ for inhibiting GDF11 and/or GDF8 that is at least 2-, 5-, 10-, 20-, 50-, 100- or even 1000-fold greater relative to the wild-type ligand-binding domain. Optionally, the altered ligand-binding domain inhibits GDF11 and/or GDF8 with an $IC_{50}$ at least 2-, 5-, 10-, 20-, 50-, 100- or even 1000-times less than the $IC_{50}$ for inhibiting activin.

In certain preferred embodiments, GDF traps of the present disclosure are designed to preferentially bind to GDF11 and/or GDF8 (also known as myostatin). Optionally, GDF11 and/or GDF8-binding traps may further bind to activin B. Optionally, GDF11 and/or GDF8-binding traps may further bind to BMP6. Optionally, GDF11 and/or GDF8-binding traps may further bind to BMP10. Optionally, GDF11 and/or GDF8-binding traps may further bind to activin B and BMP6. In certain embodiments, GDF traps of the present disclosure have diminished binding affinity for activins (e.g., activin A, activin A/B, activin B, activin C, activin E), e.g., in comparison to a wild-type ActRII polypeptide. In certain preferred embodiments, a GDF trap polypeptide of the present disclosure has diminished binding affinity for activin A.

Amino acid residues of the ActRIIB proteins (e.g., E39, K55, Y60, K74, W78, L79, D80, and F101) are in the ActRIIB ligand-binding pocket and help mediated binding to its ligands including, for example, activin A, GDF11, and GDF8. Thus the present disclosure provides GDF trap polypeptides comprising an altered-ligand binding domain (e.g., a GDF8/GDF11-binding domain) of an ActRIIB receptor which comprises one or more mutations at those amino acid residues.

As a specific example, the positively-charged amino acid residue Asp (D80) of the ligand-binding domain of ActRIIB can be mutated to a different amino acid residue to produce a GDF trap polypeptide that preferentially binds to GDF8, but not activin. Preferably, the D80 residue with respect to SEQ ID NO: 1 is changed to an amino acid residue selected from the group consisting of: an uncharged amino acid residue, a negative amino acid residue, and a hydrophobic amino acid residue. As a further specific example, the hydrophobic residue L79 of SEQ ID NO: 1 can be altered to confer altered activin-GDF11/GDF8 binding properties. For example, an L79P substitution reduces GDF11 binding to a greater extent than activin binding. In contrast, replacement of L79 with an acidic amino acid [an aspartic acid or glutamic acid; an L79D or an L79E substitution] greatly reduces activin A binding affinity while retaining GDF11 binding affinity. In exemplary embodiments, the methods described herein utilize a GDF trap polypeptide which is a variant ActRIIB polypeptide comprising an acidic amino acid (e.g., D or E) at the position corresponding to position 79 of SEQ ID NO: 1, optionally in combination with one or more additional amino acid substitutions, additions, or deletions.

In some embodiments, the present disclosure contemplates making functional variants by modifying the structure of an ActRII polypeptide for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty.

In certain embodiments, the present disclosure contemplates specific mutations of an ActRII polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sufthydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, polypeptides of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of an ActRII polypeptide as well as truncation mutants. Pools of combinatorial mutants are especially useful for identifying functionally active (e.g., TGF-beta superfamily ligand binding) ActRII sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ActRII variants may be screened for ability to bind to one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin AB, activin AC, nodal, glial cell-derived neurotrophic factor (GDNF), neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of ActRII polypeptides may also be tested in a cell-based or in vivo assay. For example, the effect of an ActRII polypeptide on the expression of genes involved in visual acuity may be assessed. This may, as needed, be performed in the presence of one or more recombinant ActRII ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty), and cells may be transfected so as to produce an ActRII polypeptide, and optionally, an ActRII ligand. Likewise, an ActRII polypeptide may be administered to a mouse or other animal and visual acuity may be assessed using art-recognized methods. Similarly, the activity of an Act RII polypeptide or a variant thereof may be tested in blood cell precursor cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference ActRII polypeptide. Such variants, when expressed from recombinant DNA constructs, can be used in gene therapy protocols. Likewise, mutagenesis can give rise to variants which have intracellular half-lives dramatically different than the corresponding unmodified ActRII polypeptide. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter the half-life of the ActRII polypeptide.

A combinatorial library may be produced by way of a degenerate library of genes encoding a library of polypeptides which each include at least a portion of potential ActRII sequences. For instance, a mixture of synthetic oligonucleotides can be enzymatically ligated into gene sequences such that the degenerate set of potential ActRII encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, SA (1983)Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; and Ike et al. (1983) Nucleic Acid Res. 11:477]. Such techniques have been employed in the directed evolution of other proteins [Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815].

Alternatively, other forms of mutagenesis can be utilized to generate a combinatorial library. For example, ActRII polypeptides of the disclosure can be generated and isolated from a library by screening using, for example, alanine scanning mutagenesis [Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232:613]; by PCR mutagenesis [Leung et al. (1989) Method Cell Mol Biol 1:11-19]; or by random mutagenesis, including chemical mutagenesis [Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ActRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty) binding assays and/or TGF-beta ligand-mediated cell signaling assays.

As will be recognized by one of skill in the art, most of the described mutations, variants or modifications described herein may be made at the nucleic acid level or, in some cases, by post-translational modification or chemical synthesis. Such techniques are well known in the art and some of which are described herein. In part, the present disclosure identifies functionally active portions (fragments) and variants of ActRII polypeptides that can be used as guidance for generating and using other variant ActRII polypeptides within the scope of the inventions described herein.

In certain embodiments, functionally active fragments of ActRII polypeptides of the present disclosure can be obtained by screening polypeptides recombinantly produced from the corresponding fragment of the nucleic acid encoding an ActRII polypeptide (e.g., SEQ ID NOs: 7, 8, 12, 13, 37, 42, 47, 60, 62, 63, 66, 67, 68, 80, 81, 82 and 83). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRII receptors and/or one or more ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty).

In certain embodiments, ActRII polypeptides of the present disclosure may further comprise post-translational modifications in addition to any that are naturally present in the ActRII (e.g. an ActRIIA or ActRIIB polypeptide). Such modifications include, but are not limited to, acetylation, carboxylation, glycosylation, phosphorylation, lipidation, and acylation. As a result, the ActRII polypeptide may contain non-amino acid elements, such as polyethylene glycols, lipids, polysaccharide or monosaccharide, and phosphates. Effects of such non-amino acid elements on the functionality of a ligand trap polypeptide may be tested as described herein for other ActRII variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ActRII polypeptides.

In certain aspects, ActRII polypeptides of the present disclosure include fusion proteins having at least a portion (domain) of an ActRII polypeptide (e.g., an ActRIIA or ActRIIB polypeptide) and one or more heterologous portions (domains). Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt- conjugated resins are used. Many of such matrices are available in "kit" form, such as the Pharmacia GST purification system and the QIAexpress™ system (Qiagen) useful with (HIS$_6$ (SEQ ID NO: 88)) fusion partners. As another example, a fusion domain may be selected so as to facilitate detection of the ActRII polypeptide. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. Other types of fusion domains that may be selected include multimerizing (e.g., dimerizing, tetramerizing) domains and functional domains (that confer an additional biological function) including, for example constant domains from immunoglobulins (e.g., Fc domains).

In certain aspects, ActRII polypeptides of the present disclosure contain one or more modifications that are capable of "stabilizing" the polypeptides. By "stabilizing" is meant anything that increases the in vitro half-life, serum half-life, regardless of whether this is because of decreased destruction, decreased clearance by the kidney, or other pharmacokinetic effect of the agent. For example, such modifications enhance the shelf-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ActRII polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol. In certain preferred embodiments, an ActRII polypeptide is fused with a heterologous domain that stabilizes the polypeptide (a "stabilizer" domain), preferably a heterologous domain that increases stability of the polypeptide in vivo. Fusions with a constant domain of an immunoglobulin (e.g., a Fc domain) are known to confer desirable pharmacokinetic properties on a wide range of proteins. Likewise, fusions to human serum albumin can confer desirable properties.

An example of a native amino acid sequence that may be used for the Fc portion of human IgG1 (G1Fc) is shown below (SEQ ID NO: 14). Dotted underline indicates the hinge region, and solid underline indicates positions with naturally occurring variants. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 14. Naturally occurring variants in G1Fc would include E134D and M136L according to the numbering system used in SEQ ID NO: 14 (see Uniprot P01857).

```
                                                        (SEQ ID NO: 14)
  1    THTCPPCPAP  ELLGGPSVFL  FPPKPKDTLM  ISRTPEVTCV  VVDVSHEDPE

51    VKFNWYVDGV  EVHNAKTKPR  EEQYNSTYRV  VSVLTVLHQD  WLNGKEYKCK

101    VSNKALPAPI  EKTISKAKGQ  PREPQVYTLP  PSREEMTKNQ  VSLTCLVKGF

151    YPSDIAVEWE  SNGQPENNYK  TTPPVLDSDG  SFFLYSKLTV  DKSRWQQGNV

201    FSCSVMHEAL  HNHYTQKSLS  LSPGK
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type IgG1 Fc domain.

An example of a native amino acid sequence that may be used for the Fc portion of human IgG2 (G2Fc) is shown below (SEQ ID NO: 15). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 15.

```
                                                            (SEQ ID NO: 15)
  1    VECPPCP APP VAGPSVFLFP PKPKDTLMIS RTPEVTCVVV DVSHEDPEVQ

51    FNWYVDGVEV HNAKTKPREE QFNSTFRVVS VLTVVHQDWL NGKEYKCKVS

101    NKGLPAPIEK TISKTKGQPR EPQVYTLPPS REEMTKNQVS LTCLVKGFYP

151    SDIAVEWESN GQPENNYKTT PPMLDSDGSF FLYSKLTVDK SRWQQGNVFS

201    CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 16) contains a short hinge region consisting of a single 15-residue segment, whereas the second G3Fc sequence (SEQ ID NO: 17) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 16 and 17.

```
                                                            (SEQ ID NO: 16)
  1    EPKSCDTPPP CPRCPAPELL GGPSVFLFPP KPKDTLMISR TPEVTCVVVD

51    VSHEDPEVQF KWYVDGVEVH NAKTKPREEQ YNSTFRVVSV LTVLHQDWLN

101    GKEYKCKVSN KALPAPIEKT ISKTKGQPRE PQVYTLPPSR EEMTKNQVSL

151    TCLVKGFYPS DIAVEWESSG QPENNYNTTP PMLDSDGSFF LYSKLTVDKS

201    RWQQGNIFSC SVMHEALHNR FTQKSLSLSP GK (SEQ ID NO: 17)
  1    ELKTPLGDTT HTCPRCPEPK SCDTPPPCPR CPEPKSCDTP PPCPRCPEPK

51    SCDTPPPCPR CPAPELLGGP SVFLFPPKPK DTLMISRTPE VTCVVVDVSH

101    EDPEVQFKWY VDGVEVHNAK TKPREEQYNS TFRVVSVLTV LHQDWLNGKE

151    YKCKVSNKAL PAPIEKTISK TKGQPREPQV YTLPPSREEM TKNQVSLTCL

201    VKGFYPSDIA VEWESSGQPE NNYNTTPPML DSDGSFFLYS KLTVDKSRWQ

251    QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 16, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 18). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 18.

```
                                                            (SEQ ID NO: 18)
  1    ESKYGPPCPS CPAPEFLGGP SVFLFPPKPK DTLMISRTPE VTCVVVDVSQ

51    EDPEVQFNWY VDGVEVHNAK TKPREEQFNS TYRVVSVLTV LHQDWLNGKE

101    YKCKVSNKGL PSSIEKTISK AKGQPREPQV YTLPPSQEEM TKNQVSLTCL
```

```
151    VKGFYPSDIA VEWESNGQPE NNYKTTPPVL DSDGSFFLYS RLTVDKSRWQ

201    EGNVFSCSVM HEALHNHYTQ KSLSLSLGK
```

A variety of engineered mutations in the Fc domain are presented herein with respect to the G1Fc sequence (SEQ ID NO: 14), and analogous mutations in G2Fc, G3Fc, and G4Fc can be derived from their alignment with G1Fc in FIG. 14. Due to unequal hinge lengths, analogous Fc positions based on isotype alignment (FIG. 14) possess different amino acid numbers in SEQ ID NOs: 14, 15, 16, 17, and 18. It can also be appreciated that a given amino acid position in an immunoglobulin sequence consisting of hinge, $C_H2$, and $C_H3$ regions (e.g., SEQ ID NOs: 14, 15, 16, 17, and 18) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 14), the human IgG1 heavy chain constant domain (Uniprot P01857), and the human IgG1 heavy chain is as follows.

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| --- | --- | --- |
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in *Sequences of Proteins of Immunological Interest*, 5th ed., Vol. 1, NIH, Bethesda, MD.

It is understood that different elements of the fusion proteins (e.g., immunoglobulin Fc fusion proteins) may be arranged in any manner that is consistent with desired functionality. For example, an ActRII polypeptide domain may be placed C-terminal to a heterologous domain, or alternatively, a heterologous domain may be placed C-terminal to an ActRII polypeptide domain. The ActRII polypeptide domain and the heterologous domain need not be adjacent in a fusion protein, and additional domains or amino acid sequences may be included C- or N-terminal to either domain or between the domains.

For example, an ActRII receptor fusion protein may comprise an amino acid sequence as set forth in the formula A-B-C. The B portion corresponds to an ActRII polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 19), GGGG (SEQ ID NO: 20), TGGGG (SEQ ID NO: 21), SGGGG (SEQ ID NO: 22), TGGG (SEQ ID NO: 23), SGGG (SEQ ID NO: 24), or GGGGS (SEQ ID NO: 25) singlets, or repeats. In certain embodiments, an ActRII fusion protein comprises an amino acid sequence as set forth in the formula A-B-C, wherein A is a leader (signal) sequence, B consists of an ActRII polypeptide domain, and C is a polypeptide portion that enhances one or more of in vivo stability, in vivo half-life, uptake/administration, tissue localization or distribution, formation of protein complexes, and/or purification. In certain embodiments, an ActRII fusion protein comprises an amino acid sequence as set forth in the formula A-B-C, wherein A is a TPA leader sequence, B consists of an ActRII receptor polypeptide domain, and C is an immunoglobulin Fc domain. Preferred fusion proteins comprise the amino acid sequence set forth in any one of SEQ ID NOs: 32, 36, 39, 40, 41, 44, 45, 46, 50, 61, 64, 78 and 79.

In preferred embodiments, ActRII polypeptides to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [see, e.g., Flatman et al., (2007) J. Chromatogr. B 848:79-87]. In some embodiments, ActRII polypeptides to be used in accordance with the methods described herein are recombinant polypeptides.

ActRII polypeptides of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the polypeptides of the disclosure, including fragments or variants thereof, may be recombinantly produced using various expression systems [e.g., *E. coli*, Chinese Hamster Ovary (CHO) cells, COS cells, baculovirus] as is well known in the art. In a further embodiment, the modified or unmodified polypeptides of the disclosure may be produced by digestion of recombinantly produced full-length ActRII polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites. Alternatively, such polypeptides may be produced from recombinantly generated full-length ActRII polypeptides using chemical cleavage (e.g., cyanogen bromide, hydroxylamine, etc.).

Any of the ActRII polypeptides described herein (e.g., ActRIIA or ActRIIB polypeptides as well as variants thereof such as GDF traps) can be combined with one or more additional ActRII antagonists to achieve the desired effect (e.g., increasing red blood cell levels, treating or preventing an anemia, and/or treating or preventing ineffective erythropoiesis in a subject in need thereof). For example, an ActRII polypeptide can be used in combination with i) one or more additional ActRII polypeptides, ii) one or more ActRII antagonist antibodies disclosed herein (e.g., an anti-GDF11 antibody, an anti-GDF8 antibody, an anti-BMP6 antibody, an anti-BMP10, and anti-activin antibody, an anti-ActRIIA antibody, and/or or an anti-ActRIIB antibody); iii) one or more small molecule ActRII antagonists (e.g., a small molecule antagonist of one or more of GDF11, GDF8, activin, BMP6, BMP10, ActRIIA, and/or ActRIIB); iv) one or more polynucleotide ActRII antagonists (e.g., a polynucleotide antagonist of one or more of GDF11, GDF8, activin, BMP6, BMP10, ActRIIA, and/or ActRIIB); v) one or more follistatin polypeptides; and/or vi) one or more FLRG polypeptides.

B. Nucleic Acids Encoding ActRII Polypeptides

In certain embodiments, the present disclosure provides isolated and/or recombinant nucleic acids encoding the ActRII polypeptides (including fragments, functional variants (e.g., GDF traps), and fusion proteins thereof). For example, SEQ ID NO: 12 encodes the naturally occurring human ActRIIA precursor polypeptide, while SEQ ID NO: 13 encodes the processed extracellular domain of ActRIIA. In addition, SEQ ID NO: 7 encodes a naturally occurring human ActRIIB precursor polypeptide (the R64 variant described above), while SEQ ID NO: 8 encodes the processed extracellular domain of ActRIIB (the R64 variant described above). The subject nucleic acids may be single-stranded or double stranded. Such nucleic acids may be DNA or RNA molecules. These nucleic acids may be used, for example, in methods for making ActRII-based ligand trap polypeptides as described herein.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ActRII polypeptides of the disclosure are understood to include nucleic acids that are variants of any one of SEQ ID NOs: 7, 8, 12, 13, 37, 42, 47, 60, 62, 63, 66, 67, 68, 80, 81, 82, and 83. Variant nucleotide sequences include sequences that differ by one or more nucleotide substitutions, additions, or deletions including allelic variants, and therefore, will include coding sequence that differ from the nucleotide sequence designated in any one of SEQ ID NOs: 7, 8, 12, 13, 37, 42, 47, 60, 62, 63, 66, 67, 68, 80, 81, 82, and 83.

In certain embodiments, ActRII polypeptides of the disclosure are encoded by isolated and/or recombinant nucleic acid sequences that are at least 70%, 75%, 80%, 85%, 90%, 91%, 92%, 93%, 94% 95%, 96%, 97%, 98%, 99%, or 100% identical to any one of SEQ ID NOs: 7, 8, 12, 13, 37, 42, 47, 60, 62, 63, 66, 67, 68, 80, 81, 82, and 83. One of ordinary skill in the art will appreciate that nucleic acid sequences that are at least 70%, 75%, 80%, 85%, 90%, 91%, 92%, 93%, 94% 95%, 96%, 97%, 98%, 99%, or 100% identical to the sequences complementary to SEQ ID NOs: 7, 8, 12, 13, 37, 42, 47, 60, 62, 63, 66, 67, 68, 80, 81, 82, and 83, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NOs: 7, 8, 12, 13, 37, 42, 47, 60, 62, 63, 66, 67, 68, 80, 81, 82, and 83, complement sequences of SEQ ID NOs: 7, 8, 12, 13, 37, 42, 47, 60, 62, 63, 66, 67, 68, 80, 81, 82, and 83, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0 x sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 37, 42, 47, 60, 62, 63, 66, 67, 68, 80, 81, 82, and 83 to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art and can be used in a variety of host cells. Typically, one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and can vary with the host cell used.

In certain aspects, the subject nucleic acid disclosed herein is provided in an expression vector comprising a nucleotide sequence encoding an ActRII polypeptide and operably linked to at least one regulatory sequence. Regulatory sequences are art-recognized and are selected to direct expression of the ActRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRII polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRII polypeptides in cells propagated in culture, e.g., to produce proteins, including fusion proteins or variant proteins, for purification.

This disclosure also pertains to a host cell transfected with a recombinant gene including a coding sequence for one or more of the subject ActRII polypeptides. The host cell may be any prokaryotic or eukaryotic cell. For example, an ActRII polypeptide of the disclosure may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ActRII polypeptides. For example, a host cell transfected with an expression vector encoding an ActRII polypeptide can be cultured under appropriate conditions to allow expression of the ActRII polypeptide to occur. The polypeptide may be secreted and isolated from a mixture of cells and medium containing the polypeptide. Alternatively, the ActRII polypeptide may be retained cytoplasmically or in a membrane fraction and the cells harvested, lysed and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRII polypeptides, and affinity purification with an agent that binds to a domain fused to the ActRII polypeptide (e.g., a protein A column may be used to purify an ActRII-Fc fusion protein). In some embodiments, the ActRII polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ActRII protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ActRII polypeptide, can allow purification of the expressed fusion protein by affinity chromatography using a Ni$^{2+}$ metal resin. The purification leader sequence can then be subsequently removed by treatment with enterokinase to provide the purified ActRII polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

iii. Antibody Antagonists

In other aspects, the present disclosure relates to an antibody, or combination of antibodies, that antagonize ActRII activity (e.g., inhibition of ActRII signaling transduction via Smads 1, 2, 3, 5, and 8). Such antibodies may bind to one or more ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty) or one or more type I and/or type II receptors (e.g., ActRIIA, ActRIIB, ALK4, ALK5). In particular, the disclosure provides methods of using an antibody ActRII antagonist, or combination of antibody ActRII antagonists, alone or in combination with one or more additional supportive therapies, to increase red blood cell levels, treat or prevent an anemia, and/or treat or prevent ineffective erythropoiesis, e.g., ineffective erythropoiesis associated with any of the following: anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficiency, megaloblastic anemias, myelophthisic anemias including, for example, myelofibrosis (myeloid metaplasia) and myelophthisis, congenital erythropoietic porphyria, and/or lead poisoning.

In certain aspects, a preferred antibody ActRII antagonist of the disclosure is an antibody, or combination of antibodies, that binds to and/or inhibits activity of at least GDF11. In certain embodiments, a preferred antibody ActRII antagonist of the disclosure is an antibody, or combination of antibodies, that binds to and/or inhibits activity of at least GDF8. In some embodiments, a preferred antibody ActRII antagonist of the disclosure is an antibody, or combination of antibodies, that binds to and/or inhibits activity of at least GDF11 and GDF8, particularly in the case of a multispecific antibody that has binding affinity for both GDF11 and GDF8 or in the context of a combination of one or more anti-GDF11 antibodies and one or more anti-GDF8 antibodies. In some embodiments, an antibody, or combination of antibodies, of the disclosure that binds to and/or inhibits the activity of GDF11 and/or GDF8 further binds to and/or inhibits activity of activin (e.g., activin A, activin B, activin AB, activin C, and/or activin E). In some embodiments, an antibody, or combination of antibodies, of the disclosure that binds to and/or inhibits the activity of GDF11 and/or GDF8 further binds to and/or inhibits activity of activin B. In some embodiments, an antibody, or combination of antibodies, of the disclosure that binds to and/or inhibits the activity of GDF11 and/or GDF8 does not bind to and/or inhibit, or does not substantially bind to and/or inhibit, activity of activin A (e.g., an antibody that has a $K_D$ of greater than $1 \times 10^{-7}$ for activin A). In some embodiments, an antibody, or combination of antibodies, of the disclosure that binds to and/or inhibits the activity of GDF11 and/or GDF8 further binds to and/or inhibits activity of BMP6. In some embodiments, an antibody, or combination of antibodies, of the disclosure that binds to and/or inhibits the activity of GDF11 and/or GDF8 further binds to and/or inhibits activity of BMP10. In some embodiments, an antibody, or combination of antibodies, of the disclosure that binds to and/or inhibits the activity of GDF11 and/or GDF8 further binds to and/or inhibits activity of BMP6 and BMP10. In some embodiments, an antibody, or combination of antibodies, of the disclosure that binds to and/or inhibits the activity of GDF11 and/or GDF8 further binds to and/or inhibits activity of activin (e.g., activin B) and BMP6. In some embodiments, an antibody, or combination of antibodies, of the disclosure that binds to and/or inhibits the activity of GDF11 and/or GDF8 further binds to and/or inhibits activity of activin (e.g., activin B) and BMP10. In some embodiments, an antibody, or combination of antibodies, of the disclosure that binds to and/or inhibits the activity of GDF11 and/or GDF8 further binds to and/or inhibits activity of activin (e.g., activin B), BMP6, and BMP10. In some embodiments, an antibody, or combination of antibodies, of the disclosure that binds to and/or inhibits the activity of GDF11 and/or GDF8 further binds to and/or inhibits activity of activin B, BMP6, and BMP10 but does not bind to and/or inhibit activin A (e.g., an antibody that has a $K_D$ of greater than $1 \times 10^{-7}$ for activin A).

In another aspect, an ActRII antagonist of the present disclosure is an antibody, or combination of antibodies, that binds to and/or inhibits activity of an ActRII receptor (e.g. an ActRIIA and/or ActRIIB receptor). In some embodiments, an anti-ActRII receptor antibody, or combination of antibodies, of the disclosure binds to an ActRII receptor and prevents binding and/or activation of the ActRII receptor by at least GDF11. In some embodiments, an anti-ActRII receptor antibody, or combination of antibodies, of the disclosure binds to an ActRII receptor and prevents binding and/or activation of the ActRII receptor by at least GDF8. In some embodiments, an anti-ActRII receptor antibody, or combination of antibodies, of the disclosure binds to an ActRII receptor and prevents binding and/or activation of the ActRII receptor by at least GDF11 and GDF8. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by activin (e.g., activin A, activin B, activin AB, activin C, and/or activin E). In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by BMP6. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by BMP10. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by BMP6 and BMP10. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by activin (e.g., activin B) and BMP6. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by activin (e.g., activin B) and BMP10. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by activin B, BMP6, and BMP10 but does not inhibit binding and/or activation, or does not substantially inhibit binding and/or activation of the ActRII receptor by activin A.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. See, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In preferred embodiments, the antibodies of the present disclosure are isolated antibodies.

Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134.

Single-domain antibodies are antibody fragments comprising all or a portion of the heavy-chain variable domain or all or a portion of the light-chain variable domain of an antibody. In certain embodiments, a single-domain antibody is a human single-domain antibody. See, e.g., U.S. Pat. No. 6,248,516.

Antibody fragments can be made by various techniques, including but not limited to proteolytic digestion of an intact antibody as well as production by recombinant host cells (e.g., *E. coli* or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, IgG$_1$, IgG$_2$, IgG$_3$, IgG$_4$, IgA$_1$, and IgA$_2$. The heavy-chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens (e.g. GDF11, GDF8, ActRIIA, ActRIIB, etc.) with at least a $K_D$ of $1 \times 10^{-7}$ or stronger, $1 \times 10^{-8}$ or stronger, $1 \times 10^{-9}$ or stronger, $1 \times 10^{-10}$ or stronger, $1 \times 10^{-11}$ or stronger, $1 \times 10^{-12}$ or stronger, $1 \times 10^{-13}$ or stronger, or $1 \times 10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (e.g., approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NHS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophotometer (Aviv Instruments) or a 8000-series SLM-AMINCO® spectrophotometer (ThermoSpectronic) with a stirred cuvette.

As used herein, anti-GDF11 antibody generally refers to an antibody that is capable of binding to GDF11 with sufficient affinity such that the antibody is useful as a diagnostic and/or therapeutic agent in targeting GDF11. In certain embodiments, the extent of binding of an anti-GDF11 antibody to an unrelated, non-GDF11 protein is less than about 10%, 9%, 8%, 7%, 6%, 5%, 4%, 3%, 2%, or less than 1% of the binding of the antibody to GDF11 as measured, for example, by a radioimmunoassay (RIA). In certain embodiments, an anti-GDF11 antibody binds to an epitope of GDF11 that is conserved among GDF11 from different species. In certain preferred embodiments, an anti-GDF11 antibody of the present disclosure is an antagonist antibody that can inhibit GDF11 activity. For example, an anti-GDF11 antibody of the disclosure may inhibit GDF11 from binding to a cognate receptor (e.g., ActRIIA or ActRIIB receptor) and/or inhibit GDF11-mediated signal transduction (activation) of a cognate receptor, such as Smad signaling by an ActRII receptor. In some embodiments, anti-GDF11 antibodies of the present disclosure, particularly in the case of multispecific antibodies, do not substantially bind to and/or inhibit activity of activin A (e.g., bind to activin A with a $K_D$ of greater than $1\times10^{-7}$). It should be noted that GDF11 has high sequence homology to GDF8 and therefore antibodies that bind and/or to GDF11, in some cases, may also bind to and/or inhibit GDF8.

As used herein, anti-GDF8 antibody generally refers to an antibody that is capable of binding to GDF8 with sufficient affinity such that the antibody is useful as a diagnostic and/or therapeutic agent in targeting GDF8. In certain embodiments, the extent of binding of an anti-GDF8 antibody to an unrelated, non-GDF8 protein is less than about 10%, 9%, 8%, 7%, 6%, 5%, 4%, 3%, 2%, or less than 1% of the binding of the antibody to GDF8 as measured, for example, by a radioimmunoassay (RIA). In certain embodiments, an anti-GDF8 antibody binds to an epitope of GDF8 that is conserved among GDF8 from different species. In certain preferred embodiments, an anti-GDF8 antibody of the present disclosure is an antagonist antibody that can inhibit GDF8 activity. For example, an anti-GDF8 antibody of the disclosure may inhibit GDF8 from binding to a cognate receptor (e.g., ActRIIA or ActRIIB receptor) and/or inhibit GDF8-mediated signal transduction (activation) of a cognate receptor, such as Smad signaling by an ActRII receptor. In some embodiments, anti-GDF8 antibodies of the present disclosure, particularly in the case of multispecific antibodies, do not substantially bind to and/or inhibit activity of activin A (e.g., bind to activin A with a $K_D$ of greater than $1\times10^{-7}$). It should be noted that GDF8 has high sequence homology to GDF11 and therefore antibodies that bind and/or to GDF8, in some cases, may also bind to and/or inhibit GDF11.

As used herein, anti-activin antibody generally refers to an antibody that is capable of binding to activin (e.g., one or more of activin A, activin B, activin C, activin AB, and/or activin E) with sufficient affinity such that the antibody is useful as a diagnostic and/or therapeutic agent in targeting activin. In certain embodiments, the extent of binding of an anti-activin antibody to an unrelated, non-activin protein is less than about 10%, 9%, 8%, 7%, 6%, 5%, 4%, 3%, 2%, or less than 1% of the binding of the antibody to activin as measured, for example, by a radioimmunoassay (RIA). In certain embodiments, an anti-activin antibody binds to an epitope of activin that is conserved among activin from different species. In certain preferred embodiments, an anti-activin antibody of the present disclosure is an antagonist antibody that can inhibit activin activity. For example, an anti-activin antibody of the disclosure may inhibit activin from binding to a cognate receptor (e.g., ActRIIA or ActRIIB receptor) and/or inhibit activin-mediated signal transduction (activation) of a cognate receptor, such as Smad signaling by an ActRII receptor. In some embodiments, anti-activin antibodies of the present disclosure bind to and/or inhibit activity of activin B. In some embodiments, anti-activin antibodies of the present disclosure, particularly in the case of multispecific antibodies, do not substantially bind to and/or inhibit activity of activin A (e.g., bind to activin A with a $K_D$ of greater than $1\times10^{-7}$).

As used herein, anti-BMP6 antibody generally refers to an antibody that is capable of binding to BMP6 with sufficient affinity such that the antibody is useful as a diagnostic and/or therapeutic agent in targeting BMP6. In certain embodiments, the extent of binding of an anti-BMP6 antibody to an unrelated, non-BMP6 protein is less than about 10%, 9%, 8%, 7%, 6%, 5%, 4%, 3%, 2%, or less than 1% of the binding of the antibody to BMP6 as measured, for example, by a radioimmunoassay (RIA). In certain embodiments, an anti-BMP6 antibody binds to an epitope of BMP6 that is conserved among BMP6 from different species. In certain preferred embodiments, an anti-BMP6 antibody of the present disclosure is an antagonist antibody that can inhibit BMP6 activity. For example, an anti-BMP6 antibody of the disclosure may inhibit BMP6 from binding to a cognate receptor (e.g., ActRIIA or ActRIIB receptor) and/or inhibit BMP6-mediated signal transduction (activation) of a cognate receptor, such as Smad signaling by an ActRII receptor. In some embodiments, anti-BMP6 antibodies of the present disclosure, particularly in the case of multispecific antibodies, do not substantially bind to and/or inhibit activity of activin A (e.g., bind to activin A with a $K_D$ of greater than $1 \times 10^{-7}$).

As used herein, anti-BMP10 antibody generally refers to an antibody that is capable of binding to BMP10 with sufficient affinity such that the antibody is useful as a diagnostic and/or therapeutic agent in targeting BMP10. In certain embodiments, the extent of binding of an anti-BMP10 antibody to an unrelated, non-BMP10 protein is less than about 10%, 9%, 8%, 7%, 6%, 5%, 4%, 3%, 2%, or less than 1% of the binding of the antibody to BMP10 as measured, for example, by a radioimmunoassay (RIA). In certain embodiments, an anti-BMP10 antibody binds to an epitope of BMP10 that is conserved among BMP10 from different species. In certain preferred embodiments, an anti-BMP10 antibody of the present disclosure is an antagonist antibody that can inhibit BMP6 activity. For example, an anti-BMP10 antibody of the disclosure may inhibit BMP10 from binding to a cognate receptor (e.g., ActRIIA or ActRIIB receptor) and/or inhibit BMP10-mediated signal transduction (activation) of a cognate receptor, such as Smad signaling by an ActRII receptor. In some embodiments, anti-BMP10 antibodies of the present disclosure, particularly in the case of multispecific antibodies, do not substantially bind to and/or inhibit activity of activin A (e.g., bind to activin A with a $K_D$ of greater than $1 \times 10^{-7}$).

An anti-ActRII antibody refers to an antibody that is capable of binding to ActRII (ActRIIA and/or ActRIIB) with sufficient affinity such that the antibody is useful as a diagnostic and/or therapeutic agent in targeting ActRII. In certain embodiments, the extent of binding of an anti-ActRII antibody to an unrelated, non-ActRII protein is less than about 10%, 9%, 8%, 7%, 6%, 5%, 4%, 3%, 2%, or less than 1% of the binding of the antibody to ActRII as measured, for example, by a radioimmunoassay (RIA). In certain embodiments, an anti-ActRII antibody binds to an epitope of ActRII that is conserved among ActRII from different species. In preferred embodiments, an anti-ActRII antibody of the present disclosure is an antagonist antibody that can inhibit ActRII activity. For example, an anti-ActRII antibody of the present disclosure may inhibit one or more ActRII ligands selected from activin A, activin B, activin AB, activin C, activin E, GDF11, GDF8, activin A, BMP6, and BMP7 from binding to the ActRII receptor and/or inhibit one of these ligands from activating ActRII signaling (e.g., Smad 1, 2, 3, 5, and 8 signaling). In some embodiments, anti-ActRII antibodies of the present disclosure inhibit GDF11 from binding to the ActRII receptor and/or inhibit GDF11 from activating ActRII signaling. In some embodiments, anti-ActRII antibodies of the present disclosure inhibit GDF8 from binding to the ActRII receptor and/or inhibit GDF8 from activating ActRII signaling. In some embodiments, anti-ActRII antibodies of the present disclosure inhibit GDF8 and GDF11 from binding to the ActRII receptor and/or inhibit GDF8 and GDF11 from activating ActRII signaling. In some embodiments, an anti-ActRII antibody of the disclosure that inhibits GDF11 and/or GDF8 from binding to and/or activating an ActRII receptor further inhibits activin (e.g., activin A, activin B, activin AB, activin C, activin E) from binding to and/or activating the ActRII receptor. In some embodiments, an anti-ActRII antibody of the disclosure that inhibits GDF11 and/or GDF8 from binding to and/or activating an ActRII receptor further inhibits BMP6 from binding to and/or activating the ActRII receptor. In some embodiments, an anti-ActRII antibody of the disclosure that inhibits GDF11 and/or GDF8 from binding to and/or activating an ActRII receptor further inhibits BMP10 from binding to and/or activating the ActRII receptor. In some embodiments, an anti-ActRII antibody of the disclosure that inhibits GDF11 and/or GDF8 from binding to and/or activating an ActRII receptor further inhibits BMP6 and BMP10 from binding to and/or activating the ActRII receptor. In some embodiments, an anti-ActRII antibody of the disclosure that inhibits GDF11 and/or GDF8 from binding to and/or activating an ActRII receptor further inhibits activin (e.g., activin B) and BMP6 from binding to and/or activating the ActRII receptor. In some embodiments, an anti-ActRII antibody of the disclosure that inhibits GDF11 and/or GDF8 from binding to and/or activating an ActRII receptor further inhibits activin (e.g., activin B) and BMP10 from binding to and/or activating the ActRII receptor. In some embodiments, an anti-ActRII antibody of the disclosure that inhibits GDF11 and/or GDF8 from binding to and/or activating an ActRII receptor further inhibits activin (e.g., activin B), BMP6, and BMP10 from binding to and/or activating the ActRII receptor. In some embodiments, anti-ActRIIA antibodies of the present disclosure do not substantially inhibit activin A from binding to the ActRII receptor and/or do not substantially inhibit activin A-mediated activation of ActRII signaling.

The nucleic acid and amino acid sequences of human ActRII receptors and ligands (e.g., GDF11, GDF8, activin A, activin B, activin C, activin E, BMP6, BMP10, ActRIIB, and ActRIIA) are well known in the art and thus antibody antagonists for use in accordance with this disclosure may be routinely made by the skilled artisan based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-

10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et cd., (1997) J. Biol. Chem. 272:10678-10684; and Rosok et cd., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2001) Curr. Opin. Pharmacol. 5: 368-74 and Lonberg (2008) Curr. Opin. Immunol. 20:450-459.

Human antibodies may be prepared by administering an immunogen (e.g., a GDF11 polypeptide, GDF8 polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals, see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage-display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., GDF11, activin B, ActRIIA, or ActRIIB) without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning unrearranged V-gene segments from stem cells and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) have binding specificities for at least two different epitopes (e.g., two, three, four, five, or six or more) on one or more (e.g., two, three, four, five, six or more) antigens.

In certain embodiments, a multispecific antibody of the present disclosure comprises two or more binding specificities, with at least one of the binding specificities being for a GDF11 epitope, and optionally one or more additional binding specificities being for an epitope on a different ActRII ligand (e.g., GDF8, activin, BMP6, and/or BMP10)

and/or an ActRII receptor (e.g., an ActRIIA and/or ActRIIB receptor). In certain embodiments, multispecific antibodies may bind to two or more different epitopes of GDF11. Preferably a multispecific antibody of the disclosure that has binding affinity, in part, for a GDF11 epitope can be used to inhibit a GDF11 activity (e.g., the ability to bind to and/or activate an ActRII receptor), and optionally inhibit the activity of one or more different ActRII ligands (e.g., GDF8, activin, BMP6, and/or BMP10) and/or an ActRII receptor (e.g., an ActRIIA or ActRIIB receptor). In certain preferred embodiments, multispecific antibodies of the present disclosure that bind to and/or inhibit GDF11 further bind to and/or inhibit at least GDF8. Optionally, multispecific antibodies of the disclosure that bind to and/or inhibit GDF11 do not substantially bind to and/or substantially inhibit activin A.

In certain embodiments, a multispecific antibody of the present disclosure comprises two or more binding specificities, with at least one of the binding specificities being for a GDF8 epitope, and optionally one or more additional binding specificities being for an epitope on a different ActRII ligand (e.g., GDF8, activin, BMP6, and/or BMP10) and/or an ActRII receptor (e.g., an ActRIIA and/or ActRIIB receptor). In certain embodiments, multispecific antibodies may bind to two or more different epitopes of GDF8. Preferably a multispecific antibody of the disclosure that has binding affinity, in part, for an GDF8 epitope can be used to inhibit an GDF8 activity (e.g., the ability to bind to and/or activate an ActRII receptor), and optionally inhibit the activity of one or more different ActRII ligands (e.g., GDF8, activin, BMP6, and/or BMP10) and/or an ActRII receptor (e.g., an ActRIIA or ActRIIB receptor). In certain preferred embodiments, multispecific antibodies of the present disclosure that bind to and/or inhibit GDF8 further bind to and/or inhibit at least GDF11. Optionally, multispecific antibodies of the disclosure that bind to and/or inhibit GDF8 do not substantially bind to and/or substantially inhibit activin A.

Engineered antibodies with three or more functional antigen binding sites, including "octopus antibodies," are also included herein (see, e.g., US 2006/0025576A1).

In certain embodiments, the antibodies disclosed herein are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from GDF11, anti-protein/anti-peptide antisera or monoclonal antibodies can be made by standard protocols [see, e.g., Antibodies: A Laboratory Manual (1988) ed. by Harlow and Lane, Cold Spring Harbor Press]. A mammal, such as a mouse, hamster, or rabbit can be immunized with an immunogenic form of the GDF11 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF11 polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of GDF11, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a GDF11 polypeptide, and monoclonal antibodies isolated from a culture comprising such hybridoma cells.

In certain embodiments, one or more amino acid modifications may be introduced into the Fc region of an antibody provided herein thereby generating an Fc-region variant. The Fc-region variant may comprise a human Fc-region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assay methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Int. Immunol. 18(12):1759-1769].

Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine-engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy-chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within, the amino acid sequences of the antibody and/or binding polypeptide. Any combination of deletion, insertion, and substitution can be made to arrive at the final construct, provided that the final construct possesses the desired characteristics, e.g., target-binding (GDF11, GDF8, ActRIIA, and/or ActRIIB binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001)]. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis", as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or binding polypeptide with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino-acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

Any of the ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP10 antibody, an anti-ActRIIA antibody, and/or or an anti-ActRIIB antibody) can be combined with one or more additional ActRII antagonist agents to achieve the desired effect [increasing red blood cell levels, treating or preventing an anemia, and/or treating or preventing ineffective erythropoiesis, e.g., ineffective erythropoiesis associated with anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficienc, megaloblastic anemias, myelophthisic anemias including, for example, myelofibrosis (myeloid metaplasia) and myelophthisis, congenital erythropoietic porphyria, and/or lead poisoning. For example, an ActRII antagonist antibody can be used in combination with i) one or more additional ActRII antagonist antibodies, ii) one or more ActRII polypeptides; iii) one or more small molecule ActRII antagonists (e.g., a small molecule antagonist of one or more of GDF11, GDF8, activin, BMP6, BMP10, ActRIIA, and/or ActRIIB); iv) one or more polynucleotide ActRII antagonists (e.g., a polynucleotide antagonist of one or more of GDF11, GDF8, activin, BMP6, BMP10, ActRIIA, and/or ActRIIB); v) one or more follistatin polypeptides; and/or vi) one or more FLRG polypeptides.

iv. Small Molecule Antagonists

In another aspect, the present disclosure relates to a small molecule, or combination of small molecules, that antagonizes ActRII activity (e.g., inhibition of ActRII signaling transduction via Smads 1, 2, 3, 5, and 8). In particular, the disclosure provides methods of using a small molecule antagonist (inhibitors), or combination of small molecule antagonists, of ActRII, alone or in combination with one or more additional supportive therapies, to increase red blood cell levels, treat or prevent an anemia, and/or treat or prevent ineffective erythropoiesis, e.g., ineffective erythropoiesis associated with anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficienc, megaloblastic anemias, myelophthisic anemias including, for example, myelofibrosis (myeloid metaplasia) and myelophthisis, congenital erythropoietic porphyria, and/or lead poisoning.

In some embodiments, a preferred ActRII antagonist of the present disclosure is a small molecule antagonist, or combination of small molecule antagonists, that inhibits at least GDF11 activity. In some embodiments, a preferred ActRII antagonist of the present disclosure is a small molecule antagonist, or combination of small molecule antagonists, that inhibits at least GDF8 activity. In some embodiments, a preferred ActRII antagonist of the present disclosure is a small molecule antagonist, or combination of small molecule antagonists, that inhibits at least GDF11 and GDF8 activity. In some embodiments, a small molecule antagonist, or combination of small molecule antagonists, of the present disclosure that inhibits GDF11 and/or GDF8 activity further inhibits activin (e.g., activin A, activin B, activin AB, activin C, activin E). In some embodiments, a small molecule antagonist, or combination of small molecule antagonists, of the present disclosure that inhibits GDF11 and/or GDF8 activity further inhibits BMP6. In some embodiments, a small molecule antagonist, or combination of small molecule antagonists, of the present disclosure that inhibits GDF11 and/or GDF8 activity further inhibits BMP10. In some embodiments, a small molecule antagonist, or combination of small molecule antagonists, of the present disclosure that inhibits GDF11 and/or GDF8 activity further inhibits BMP6 and BMP10. In some embodiments, a small molecule antagonist, or combination of small molecule antagonists, of the present disclosure that inhibits GDF11 and/or GDF8 activity further inhibits activin (e.g., activin B) and BMP6. In some embodiments, a small molecule antagonist, or combination of small molecule antagonists, of the present disclosure that inhibits GDF11 and/or GDF8 activity further inhibits activin (e.g., activin B) and BMP10. In some embodiments, a small molecule antagonist, or combination of small molecule antagonists, of the present disclosure that inhibits GDF11 and/or GDF8 activity further inhibits activin (e.g., activin B), BMP6, and BMP10. In some embodiments, a small molecule antagonist, or combination of small molecule antagonists, of the present disclosure that inhibits GDF11 and/or GDF8 activity do not inhibit activin A.

In some embodiments, a small molecule antagonist, or combination of small molecule antagonists, of the present disclosure inhibits an ActRII receptor (e.g. ActRII-mediated Smad 1, 2, 3, 5, and 8 signaling transduction). For example, in some embodiments, a small molecule antagonist, or combination of small molecule antagonists, of the disclosure inhibits GDF11 from binding to and/or activating an ActRII receptor (ActRIIA and/or ActRIIB). In some embodiments, a small molecule antagonist, or combination of small molecule antagonists, of the disclosure inhibits GDF8 from binding to and/or activating an ActRII receptor. In some embodiments, a small molecule antagonist, or combination of small molecule antagonists, of the disclosure inhibits GDF11 and GDF8 from binding to and/or activating an ActRII receptor. In some embodiments, a small molecule antagonist, or combination of small molecule antagonists, that inhibits GDF11 and/or GDF8 from binding to and/or activating an ActRII receptor further inhibits activin (e.g., activin A, activin B, activin AB, activin C, and/or activin E) from binding to and/or activation an ActRII receptor. In some embodiments, a small molecule antagonist, or combination of small molecule antagonists, that inhibits GDF11 and/or GDF8 from binding to and/or activating an ActRII receptor further inhibits BMP6 from binding to and/or activation an ActRII receptor. In some embodiments, a small molecule antagonist, or combination of small molecule antagonists, that inhibits GDF11 and/or GDF8 from binding to and/or activating an ActRII receptor further inhibits BMP10 from binding to and/or activation an ActRII receptor. In some embodiments, a small molecule antagonist, or combination of small molecule antagonists, that inhibits GDF11 and/or GDF8 from binding to and/or activating an ActRII receptor further inhibits BMP6 and BMP10 from binding to and/or activation an ActRII receptor. In some embodiments, a small molecule antagonist, or combination of small molecule antagonists, that inhibits GDF11 and/or GDF8 from binding to and/or activating an ActRII receptor further inhibits activin (e.g., activin B) and BMP6 from binding to and/or activation an ActRII receptor. In some embodiments, a small molecule antagonist, or combination of small molecule antagonists, that inhibits GDF11 and/or GDF8 from binding to and/or activating an ActRII receptor further inhibits activin (e.g., activin B) and BMP10 from binding to and/or activation an ActRII receptor. In some embodiments, a small molecule antagonist, or combination of small molecule antagonists, that inhibits GDF11 and/or GDF8 from binding to and/or activating an ActRII receptor further inhibits activin (e.g., activin B), BMP6, and BMP10 from binding to and/or activation an ActRII receptor. In some embodiments, a small molecule antagonist, or combination of small molecule antagonists, that inhibits GDF11 and/or GDF8 from binding to and/or activating an ActRII receptor does not inhibit activin A from binding to and/or activation an ActRII receptor.

Small molecule ActRII antagonists can be direct or indirect inhibitors. For example, an indirect small molecule ActRII antagonist, or combination of small molecule ActRII antagonists, may inhibit the expression (e.g., transcription, translation, cellular secretion, or combinations thereof) of at least one or more of GDF11, GDF8, activin (e.g., activin A, activin B, activin AB, activin C, activin E) BMP6, BMP10, ActRIIA and/or ActRIIB. Alternatively, a direct small molecule ActRII antagonist, or combination of small molecule ActRII antagonists, may directly bind to, for example, one or more ligand [e.g., GDF11, GDF8, activin (e.g., activin A, activin B, activin AB, activin C, activin E) BMP6, and/or BMP10], receptor (ActRIIA and/or ActRIIB), or signaling component (e.g., one or more of Smad 1, 2, 3, 5, and 8) of an ActRII-ligand signaling pathway. Combinations of one or more indirect and one or more direct small molecule ActRII antagonists may be used in accordance with the methods disclosed herein.

Binding organic small molecule antagonists of the present disclosure may be identified and chemically synthesized using known methodology (see, e.g., PCT Publication Nos. WO 00/00823 and WO 00/39585). In general, small molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein (e.g., GDF11, GDF8, ActRIIA, and ActRIIB). Such small molecule antagonists may be identified without undue experimentation using well-known techniques. In this regard, it is noted that techniques for screening organic small molecule libraries for molecules that are capable of binding to a polypeptide target are well-known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

Any of the small molecule ActRII antagonists disclosed herein (e.g., a small molecule antagonist of one or more of GDF11, GDF8, activin A, activin B, activin AB, activin C, activin E, BMP6, BMP10, ActRIIA, and/or ActRIIB) can be combined with one or more additional ActRII antagonist agents to achieve the desired effect [e.g., to treat or prevent anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficienc, megaloblastic anemias, myelophthisic anemias including, for example, myelofibrosis (myeloid metaplasia) and myelophthisis, congenital erythropoietic porphyria, and/or lead poisoning. For example, a small molecule ActRII antagonist can be used in combination with i) one or more additional small molecule ActRII antagonists, ii) one or more ActRII antagonist antibodies disclosed herein (e.g., an anti-GDF11 antibody, an anti-GDF8 antibody, an anti-BMP6 antibody, an anti-BMP10, and anti-activin antibody, an anti-ActRIIA antibody, and/or or an anti-ActRIIB antibody); iii) one or more ActRII polypeptides (e.g., ActRIIA and ActRIIB polypeptides and variants thereof); iv) one or more polynucleotide ActRII antagonists (e.g., a polynucleotide antagonist of one or more of GDF11, GDF8, activin, BMP6, BMP10, ActRIIA, and/or ActRIIB); v) one or more follistatin polypeptides; and/or vi) one or more FLRG polypeptides.

v. Antagonist Polynucleotides

In another aspect, the present disclosure relates to a polynucleotide, or combination of polynucleotides, that antagonizes ActRII activity (e.g., inhibition of ActRII signaling transduction via Smads 1, 2, 3, 5, and 8). In particular, the disclosure provides methods of using a polynucleotide ActRII antagonist, or combination of polynucleotide ActRII antagonists, alone or in combination with one or more additional supportive therapies, to increase red blood cell levels, treat or prevent an anemia, and/or treat or preventing ineffective erythropoiesis, e.g., ineffective erythropoiesis associated with anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficienc, megaloblastic anemias, myelophthisic anemias including, for example, myelofibrosis (myeloid metaplasia) and myelophthisis, congenital erythropoietic porphyria, and/or lead poisoning.

In some embodiments, a polynucleotide ActRII antagonist, or combination of polynucleotide ActRII antagonists, of the present disclosure can be used to inhibit the activity and/or expression (e.g., transcription, translation, secretion, or combinations thereof) of GDF11. In some embodiments, a polynucleotide ActRII antagonist, or combination of polynucleotide ActRII antagonists, of the present disclosure can be used to inhibit the activity and/or expression of GDF8. In some embodiments, a polynucleotide ActRII antagonist, or combination of polynucleotide ActRII antagonists, of the present disclosure can be used to inhibit the activity and/or expression of GDF11 and GDF8. In some embodiments, a polynucleotide ActRII antagonist, or combination of polynucleotide ActRII antagonists, that inhibits the activity and/or expression of GDF11 and/or GDF8 further inhibits the activity and/or expression of activin (e.g., activin A, activin B, activin AB, activin C, and/or activin E). In some embodiments, a polynucleotide ActRII antagonist, or combination of polynucleotide ActRII antagonists, that inhibits the activity and/or expression of GDF11 and/or GDF8 further inhibits the activity and/or expression of BMP6. In some embodiments, a polynucleotide ActRII antagonist, or combination of polynucleotide ActRII antagonists, that inhibits the activity and/or expression of GDF11 and/or GDF8 further inhibits the activity and/or expression of BMP10. In some embodiments, a polynucleotide ActRII antagonist, or combination of polynucleotide ActRII antagonists, that inhibits the activity and/or expression of GDF11 and/or GDF8 further inhibits the activity and/or expression of BMP6 and BMP10. In some embodiments, a polynucleotide ActRII antagonist, or combination of polynucleotide ActRII antagonists, that inhibits the activity and/or expression of GDF11 and/or GDF8 further inhibits the activity and/or expression of activin (e.g., activin B) and BMP6. In some embodiments, a polynucleotide ActRII antagonist, or combination of polynucleotide ActRII antagonists, that inhibits the activity and/or expression of GDF11 and/or GDF8 further inhibits the activity and/or expression of activin (e.g., activin B) and BMP10. In some embodiments, a polynucleotide ActRII antagonist, or combination of polynucleotide ActRII antagonists, that inhibits the activity and/or expression of GDF11 and/or GDF8 further inhibits the activity and/or expression of activin (e.g., activin B), BMP6, and BMP10. In some embodiments, a polynucleotide ActRII antagonist, or combination of polynucleotide ActRII antagonists, that inhibits the activity and/or expression of GDF11 and/or GDF8 does not inhibit the activity and/or expression of activin A.

In some embodiments, a polynucleotide antagonist, or combination of polynucleotide antagonists, of the disclosure inhibits the activity and/or expression (e.g., transcription, translation, secretion, or combinations thereof) of at ActRII (ActRIIA and/or ActRIIB. In some embodiments, a polynucleotide antagonist, or combination of polynucleotide antagonists, of the disclosure that inhibits the activity and/or expression of ActRII may further inhibit the activity and or expression of one or more of ligands (e.g., activin A, activin B, activin AB, activin C, activin E, BMP6, and BMP10). In some embodiments, a polynucleotide antagonist, or combination of polynucleotide antagonists, of the disclosure that inhibits the activity and/or expression of ActRII does not inhibit the activity and or expression of activin A.

The polynucleotide antagonists of the present disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human GDF11, GDF8, activin A, activin B, activin C, activin E, BMP6, BMP10, ActRIIA, and ActRIIB are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991) Science 251:1300. The methods are based on binding of a polynucleotide to a complementary DNA or RNA. In some embodiments, the antisense nucleic acids comprise a single-stranded RNA or DNA sequence that is complementary to at least a portion of an RNA transcript of a desired gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-untranslated, noncoding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated, or coding regions of an mRNA of the disclosure, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 29:304-310], the promoter contained in the 3' long terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA or RNAi molecules that target the expression of one or more genes. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Left 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as *E. coli* RNase III(Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule, such as a GDF11, GDF8, activin A, activin B, activin C, activin E, BMP6, BMP7, Nodal, ActRIIA, and ActRIIB polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707,796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

Any of the polynucleotide ActRII antagonists disclosed herein (e.g., a polynucleotide antagonist of one or more of GDF11, GDF8, activin A, activin B, activin AB, activin C, activin E, BMP6, BMP10, ActRIIA, and/or ActRIIB) can be combined with one or more additional ActRII antagonists to achieve the desired effect [e.g., treat or prevent anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficienc, megaloblastic anemias, myelophthisic anemias including, for example, myelofibrosis (myeloid metaplasia) and myelophthisis, congenital erythropoietic porphyria, and/or lead poisoning. For example, a polynucleotide ActRII antagonist disclosed herein (e.g., a polynucleotide antagonist of one or more of GDF11, GDF8, activin A, activin B, activin AB, activin C, activin E, BMP6, BMP1-, ActRIIA, and/or ActRIIB) can be used in combination with i) one or more additional polynucleotide ActRII antagonists, ii) one or more ActRII polypeptides (e.g., ActRIIA and/or ActRIIB polypeptides and variants thereof); iii) one or more ActRII antagonist antibodies (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP10 antibody, an anti-ActRIIA antibody, or an anti-ActRIIB antibody); iv) one or more small molecule ActRII antagonists (e.g., a small molecule antagonist of one or more of GDF11, GDF8, activin A, activin B, activin AB, activin C, activin E, BMP6, BMP10, ActRIIA, and/or ActRIIB); v) one or more follistatin polypeptides; and/or vi) one or more FLRG polypeptides.

vi. Follistatin and FLRG Antagonists

In other aspects, an ActRII antagonist (inhibitor) for use in accordance with the methods disclosed herein is a follistatin or FLRG polypeptide, which may be used alone or in combination with one or more additional supportive therapies to increase red blood cell levels, treat or prevent an anemia, and/or treat or prevent ineffective erythropoiesis, e.g., ineffective erythropoiesis associated with anemia (e.g., anemia caused by or associated with blood loss, nutrient (e.g., iron) deficiency, medication reaction, kidney disease, and/or tumors or cancer), hemoglobinopathies including, for example, sickle cell disease (anemia), Hemoglobin C disease, Hemoglobin S-C Disease, thalassemias (e.g., any one of the various forms of alpha-, beta- or delta-beta-thalassemias), myelodysplastic syndrome (MDS), sideroblastic anemia (inherited or acquired); dyserythropoietic anemia (Types I and II), sickle cell anemia, hereditary spherocytosis; pyruvate kinase deficienc, megaloblastic anemias, myelophthisic anemias including, for example, myelofibrosis (myeloid metaplasia) and myelophthisis, congenital erythropoietic porphyria, and/or lead poisoning.

The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain preferred embodiments, follistatin polypeptides of the disclosure bind to and/or inhibit activin activity, particularly activin A. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 28-30, the follistatin N-terminal domain ("FSND" SEQ ID NO: 28), FSD2 (SEQ ID NO: 30), and to a lesser extent FSD1 (SEQ ID NO: 29) represent exemplary domains within follistatin that are important for activin binding. In addition, methods for making and testing libraries of polypeptides are described above in the context of ActRII polypeptides, and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide (SEQ ID NO: 26) as described, for example, in WO2005/025601.

The human follistatin precursor polypeptide isoform FST344 is as follows:

```
(SEQ ID NO: 26; NCBI Reference No. NP_037541.1)
  1    mvrarhqpgg lclllllllcq fmedrsaqag ncwlrqakng rcqvlyktel 51    skeeccstgr lstswteedv ndntlfkwmi fnggapncip cketcenvdc 101    gpgkkcrmnk knkprcvcap dcsnitwkgp vcgldgktyr necallkarc 151    keqpelevqy qgrckktcrd vfcpgsstcv vdqtrmaycv tcnricpepa 201    sseqylcgnd gvtyssachl rkatcllgrs iglayegkci kakscediqc 251    tggkkclwdf kvgrgrcslc delcpdsksd epvcasdnat yasecamkea 301    acssgvllev khsgscnsis edteeeeede dqdysfpiss ilew
```

The signal peptide is underlined; also underlined above are the last 27 residues which represent the C-terminal extension distinguishing this follistatin isoform from the shorter follistatin isoform FST317 shown below.

The human follistatin precursor polypeptide isoform FST317 is as follows:

```
(SEQ ID NO: 27; NCBI Reference No. NP_006341.1)
  1    MVRARHQPGG LCLLLLLLCQ FMEDRSAQAG NCWLRQAKNG RCQVLYKTEL

51    SKEECCSTGR LSTSWTEEDV NDNTLFKWMI FNGGAPNCIP CKETCENVDC

101    GPGKKCRMNK KNKPRCVCAP DCSNITWKGP VCGLDGKTYR NECALLKARC

151    KEQPELEVQY QGRCKKTCRD VFCPGSSTCV VDQTNNAYCV TCNRICPEPA

201    SSEQYLCGND GVTYSSACHL RKATCLLGRS IGLAYEGKCI KAKSCEDIQC

251    TGGKKCLWDF KVGRGRCSLC DELCPDSKSD EPVCASDNAT YASECAMKEA

301    ACSSGVLLEV KHSGSCN
```

The signal peptide is underlined.

The follistatin N-terminal domain (FSND) sequence is as follows:

```
(SEQ ID NO: 28; FSND)
GNCWLRQAKNGRCQVLYKTELSKEECCSTGRLSTSWTEEDVNDN

TLFKWMIFNGGAPNCIPCK
```

The FSD1 and FSD2 sequences are as follows:

```
(SEQ ID NO: 29; FSD1)
ETCENVDCGPGKKCRMNKKNKPRCV (SEQ ID NO: 30; FSD2)
KTCRDVFCPGSSTCVVDQTNNAYCVT
```

In other aspects, an agent for use in accordance with the methods disclosed herein is a follistatin-like related gene (FLRG), also known as follistatin-related protein 3 (FSTL3). The term "FLRG polypeptide" includes polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activin activity, particularly activin A. Variants of FLRG polypeptides that retain activin binding properties can be identified using routine methods to assay FLRG and activin interactions (see, e.g., U.S. Pat. No. 6,537,966). In addition, methods for making and testing libraries of polypeptides are described above in the context of ActRII polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor (follistatin-related protein 3 precursor) polypeptide is as follows:

```
(SEQ ID NO: 31; NCBI Reference No. NP_005851.1)
  1    MRPGAPGPLW PLPWGALAWA VGFVSSMGSG NPAPGGVCWL QQGQEATCSL

51    VLQTDVTRAE CCASGNIDTA WSNLTHPGNK INLLGFLGLV HCLPCKDSCD

101    GVECGPGKAC RMLGGRPRCE CAPDCSGLPA RLQVCGSDGA TYRDECELRA
```

```
151    ARCRGHPDLS VMYRGRCRKS CEHVVCPRPQ SCVVDQTGSA HCVVCRAAPC

201    PVPSSPGQEL CGNNNVTYIS SCHMRQATCF LGRSIGVRHA GSCAGTPEEP

251    PGGESAEEEE NFV
```

The signal peptide is underlined.

In certain embodiments, functional variants or modified forms of the follistatin polypeptides and FLRG polypeptides include fusion proteins having at least a portion of the follistatin polypeptide or FLRG polypeptide and one or more fusion domains, such as, for example, domains that facilitate isolation, detection, stabilization or multimerization of the polypeptide. Suitable fusion domains are discussed in detail above with reference to the ActRII polypeptides. In some embodiment, an agent of the disclosure is a fusion protein comprising an activin-binding portion of a follistatin polypeptide fused to an Fc domain. In another embodiment, an agent of the disclosure is a fusion protein comprising an activin binding portion of an FLRG polypeptide fused to an Fc domain.

Any of the follistatin polypeptides disclosed herein may be combined with one or more additional ActRII antagonists agents of the disclosure to achieve the desired effect (e.g., to increase red blood cell levels, treat or prevent an anemia, and/or treat or prevent ineffective erythropoiesis). For example, a follistatin polypeptide can be used in combination with i) one or more additional follistatin polypeptides, ii) one or more ActRII polypeptides disclosed herein (e.g., ActRIIA and/or ActRIIB polypeptides and variants thereof), iii) one or more ActRII antagonist antibodies (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); iv) one or more small molecule ActRII antagonists (e.g., a small molecule antagonist of one or more of GDF11, GDF8, activin A, activin B, activin AB, activin C, activin E, BMP6, BMP7, Nodal, ActRIIA, and/or ActRIIB); v) one or more polynucleotide ActRII antagonists (e.g., a polynucleotide antagonist of one or more of GDF11, GDF8, activin A, activin B, activin AB, activin C, activin E, BMP6, BMP7, Nodal, ActRIIA, and/or ActRIIB); and/or vi) one or more FLRG polypeptides.

Similarly, any of the FLRG polypeptides disclosed herein may be combined with one or more additional ActRII antagonists agents of the disclosure to achieve the desired effect increase red blood cell levels, treat or prevent an anemia, and/or treat or prevent ineffective erythropoiesis. For example, a FLRG polypeptide can be used in combination with i) one or more additional FLRG polypeptides, ii) one or more ActRII polypeptides disclosed herein (e.g., ActRIIA and/or ActRIIB polypeptides and variants thereof), iii) one or more ActRII antagonist antibodies (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); iv) one or more small molecule ActRII antagonists (e.g., a small molecule antagonist of one or more of GDF11, GDF8, activin A, activin B, activin AB, activin C, activin E, BMP6, BMP7, Nodal, ActRIIA, and/or ActRIIB); v) one or more polynucleotide ActRII antagonists (e.g., a polynucleotide antagonist of one or more of GDF11, GDF8, activin A, activin B, activin AB, activin C, activin E, BMP6, BMP7, Nodal, ActRIIA, and/or ActRIIB); and/or vi) one or more follistatin polypeptides.

3. Screening Assays

In certain aspects, the present disclosure relates to the use of GATA-1, NFE2 and/or heat shock factor proteins to identify agonists of any one or more of GATA-1, NFE2 and/or heat shock factor proteins. Compounds identified through the screening assays disclosed herein can be tested to assess their ability to modulate red blood cell, hemoglobin and/or reticulocyte levels in vivo or in vitro. These compounds can be tested, for example, in animal models.

There are numerous approaches to screening for therapeutic agents for increasing red blood cell or hemoglobin levels by increasing GATA-1, NFE2 and or heat shock factor proteins. In certain embodiments, high-throughput screening of compounds can be carried out to identify agents that increase expression of reporter genes (e.g., luciferase) under the control of GATA-1 and/or NFE2. Alternatively, the assay can be used to identify compounds that increase expression of GATA-1, NFE2 and/or heat shock factor proteins, as detected by methods available in the art, e.g., rtPCR, Western Blot and/or ELISA analysis. In some embodiments, the assay can be used to identify compounds that increase the expression of GATA-1 target genes such as one or more heme biosynthesis genes (e.g., Ppox, Fech, Alas2, and Abcb10l) and/or one or more erythroid differentiation factors (e.g., KLF1, NFE2, GYPA, Bcl21, Bnip31, Bach1, and ANK1) using detection methods available in the art, e.g., rtPCR, Western Blot and/or ELISA analysis.

In certain embodiments, the assay is carried out to screen and identify compounds that specifically inhibit or reduce binding of an ActRII polypeptide to its binding partner, such as an ActRII ligand (e.g., GDF11, activin A, activin B, activin C, activin E, GDF8, activin A, BMP6, GDF15, Nodal, GDF3, BMP3, BMP3B, BMP9, and BMP10), as inhibition of ActRII signaling was demonstrated herein to increase expression of GATA-1, NFE2 and heat shock factor proteins. Alternatively, the assay can be used to identify compounds that do not substantially affect binding of an ActRII polypeptide to its binding partner, such as an ActRII ligand (e.g., activin A). In a further embodiment, the compounds can be identified by their ability to interact with an ActRII polypeptide.

A variety of assay formats will suffice and, in light of the present disclosure, those not expressly described herein will nevertheless be comprehended by one of ordinary skill in the art. As described herein, the test compounds (agents) of the disclosure may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present disclosure include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between, e.g., an ActRII polypeptide and its binding partner (e.g., GDF11, activin A, activin B, etc.).

Merely to illustrate, in an exemplary screening assay of the present disclosure, the compound of interest is contacted with an isolated and purified ActRIIB polypeptide which is ordinarily capable of binding to an ActRIIB ligand (e.g., GDF11, activin A, activin B, activin C, activin E, GDF8, BMP6, activin A, BMP6, GDF15, Nodal, GDF3, BMP3, BMP3B, BMP9, and/or BMP10), as appropriate for the intention of the assay. To the mixture of the compound and ActRIIB polypeptide is then added to a composition containing an ActRIIB ligand. Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the polypeptide (e.g., ActRII, GATA-1, NFE2, heat shock factor, HSP70, HSF1 and/or HSP90) and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRII polypeptide or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between an ActRII polypeptide and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two hybrid assay," for identifying agents that disrupt or potentiate interaction between an ActRIIB polypeptide and its binding partner [see, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696)]. In certain embodiments, the present disclosure contemplates the use of reverse two hybrid systems to identify compounds (e.g., small molecules or peptides) that dissociate interactions between an polypeptide (e.g., ActRII, GATA-1, NFE2, heat shock factor, HSP70, HSF1 and/or HSP90) and its binding protein [see, e.g., Vidal and Legrain, (1999) Nucleic Acids Res 27:919-29; Vidal and Legrain (1999) Trends Biotechnol 17:374-81; and U.S. Pat. Nos. 5,525,490; 5,955,280; and 5,965,368].

In certain embodiments, the subject compounds are identified by their ability to interact with a polypeptide (e.g., ActRII, GATA-1, NFE2, heat shock factor, HSP70, HSF1 and/or HSP90). The interaction between the compound and the polypeptide may be covalent or non-covalent. For example, such interaction can be identified at the protein level using in vitro biochemical methods, including photo-crosslinking, radiolabeled ligand binding, and affinity chromatography [see, e.g., Jakoby W B et al. (1974) Methods in Enzymology 46: 1]. In certain cases, the compounds may be screened in a mechanism based assay, such as an assay to detect compounds which bind to a polypeptide (e.g., ActRII, GATA-1, NFE2, heat shock factor, HSP70, HSF1 and/or HSP90). This may include a solid phase or fluid phase binding event. Alternatively, the gene encoding a polypeptide (e.g., ActRII, GATA-1, NFE2, heat shock factor, HSP70, HSF1 and/or HSP90) can be transfected with a reporter system (e.g., β-galactosidase, luciferase, or green fluorescent protein) into a cell and screened against the library preferably by a high-throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

4. Exemplary Therapeutic Uses

In certain aspects, agents, or combination of agents, of the disclosure that agonize (activate), reduce inhibition of, and/ or supplement the activity of any one of, or combination of, GATA-1, heat shock factor, and/or NFE2 can be used to increase red blood cell levels, treat and/or prevent an anemia, and/or treat or prevent ineffective erythropoiesis in a subject in need thereof.

The terms "subject," an "individual," or a "patient" are interchangeable throughout the specification and generally refer to mammals. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, an agent of the present disclosure may be used in combination with conventional therapeutic approaches for increasing red blood cell levels, particularly those used to treat anemias of multifactorial origin. Conventional therapeutic approaches for increasing red blood cell levels include, for example, red blood cell transfusion, administration of one or more EPO receptor activators, hematopoietic stem cell transplantation, immunosuppressive biologics and drugs (e.g., corticosteroids). In certain embodiments, an agent of the present disclosure can be used to treat or prevent an anemia in a subject in need thereof. In certain embodiments, an agent of the present disclosure can be used to increase red blood cell levels, treat or prevent an anemia, and/or treat or prevent ineffective erythropoiesis in a subject in need thereof. In certain aspects, an agent of the present disclosure can be used in combination with conventional therapeutic approaches for treating or preventing an anemia or ineffective erythropoiesis disorder, particularly those used to treat anemias of multifactorial origin.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" as used herein includes amelioration or elimination of the condition once it has been established.

In either case, prevention or treatment may be discerned in the diagnosis provided by a physician or other health care provider and the intended result of administration of the therapeutic agent. In some embodiments, the levels of GATA-1, heat shock factor and/or NFE2 expression are determined in a test subject. In some embodiments, if the levels of GATA-1, heat shock factor and/or NFE2 expression are determined to be reduced in the test subject as compared to the reference population, the subject is administered any of the agents disclosed herein.

In general, treatment or prevention of a disease or condition as described in the present disclosure is achieved by administering one or more agents of the disclosure that agonize (activate), reduce inhibition of, and/or supplement the activity of any one of, or combination of, GATA-1, heat shock factor, and/or NFE2 in an "effective amount." An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain embodiments, one or more of the agents of the disclosure may be used to increase red blood cell, hemoglobin, or reticulocyte levels in healthy individuals and selected patient populations. Examples of appropriate patient populations include those with undesirably low red blood cell or hemoglobin levels, such as patients having an anemia, and those that are at risk for developing undesirably low red blood cell or hemoglobin levels, such as those patients who are about to undergo major surgery or other procedures that may result in substantial blood loss. In one embodiment, a patient with adequate red blood cell levels is treated with one or more agents of the disclosure that agonize (activate), reduce inhibition of, and/or supplement the activity of any one of, or combination of, GATA-1, heat shock factor, and/or NFE2 to increase red blood cell levels, and then blood is drawn and stored for later use in transfusions.

One or more of the agents of the disclosure may be used to increase red blood cell levels, hemoglobin levels, and/or hematocrit levels in a patient having an anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects [see, e.g., Jacobs et al. (2000) Nephrol Dial Transplant 15, 15-19]. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow [see, e.g., Adamson (2008) Harrison's Principles of Internal Medicine, 17th ed.; McGraw Hill, N.Y., pp 628-634]. Potential causes of anemia include, for example, blood loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkins lymphoma, and Hodgkins lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or auto-antibodies and/or for religious reasons (e.g., some Jehovah's Witnesses); infections (e.g., malaria and osteomyelitis); hemoglobinopathies including, for example, sickle cell disease (anemia), Hemoglobin C disease, Hemoglobin S-C Disease, thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload [see, e.g., Adamson (2008) Harrison's Principles of Internal Medicine, 17th ed.; McGraw Hill, N.Y., pp 628-634]. In some embodiments, one or more agents of the disclosure that agonize (activate), reduce inhibition of, and/or supplement the activity of any one of, or combination of, GATA-1, heat shock factor, and/or NFE2 could be used to treat or prevent anemia associated with one or more of the disorders or conditions disclosed herein.

Many factors can contribute to cancer-related anemia. Some are associated with the disease process itself and the generation of inflammatory cytokines such as interleukin-1, interferon-gamma, and tumor necrosis factor [Bron et al. (2001) Semin Oncol 28(Suppl 8):1-6]. Among its effects, inflammation induces the key iron-regulatory peptide hepcidin, thereby inhibiting iron export from macrophages and generally limiting iron availability for erythropoiesis [see, e.g., Ganz (2007) J Am Soc Nephrol 18:394-400]. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more agents of the disclosure that agonize (activate), reduce inhibition of, and/or supplement the activity of any one of, or combination of, GATA-1, heat shock factor, and/or NFE2 could be used to treat a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients [see, e.g., Groopman et al. (1999) J Natl Cancer Inst 91:1616-1634]. Myelosuppressive drugs include, for example: 1)alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more agents of the disclosure that agonize (activate), reduce inhibition of, and/or supplement the activity of any one of, or combination of, GATA-1, heat shock factor, and/or NFE2 could be used to treat a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function [see, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231]. In some embodiments, one or more agents of the disclosure that agonize (activate), reduce inhibition of, and/or supplement the activity of any one of, or combination of, GATA-1, heat shock factor, and/or NFE2 could be used to treat anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more GDF11 and/or activin B antagonist agents of the disclosure that agonize (activate), reduce inhibition of, and/or supplement the activity of any one of, or combination of, GATA-1, heat shock factor, and/or NFE2 could be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs [see, e.g., Adamson (2008) Harrison's Principles of Internal Medicine, 17th ed.; McGraw Hill, N.Y., pp 628-634]. Appropriate therapy for iron-deficiency anemia depends on its cause and severity, with oral iron preparations, parenteral iron formulations, and RBC transfusion as major conventional options. In some embodiments, one or more agents of the disclosure that agonize (activate), reduce inhibition of, and/or supplement the activity of any one of, or combination of, GATA-1, heat shock factor, and/or NFE2 could be used to treat a chronic iron-deficiency.

Myelodysplastic syndromes (MDS) are a diverse collection of hematological disorders characterized by ineffective production of myeloid blood cells and risk of transformation to acute myeloid leukemia. In MDS patients, hematopoietic stem cells do not mature into healthy red blood cells, white blood cells, or platelets. MDS disorders include, for example, refractory anemia, refractory cytopenia with unilineage dysplasia (RCUD), refractory anemia with ringed sideroblasts (RARS), refractory anemia with ringed sideroblasts associated with marked thrombocytosis (RARS-T), refractory anemia with excess blasts (RAEB-1), refractory anemia with excess blasts in transformation (RAEB-2), refractory cytopenia with multilineage dysplasia (RCMD), MDS unclassified (MDS-U), and myelodysplastic syndrome associated with an isolated 5q chromosome abnormality [MDS with del(5q)].

MDS patients eventually require blood transfusions and/or treatment with erythropoietic growth factors (e.g., ESAs such as EPO) alone or in combination with a colony-stimulating factor [e.g., an analog of granulocyte colony-stimulating factor (G-CSF) such as filgrastim or an analog of granulocyte macrophage colony-stimulating factor (GM-GSF) such as sargramostim] to increase red blood cell levels. The frequency of transfusions depends on the extent of the disease and on the presence of comorbidities. Chronic transfusions are known to increase hemoglobin levels, which in turn improve brain and peripheral tissue oxygenation, thereby improving physical activity and mental alertness. However, many MDS patients develop side-effects from the use of such therapies. For example, patients who receive frequent red blood cell transfusions can develop tissue and organ damage from iron accumulation and generation of toxic reactive oxygen species. Accordingly, one or more agents of the disclosure that agonize (activate), reduce inhibition of, and/or supplement the activity of any one of, or combination of, GATA-1, heat shock factor, and/or NFE2 may be used to treat patients with MDS or sideroblastic anemias. In some embodiments, patients suffering from MDS or a sideroblastic anemia may be treated using a combination of one or more agents of the disclosure that agonize (activate), reduce inhibition of, and/or supplement the activity of any one of, or combination of, GATA-1, heat shock factor, and/or NFE2 and one or more additional therapeutic agents for treating MDS including, for example, ESAs; G-CSF analogs, including filgrastim; GM-CSF analogs, including sargramostim; lenalidomide; thalidomide; pomalidomide, hypomethylating agents, including azacitidine and decitabine; iron-chelating agents, including deferoxamine and deferasirox; thrombopoietin mimetics, including romiplostim and eltrombopag; chemotherapeutic agents, including cytarabine (ara-C) alone or in combination with idarubicin, topotecan, or fludarabine; immunosuppressants, including antithymocyte globulin, alemtuzumab, and cyclosporine; histone deacetylase inhibitors (HDAC inhibitors), including vorinostat, valproic acid, phenylbutyrate, entinostat, MGCD0103, and other class I nuclear HDAC inhibitors, class II non-nuclear HDAC inhibitors, pan HDAC inhibitors, and isoform-specific HDAC inhibitors; farnesyltransferase inhibitors, including as tipifarnib and lonafarnib; tumor necrosis factor-alpha (TNF-α) inhibitors, including etanercept or infliximab; inhibitors of glutathione-S-transferase (GST) P1-1, including ezatiostat; and inhitors of CD33, including gemtuzumab ozogamicin.

As described herein, patients that exhibit ring sideroblasts may be particularly suited to treatment with ActRII antagonists. Sideroblastic anemias can be classified broadly into congenital (inherited) and acquired forms, which can be further subdivided as shown in Table 1.

TABLE 1

Classification of Sideroblastic Anemias*

| Class | Gene | Anemia Severity | Iron Homeostasis |
|---|---|---|---|
| Congenital | | | |
| Nonsyndromic | | | |
| X-linked | ALAS2 | Mild to severe | Iron overload |
| SLC25A38 deficiency | SLC25A38 | Severe | Iron overload |
| Glutaredoxin 5 deficiency | GLRX5 | Mild to severe | Iron overload |
| Erythropoietic protoporphyria | FECH | Mild | — |
| Syndromic | | | |
| X-linked with ataxia | ABCB7 | Mild to moderate | — |
| SIFD | Unknown | Severe | Iron overload |
| Pearson marrow-pancreas Syndrome | mtDNA | Severe | — |
| Myopathy, lactic acidosis, and sideroblastic anemia (MLASA) | PUS1/YARS2 | Mild to severe | — |
| Thiamine-responsive megaloblastic anemia (TRMA) | SLC19A2 | Severe | — |
| Syndromic/nonsyndromic of unknown cause | Unknown | Variable | — |
| Acquired | | | |
| Clonal/Neoplastic | | | |
| MDS** | Variable | Mild to severe | Iron overload |
| Metabolic | | | |
| Alcoholism | — | Variable | — |
| Drug-induced | — | Variable | — |
| Copper deficiency (zinc toxicity) | — | Variable | — |
| Hypothermia | — | Variable | — |

*See Bottomley et al., 2014, Hematol Oncol Clin N Am 28: 653-670.
**See table below for MDS subclassifications according to the World Health Organization.

Novel sequencing techniques have led in the past few years to identification of dozens of genes that are recurrently mutated in MDS. A 2013 list of such genes classified by type is shown in Table 3. One or more such mutations can be found in almost all patients with MDS, and knowing the nature of the genes involved has improved understanding of how MDS develops and evolves, although it has not yet had an impact on treatment. Whole-genome sequencing applied to MDS patient samples has identified an entirely novel class of cancer-associated genes encoding mRNA splicing (spliceosome) factors. The first such gene identified in MDS was SF3B1, which is mutated particularly frequently in patients with RARS [Papaemmanuil et al. (2011) N Engl J Med 365:1384-1395]. Other major categories of mutated genes are epigenetic (DNA methylation) regulators, transcription factors, and signaling molecules [Cazzola et al. (2013) Blood 122:4021-4034; Bejar et al. (2014) Blood 124:2793-2803]. The extent to which these mutations co-occur in MDS patients seems to vary with gene type. For example, approximately 50% of MDS patients possess one of ten genes identified to date encoding mutant splicing factors, but these mutant genes rarely co-occur in the same patient [Bejar et al. (2014) Blood 124:2793-2803]. Thus, these mutant genes are seldom redundant markers for the same individuals. Genes encoding mutant epigenetic regulators co-occur more frequently with each other and with mutant splicing factor genes in the same patient. As disclosed herein, the differential occurrence of mutant genes such as those listed in Table 3 provides a genetic signature that can assist in predicting which patients with MDS or sideroblastic anemia are likely to be either responsive or nonresponsive therapeutically to agents of the disclosure that agonize (activate), reduce inhibition of, and/or supplement the activity of any one of, or combination of, GATA-1, heat shock factor, and/or NFE2.

TABLE 3

MDS-Associated Somatic Mutations*

| Gene | Frequency in MDS (% cases) |
|---|---|
| RNA Splicing | |
| SF3B1 | 14-28 |
| SRSF2 | 15 |
| U2AF1 | 8 |
| ZRSR2 | 6 |
| PRPF40B | 1 |
| SF3A1 | 1 |
| SF1 | 1 |
| U2AF65 | <1 |
| LUC7L2 | Rare |
| PRPF8 | Rare |
| Epigenetic Regulators | |
| TET2 | 19-26 |
| ASXL1 | 10-20 |
| DNMT3A | 10 |
| IDH1/IDH2 | 4-12 |
| EZH2 | 6 |
| UTX | 1 |
| ATRX | <1 |
| Transcription Factors | |
| RUNX1 | 10-20 |
| TP53 | 4-14 |
| ETV6 | 1-3 |
| PHF6 | Rare |
| WT1 | Rare |

TABLE 3-continued

MDS-Associated Somatic Mutations*

| Gene | Frequency in MDS (% cases) |
|---|---|
| Signaling | |
| NRAS | 10 |
| CBL | 3 |
| JAK2 | 3 |
| FLT3 | 2-3 |
| KRAS | 1-2 |
| c-KIT | 1 |
| BRAF | <1 |
| CDKN2A | <1 |
| GNAS | <1 |
| PTEN | <1 |
| PTPN11 | <1 |
| CBLB | Rare |
| MPL, CSF1R | Rare |
| Others | |
| NPM1 | 2-3 |

*From Tothova et al. (2013) Clin Cancer Res 19: 1637-1643.

Among the genes listed in Table 3, the gene encoding splicing factor 3B1 (SF3B1) has been implicated recently as critical in MDS, particularly in the RARS, RARS-T, and RCMD-RS subtypes [Malcovati et al. (2011) Blood 118: 6239-6246; Dolatshad et al. (2014) Leukemia doi: 10.1038/leu.2014.331 epub ahead of print]. Somatic mutations in SF3B1 also occur in hematologic cancers including chronic lymphocytic leukemia (CLL), and acute myeloid leukemia (AML) as well as in breast cancer, pancreatic cancer, gastric cancer, prostate cancer, and uveal melanoma [Malcovati et al. (2011) Blood 118:6239-6246; Wang et al. (2011) N Engl J Med 365:2497-2506; The Cancer Genome Atlas Network (2012) Nature 490:61-70; Biankin et al. (2012) Nature 491:399-405; Chesnais et al. (2012) Oncotarget 3:1284-1293; Furney et al. (2013) Cancer Discov 3:1122-1129; Je et al. (2013) Int J Cancer 133:260-266]. A spectrum of SF3B1 mutations, many clustered at a few locations in the protein, have been identified in clinical samples or in cell lines exposed to high concentrations of pladienolide [Webb et al. (2013) Drug Discov Today 18:43-49]. SF3B1 mutations identified in MDS include, for example, K182E, E491G, R590K, E592K, R625C, R625G, N626D, N626S, H662Y, T663A, K666M, K666Q, K666R, Q670E, G676D, V701I, I704N, I704V, G740R, A744P, D781G, and A1188V. SF3B1 mutations identified in cancer include, for example, N619K, N626H, N626Y, R630S, I704T, G740E, K741N, G742D, D894G, Q903R, R1041H, and I1241T. Finally, SF3B1 mutations found in both MDS and cancer include, for example, G347V, E622D, Y623C, R625H, R625L, H662D, H662Q, T663I, K666E, K666N, K666T, K700E, and V701F.

In one embodiment of the disclosure, agents of the disclosure that agonize (activate), reduce inhibition of, and/or supplement the activity of any one of, or combination of, GATA-1, heat shock factor, and/or NFE2 are useful for treating MDS patients or patients with sideroblastic anemia, in whom more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% of erythroid precursors are ring sideroblasts, e.g., in refractory anemia with ring sideroblasts (RARS), RARS associated with marked thrombocytosis (RARS-T), or refractory cytopenia with multilineage dysplasia (RCMD, also known as RCMD-RS in patients where ring sideroblasts are prominent).

Accordingly, one or more agents of the disclosure that agonize (activate), reduce inhibition of, and/or supplement the activity of any one of, or combination of, GATA-1, heat shock factor, and/or NFE2, may be used to treat patients having MDS. In certain embodiments, patients suffering from MDS may be treated using one or more agents of the disclosure that agonize (activate), reduce inhibition of, and/or supplement the activity of any one of, or combination of, GATA-1, heat shock factor, and/or NFE2. In other embodiments, patient suffering from MDS may be treated using a combination of one or more agents of the disclosure that agonize (activate), reduce inhibition of, and/or supplement the activity of any one of, or combination of, GATA-1, heat shock factor, and/or NFE2 and one or more additional therapeutic agents for treating MDS including, for example, thalidomide, lenalidomide, azacitadine, decitabine, erythropoietins, deferoxamine, antithymocyte globulin, and filgrastrim (G-CSF).

Originally distinguished from aplastic anemia, hemorrhage, or peripheral hemolysis on the basis of ferrokinetic studies [see, e.g., Ricketts et al. (1978) Clin Nucl Med 3:159-164], ineffective erythropoiesis describes a diverse group of anemias in which production of mature RBCs is less than would be expected given the number of erythroid precursors (erythroblasts) present in the bone marrow [Tanno et al. (2010) Adv Hematol 2010:358283]. In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis [see, e.g., Aizawa et al. (2003) Am J Hematol 74:68-72], erythroblast-induced bone pathology [see, e.g., Di Matteo et al. (2008) J Biol Regul Homeost Agents 22:211-216], and tissue iron overload, even in the absence of therapeutic RBC transfusions [see, e.g., Pippard et al. (1979) Lancet 2:819-821]. Thus, by boosting erythropoietic effectiveness, a GDF11 and/or activin B antagonist of the present disclosure may break the aforementioned cycle and thus alleviate not only the underlying anemia but also the associated complications of elevated erythropoietin levels, splenomegaly, bone pathology, and tissue iron overload. In some embodiments, one or more agents of the disclosure that agonize (activate), reduce inhibition of, and/or supplement the activity of any one of, or combination of, GATA-1, heat shock factor, and/or NFE2 can be used to treat or prevent ineffective erythropoiesis, including anemia and elevated EPO levels as well as complications such as splenomegaly, erythroblast-induced bone pathology, iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors [see, e.g., Musallam et al. (2012) Cold Spring Harb Perspect Med 2:a013482]. With erythroblast-induced bone pathology, attendant pathologies include low bone mineral density, osteoporosis, and bone pain [see, e.g., Haidar et al. (2011) Bone 48:425-432]. With iron overload, attendant pathologies include hepcidin suppression and hyperabsorption of dietary iron [see, e.g., Musallam et al. (2012) Blood Rev 26(Suppl 1):S16-S19], multiple endocrinopathies and liver fibrosis/cirrhosis [see, e.g., Galanello et al. (2010) Orphanet J Rare Dis 5:11], and iron-overload cardiomyopathy [Lekawanvijit et al., 2009, Can J Cardiol 25:213-218].

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation [see, e.g., Schrier (2002) Curr Opin Hematol 9:123-126]. Thalassemias are collectively among the most frequent genetic disorders worldwide, with changing epidemiologic patterns predicted to contribute to a growing public health problem in both the U.S. and globally [Vichinsky (2005) Ann NY Acad Sci 1054:18-24]. Thalassemia syndromes are named according to their severity. Thus, α-thalassemias include α-thalassemia minima, α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia [see, e.g., Rund et al. (2005) N Engl J Med 353:1135-1146]. 0.5-β Thalassemia is a form of β-thalassemia characterized by decreased or absent synthesis of the delta- and beta-globin chains with a compensatory increase in expression of fetal gamma-chain synthesis. Subjects heterozygous for δ-β thalassemia are clinically asymptomatic, but subjects homozygous for δ-β thalassemia have mild clinical presentation. In certain embodiments, one or more agents of the disclosure that agonize (activate), reduce inhibition of, and/or supplement the activity of any one of, or combination of, GATA-1, heat shock factor, and/or NFE2 can be used to treat or prevent a thalassemia syndrome.

In some embodiments, one or more agents of the disclosure that agonize (activate), reduce inhibition of, and/or supplement the activity of any one of, or combination of, GATA-1, heat shock factor, and/or NFE2 can be used for treating disorders of ineffective erythropoiesis besides thalassemia syndromes. Such disorders include sideroblastic anemia (inherited or acquired); dyserythropoietic anemia (Types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias including, for example, myelofibrosis (myeloid metaplasia) and myelophthisis; congenital erythropoietic porphyria; and/or lead poisoning. In some embodiments, the sideroblastic anemia is any one or more of congenital sideroblastic anemia, clonal sideroblastic anemia, acquired reversible sideroblastic anemia, X-linked sideroblastic anemia, sideroblastic anemia with spinocerebellar ataxia, and/or pyridoxine-responsive sideroblastic anemia.

Numerous genes contribute to classical sickle-cell disease (SCD; drepanocytosis). Primarily, sickle-cell disease is an inherited disorder caused by a mutation in the β-globin gene (a mutation of a glutamate to a valine at codon 6). See, e.g., Kassim et al. (2013) Annu Rev Med, 64: 451-466. Sickle-cell anemia refers to the most common form of sickle-cell disease, with a homozygous mutation in the $β^S$ allele (HbSS), affecting 60 to 70% of people with sickle-cell disease. Because of the mutation in the β-globin gene, abnormal hemoglobin molecules are produced with a hydrophobic motif that is exposed when it is in a deoxygenated state [see, e.g., Eaton et al. (1990) Adv Protein Chem, 40: 63-279; Steinberg, MH (1999) N Engl J Med 340(13): 1021-1030; and Ballas et al. (1992) Blood, 79(8): 2154-63]. Once exposed, the chains of the separate hemoglobin molecules polymerize, which results in damage to the red blood cell membrane and cellular dehydration. The membrane damage is manifested, in part, by a redistribution of membrane lipids leading to the expression of phosphatidylserine on the outer leaflet of the erythrocyte membrane [see, e.g., (2002) Blood 99(5): 1564-1571]. Externalized phosphatidylserine promotes adhesion to both macrophages and activated endothelial cells, which contributes to vascular (vaso) occlusion. Thus, at low oxygen states, the red cell's hemoglobin precipitates into long crystals that cause it to elongate, morphologically switching into a "sickled" red blood cell. Both genotype and the extent and degree of deoxygenation contribute to the severity of hemoglobin polymerization. It has been demonstrated that the presence of fetal hemoglobin proportionally reduces the amount of pathological hemoglobin polymers and is protective from vaso-occlusive crises.

In some embodiments, patients suffering from sickle-cell disease may be treated using a combination of one or more agents of the disclosure that agonize (activate), reduce inhibition of, and/or supplement the activity of any one of, or combination of, GATA-1, heat shock factor, and/or NFE2, optionally in combination with one or more additional supportive therapies for treating sickle-cell disease including, for example, antibiotics, pain management [e.g., treatment with one or more narcotics, non-steroid anti-inflammatory drugs, and/or corticosteroids), intravenous fluids, blood transfusion, surgery, iron chelation therapy (e.g., deferroxamine) and hydroxyurea (e.g. Droxia®)]. In some embodiments, one or more ActRII antagonist agents of the disclosure (e.g., a GDF-ActRII antagonist, an ActRIIA polypeptide, an ActRIIB polypeptide, a GDF trap, etc.), may be used to treat sickle-cell disease in a patient in need thereof in combination with one or more additional agents and/or supportive therapies for treating sickle-cell disease (e.g., treatment with one or more narcotics, non-steroid anti-inflammatory drugs, and/or corticosteroids), intravenous fluids, blood transfusion, surgery, iron chelation therapy (e.g., deferroxamine) and hydroxyurea).

In certain embodiments, a subject, prior to the administration of any of the agents disclosed herein, has decreased levels of GATA-1 compared to levels of GATA-1 in a reference population. In certain embodiments, any of the agents disclosed herein is administered to a subject in whom it has been determined has decreased levels of GATA-1 protein compared to levels of GATA-1 in a reference population. In some embodiments, a subject, prior to the administration of any of the agents disclosed herein, has decreased levels of one or more heme biosynthesis genes selected from the group consisting of: Ppox, Fech, Alas2, and Abcb10l, compared to levels of Ppox, Fech, Alas2, and Abcb10l in a reference population. In some embodiments, a subject, prior to the administration of any of the agents disclosed herein, has decreased levels of one or more erythroid differentiation factors selected from the group consisting of: KLF1, NFE2, GYPA, Bcl21, Bnip31, Bach1, and ANK1, compared to levels of KLF1, NFE2, GYPA, Bcl21, Bnip31, Bach1, and ANK1, in a reference population. In some embodiments, the subject is a human, and the reference population consists of one or more humans. In some embodiments, the reference population consists of 1, 2, 3, 5, 10, 20, 25, 30, 50, 70, 75, 80, 90, 100, 200, 250, 500, or 1000 individuals. In some embodiments, the reference population consists of healthy individuals. In some embodiments, the reference population consists of people of the same gender, age, and/or weight as the subject. In some embodiments, the reference population consists of people without ineffective erythropoiesis. In some embodiments, the reference population consists of people without MDS. In some embodiments, the reference population consists of people without a hemoglobinopathy. In some embodiments, the reference population consists of people without sickle-cell disease. In some embodiments, the reference population consists of people without beta-thalassemia. In some embodiments, the decreased levels of GATA-1 are about 10%, 20%, 25%, 30%, 40%, 50%, 60%, 70%, 75%, 80%, 90%, 100%, 200%, or 500% lower than the levels of GATA-1 in the reference population. In some embodiments, the decreased levels of Ppox, Fech, Alas2, and Abcb10l are about 10%, 20%, 25%, 30%, 40%, 50%, 60%, 70%, 75%, 80%, 90%, 100%, 200%, or 500% lower than the levels of Ppox, Fech, Alas2, and/or Abcb10l in the reference population. In some embodiments, the decreased levels of KLF1, NFE2, GYPA, Bcl21, Bnip31, Bach1, and/or ANK1 are about 10%, 20%, 25%, 30%, 40%, 50%, 60%, 70%, 75%, 80%, 90%, 100%, 200%, or 500% lower than the levels of KLF1, NFE2, GYPA, Bcl21, Bnip31, Bach1, and/or ANK1 in the reference population. In some embodiments, the decreased levels of GATA-1 are about 10%, 20%, 25%, 30%, 40%, 50%, 60%, 70%, 75%, 80%, 90%, 100%, 200%, or 500% lower than the levels of GATA-1 in the bottom 10%, bottom 5%, bottom 4%, bottom 3%, bottom 2%, or bottom 1% of the reference population. In some embodiments, the decreased levels of Ppox, Fech, Alas2, and/or Abcb10l are about 10%, 20%, 25%, 30%, 40%, 50%, 60%, 70%, 75%, 80%, 90%, 100%, 200%, or 500% lower than the levels of Ppox, Fech, Alas2, and/or Abcb10l in the bottom 10%, bottom 5%, bottom 4%, bottom 3%, bottom 2%, or bottom 1% of the reference population. In some embodiments, the decreased levels of KLF1, NFE2, GYPA, Bcl21, Bnip31, Bach1, and/or ANK1 are about 10%, 20%, 25%, 30%, 40%, 50%, 60%, 70%, 75%, 80%, 90%, 100%, 200%, or 500% lower than the levels of KLF1, NFE2, GYPA, Bcl21, Bnip31, Bach1, and/or ANK1 in the bottom 10%, bottom 5%, bottom 4%, bottom 3%, bottom 2%, or bottom 1% of the reference population.

In certain embodiments, a subject, prior to the administration of any of the agents disclosed herein, has decreased levels of heat shock factor compared to levels of heat shock factor in a reference population. In certain embodiments, any of the agents disclosed herein is administered to a subject in whom it has been determined has decreased levels of heat shock factor protein compared to levels of heat shock factor protein in a reference population. In some embodiments, the subject is a human, and the reference population consists of one or more humans. In some embodiments, the reference population consists of 1, 2, 3, 5, 10, 20, 25, 30, 50, 70, 75, 80, 90, 100, 200, 250, 500, or 1000 individuals. In some embodiments, the reference population consists of healthy individuals. In some embodiments, the reference population consists of people of the same gender, age, and/or weight as the subject. In some embodiments, the reference population consists of people without ineffective erythropoiesis. In some embodiments, the reference population consists of people without MDS. In some embodiments, the reference population consists of people without a hemoglobinopathy. In some embodiments, the reference population consists of people without sickle-cell disease. In some embodiments, the reference population consists of people without beta-thalassemia. In some embodiments, the decreased levels of heat shock factor are about 10%, 20%, 25%, 30%, 40%, 50%, 60%, 70%, 75%, 80%, 90%, 100%, 200%, or 500% lower than the levels of heat shock factor in the reference population. In some embodiments, the decreased levels of heat shock factor are about 10%, 20%, 25%, 30%, 40%, 50%, 60%, 70%, 75%, 80%, 90%, 100%, 200%, or 500% lower than the levels of heat shock factor in the bottom 10%, bottom 5%, bottom 4%, bottom 3%, bottom 2%, or bottom 1% of the reference population. In certain embodiments, a subject, prior to the administration of any of the agents disclosed herein, has decreased levels of NFE2 compared to levels of NFE2 in a reference population. In certain embodiments, any of the agents disclosed herein is administered to a subject in whom it has been determined has decreased levels of NFE2 compared to levels of NFE2 in a reference population. In some embodiments, the subject is a human, and the reference population consists of one or more humans. In some embodiments, the reference population consists of 1, 2, 3, 5, 10, 20, 25, 30, 50, 70, 75, 80, 90, 100, 200, 250, 500, or 1000 individuals. In some embodiments, the reference population consists of healthy individuals. In some embodiments, the reference population consists of people of the same gender, age, and/or weight as the subject. In some embodiments, the reference population consists of people without ineffective erythropoiesis. In some embodiments, the reference population consists of people without MDS. In some embodiments, the reference population consists of people without a hemoglobinopathy. In some embodiments, the reference population consists of people without sickle-cell disease. In some embodiments, the reference population consists of people without beta-thalassemia. In some embodiments, the decreased levels of NFE2 are about 10%, 20%, 25%, 30%, 40%, 50%, 60%, 70%, 75%, 80%, 90%, 100%, 200%, or 500% lower than the levels of NFE2 in the reference population. In some embodiments, the decreased levels of NFE2 are about 10%, 20%, 25%, 30%, 40%, 50%, 60%, 70%, 75%, 80%, 90%, 100%, 200%, or 500% lower than the levels of NFE2 in the bottom 10%, bottom 5%, bottom 4%, bottom 3%, bottom 2%, or bottom 1% of the reference population.

In certain embodiments, any of the methods disclosed herein incorporate a diagnostic step in which the subject is first assessed for levels of GATA-1, heat shock factor and/or NFE2 prior to being administered any of the agents disclosed herein. In certain embodiments, the subject is first assessed for levels of GATA-1, heat shock factor and/or NFE2 prior to a first administration of any of the agents disclosed herein, and then the subject is assessed a second time for levels of GATA-1, heat shock factor and/or NFE2 followed by a second administration of any of the agents disclosed herein. In certain embodiments, the dose of the agent for the second administration is modified depending on the levels of GATA-1, heat shock factor and/or NFE2 determined during the second assessment. In some embodiments, the dose of the agent for the second administration is increased depending on the levels of GATA-1, heat shock factor and/or NFE2 determined during the second assessment. In some embodiments, the dose of the agent for the second administration is decreased depending on the levels of GATA-1, heat shock factor and/or NFE2 determined during the second assessment.

In particular embodiments, the application provides for a method for treating or preventing ineffective erythropoiesis in a subject comprising: a) taking a first measurement of level of GATA-1 in the subject, b) administering to the subject an initial dose of an ActRII antagonist to the subject, c) taking a second measurement of the level of GATA-1 in the subject, d) administering to the patient an additional dose of the ActRII antagonist that is the same as the initial dose or an adjusted dose of the ActRII antagonist. In some embodiments, the application provides for a method for treating or preventing ineffective erythropoiesis in a subject comprising: a) administering to the subject an initial dose of an ActRII antagonist to the subject, b) taking a measurement of the level of GATA-1 in the subject, c) administering to the patient an additional dose of the ActRII antagonist that is the same as the initial dose or an adjusted dose of the ActRII antagonist. In some embodiments, the level of GATA-1 in the subject is compared to a reference population. In some embodiments, the initial dose of the ActRII antagonist is about 0.1 mg/kg, about 0.3 mg/kg, about 0.5 mg/kg, about 0.7 mg/kg, about 0.8 mg/kg, about 0.9 mg/kg, about 1.0 mg/kg, about 2.0 mg/kg, about 3 mg/kg, about 5 mg/kg, about 10 mg/kg. In some embodiments, the initial and/or adjusted dose is administered about twice a week, about once a week, about once every two weeks, about once a month, about once every two months, about once every three months, about once every six months, about once every five weeks, about once every six weeks, about once every seven weeks, about every 5 days, about every 10 days, about every 15 days, about every 20 days, about every 25 days, about every 30 days, about every 35 days, or about ever 40 days. In some embodiments, the adjusted dose of the ActRII antagonist is greater than the initial dose if the level of GATA-1 is decreased compared to the level of GATA-1 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg greater than the initial dose. In some embodiments, the adjusted dose is administered more frequently than the initial dose. In some embodiments, the additional dose of the ActRII antagonist is the same as the initial dose, and wherein the additional dose is administered more frequently than the initial dose if the level of GATA-1 is decreased compared to the level of GATA-1 in the reference population. In some embodiments, the first measurement of the levels of GATA-1 in the subject is compared to the second measurement of the levels of GATA-1 in the subject. In some embodiments, the adjusted dose of the ActRII antagonist is greater than the initial dose if the level of GATA-1 in the second measurement is about the same as or lower than the level of GATA-1 in the first measurement. In some embodiments, the additional dose is administered more frequently than the initial dose if the level of GATA-1 in the second measurement is about the same as or lower than the level of GATA-1 in the first measurement. In some embodiments, the additional dose is the same as the initial dose. In some embodiments, the adjusted dose of the ActRII antagonist is less than the initial dose if the level of GATA-1 is elevated compared to the level of GATA-1 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg less than the initial dose. In some embodiments, the adjusted dose is administered less frequently than the initial dose. In some embodiments, the dose is the same as the initial dose, and wherein the additional dose is administered less frequently than the initial dose if the level of GATA-1 is elevated compared to the level of GATA-1 in the reference population. In some embodiments, the adjusted dose is administered continuously. In some embodiments, the first measurement is taken prior to commencement of the treatment. In some embodiments, the first measurement is taken immediately after commencement of the treatment. In some embodiments, the first measurement is taken within about 1 day, about 2 days, about 3 days, about 4 days, about 5 days, about 6 days, about 7 days, about 10 days, about 14 days, about 21 days, about 28 days, about 30 days, or about 60 days after commencement of treatment. In some embodiments, the second measurement is taken immediately after commencement of the treatment. In some embodiments, the second measurement is taken within about 1 day, about 2 days, about 3 days, about 4 days, about 5 days, about 6 days, about 7 days, about 10 days, about 14 days, about 21 days, about 28 days, about 30 days, or about two months, about three months, about four months, about five months, about six months, about eight months, about 10 months, or about 12 months after commencement of treatment. In some embodiments, the decreased level of GATA-1 is about 10%, 20%, 25%, 30%, 40%, 50%, 60%, 70%, 75%, 80%, 90%, 100%, 200%, or 500% lower than the level of GATA-1 in the reference population. In some embodiments, the decreased level of GATA-1 is about 10%, 20%, 25%, 30%, 40%, 50%, 60%, 70%, 75%, 80%, 90%, 100%, 200%, or 500% lower than the level of GATA-1 in the bottom 10%, bottom 5%, bottom 4%, bottom 3%, bottom 2%, or bottom 1% of the reference population. In some embodiments, the elevated level of GATA-1 is about 10%, 20%, 25%, 30%, 40%, 50%, 60%, 70%, 75%, 80%, 90%, 100%, 200%, or 500% higher than the level of GATA-1 in the reference population. In some embodiments, the elevated level of GATA-1 is about 10%, 20%, 25%, 30%, 40%, 50%, 60%, 70%, 75%, 80%, 90%, 100%, 200%, or 500% higher than the level of GATA-1 in the bottom 10%, bottom 5%, bottom 4%, bottom 3%, bottom 2%, or bottom 1% of the reference population. In some embodiments, the level of GATA-1 is the protein level of GATA-1. In some embodiments, the protein level of GATA-1 is determined by ELISA. In some embodiments, the level of GATA-1 is the mRNA level of GATA-1. In some embodiments, the mRNA level of GATA-1 is determined by qRT-PCR. In some embodiments, the levels are measured in a tissue. In some embodiments, the levels are measured in serum. In some embodiments, the levels are measured in bone marrow. In some embodiments, the levels are measured in erythroblasts.

In particular embodiments, the application provides for a method for treating or preventing ineffective erythropoiesis in a subject comprising: a) taking a first measurement of level of heat shock factor protein in the subject, b) administering to the subject an initial dose of an ActRII antagonist to the subject, c) taking a second measurement of the level of heat shock factor protein in the subject, d) administering to the patient an additional dose of the ActRII antagonist that is the same as the initial dose or an adjusted dose of the ActRII antagonist. In some embodiments, the application provides for a method for treating or preventing ineffective erythropoiesis in a subject comprising: a) administering to the subject an initial dose of an ActRII antagonist to the subject, b) taking a measurement of the level of heat shock factor in the subject, c) administering to the patient an additional dose of the ActRII antagonist that is the same as the initial dose or an adjusted dose of the ActRII antagonist. In some embodiments, the level of heat shock factor in the subject is compared to a reference population. In some embodiments, the initial dose of the ActRII antagonist is about 0.1 mg/kg, about 0.3 mg/kg, about 0.5 mg/kg, about 0.7 mg/kg, about 0.8 mg/kg, about 0.9 mg/kg, about 1.0 mg/kg, about 2.0 mg/kg, about 3 mg/kg, about 5 mg/kg, about 10 mg/kg. In some embodiments, the initial and/or adjusted dose is administered about twice a week, about once a week, about once every two weeks, about once a month, about once every two months, about once every three months, about once every six months, about once every five weeks, about once every six weeks, about once every seven weeks, about every 5 days, about every 10 days, about every 15 days, about every 20 days, about every 25 days, about every 30 days, about every 35 days, or about ever 40 days. In some embodiments, the adjusted dose of the ActRII antagonist is greater than the initial dose if the level of heat shock factor protein is decreased compared to the level of heat shock factor protein in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg greater than the initial dose. In some embodiments, the adjusted dose is administered more frequently than the initial dose. In some embodiments, the additional dose of the ActRII antagonist is the same as the initial dose, and wherein the additional dose is administered more frequently than the initial dose if the level of heat shock factor is decreased compared to the level of heat shock factor in the reference population. In some embodiments, the first measurement of the levels of heat shock factor in the subject is compared to the second measurement of the levels of heat shock factor in the subject. In some embodiments, the adjusted dose of the ActRII antagonist is greater than the initial dose if the level of heat shock factor in the second measurement is about the same as or lower than the level of heat shock factor in the first measurement. In some embodiments, the additional dose is administered more frequently than the initial dose if the level of heat shock factor in the second measurement is about the same as or lower than the level of heat shock factor in the first measurement. In some embodiments, the additional dose is the same as the initial dose. In some embodiments, the adjusted dose of the ActRII antagonist is less than the initial dose if the level of heat shock factor is elevated compared to the level of heat shock factor in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg less than the initial dose. In some embodiments, the adjusted dose is administered less frequently than the initial dose. In some embodiments, the adjusted dose is administered continuously. In some embodiments, the dose is the same as the initial dose, and wherein the additional dose is administered less frequently than the initial dose if the level of heat shock factor is elevated compared to the level of heat shock factor in the reference population. In some embodiments, the first measurement is taken prior to commencement of the treatment. In some embodiments, the first measurement is taken immediately after commencement of the treatment. In some embodiments, the first measurement is taken within about 1 day, about 2 days, about 3 days, about 4 days, about 5 days, about 6 days, about 7 days, about 10 days, about 14 days, about 21 days, about 28 days, about 30 days, or about 60 days after commencement of treatment. In some embodiments, the second measurement is take immediately after commencement of the treatment. In some embodiments, the second measurement is taken within about 1 day, about 2 days, about 3 days, about 4 days, about 5 days, about 6 days, about 7 days, about 10 days, about 14 days, about 21 days, about 28 days, about 30 days, or about two months, about three months, about four months, about five months, about six months, about eight months, about 10 months, or about 12 months after commencement of treatment. In some embodiments, the decreased level of heat shock factor is about 10%, 20%, 25%, 30%, 40%, 50%, 60%, 70%, 75%, 80%, 90%, 100%, 200%, or 500% lower than the level of heat shock factor in the reference population. In some embodiments, the decreased level of heat shock factor is about 10%, 20%, 25%, 30%, 40%, 50%, 60%, 70%, 75%, 80%, 90%, 100%, 200%, or 500% lower than the level of heat shock factor in the bottom 10%, bottom 5%, bottom 4%, bottom 3%, bottom 2%, or bottom 1% of the reference population. In some embodiments, the elevated level of heat shock factor is about 10%, 20%, 25%, 30%, 40%, 50%, 60%, 70%, 75%, 80%, 90%, 100%, 200%, or 500% higher than the level of heat shock factor in the reference population. In some embodiments, the elevated level of heat shock factor is about 10%, 20%, 25%, 30%, 40%, 50%, 60%, 70%, 75%, 80%, 90%, 100%, 200%, or 500% higher than the level of heat shock factor in the bottom 10%, bottom 5%, bottom 4%, bottom 3%, bottom 2%, or bottom 1% of the reference population. In some embodiments, the level of heat shock factor is the protein level of heat shock factor. In some embodiments, the protein level of heat shock factor is determined by ELISA. In some embodiments, the level of heat shock factor is the mRNA level of heat shock factor. In some embodiments, the mRNA level of heat shock factor is determined by qRT-PCR. In some embodiments, the levels are measured in a tissue. In some embodiments, the levels are measured in serum. In some embodiments, the levels are measured in bone marrow. In some embodiments, the levels are measured in erythroblasts.

In particular embodiments, the application provides for a method for treating or preventing ineffective erythropoiesis in a subject comprising: a) taking a first measurement of level of NFE2 in the subject, b) administering to the subject an initial dose of an ActRII antagonist to the subject, c) taking a second measurement of the level of NFE2 in the subject, d) administering to the patient an additional dose of the ActRII antagonist that is the same as the initial dose or an adjusted dose of the ActRII antagonist. In some embodiments, the application provides for a method for treating or preventing ineffective erythropoiesis in a subject comprising: a) administering to the subject an initial dose of an ActRII antagonist to the subject, b) taking a measurement of the level of NFE2 in the subject, c) administering to the patient an additional dose of the ActRII antagonist that is the same as the initial dose or an adjusted dose of the ActRII antagonist. In some embodiments, the level of NFE2 in the subject is compared to a reference population. In some embodiments, the initial dose of the ActRII antagonist is about 0.1 mg/kg, about 0.3 mg/kg, about 0.5 mg/kg, about 0.7 mg/kg, about 0.8 mg/kg, about 0.9 mg/kg, about 1.0 mg/kg, about 2.0 mg/kg, about 3 mg/kg, about 5 mg/kg, about 10 mg/kg. In some embodiments, the initial and/or adjusted dose is administered about twice a week, about once a week, about once every two weeks, about once a month, about once every two months, about once every three months, about once every six months, about once every five weeks, about once every six weeks, about once every seven weeks, about every 5 days, about every 10 days, about every 15 days, about every 20 days, about every 25 days, about every 30 days, about every 35 days, or about ever 40 days. In some embodiments, the adjusted dose of the ActRII antagonist is greater than the initial dose if the level of NFE2 is decreased compared to the level of NFE2 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg greater than the initial dose. In some embodiments, the adjusted dose is administered more frequently than the initial dose. In some embodiments, the additional dose of the ActRII antagonist is the same as the initial dose, and wherein the additional dose is administered more frequently than the initial dose if the level of NFE2 is decreased compared to the level of NFE2 in the reference population. In some embodiments, the first measurement of the levels of NFE2 in the subject is compared to the second measurement of the levels of NFE2 in the subject. In some embodiments, the adjusted dose of the ActRII antagonist is greater than the initial dose if the level of NFE2 in the second measurement is about the same as or lower than the level of NFE2 in the first measurement. In some embodiments, the additional dose is administered more frequently than the initial dose if the level of NFE2 in the second measurement is about the same as or lower than the level of NFE2 in the first measurement. In some embodiments, the additional dose is the same as the initial dose. In some embodiments, the adjusted dose of the ActRII antagonist is less than the initial dose if the level of NFE2 is elevated compared to the level of NFE2 in a reference population. In some embodiments, the adjusted dose is about 0.05 mg/kg, about 0.1 mg/kg, about 0.15 mg/kg, about 0.2 mg/kg, about 0.25 mg/kg, about 0.3 mg/kg, about 0.4 mg/kg, about 0.5, mg/kg, about 0.75 mg/kg, about 1 mg/kg, about 1.5 mg/kg, about 2 mg/kg, about 3 mg/kg, about 4 mg/kg, about 5 mg/kg, about 7 mg/kg, or about 10 mg/kg less than the initial dose. In some embodiments, the adjusted dose is administered less frequently than the initial dose. In some embodiments, the adjusted dose is administered continuously. In some embodiments, the dose is the same as the initial dose, and wherein the additional dose is administered less frequently than the initial dose if the level of NFE2 is elevated compared to the level of NFE2 in the reference population. In some embodiments, the first measurement is taken prior to commencement of the treatment. In some embodiments, the first measurement is taken immediately after commencement of the treatment. In some embodiments, the first measurement is taken within about 1 day, about 2 days, about 3 days, about 4 days, about 5 days, about 6 days, about 7 days, about 10 days, about 14 days, about 21 days, about 28 days, about 30 days, or about 60 days after commencement of treatment. In some embodiments, the second measurement is take immediately after commencement of the treatment. In some embodiments, the second measurement is taken within about 1 day, about 2 days, about 3 days, about 4 days, about 5 days, about 6 days, about 7 days, about 10 days, about 14 days, about 21 days, about 28 days, about 30 days, or about two months, about three months, about four months, about five months, about six months, about eight months, about 10 months, or about 12 months after commencement of treatment. In some embodiments, the decreased level of NFE2 is about 10%, 20%, 25%, 30%, 40%, 50%, 60%, 70%, 75%, 80%, 90%, 100%, 200%, or 500% lower than the level of NFE2 in the reference population. In some embodiments, the decreased level of NFE2 is about 10%, 20%, 25%, 30%, 40%, 50%, 60%, 70%, 75%, 80%, 90%, 100%, 200%, or 500% lower than the level of NFE2 in the bottom 10%, bottom 5%, bottom 4%, bottom 3%, bottom 2%, or bottom 1% of the reference population. In some embodiments, the elevated level of NFE2 is about 10%, 20%, 25%, 30%, 40%, 50%, 60%, 70%, 75%, 80%, 90%, 100%, 200%, or 500% higher than the level of NFE2 in the reference population. In some embodiments, the elevated level of NFE2 is about 10%, 20%, 25%, 30%, 40%, 50%, 60%, 70%, 75%, 80%, 90%, 100%, 200%, or 500% higher than the level of NFE2 in the bottom 10%, bottom 5%, bottom 4%, bottom 3%, bottom 2%, or bottom 1% of the reference population. In some embodiments, the level of NFE2 is the protein level of NFE2. In some embodiments, the protein level of NFE2 is determined by ELISA. In some embodiments, the level of NFE2 is the mRNA level of NFE2. In some embodiments, the mRNA level of NFE2 is determined by qRT-PCR. In some embodiments, the levels are measured in a tissue. In some embodiments, the levels are measured in serum. In some embodiments, the levels are measured in bone marrow. In some embodiments, the levels are measured in erythroblasts.

In certain embodiments, agents of the disclosure that agonize (activate), reduce inhibition of, and/or supplement the activity of any one of, or combination of, GATA-1, heat shock factor, and/or NFE2 may be used in combination with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload [see, e.g., Hershko (2006) Haematologica 91:1307-1312; Cao et al. (2011), Pediatr Rep 3(2):e17]. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; Galanello et al. (2010) Ann NY Acad Sci 1202:79-86].

As used herein, "in combination with" or "conjoint administration" refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more agents of the disclosure that agonize (activate), reduce inhibition of, and/or supplement the activity of any one of, or combination of, GATA-1, heat shock factor, and/or NFE2 can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, any of the agents disclosed herein that is a Smad antagonist is combined with an additional agent, wherein the additional agent is any of the agents disclosed herein that acts downstream of Smad signaling. In some embodiments, the additional agent is an estrogen receptor antagonist. In some embodiments, the additional agent is an estrogen receptor inhibitor. In some embodiments, the additional agent inhibits the binding of ErbB2/HER2 to the estrogen receptor. In some embodiments, the additional agent inhibits the binding of endogenous estrogen to the estrogen receptor. In some embodiments, the additional agent is an estrogen receptor activator. In some embodiments, the additional agent is an agonist of estrogen receptor alpha (ERα) and estrogen receptor beta (ERβ). In some embodiments, the additional agent is an agonist of membrane estrogen receptors (mER). In some embodiments, the additional agent is an estrogen sex hormone. In some embodiments, the additional agent is chemotherapeutic. In some embodiments, the additional agent inhibits the synthesis of DNA or RNA. In some embodiments, the additional agent inhibits the topoisomerase II enzyme. In some embodiments, the additional agent results in iron-mediated generation of free oxygen radicals. In some embodiments, the additional agent induces histone eviction from chromatin. In some embodiments, the additional agent that acts downstream of Smad signaling is one or more of erythropoietin, tamoxifen, oestradiol, an anthracycline (e.g., aclacinomycin A, daunorubicin, doxorubicin, epirubicin, idarubicin, valrubicin, mitoxantrone, and any analogs thereof), a vector comprising a polynucleotide encoding recombinant GATA-1 protein, and/or recombinant GATA-1. In some embodiments, the additional agent that acts downstream of Smad signaling is a vector comprising a polynucleotide encoding recombinant NFE2 protein and/or a recombinant NFE2. In some embodiments, the additional agent is an antibiotic. In some embodiments, the additional agent inhibits the function of Hsp90. In some embodiments, the additional agent is an antitumor antibiotic. In some embodiments the additional agent that acts downstream of Smad signaling is a vector comprising a polynucleotide encoding recombinant heat shock factor protein, recombinant heat shock factor, an inducer of HSF1 activity (e.g., a pentacyclic triterpenoid, tricyclic bis(cyanoenone), celastrol, HSF1A, gedunin, sappanone A, and/or derivatives thereof), an inhibitor of HSP90 (e.g., geldanamycin, radicicol, 17-AAG, 17-DMAG, IPI-493, $OCH_3$, $NHCH_2$ $CH=CH_2$, $NHCH_2CH_2N(CH_3)_2$, $NH_2$, NVP-AUY922, KW-2478, AT13387, BIIB021, PU-H71, SNX-5422, NVP-BEP800, CUDC-305, XL888, and/or derivatives thereof), 115-7c and/or Compound A, or derivatives thereof, a vector comprising a polynucleotide encoding recombinant HSP70, and/or recombinant HSP70. In some embodiments, the Smad signaling antagonists are any of the agents of the disclosure that antagonize any one or more of GDF11 and/or activin B, GDF8, activin A, activin C, activin E, BMP6, GDF15, Nodal, GDF3, BMP3, BMP3B, BMP9, and BMP10).

In certain embodiments, one or more agents of the disclosure that agonize (activate), reduce inhibition of, and/or supplement the activity of any one of, or combination of, GATA-1, heat shock factor, and/or NFE2 may be used in combination with hepcidin or a hepcidin agonist for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis [see, e.g., Nemeth (2010) Adv Hematol 2010:750643]. This view is supported by beneficial effects of increased hepcidin expression in a mouse model of β-thalassemia [Gardenghi et al. (2010) J Clin Invest 120:4466-4477].

One or more agents of the disclosure that agonize (activate), reduce inhibition of, and/or supplement the activity of any one of, or combination of, GATA-1, heat shock factor, and/or NFE2 would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more agents of the disclosure that agonize (activate), reduce inhibition of, and/ or supplement the activity of any one of, or combination of, GATA-1, heat shock factor, and/or NFE2. In certain embodiments, one or more agents of the disclosure that agonize (activate), reduce inhibition of, and/or supplement the activity of any one of, or combination of, GATA-1, heat shock factor, and/or NFE2 of the disclosure may be used in combination with EPO receptor activators to reduce the required dose of these activators in patients that are susceptible to adverse effects of EPO. These methods may be used for therapeutic and prophylactic treatments of a patient.

One or more agents of the disclosure that agonize (activate), reduce inhibition of, and/or supplement the activity of any one of, or combination of, GATA-1, heat shock factor, and/or NFE2 may be used in combination with EPO receptor activators to achieve an increase in red blood cells, particularly at lower dose ranges of EPO receptor activators. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that antagonists of the present disclosure act by a different mechanism than EPO, these antagonists may be useful for increasing red blood cell and hemoglobin levels in patients that do not respond well to EPO. For example, an antagonist of the present disclosure may be beneficial for a patient in which administration of a normal-to-increased dose of EPO (>300 IU/kg/week) does not result in the increase of hemoglobin level up to the target level. Patients with an inadequate EPO response are found in all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more agents of the disclosure that agonize (activate), reduce inhibition of, and/ or supplement the activity of any one of, or combination of, GATA-1, heat shock factor, and/or NFE2 by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more agents of the disclosure that agonize (activate), reduce inhibition of, and/or supplement the activity of any one of, or combination of, GATA-1, heat shock factor, and/or NFE2 may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more agents of the disclosure that agonize (activate), reduce inhibition of, and/or supplement the activity of any one of, or combination of, GATA-1, heat shock factor, and/or NFE2, then onset of administration of the one or more antagonists of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more antagonists of the disclosure may be delayed until the levels have returned to a normal or acceptable level.

In certain embodiments, if one or more hematologic parameters are outside the normal range or on the high side of normal in a patient who is a candidate to be treated with one or more agents of the disclosure that agonize (activate), reduce inhibition of, and/or supplement the activity of any one of, or combination of, GATA-1, heat shock factor, and/or NFE2, then the onset of administration may not be delayed. However, the dosage amount or frequency of dosing of the one or more antagonists of the disclosure may be set at an amount that would reduce the risk of an unacceptable increase in the hematologic parameters arising upon administration of the one or more antagonists of the disclosure. Alternatively, a therapeutic regimen may be developed for the patient that combines one or more agents of the disclosure that agonize (activate), reduce inhibition of, and/or supplement the activity of any one of, or combination of, GATA-1, heat shock factor, and/or NFE2 with a therapeutic agent that addresses the undesirable level of the hematologic parameter. For example, if the patient has elevated blood pressure, then a therapeutic regimen involving administration of one or more agents of the disclosure that agonize (activate), reduce inhibition of, and/or supplement the activity of any one of, or combination of, GATA-1, heat shock factor, and/or NFE2 of the disclosure and a blood pressure-lowering agent may be designed. For a patient having lower than desired iron stores, a therapeutic regimen of one or more agents of the disclosure that agonize (activate), reduce inhibition of, and/or supplement the activity of any one of, or combination of, GATA-1, heat shock factor, and/or NFE2 and iron supplementation may be developed.

In one embodiment, baseline parameter(s) for one or more hematologic parameters may be established for a patient who is a candidate to be treated with one or more agents of the disclosure that agonize (activate), reduce inhibition of, and/or supplement the activity of any one of, or combination of, GATA-1, heat shock factor, and/or NFE2 of the disclosure and an appropriate dosing regimen established for that patient based on the baseline value(s). Alternatively, established baseline parameters based on a patient's medical history could be used to inform an appropriate antagonist-dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more agents of the disclosure that agonize (activate), reduce inhibition of, and/or supplement the activity of any one of, or combination of, GATA-1, heat shock factor, and/or NFE2 of the disclosure may also be used as the relevant comparative values for monitoring any changes to the hematologic parameters during treatment with the one or more antagonists of the disclosure.

In certain embodiments, one or more hematologic parameters are measured in patients who are being treated with a one or more agents of the disclosure that agonize (activate), reduce inhibition of, and/or supplement the activity of any one of, or combination of, GATA-1, heat shock factor, and/or NFE2 of the disclosure. The hematologic parameters may be used to monitor the patient during treatment and permit adjustment or termination of the dosing with the one or more antagonists of the disclosure or additional dosing with another therapeutic agent. For example, if administration of agents of the disclosure that agonize (activate), reduce inhibition of, and/or supplement the activity of any one of, or combination of, GATA-1, heat shock factor, and/or NFE2 results in an increase in blood pressure, red blood cell level, or hemoglobin level, or a reduction in iron stores, then the dose of the one or more antagonists of the disclosure may be reduced in amount or frequency in order to decrease the effects of the one or more antagonist of the disclosure on the one or more hematologic parameters. If administration of one or more agents of the disclosure that agonize (activate), reduce inhibition of, and/or supplement the activity of any one of, or combination of, GATA-1, heat shock factor, and/or NFE2 results in a change in one or more hematologic parameters that is adverse to the patient, then the dosing of the one or more antagonist of the disclosure may be terminated either temporarily, until the hematologic parameter(s) return to an acceptable level, or permanently. Similarly, if one or more hematologic parameters are not brought within an acceptable range after reducing the dose or frequency of administration of the one or more antagonists of the disclosure, then the dosing may be terminated. As an alternative, or in addition to, reducing or terminating the dosing with the one or more antagonists of the disclosure, the patient may be dosed with an additional therapeutic agent that addresses the undesirable level in the hematologic parameter(s), such as, for example, a blood pressure-lowering agent or an iron supplement. For example, if a patient being treated with one or more agents of the disclosure that agonize (activate), reduce inhibition of, and/or supplement the activity of any one of, or combination of, GATA-1, heat shock factor, and/or NFE2 has elevated blood pressure, then dosing with the one or more antagonists of the disclosure may continue at the same level and a blood pressure-lowering agent is added to the treatment regimen, dosing with the one or more antagonists of the disclosure may be reduced (e.g., in amount and/or frequency) and a blood pressure-lowering agent is added to the treatment regimen, or dosing with the one or more antagonists of the disclosure may be terminated and the patient may be treated with a blood pressure-lowering agent.

5. Pharmaceutical Compositions

In certain embodiments, one or more agents of the disclosure that agonize (activate), reduce inhibition of, and/or supplement the activity of any one of, or combination of, GATA-1, heat shock factor, and/or NFE2 can be administered alone or as a component of a pharmaceutical formulation (therapeutic composition or pharmaceutical composition). A pharmaceutical formation refers to a preparation which is in such form as to permit the biological activity of an active ingredient contained therein to be effective and which contains no additional components which are unacceptably toxic to a subject to which the formulation would be administered. The subject compounds may be formulated for administration in any convenient way for use in human or veterinary medicine. For example, one or more agents of the disclosure that agonize (activate), reduce inhibition of, and/or supplement the activity of any one of, or combination of, GATA-1, heat shock factor, and/or NFE2 may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, or preservative. In general, pharmaceutical formulations for use in the present disclosure are in a pyrogen-free, physiologically acceptable form when administered to a subject. Therapeutically useful agents other than the antagonist of the disclosure, which may optionally be included in the formulation as described above, may be administered in combination with the subject compounds in the methods of the present disclosure.

Typically, compounds will be administered parenterally [e.g., by intravenous (I.V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure that agonize (activate), reduce inhibition of, and/or supplement the activity of any one of, or combination of, GATA-1, heat shock factor, and/or NFE2 of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In certain embodiments, a therapeutic method of the present disclosure includes administering the formulation systemically, or locally, from an implant or device. Further, the composition may be encapsulated or injected in a form for delivery to a target tissue site (e.g., bone marrow or muscle). In certain embodiments, compositions of the present disclosure may include a matrix capable of delivering one or more agents of the disclosure that agonize (activate), reduce inhibition of, and/or supplement the activity of any one of, or combination of, GATA-1, heat shock factor, and/or NFE2 to a target tissue site (e.g., bone marrow or muscle), providing a structure for the developing tissue and optimally capable of being resorbed into the body. For example, the matrix may provide slow release of one or more agents of the disclosure that agonize (activate), reduce inhibition of, and/or supplement the activity of any one of, or combination of, GATA-1, heat shock factor, and/or NFE2. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, formulations (compositions) of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the present formulations (compositions) may include pharmaceutically acceptable emulsions, microemulsions, solutions, suspensions, syrups, and elixirs. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more agents of the disclosure that agonize (activate), reduce inhibition of, and/or supplement the activity of any one of, or combination of, GATA-1, heat shock factor, and/or NFE2. The various factors include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more agents of the disclosure that agonize (activate), reduce inhibition of, and/or supplement the activity of any one of, or combination of, GATA-1, heat shock factor, and/or NFE2. Such therapy would achieve its therapeutic effect by introduction of the antagonist sequences into cells or tissues having one or more of the disorders as listed above. Delivery of the antagonist sequences can be achieved, for example, by using a recombinant expression vector such as a chimeric virus or a colloidal dispersion system. Preferred therapeutic delivery of one or more agents of the disclosure that agonize (activate), reduce inhibition of, and/or supplement the activity of any one of, or combination of, GATA-1, heat shock factor, and/or NFE2 is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous sarcoma virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more agents of the disclosure that agonize (activate), reduce inhibition of, and/or supplement the activity of any one of, or combination of, GATA-1, heat shock factor, and/or NFE2.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more agents of the disclosure that agonize (activate), reduce inhibition of, and/or supplement the activity of any one of, or combination of, GATA-1, heat shock factor, and/or NFE2 is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form [see, e.g., Fraley, et al. (1981) Trends Biochem. Sci., 6:77]. Methods for efficient gene transfer using a liposome vehicle are known in the art [see, e.g., Mannino, et al. (1988) Biotechniques, 6:682, 1988].

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example, a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1: ActRIIa-Fc Fusion Proteins

Applicants constructed a soluble ActRIIA fusion protein that has the extracellular domain of human ActRIIa fused to a human or mouse Fc domain with a minimal linker in between. The constructs are referred to as ActRIIA-hFc and ActRIIA-mFc, respectively.

ActRIIA-hFc is shown below as purified from CHO cell lines (SEQ ID NO: 32):

```
ILGRSETQECLFFNANWEKDRTNQTGVEPCYGDKDKRRHCFATWK
NISGSIEIVKQGCWLDDINCYDRTDCVEKKDSPEVYFCCCEGNMCNEKFS
YFPEMEVTQPTSNPVTPKPPTGGGTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPVPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK
```

The ActRIIA-hFc and ActRIIA-mFc proteins were expressed in CHO cell lines. Three different leader sequences were considered:
(i) Honey bee mellitin (HBML): MKFLVNVALVFMV-VYISYIYA (SEQ ID NO: 33)
(ii) Tissue plasminogen activator (TPA): MDAMKR-GLCCVLLLCGAVFVSP (SEQ ID NO: 34)
(iii) Native: MGAAAKLAFAVFLISCSSGA (SEQ ID NO: 35).

The selected form employs the TPA leader and has the following unprocessed amino acid sequence:

```
                                        (SEQ ID NO: 36)
MDAMKRGLCCVLLLCGAVFVSPGAAILGRSETQECLFFNANWEKD
RTNQTGVEPCYGDKDKRRHCFATWKNISGSIEIVKQGCWLDDINCYDRTD
CVEKKDSPEVYFCCCEGNMCNEKFSYFPEMEVTQPTSNPVTPKPPTGGGT
HTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKV
SNKALPVPIEKTISKAKGQPREPQVYTLPPSREEMTKNQVSLTCLVKGFY
PSDIAVEWESNGQPENNYKTTPPVLDSDGSFFLYSKLTVDKSRWQQGNVF
SCSVMHEALHNHYTQKSLSLSPGK
```

This polypeptide is encoded by the following nucleic acid sequence:

```
                                        (SEQ ID NO: 37)
ATGGATGCAATGAAGAGAGGGCTCTGCTGTGTGCTGCTGCTGTGT
GGAGCAGTCTTCGTTTCGCCCGGCGCCGCTATACTTGGTAGATCAGAAAC
TCAGGAGTGTCTTTTTTTAATGCTAATTGGGAAAAAGACAGAACCAATCA
AACTGGTGTTGAACCGTGTTATGGTGACAAAGATAAACGGCGGCATTGTT
TTGCTACCTGGAAGAATATTTCTGGTTCCATTGAATAGTGAAACAAGGTT
GTTGGCTGGATGATATCAACTGCTATGACAGGACTGATTGTGTAGAAAAA
AAAGACAGCCCTGAAGTATATTTCTGTTGCTGTGAGGGCAATATGTGTAA
TGAAAAGTTTTCTTATTTTCCGGAGATGGAAGTCACACAGCCCACTTCAA
ATCCAGTTACACCTAAGCCACCCACCGGTGGTGGAACTCACACATGCCCA
CCGTGCCCAGCACCTGAACTCCTGGGGGGACCGTCAGTCTTCCTCTTCCC
CCCAAAACCCAAGGACACCCTCATGATCTCCCGGACCCCTGAGGTCACAT
GCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGA
GCAGTACAACAGCACGTACCGTGTGGTCAGCGTCCTCACCGTCCTGCACC
AGGACTGGCTGAATGGCAAGGAGTACAAGTGCAAGGTCTCCAACAAAGCC
CTCCCAGTCCCCATCGAGAAAACCATCTCCAAAGCCAAAGGGCAGCCCCG
AGAACCACAGGTGTACACCCTGCCCCCATCCCGGGAGGAGATGACCAAGA
ACCAGGTCAGCCTGACCTGCCTGGTCAAAGGCTTCTATCCCAGCGACATC
GCCGTGGAGTGGGAGAGCAATGGGCAGCCGGAGAACAACTACAAGACCAC
GCCTCCCGTGCTGGACTCCGACGGCTCCTTCTTCCTCTATAGCAAGCTCA
CCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTC
TCCGGGTAAATGAGAATTC
```

Figure 3:
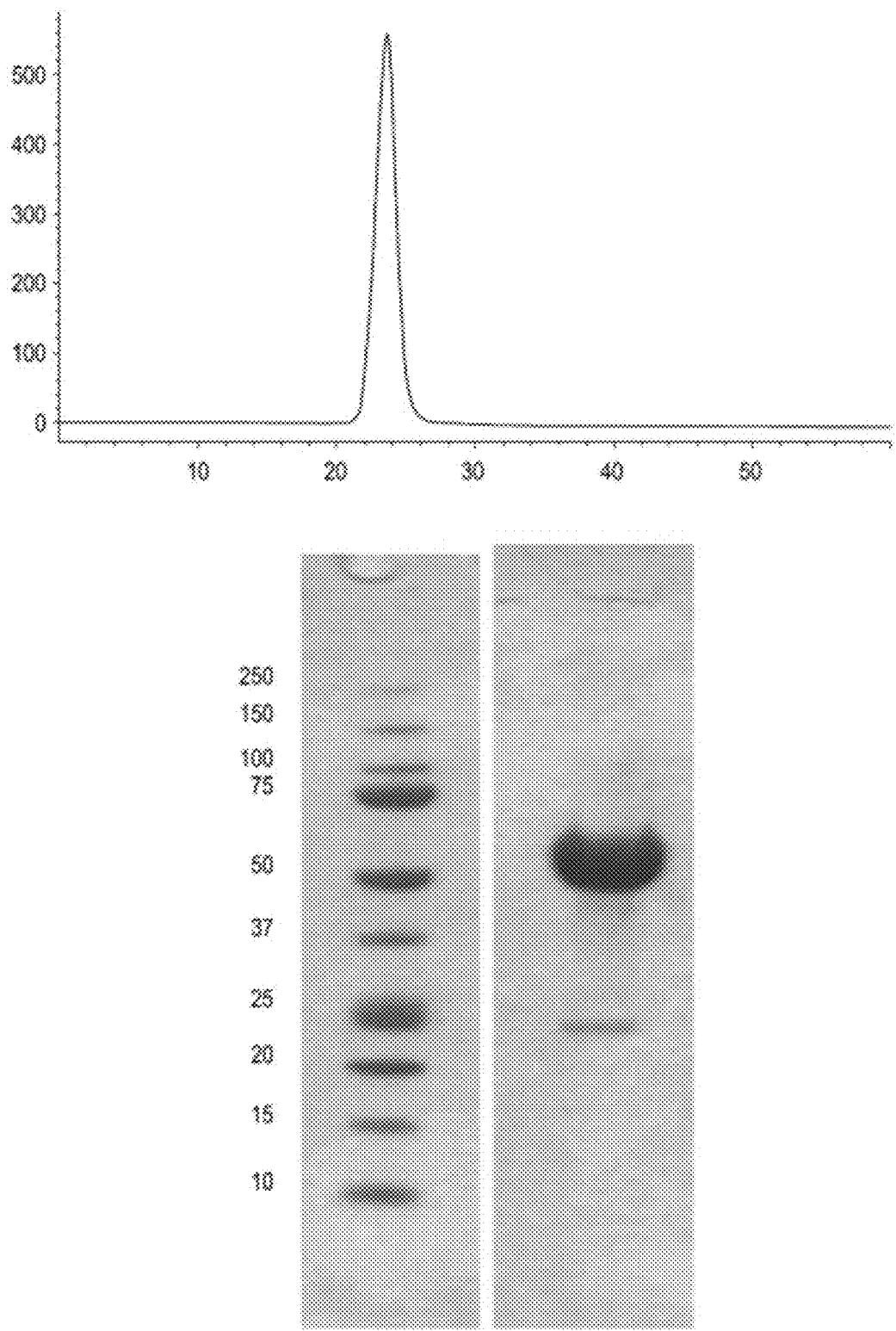
FIG. 3 shows the purification of ActRIIA-hFc expressed in CHO cells. The protein purifies as a single, well-defined peak as visualized by sizing column (top panel) and Coomassie stained SDS-PAGE (bottom panel) (left lane: molecular weight standards; right lane: ActRIIA-hFc).

Both ActRIIA-hFc and ActRIIA-mFc were remarkably amenable to recombinant expression. As shown in FIG. 3, the protein was purified as a single, well-defined peak of protein. N-terminal sequencing revealed a single sequence of -ILGRSETQE (SEQ ID NO: 38). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE.

ActRIIA-hFc and ActRIIA-mFc showed a high affinity for ligands. GDF-11 or activin A were immobilized on a Biacore™ CM5 chip using standard amine-coupling procedure. ActRIIA-hFc and ActRIIA-mFc proteins were loaded onto the system, and binding was measured. ActRIIA-hFc bound to activin with a dissociation constant ($K_D$) of $5 \times 10^{-12}$ and bound to GDF11 with a $K_D$ of $9.96 \times 10^{-9}$. See FIG. 4. ActRIIA-mFc behaved similarly.

The ActRIIA-hFc was very stable in pharmacokinetic studies. Rats were dosed with 1 mg/kg, 3 mg/kg, or 10 mg/kg of ActRIIA-hFc protein, and plasma levels of the protein were measured at 24, 48, 72, 144 and 168 hours. In a separate study, rats were dosed at 1 mg/kg, 10 mg/kg, or 30 mg/kg. In rats, ActRIIA-hFc had an 11-14 day serum half-life, and circulating levels of the drug were quite high after two weeks (11 µg/ml, 110 µg/ml, or 304 µg/ml for initial administrations of 1 mg/kg, 10 mg/kg, or 30 mg/kg, respectively.) In cynomolgus monkeys, the plasma half-life was substantially greater than 14 days, and circulating levels of the drug were 25 µg/ml, 304 µg/ml, or 1440 µg/ml for initial administrations of 1 mg/kg, 10 mg/kg, or 30 mg/kg, respectively.

Example 2: Characterization of an ActRIIA-hFc Protein

ActRIIA-hFc fusion protein was expressed in stably transfected CHO-DUKX B11 cells from a pAID4 vector (SV40 ori/enhancer, CMV promoter), using a tissue plasminogen leader sequence of SEQ ID NO: 34. The protein, purified as described above in Example 1, had a sequence of SEQ ID NO: 32. The Fc portion is a human IgG1 Fc sequence, as shown in SEQ ID NO: 32. Protein analysis reveals that the ActRIIA-hFc fusion protein is formed as a homodimer with disulfide bonding.

The CHO-cell-expressed material has a higher affinity for activin B ligand than that reported for an ActRIIa-hFc fusion protein expressed in human 293 cells [see, del Re et al. (2004) J Biol Chem. 279(51):53126-53135]. Additionally, the use of the TPA leader sequence provided greater production than other leader sequences and, unlike ActRIIA-Fc expressed with a native leader, provided a highly pure N-terminal sequence. Use of the native leader sequence resulted in two major species of ActRIIA-Fc, each having a different N-terminal sequence.

Example 3: Alternative ActRIIA-Fc Proteins

A variety of ActRIIA variants that may be used according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIA. The sequence for such a construct is presented below (Fc portion underlined) (SEQ ID NO: 39):

ILGRSETQECLFFNANWEKDRTNQTGVEPCYGDKDKRRHCFATWKNISGS
IEIVKQGCWLDDINCYDRTDCVEKKDSPEVYFCCCEGNMCNEKFSYFPEM
TGGGTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPVPIEKTISKAKGQPREPQVYTLPPSREEMTKNQVSLTCL
VKGFYPSDIAVEWESNGQPENNYKTTPPVLDSDGSFFLYSKLTVDKSRWQ
QGNVFSCSVMHEALHNHYTQKSLSLSPGK

Example 4: Generation of ActRIIB-Fc Fusion Proteins

Applicants constructed a soluble ActRIIB fusion protein that has the extracellular domain of human ActRIIB fused to a human or mouse Fc domain with a minimal linker (three glycine amino acids) in between. The constructs are referred to as ActRIIB-hFc and ActRIIB-mFc, respectively.

ActRIIB-hFc is shown below as purified from CHO cell lines (SEQ ID NO: 40):

GRGEAETRECIYYNANWELERTNQSGLERCEGEQDKRLHCYASWRNSSGT
IELVKKGCWLDDFNCYDRQECVATEENPQVYFCCCEGNFCNERFTHLPEA
GGPEVTYEPPPTAPTGGGTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPVPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

The ActRIIB-hFc and ActRIIB-mFc proteins were expressed in CHO cell lines. Three different leader sequences were considered: (i) Honey bee mellitin (HBML), ii) Tissue plasminogen activator (TPA), and (iii) Native: MGAAAKLAFAVFLISCSSGA (SEQ ID NO: 77).

The selected form employs the TPA leader and has the following unprocessed amino acid sequence (SEQ ID NO: 41):

MDAMKRGLCCVLLLCGAVFVSPGASGRGEAETRECIYYNANWELERTNQS
GLERCEGEQDKRLHCYASWRNSSGTIELVKKGCWLDDFNCYDRQECVATE
ENPQVYFCCCEGNFCNERFTHLPEAGGPEVTYEPPPTAPTGGGTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
VPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMH
EALHNHYTQKSLSLSPGK

This polypeptide is encoded by the following nucleic acid sequence (SEQ ID NO: 42):

```
A TGGATGCAAT GAAGAGAGGG CTCTGCTGTG TGCTGCTGCT
GTGTGGAGCA GTCTTCGTTT CGCCCGGCGC CTCTGGGCGT
GGGGAGGCTG AGACACGGGA GTGCATCTAC TACAACGCCA
ACTGGGAGCT GGAGCGCACC AACCAGAGCG GCCTGGAGCG
CTGCGAAGGC GAGCAGGACA AGCGGCTGCA CTGCTACGCC
TCCTGGCGCA ACAGCTCTGG CACCATCGAG CTCGTGAAGA
AGGGCTGCTG GCTAGATGAC TTCAACTGCT ACGATAGGCA
GGAGTGTGTG GCCACTGAGG AGAACCCCCA GGTGTACTTC
TGCTGCTGTG AAGGCAACTT CTGCAACGAG CGCTTCACTC
ATTTGCCAGA GGCTGGGGGC CCGGAAGTCA CGTACGAGCC
ACCCCCGACA GCCCCCACCG GTGGTGGAAC TCACACATGC
CCACCGTGCC CAGCACCTGA ACTCCTGGGG GGACCGTCAG
TCTTCCTCTT CCCCCCAAAA CCCAAGGACA CCCTCATGAT
CTCCCGGACC CCTGAGGTCA CATGCGTGGT GGTGGACGTG
AGCCACGAAG ACCCTGAGGT CAAGTTCAAC TGGTACGTGG
ACGGCGTGGA GGTGCATAAT GCCAAGACAA AGCCGCGGGA
GGAGCAGTAC AACAGCACGT ACCGTGTGGT CAGCGTCCTC
ACCGTCCTGC ACCAGGACTG GCTGAATGGC AAGGAGTACA
AGTGCAAGGT CTCCAACAAA GCCCTCCCAG TCCCCATCGA
GAAAACCATC TCCAAAGCCA AAGGGCAGCC CCGAGAACCA
CAGGTGTACA CCCTGCCCCC ATCCCGGGAG GAGATGACCA
AGAACCAGGT CAGCCTGACC TGCCTGGTCA AAGGCTTCTA
TCCCAGCGAC ATCGCCGTGG AGTGGGAGAG CAATGGGCAG
CCGGAGAACA ACTACAAGAC CACGCCTCCC GTGCTGGACT
CCGACGGCTC CTTCTTCCTC TATAGCAAGC TCACCGTGGA
CAAGAGCAGG TGGCAGCAGG GGAACGTCTT CTCATGCTCC
GTGATGCATG AGGCTCTGCA CAACCACTAC ACGCAGAAGA
GCCTCTCCCT GTCTCCGGGT AAATGA
```

N-terminal sequencing of the CHO-cell-produced material revealed a major sequence of-GRGEAE (SEQ ID NO: 43). Notably, other constructs reported in the literature begin with an-SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Applicants generated a series of mutations in the extracellular domain of ActRIIB and produced these mutant proteins as soluble fusion proteins between extracellular ActRIIB and an Fc domain. The background ActRIIB-Fc fusion has the sequence of SEQ ID NO: 40.

Various mutations, including N- and C-terminal truncations, were introduced into the background ActRIIB-Fc protein. Based on the data presented herien, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into E. coli DH5 alpha, colonies were picked and DNAs were isolated. For murine constructs (mFc), a murine IgG2a was substituted for the human IgG1. Sequences of all mutants were verified. All of the mutants were produced in HEK293T cells by transient transfection. In summary, in a 500 ml spinner, HEK293T cells were set up at $6\times10^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, a protein A column, and eluted with low pH (3.0)glycine buffer. After neutralization, these were dialyzed against PBS.

Mutants were also produced in CHO cells by similar methodology. Mutants were tested in binding assays and/or bioassays described in WO 2008/097541 and WO 2006/012627 incorporated by reference herein. In some instances, assays were performed with conditioned medium rather than purified proteins. Additional variations of ActRIIB are described in U.S. Pat. No. 7,842,663.

Applicant generated an ActRIIB(25-131)-hFc fusion protein, which comprises the human ActRIIB extracellular domain with N-terminal and C-terminal truncations (residues 25-131 of the native protein SEQ ID NO: 1) fused N-terminally with a TPA leader sequence substituted for the native ActRIIB leader and C-terminally with a human Fc domain via a minimal linker (three glycine residues) (FIG. 15). A nucleotide sequence encoding this fusion protein is shown in FIG. 16. Applicants modified the codons and found a variant nucleic acid encoding the ActRIIB(25-131)-hFc protein that provided substantial improvement in the expression levels of initial transformants (FIG. 17).

The mature protein has an amino acid sequence as follows (N-terminus confirmed by N-terminal sequencing)(SEQ ID NO: 78):

```
ETRECIYYNA NWELERTNQS GLERCEGEQD KRLHCYASWR

NSSGTIELVK KGCWLDDFNC YDRQECVATE ENPQVYFCCC

EGNFCNERFT HLPEAGGPEV TYEPPPTGGG THTCPPCPAP

ELLGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
Amino acids 1-107 are derived from ActRIIB.
```

The expressed molecule was purified using a series of column chromatography steps, including for example, three or more of the following, in any order: Protein A chromatography, Q sepharose chromatography, phenylsepharose chromatography, size exclusion chromatography and cation exchange chromatography. The purification could be completed with viral filtration and buffer exchange.

Affinities of several ligands for ActRIIB(25-131)-hFc and its full-length counterpart ActRIIB(20-134)-hFc were evaluated in vitro with a Biacore™ instrument, and the results are summarized in the table below. Kd values were obtained by steady-state affinity fit due to very rapid association and dissociation of the complex, which prevented accurate determination of $k_{on}$ and $k_{off}$. ActRIIB(25-131)-hFc bound activin A, activin B, and GDF11 with high affinity.

Ligand Affinities of ActRIIB-hFc Forms:

| Fusion Construct | Activin A (e−11) | Activin B (e−11) | GDF11 (e−11) |
|---|---|---|---|
| ActRIIB(20-134)-hFc | 1.6 | 1.2 | 3.6 |
| ActRIIB(25-131)-hFc | 1.8 | 1.2 | 3.1 |

Example 5: Generation of a GDF Trap

Applicants constructed a GDF trap as follows. A polypeptide having a modified extracellular domain of ActRIIB (amino acids 20-134 of SEQ ID NO: 1 with an L79D substitution) with greatly reduced activin A binding relative to GDF11 and/or myostatin (as a consequence of a leucine-to-aspartate substitution at position 79 in SEQ ID NO:1) was fused to a human or mouse Fc domain with a minimal linker (three glycine amino acids) in between. The constructs are referred to as ActRIIB(L79D 20-134)-hFc and ActRIIB (L79D 20-134)-mFc, respectively. Alternative forms with a glutamate rather than an aspartate at position 79 performed similarly (L79E). Alternative forms with an alanine rather than a valine at position 226 with respect to SEQ ID NO: 44, below were also generated and performed equivalently in all respects tested. The aspartate at position 79 (relative to SEQ ID NO: 1, or position 60 relative to SEQ ID NO: 44) is indicated with doubleunderlining below. The valine at position 226 relative to SEQ ID NO: 44 is also indicated by doubleunderlining below.

The GDF trap ActRIIB(L79D 20-134)-hFc is shown below as purified from CHO cell lines (SEQ ID NO: 44).

(SEQ ID NO: 44)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEVTYEPPPTAPTGGGTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPVPIEKTISKAKGQPREPQVYTLPPS

REEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

The ActRIIB-derived portion of the GDF trap has an amino acid sequence set forth below (SEQ ID NO: 45), and that portion could be used as a monomer or as a non-Fc fusion protein as a monomer, dimer, or greater-order complex.

(SEQ ID NO: 45)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEVTYEPPPTAPT

The GDF trap protein was expressed in CHO cell lines. Three different leader sequences were considered:
(i) Honey bee melittin (HBML), (ii) Tissue plasminogen activator (TPA), and (iii) Native.
The selected form employs the TPA leader and has the following unprocessed amino acid sequence:

(SEQ ID NO: 46)
MDAMKRGLCCVLLLCGAVFVSPGASGRGEAETRECIYYNANWELERTNQS

GLERCEGEQDKRLHCYASWRNSSGTIELVKKGCWDDDFNCYDRQECVATE

ENPQVYFCCCEGNFCNERFTHLPEAGGPEVTYEPPPTAPTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

This polypeptide is encoded by the following nucleic acid sequence (SEQ ID NO: 47):

```
A TGGATGCAAT GAAGAGAGGG CTCTGCTGTG TGCTGCTGCT

GTGTGGAGCA GTCTTCGTTT CGCCCGGCGC CTCTGGGCGT

GGGGAGGCTG AGACACGGGA GTGCATCTAC TACAACGCCA

ACTGGGAGCT GGAGCGCACC AACCAGAGCG GCCTGGAGCG

CTGCGAAGGC GAGCAGGACA AGCGGCTGCA CTGCTACGCC

TCCTGGCGCA ACAGCTCTGG CACCATCGAG CTCGTGAAGA

AGGGCTGCTG GGACGATGAC TTCAACTGCT ACGATAGGCA

GGAGTGTGTG GCCACTGAGG AGAACCCCCA GGTGTACTTC
```
-continued
```
TGCTGCTGTG AAGGCAACTT CTGCAACGAG CGCTTCACTC

ATTTGCCAGA GGCTGGGGGC CCGGAAGTCA CGTACGAGCC

ACCCCCGACA GCCCCCACCG GTGGTGGAAC TCACACATGC

CCACCGTGCC CAGCACCTGA ACTCCTGGGG GGACCGTCAG

TCTTCCTCTT CCCCCCAAAA CCCAAGGACA CCCTCATGAT

CTCCCGGACC CCTGAGGTCA CATGCGTGGT GGTGGACGTG

AGCCACGAAG ACCCTGAGGT CAAGTTCAAC TGGTACGTGG

ACGGCGTGGA GGTGCATAAT GCCAAGACAA AGCCGCGGGA

GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG TCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA
```

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. In an example of a purification scheme, the cell culture medium is passed over a protein A column, washed in 150 mM Tris/NaCl (pH 8.0), then washed in 50 mM Tris/NaCl (pH 8.0) and eluted with 0.1 M glycine, pH 3.0. The low pH eluate is kept at room temperature for 30 minutes as a viral clearance step. The eluate is then neutralized and passed over a Q-sepharose ion-exchange column and washed in 50 mM Tris pH 8.0, 50 mM NaCl, and eluted in 50 mM Tris pH 8.0, with an NaCl concentration between 150 mM and 300 mM. The eluate is then changed into 50 mM Tris pH 8.0, 1.1 M ammonium sulfate and passed over a phenyl sepharose column, washed, and eluted in 50 mM Tris pH 8.0 with ammonium sulfate between 150 and 300 mM. The eluate is dialyzed and filtered for use.

Additional GDF traps (ActRIIB-Fc fusion proteins modified so as to reduce the ratio of activin A binding relative to myostatin or GDF11 binding) are described in WO 2008/097541 and WO 2006/012627, incorporated by reference herein.

Example 6: Bioassay for GDF-11- and Activin-Mediated Signaling

An A-204 reporter gene assay was used to evaluate the effects of ActRIIB-Fc proteins and GDF traps on signaling by GDF-11 and activin A. Cell line: human rhabdomyosarcoma (derived from muscle). Reporter vector: pGL3

(CAGA)12 (described in Dennler et al, 1998, EMBO 17: 3091-3100). The CAGA12 motif is present in TGF-beta responsive genes (e.g., PAI-1 gene), so this vector is of general use for factors signaling through SMAD2 and 3.

Day 1: Split A-204 cells into 48-well plate.

Day 2: A-204 cells transfected with 10 ug pGL3(CAGA) 12 or pGL3(CAGA)12(10 ug)+pRLCMV (1 µg) and Fugene.

Day 3: Add factors (diluted into medium+0.1% BSA). Inhibitors need to be preincubated with factors for 1 hr before adding to cells. Six hrs later, cells were rinsed with PBS and lysed.

This is followed by a luciferase assay. In the absence of any inhibitors, activin A showed 10-fold stimulation of reporter gene expression and an ED50~2 ng/ml. GDF-11: 16 fold stimulation, ED50: ~1.5 ng/ml.

ActRIIB(20-134) is a potent inhibitor of activin A, GDF-8, and GDF-11 activity in this assay. As described below, ActRIIB variants were also tested in this assay.

Example 7: ActRIIB-Fc Variants, Cell-Based Activity

Activity of ActRIIB-Fc proteins and GDF traps was tested in a cell-based assay as described above. Results are summarized in the table below. Some variants were tested in different C-terminal truncation constructs. As discussed above, truncations of five or fifteen amino acids caused reduction in activity. The GDF traps (L79D and L79E variants) showed substantial loss of activin A inhibition while retaining almost wild-type inhibition of GDF-11.

Soluble ActRIIB-Fc Binding to GDF11 and Activin A:

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 | 20-134 | +++ (approx. $10^{-8}$M $K_I$) | +++ (approx. $10^{-8}$M $K_I$) |
| A64 | 20-134 | + (approx. $10^{-6}$M $K_I$) | + (approx. $10^{-6}$M $K_I$) |
| R64 | 20-129 | +++ | +++ |
| R64 K74A | 20-134 | ++++ | ++++ |
| R64 A24N | 20-134 | +++ | +++ |
| R64 A24N | 20-119 | ++ | ++ |
| R64 A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |
| R64K | 20-134 | +++ | +++ |
| R64K | 20-129 | +++ | +++ |
| R64 P129S P130A | 20-134 | +++ | +++ |
| R64N | 20-134 | + | + |

Poor activity (roughly 1 × $10^{-6}$ $K_I$) Moderate activity (roughly 1 × $10^{-7}$ $K_I$)
+++ Good (wild-type) activity (roughly 1 × $10^{-8}$ $K_I$)
++++ Greater than wild-type activity Several variants have been assessed for serum half-life in rats. ActRIIB(20-134)-Fc has a serum half-life of approximately 70 hours. ActRIIB(A24N 20-134)-Fc variant has activity in the cell-based assay (above) and that is equivalent to the wild-type molecule. The A24N variant, and any of the other variants tested above, may be combined with the GDF trap molecules, such as the L79D or L79E variants.

Example 8: GDF-11 and Activin A Binding

Binding of certain ActRIIB-Fc proteins and GDF traps to ligands was tested in a Biacore assay.

The ActRIIB-Fc variants or wild-type protein were captured onto the system using an anti-hFc antibody. Ligands were injected and flowed over the captured receptor proteins. Results are summarized in the tables below.

Ligand-Binding Specificity IIB Variants.

| Protein | Kon (1/Ms) | Koff (1/s) | KD (M) |
|---|---|---|---|
| | GDF11 | | |
| ActRIIB(20-134)-hFc | 1.34e–6 | 1.13e–4 | 8.42e–11 |
| ActRIIB(A24N 20-134)-hFc | 1.21e–6 | 6.35e–5 | 5.19e–11 |
| ActRIIB(L79D 20-134)-hFc | 6.7e–5 | 4.39e–4 | 6.55e–10 |
| ActRIIB(L79E 20-134)-hFc | 3.8e–5 | 2.74e–4 | 7.16e–10 |
| ActRIIB(R64K 20-134)-hFc | 6.77e–5 | 2.41e–4 | 3.56e–11 |
| | GDF8 | | |
| ActRIIB(20-134)-hFc | 3.69e–5 | 3.45e–5 | 9.35e–11 |
| ActRIIB(A24N 20-134)-hFc | | | |
| ActRIIB(L79D 20-134)-hFc | 3.85e–5 | 8.3e–4 | 2.15e–9 |
| ActRIIB(L79E 20-134)-hFc | 3.74e–5 | 9e–4 | 2.41e–9 |
| ActRIIB(R64K 20-134)-hFc | 2.25e–5 | 4.71e–5 | 2.1e–10 |
| ActRIIB(R64K 20-129)-hFc | 9.74e–5 | 2.09e–4 | 2.15e–9 |
| ActRIIB(P129S, P130R 20-134)-hFc | 1.08e–5 | 1.8e–4 | 1.67e–9 |
| ActRIIB(K74A 20-134)-hFc | 2.8e–5 | 2.03e–5 | 7.18e–11 |
| | Activin A | | |
| ActRIIB(20-134)-hFc | 5.94e6 | 1.59e–4 | 2.68e–11 |
| ActRIIB(A24N 20-134)-hFc | 3.34e6 | 3.46e–4 | 1.04e–10 |
| ActRIIB(L79D 20-134)-hFc | | | Low binding |
| ActRIIB(L79E 20-134)-hFc | | | Low binding |
| ActRIIB(R64K 20-134)-hFc | 6.82e6 | 3.25e–4 | 4.76e–11 |
| ActRIIB(R64K 20-129)-hFc | 7.46e6 | 6.28e–4 | 8.41e–11 |
| ActRIIB(P129S, P130R 20-134)-hFc | 5.02e6 | 4.17e–4 | 8.31e–11 |

These data obtained in a cell-free assay confirm the cell-based assay data, demonstrating that the L79D or L79E molecule retains myostatin and GDF11 binding but shows markedly decreased (non-quantifiable) binding to activin A.

Other variants have been generated and tested, as reported in WO2006/012627 (incorporated herein by reference in its entirety). See, e.g., pp. 59-60, using ligands coupled to the device and flowing receptor over the coupled ligands. Notably, K74Y, K74F, K74I (and presumably other hydrophobic substitutions at K74, such as K74L), and D80I, cause a decrease in the ratio of activin A (ActA) binding to GDF11 binding, relative to the wild-type K74 molecule. A table of data with respect to these variants is reproduced below:

Soluble ActRIIB-Fc Variants Binding to GDF11 and Activin a (Biacore™ Assay)

| ActRIIB | ActA | GDF11 |
|---|---|---|
| WT (64A) | KD = 1.8e–7M (+) | KD = 2.6e–7M (+) |
| WT (64R) | na | KD = 8.6e–8M (+++) |
| +15tail | KD ~2.6e–8M (+++) | KD = 1.9e–8M (++++) |
| E37A | * | * |
| R40A | – | – |
| D54A | – | * |
| K55A | ++ | * |
| R56A | * | * |
| K74A | KD = 4.35e–9M +++++ | KD = 5.3e–9M +++++ |

-continued

| ActRIIB | ActA | GDF11 |
|---|---|---|
| K74Y | * | -- |
| K74F | * | -- |
| K74I | * | -- |
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | -- |
| F82A | ++ | - |

\* No observed binding
-- <⅓ WT binding
- ~½ <2x increased binding
+++ ~5x increased binding
++++ ~10x increased binding
+++++ ~40x increased binding

Example 9: Generation of a GDF Trap with Truncated ActRIIB Extracellular Domain A GDF trap with truncated ActRIIB extracellular domain, referred to as ActRIIB(L79D 25-131)-hFc, was generated by N-terminal fusion of TPA leader to truncated extracellular domain (residues 25-131 in SEQ ID NO:1) containing a leucine-to-aspartate substitution (at residue 79 in SEQ ID NO:1) and C-terminal fusion of human Fc domain with minimal linker (three glycine residues) (FIG. 7, SEQ ID NO: 61). One nucleotide sequence encoding this fusion protein is shown in FIG. 8 (SEQ ID NO: 62), and an alternative nucleotide sequence encoding exactly the same fusion protein is shown in FIG. 11 (SEQ ID NO: 66).

Example 10: Selective Ligand Binding by GDF Trap with Double-Truncated ActRIIB Extracelluar Domain The affinity of GDF traps and other ActRIIB-hFc proteins for several ligands was evaluated in vitro with a Biacore™ instrument. Results are summarized in the table below. Kd values were obtained by steady-state affinity fit due to the very rapid association and dissociation of the complex, which prevented accurate determination of $k_{on}$ and $k_{off}$.

Ligand Selectivity of ActRIIB-hFc Variants:

| Fusion Construct | Activin A (Kd e-11) | Activin B (Kd e-11) | GDF11 (Kd e-11) |
|---|---|---|---|
| ActRIIB(L79 20-134)-hFc | 1.6 | 1.2 | 3.6 |
| ActRIIB(L79D 20-134)-hFc | 1350.0 | 78.8 | 12.3 |
| ActRIIB(L79 25-131)-hFc | 1.8 | 1.2 | 3.1 |
| ActRIIB(L79D 25-131)-hFc | 2290.0 | 62.1 | 7.4 |

The GDF trap with a truncated extracellular domain, ActRIIB(L79D 25-131)-hFc, equaled or surpassed the ligand selectivity displayed by the longer variant, ActRIIB (L79D 20-134)-hFc, with pronounced loss of activin A binding, partial loss of activin B binding, and nearly full retention of GDF11 binding compared to ActRIIB-hFc counterparts lacking the L79D substitution. Note that truncation alone (without L79D substitution) did not alter selectivity among the ligands displayed here [compare ActRIIB (L79 25-131)-hFc with ActRIIB(L79 20-134)-hFc].

ActRIIB(L79D 25-131)-hFc also retains strong to intermediate binding to the Smad 2/3 signaling ligand GDF8 and the Smad 1/5/8 ligands BMP6 and BMP10.

Example 11: GDF Trap Derived from ActRIIB5

Others have reported an alternate, soluble form of ActRIIB (designated ActRIIB5), in which exon 4, including the ActRIIB transmembrane domain, has been replaced by a different C-terminal sequence (see, e.g., WO 2007/053775).

The sequence of native human ActRIIB5 without its leader is as follows:

(SEQ ID NO: 48)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEGPWASTTIPSGGPEATAAAGDQGSGALWLCLEGPAHE

An leucine-to-aspartate substitution, or other acidic substitutions, may be performed at native position 79 (underlined) as described to construct the variant ActRIIB5(L79D), which has the following sequence:

(SEQ ID NO: 49)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE

This variant may be connected to human Fc (double underline) with a TGGG linker (SEQ ID NO: 23) (single underline) to generate a human ActRIIB5(L79D)-hFc fusion protein with the following sequence:

(SEQ ID NO: 50)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE<u>TGGG</u><u>THTCP</u>

<u>PCPAPELLGGPSVFLFPPKPKDTLMISRTPEVTCVVVDVSHEDPEVKFNW</u>

<u>YVDGVEVHNAKTKPREEQYNSTYRVVSVLTVLHQDWLNGKEYKCKVSNKA</u>

<u>LPAPIEKTISKAKGQPREPQVYTLPPSREEMTKNQVSLTCLVKGFYPSDI</u>

<u>AVEWESNGQPENNYKTTPPVLDSDGSFFLYSKLTVDKSRWQQGNVFSCSV</u>

<u>MHEALHNHYTQKSLSLSPGK</u>.

This construct may be expressed in CHO cells.

Example 12: Inhibition of Smad Signaling in a Murine β-Thalassemia Model Result in Upregulation of GATA-1, NFE2 and Heat Shock Factor Protein It has been previously reported that Smad2/3 signaling (of the TGFβ superfamily) is elevated in myelodysplastic syndromes (MDS) and β-thalassemia, diseases that are characterized by ineffective erythropoiesis (Suragani et al., 2014, Nat Med, 20(4):408-14). Smad pathway inhibition using ActRIIB(L79D 25-131)-mFca modified activin receptor type IIB ligand trap, decreased ineffective erythropoiesis and alleviated disease pathology in a murine model of β-thalassemia. In order to better understand the therapeutic effects behind Smad pathway inhibition in a representative model of ineffective erythropoiesis, the molecular mechanism of ActRIIB(L79D 25-131)-mFc therapy in the murine model of β-thalassemia was examined.

β-thalassemic mice (Hbb$^{th3/+}$) were administered a single bolus of vehicle (VEH) or ActRIIB(L79D 25-131)-mFc (30 mg/kg, i.p). At 16 hours following administration the splenic basophilic erythroblasts (CD71$^+$Ter119$^+$FSC$^{high}$) were sorted by flow cytometry and RNA was isolated and subjected to genome wide transcriptome profiling using RNA sequencing analysis.

Transcriptome analysis of β-thalassemic erythroblasts revealed a total of 74 genes that were differentially expressed (absolute fold change >1.5, false discovery rate adjusted P value <0.05) in ActRIIB(L79D 25-131)-mFc treated samples compared to VEH treatment. To identify molecular mechanisms, gene set enrichment analysis (GSEA) (Subramanian et al., 2005, PNAS, 102(43):15545-15550) was performed on data from ActRIIB(L79D 25-131)-mFc and VEH treated samples. The analysis depicted significant upregulation of target genes of multiple transcriptional regulators including GATA-1 (erythroid differentiation), NFE2 and heat shock factor (involved in globin expression and protein quality-control). Multiple studies have established GATA-1 as a master transcriptional regulator of terminal erythroid differentiation. The individual gene symbols based comparative analysis revealed up-regulation of 53/478 GATA-1 activators and down regulation of 9/342 GATA-1 repressors. The GATA-1 target genes that were up regulated by ActRIIB(L79D 25-131)-mFc treatment are involved in heme biosynthesis (such as Ppox, Fech, Alas2 and Abcb10) and erythroid differentiation (such as Klf1, Nfe2, Gypa, Bcl21, Bnip31, Bach1, and Ank1). Further GSEA of GATA-1 activator and repressor signatures against ActRIIB(L79D 25-131)-mFc treatment data revealed a significant up-regulation of 158/328 activated genes (Normalized Enrichment Score=2.7, P=0) involved in heme biosynthesis, and cell cycle regulation whereas there was no statistically significant down regulation of GATA-1 repressed genes. Consistent with this data, these results in differentiating mouse erythroleukemic (MEL) cells showed increased Smad2/3 phosphorylation that is correlated with reduced GATA-1 protein levels.

Together, the data provide a potential mechanistic role for ActRIIB(L79D 25-131)-Fc treatment in β-thalassemia. In particular, the data indicate that ActRIIB(L79D 25-131)-Fc treatment results in transcriptional upregulation of genes known to promote erythroid differentiation and processing of unpaired α-globins. By inhibiting Smad signaling, ActRIIB(L79D 25-131)-Fc relieves the block of terminal erythroid maturation and decreases ineffective erythropoiesis in β-thalassemia.

Therefore, the data suggest that other agents which agonize (activate), reduce inhibition of, and/or supplement the activity of, for example, any one of, or combination of, GATA-1, heat shock factor, and/or NFE2, or one or more downstream factors of any one of GATA-1, heat shock factor, and/or NFE2, may be useful in the treatment of ineffective erythropoiesis associated with a variety of disorders including, for example, β-thalassemia and MDS. Moreover, the data indicate ineffective erythropoiesis patients that may particularly benefit from treatment with one or more Smad inhibitors disclosed herein [e.g., ActRII inhibitors such as ActRIIB(L79D 25-131)-Fc] are patients that have low levels and/or activity of one or more GATA-1, heat shock factor, and/or NFE2. In such ineffective erythropoiesis patients with low levels and/or activity of one or more GATA-1, heat shock factor, and/or NFE2, these biomarkers may be useful for determining the therapeutically effectiveness of an agent, or combination of agents, and thus be useful in managing dosing of a patient (e.g., dose amount administered and/or interval of dosing) particularly when administering one or more Smad antagonists as described herein [e.g., ActRIIB(L79D 25-131)-Fc].

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating or preventing ineffective erythropoiesis in a subject in need thereof, the method comprising:
   i) determining the level of GATA-1 in the subject;
   ii) identifying the subject who has a decreased level of GATA-1 as compared to a reference population; and
   iii) administering to the subject identified in ii) a pharmaceutically effective amount of an agent, or combination of agents, selected from the group consisting of an ActRIIA polypeptide comprising a sequence that is at least 90% identical to the amino acid sequence corresponding to positions 21-135 of SEQ ID NO: 9, and an ActRIIB polypeptide comprising a sequence that is at least 90% identical to the amino acid sequnce corresponding to positions 29-109 of SEQ ID NO: 1, wherein the ActRIIA and ActRIIB polypeptides are capable of binding to GDF11; and wherein the reference population consists of people without ineffective erythropoiesis.

2. The method of claim 1, wherein the subject has a decreased level of one or more:

a) heme biosynthesis genes selected from the group consisting of: Ppox, Fech, Alas2, and Abcb10, compared to levels of Ppox, Fech, Alas2, and Abcb10 in a reference population; and/or
b) erythroid differentiation factors selected from the group consisting of: KLF1, NFE2, GYPA, Bcl2l, Bnip3l, Bach1, and ANK1, compared to levels of KLF1, NFE2, GYPA, Bcl2l, Bnip3l, Bach1, and ANK1 in a reference population.

3. The method of claim 1, wherein the reference population consists of healthy individuals.

4. The method of claim 1, wherein the agent agonizes, reduces the inhibition of, supplements the activity of, increases the levels of and/or increases the activity of one or more:
a) heme biosynthesis genes selected from the group consisting of: Ppox, Fech, Alas2, and Abcb 10; and/or
b) erythroid differentiation factors selected from the group consisting of: KLF1, NFE2, GYPA, Bcl2l, Bnip3l, Bach1, and ANK1.

5. The method of claim 1, wherein the agent is an ActRIIA polypeptide comprising an amino acid sequence that is at least 90% identical to the sequence of amino acids 21-135 of SEQ ID NO: 9.

6. The method of claim 1, wherein the agent is an ActRIIA polypeptide comprising an amino acid sequence that is at least 95% identical to SEQ ID NO: 10.

7. The method of claim 1, wherein the agent is an ActRIIA polypeptide comprising the amino acid sequence of SEQ ID NO: 10.

8. The method of claim 1, wherein the agent is an ActRIIB polypeptide comprising an amino acid sequence that is at least 90% identical to the sequence of amino acids 29-109 of SEQ ID NO: 1.

9. The method of claim 1, wherein the agent is an ActRIIB polypeptide comprising an amino acid sequence that is at least 90% identical to the amino acid sequence corresponding to positions 25-131 of SEQ ID NO: 1.

10. The method of claim 1, wherein the agent is an ActRIIB polypeptide comprising an amino acid sequence that is at least 95% identical to the amino acid sequence corresponding to positions 25-131 of SEQ ID NO: 1.

11. The method of claim 1, wherein the agent is an ActRIIB polypeptide comprising the amino acid sequence corresponding to positions 25-131 of SEQ ID NO: 1.

12. The method of claim 1, wherein the agent is an ActRIIA polypeptide comprising a polypeptide selected from:
a) a polypeptide comprising the amino acid sequence of SEQ ID NO: 32 or comprising an amino acid sequence that is at least 90% identical to the amino acid sequence of SEQ ID NO: 32; and
b) a polypeptide comprising the amino acid sequence of SEQ ID NO: 36 or comprising an amino acid sequence that is at least 90% identical to the amino acid sequence of SEQ ID NO: 36.

13. The method of claim 1, wherein the agent is an ActRIIB polypeptide comprising a polypeptide selected from:

a) a polypeptide comprising the amino acid sequence of SEQ ID NO: 40 or comprising an amino acid sequence that is at least 90% identical to the amino acid sequence of SEQ ID NO: 40;
b) a polypeptide comprising the amino acid sequence of SEQ ID NO: 41 or comprising an amino acid sequence that is at least 90% identical to the amino acid sequence of SEQ ID NO: 41;
c) a polypeptide comprising the amino acid sequence of SEQ ID NO: 44 or comprising an amino acid sequence that is at least 90% identical to the amino acid sequence of SEQ ID NO: 44;
d) a polypeptide comprising the amino acid sequence of SEQ ID NO: 46 or comprising an amino acid sequence that is at least 90% identical to the amino acid sequence of SEQ ID NO: 46;
e) a polypeptide comprising the amino acid sequence of SEQ ID NO: 50 or comprising an amino acid sequence that is at least 90% identical to the amino acid sequence of SEQ ID NO: 50;
f) a polypeptide comprising the amino acid sequence of SEQ ID NO: 78 or comprising an amino acid sequence that is at least 90% identical to the amino acid sequence of SEQ ID NO: 78;
g) a polypeptide comprising the amino acid sequence of SEQ ID NO: 61 or comprising an amino acid sequence that is at least 90% identical to the amino acid sequence of SEQ ID NO: 61;
h) a polypeptide comprising the amino acid sequence of SEQ ID NO: 64 or comprising an amino acid sequence that is at least 90% identical to the amino acid sequence of SEQ ID NO: 64; and
i) a polypeptide comprising the amino acid sequence of SEQ ID NO: 79 or comprising an amino acid sequence that is at least 90% identical to the amino acid sequence of SEQ ID NO: 79.

14. The method of claim 1, wherein the agent is an ActRIIB polypeptide comprising an amino acid sequence that is at least 90% identical to SEQ ID NO: 64.

15. The method of claim 1, wherein the agent is an ActRIIB polypeptide comprising an amino acid sequence that is at least 95% identical to SEQ ID NO: 64.

16. The method of claim 1, wherein the agent is an ActRIIB polypeptide comprising the amino acid sequence of SEQ ID NO: 64.

17. The method of claim 1, wherein the subject has myelodysplastic syndrome (MDS).

18. The method of claim 1, wherein the ineffective erythropoiesis is associated with a hemoglobinopathy.

19. The method of claim 18, wherein the hemoglobinopathy is a thalassemia selected from the group consisting of: alpha-thalassemia-minima, alpha-thalassemia minor, Hemoglobin H disease, alpha-thalassemia major, beta-thalassemia-minor, beta-thalassemia intermedia, beta-thalassemia major, Hemoglobin E disease, and delta-beta-thalassemia.

20. The method of claim 18, wherein the hemoglobinopathy is selected from the group consisting of: sickle-cell anemia, Hemoglobin C disease, and hemoglobin S-C disease.

* * * * *

UNITED STATES PATENT AND TRADEMARK OFFICE
CERTIFICATE OF CORRECTION

PATENT NO. : 11,123,430 B2
APPLICATION NO. : 15/343757
DATED : September 21, 2021
INVENTOR(S) : Ravindra Kumar et al.

It is certified that error appears in the above-identified patent and that said Letters Patent is hereby corrected as shown below:

On the Title Page

Item (72), Please delete:
"(72) Inventors: Ravindra Kumar, Acton, MA (US);
　　　　Pedro Martinez, Cambridge, MA (US);
　　　　Naga Venkata Sai Rajasekhar Suragani, Wrentham, MA (US)"
And replace with:
--Inventors: Ravindra Kumar, Acton, MA (US);
　　　　Pedro Martinez, Cambridge, MA (US);
　　　　Rajasekhar Naga Venkata Sai Suragani, Wrentham, MA (US)--

In the Claims

Column 242, Line 60, delete:
"is at least 90% identical to the amino acid sequnce"
And replace with:
--is at least 90% identical to the amino acid sequence--

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 90

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60
```

```
Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
```

```
                     485                 490                 495
Val Thr Ser Val Thr Asn Val Asp Leu Pro Pro Lys Glu Ser Ser Ile
            500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30
```

```
Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Ala
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
        210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
        290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
        370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445
```

```
Gly Leu Ala Gln Leu Cys Val Thr Ile Glu Glu Cys Trp Asp His Asp
    450                 455                 460
Ala Glu Ala Arg Leu Ser Ala Gly Cys Val Glu Glu Arg Val Ser Leu
465                 470                 475                 480
Ile Arg Arg Ser Val Asn Gly Thr Thr Ser Asp Cys Leu Val Ser Leu
                485                 490                 495
Val Thr Ser Val Thr Asn Val Asp Leu Pro Pro Lys Glu Ser Ser Ile
                500                 505                 510
```

<210> SEQ ID NO 5
<211> LENGTH: 115
<212> TYPE: PRT
<213> ORGANISM: Homo sapiens

<400> SEQUENCE: 5

```
Gly Arg Gly Glu Ala Glu Thr Arg Glu Cys Ile Tyr Tyr Asn Ala Asn
1               5                   10                  15
Trp Glu Leu Glu Arg Thr Asn Gln Ser Gly Leu Glu Arg Cys Glu Gly
                20                  25                  30
Glu Gln Asp Lys Arg Leu His Cys Tyr Ala Ser Trp Ala Asn Ser Ser
                35                  40                  45
Gly Thr Ile Glu Leu Val Lys Lys Gly Cys Trp Leu Asp Asp Phe Asn
        50                  55                  60
Cys Tyr Asp Arg Gln Glu Cys Val Ala Thr Glu Glu Asn Pro Gln Val
65                  70                  75                  80
Tyr Phe Cys Cys Cys Glu Gly Asn Phe Cys Asn Glu Arg Phe Thr His
                85                  90                  95
Leu Pro Glu Ala Gly Gly Pro Glu Val Thr Tyr Glu Pro Pro Pro Thr
                100                 105                 110
Ala Pro Thr
        115
```

<210> SEQ ID NO 6
<211> LENGTH: 100
<212> TYPE: PRT
<213> ORGANISM: Homo sapiens

<400> SEQUENCE: 6

```
Gly Arg Gly Glu Ala Glu Thr Arg Glu Cys Ile Tyr Tyr Asn Ala Asn
1               5                   10                  15
Trp Glu Leu Glu Arg Thr Asn Gln Ser Gly Leu Glu Arg Cys Glu Gly
                20                  25                  30
Glu Gln Asp Lys Arg Leu His Cys Tyr Ala Ser Trp Ala Asn Ser Ser
                35                  40                  45
Gly Thr Ile Glu Leu Val Lys Lys Gly Cys Trp Leu Asp Asp Phe Asn
        50                  55                  60
Cys Tyr Asp Arg Gln Glu Cys Val Ala Thr Glu Glu Asn Pro Gln Val
65                  70                  75                  80
Tyr Phe Cys Cys Cys Glu Gly Asn Phe Cys Asn Glu Arg Phe Thr His
                85                  90                  95
Leu Pro Glu Ala
                100
```

<210> SEQ ID NO 7
<211> LENGTH: 1536
<212> TYPE: DNA
<213> ORGANISM: Homo sapiens

<400> SEQUENCE: 7

```
atgacggcgc cctgggtggc cctcgccctc ctctggggat cgctgtgcgc cggctctggg      60
cgtggggagg ctgagacacg ggagtgcatc tactacaacg ccaactggga gctggagcgc     120
accaaccaga gcggcctgga cgctgcgaa ggcgagcagg acaagcggct gcactgctac      180
gcctcctggc gcaacagctc tggcaccatc gagctcgtga agaagggctg ctggctagat     240
gacttcaact gctacgatag caggagtgt gtggccactg aggagaaccc ccaggtgtac      300
ttctgctgct gtgaaggcaa cttctgcaac gaacgcttca ctcatttgcc agaggctggg     360
ggcccggaag tcacgtacga gccaccccg acagcccca ccctgctcac ggtgctggcc       420
tactcactgc tgcccatcgg gggcctttcc ctcatcgtcc tgctggcctt ttggatgtac     480
cggcatcgca agccccccta cggtcatgtg acatccatg aggaccctgg gcctccacca     540
ccatcccctc tggtgggcct gaagccactg cagctgctgg agatcaaggc tcggggcgc     600 tttggctgtg tctggaaggc ccagctcatg aatgactttg tagctgtcaa gatcttccca    660
ctccaggaca agcagtcgtg gcagagtgaa cgggagatct tcagcacacc tggcatgaag     720
cacgagaacc tgctacagtt cattgctgcc gagaagcgag gctccaacct cgaagtagag    780
ctgtggctca tcacggcctt ccatgacaag ggctccctca cggattacct caaggggaac    840
atcatcacat ggaacgaact gtgtcatgta gcagagacga tgtcacgagg cctctcatac    900
ctgcatgagg atgtgccctg gtgccgtggc gagggccaca gccgtctat tgcccacagg     960 gactttaaaa gtaagaatgt attgctgaag agcgacctca cagccgtgct ggctgacttt   1020
ggcttggctg ttcgatttga ccagggaaa cctccagggg acacccacgg acaggtaggc   1080
acgagacggt acatggctcc tgaggtgctc gagggagcca tcaacttcca gagagatgcc   1140
ttcctgcgca ttgacatgta tgccatgggg ttggtgctgt gggagcttgt gtctcgctgc   1200
aaggctgcag acggacccgt ggatgagtac atgctgccct tgaggaaga gattggccag    1260 caccttcgt tggaggagct gcaggaggtg gtggtgcaca agaagatgag gccccaccatt   1320 aaagatcact ggttgaaaca cccgggcctg gcccagcttt gtgtgaccat cgaggagtgc   1380
tgggaccatg atgcagaggc tcgccttgtcc gcgggctgtg tggaggagcg ggtgtccctg   1440
attcggaggt cggtcaacgg cactacctcg gactgtctcg tttccctggt gacctctgtc   1500
accaatgtgg acctgccccc taaagagtca agcatc                              1536
```

<210> SEQ ID NO 8
<211> LENGTH: 340
<212> TYPE: DNA
<213> ORGANISM: Homo sapiens

<400> SEQUENCE: 8

```
gggcgtgggg aggctgagac acgggagtgc atctactaca cgccaactg ggagctggag      60 cgcaccaacc agagcggcct ggagcgctgc gaaggcgagc aggacaagcg gctgcactgc    120
tacgcctcct ggcgcaacag ctctggcacc atcgagctcg tgaagaaggg ctgctggcta    180
gatgacttca actgctacga taggcaggag tgtgtggcca ctgaggagaa ccccaggtg     240 tacttctgct gctgtgaagg caacttctgc aacgaacgct tcactcattt gccagaggct    300
gggggcccgg aagtcacgta cgagccaccc ccgacagccc                           340
```

<210> SEQ ID NO 9
<211> LENGTH: 513
<212> TYPE: PRT
<213> ORGANISM: Homo sapiens

```
<400> SEQUENCE: 9

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
                35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
                115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
    180                 185                 190

Gln Leu Leu Glu Val Lys Ala Arg Gly Arg Phe Gly Cys Val Trp Lys
    195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
    275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
            355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
```

```
                    405                 410                 415
Glu Glu Ile Gly Gln His Pro Ser Leu Glu Asp Met Gln Glu Val Val
                420                 425                 430

Val His Lys Lys Arg Pro Val Leu Arg Asp Tyr Trp Gln Lys His
            435                 440                 445

Ala Gly Met Ala Met Leu Cys Glu Thr Ile Glu Cys Trp Asp His
        450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 10
<211> LENGTH: 115
<212> TYPE: PRT
<213> ORGANISM: Homo sapiens

<400> SEQUENCE: 10

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 11
<211> LENGTH: 100
<212> TYPE: PRT
<213> ORGANISM: Homo sapiens

<400> SEQUENCE: 11

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95
```

Phe Pro Glu Met
           100

<210> SEQ ID NO 12
<211> LENGTH: 1539
<212> TYPE: DNA
<213> ORGANISM: Homo sapiens

<400> SEQUENCE: 12

| | | | | | |
|---|---|---|---|---|---|
| atgggagctg | ctgcaaagtt | ggcgtttgcc | gtctttctta | tctcctgttc | ttcaggtgct | 60 |
| atacttggta | gatcagaaac | tcaggagtgt | cttttcttta | atgctaattg | ggaaaaagac | 120 |
| agaaccaatc | aaactggtgt | tgaaccgtgt | tatggtgaca | aagataaacg | gcggcattgt | 180 |
| tttgctacct | ggaagaatat | ttctggttcc | attgaaatag | tgaaacaagg | ttgttggctg | 240 |
| gatgatatca | actgctatga | caggactgat | tgtgtagaaa | aaaagacag | ccctgaagta | 300 |
| tattttgtt | gctgtgaggg | caatatgtgt | aatgaaaagt | tttcttattt | tccggagatg | 360 |
| gaagtcacac | agcccacttc | aaatccagtt | acacctaagc | cacccctatta | caacatcctg | 420 |
| ctctattcct | tggtgccact | tatgttaatt | gcggggattg | tcatttgtgc | attttgggtg | 480 |
| tacaggcatc | acaagatggc | ctaccctcct | gtacttgttc | caactcaaga | cccaggacca | 540 |
| ccccaccctt | ctccattact | aggttttgaaa | ccactgcagt | tattagaagt | gaaagcaagg | 600 |
| ggaagatttg | gttgtgtctg | gaaagcccag | ttgcttaacg | aatatgtggc | tgtcaaaata | 660 |
| tttccaatac | aggacaaaca | gtcatggcaa | aatgaatacg | aagtctacag | tttgcctgga | 720 |
| atgaagcatg | agaacatatt | acagttcatt | ggtgcagaaa | aacgaggcac | cagtgttgat | 780 |
| gtggatcttt | ggctgatcac | agcatttcat | gaaaagggtt | cactatcaga | ctttcttaag | 840 |
| gctaatgtgg | tctcttggaa | tgaactgtgt | catattgcag | aaaccatggc | tagaggattg | 900 |
| gcatatttac | atgaggatat | acctggccta | aaagatggcc | acaaacctgc | catatctcac | 960 |
| agggacatca | aaagtaaaaa | tgtgctgttg | aaaaacaacc | tgacagcttg | cattgctgac | 1020 |
| tttgggttgg | ccttaaaatt | tgaggctggc | aagtctgcag | gcgataccca | tggacaggtt | 1080 |
| ggtacccgga | ggtacatggc | tccagaggta | ttagagggtg | ctataaactt | ccaaagggat | 1140 |
| gcatttttga | ggatagatat | gtatgccatg | ggattagtcc | tatgggaact | ggcttctcgc | 1200 |
| tgtactgctg | cagatggacc | tgtagatgaa | tacatgttgc | catttgagga | ggaaattggc | 1260 |
| cagcatccat | ctcttgaaga | catgcaggaa | gttgttgtgc | ataaaaaaaa | gaggcctgtt | 1320 |
| ttaagagatt | attggcagaa | acatgctgga | atggcaatgc | tctgtgaaac | cattgaagaa | 1380 |
| tgttgggatc | acgacgcaga | agccaggtta | tcagctggat | gtgtaggtga | agaattacc | 1440 |
| cagatgcaga | gactaacaaa | tattattacc | acagaggaca | ttgtaacagt | ggtcacaatg | 1500 |
| gtgacaaatg | ttgactttcc | tcccaaagaa | tctagtcta | | | 1539 |

<210> SEQ ID NO 13
<211> LENGTH: 345
<212> TYPE: DNA
<213> ORGANISM: Homo sapiens

<400> SEQUENCE: 13

| | | | | | |
|---|---|---|---|---|---|
| atacttggta | gatcagaaac | tcaggagtgt | cttttcttta | atgctaattg | ggaaaaagac | 60 |
| agaaccaatc | aaactggtgt | tgaaccgtgt | tatggtgaca | aagataaacg | gcggcattgt | 120 |
| tttgctacct | ggaagaatat | ttctggttcc | attgaaatag | tgaaacaagg | ttgttggctg | 180 |
| gatgatatca | actgctatga | caggactgat | tgtgtagaaa | aaaagacag | ccctgaagta | 240 |

```
tatttttgtt gctgtgaggg caatatgtgt aatgaaaagt tttcttattt tccggagatg    300
gaagtcacac agcccacttc aaatccagtt acacctaagc caccc                   345
```

<210> SEQ ID NO 14
<211> LENGTH: 225
<212> TYPE: PRT
<213> ORGANISM: Homo sapiens

<400> SEQUENCE: 14

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 15
<211> LENGTH: 223
<212> TYPE: PRT
<213> ORGANISM: Homo sapiens

<400> SEQUENCE: 15

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
```

```
                65                  70                  75                  80
Val Leu Thr Val His Gln Asp Trp Leu Asn Gly Lys Glu Tyr Lys
                    85                  90                  95
Cys Lys Val Ser Asn Lys Gly Leu Pro Ala Pro Ile Glu Lys Thr Ile
                    100                 105                 110
Ser Lys Thr Lys Gly Gln Pro Arg Glu Pro Gln Val Tyr Thr Leu Pro
                    115                 120                 125
Pro Ser Arg Glu Glu Met Thr Lys Asn Gln Val Ser Leu Thr Cys Leu
130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Met Leu Asp Ser
                    165                 170                 175
Asp Gly Ser Phe Phe Leu Tyr Ser Lys Leu Thr Val Asp Lys Ser Arg
                    180                 185                 190
Trp Gln Gln Gly Asn Val Phe Ser Cys Ser Val Met His Glu Ala Leu
                    195                 200                 205
His Asn His Tyr Thr Gln Lys Ser Leu Ser Leu Ser Pro Gly Lys
210                 215                 220

<210> SEQ ID NO 16
<211> LENGTH: 232
<212> TYPE: PRT
<213> ORGANISM: Homo sapiens

<400> SEQUENCE: 16

Glu Pro Lys Ser Cys Asp Thr Pro Pro Pro Cys Pro Arg Cys Pro Ala
1               5                   10                  15
Pro Glu Leu Leu Gly Gly Pro Ser Val Phe Leu Phe Pro Pro Lys Pro
                20                  25                  30
Lys Asp Thr Leu Met Ile Ser Arg Thr Pro Glu Val Thr Cys Val Val
                35                  40                  45
Val Asp Val Ser His Glu Asp Pro Glu Val Gln Phe Lys Trp Tyr Val
50                  55                  60
Asp Gly Val Glu Val His Asn Ala Lys Thr Lys Pro Arg Glu Glu Gln
65                  70                  75                  80
Tyr Asn Ser Thr Phe Arg Val Val Ser Val Leu Thr Val Leu His Gln
                85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Thr Lys Gly Gln Pro
                115                 120                 125
Arg Glu Pro Gln Val Tyr Thr Leu Pro Pro Ser Arg Glu Glu Met Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Ser Gly Gln Pro Glu Asn Asn Tyr
                165                 170                 175
Asn Thr Thr Pro Pro Met Leu Asp Ser Asp Gly Ser Phe Phe Leu Tyr
                180                 185                 190
Ser Lys Leu Thr Val Asp Lys Ser Arg Trp Gln Gln Gly Asn Ile Phe
                195                 200                 205
Ser Cys Ser Val Met His Glu Ala Leu His Asn Arg Phe Thr Gln Lys
210                 215                 220
```

```
Ser Leu Ser Leu Ser Pro Gly Lys
225                 230
```

<210> SEQ ID NO 17
<211> LENGTH: 279
<212> TYPE: PRT
<213> ORGANISM: Homo sapiens

<400> SEQUENCE: 17

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275
```

<210> SEQ ID NO 18
<211> LENGTH: 229
<212> TYPE: PRT
<213> ORGANISM: Homo sapiens

<400> SEQUENCE: 18

```
Glu Ser Lys Tyr Gly Pro Pro Cys Ser Cys Pro Ala Pro Glu Phe
1               5                   10                  15

Leu Gly Gly Pro Ser Val Phe Leu Phe Pro Pro Lys Pro Lys Asp Thr
            20                  25                  30
```

```
Leu Met Ile Ser Arg Thr Pro Glu Val Thr Cys Val Val Asp Val
         35                  40                  45

Ser Gln Glu Asp Pro Gly Val Gln Phe Asn Trp Tyr Val Asp Gly Val
 50                  55                  60

Glu Val His Asn Ala Lys Thr Lys Pro Arg Glu Glu Gln Phe Asn Ser
65                   70                  75                  80

Thr Tyr Arg Val Val Ser Val Leu Thr Val Leu His Gln Asp Trp Leu
             85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly
1

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Gly Gly Gly Gly
```

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gly Gly Gly Gly
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Gly Gly Gly
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Gly Gly
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Ser
1               5

<210> SEQ ID NO 26
<211> LENGTH: 344
<212> TYPE: PRT
<213> ORGANISM: Homo sapiens

<400> SEQUENCE: 26

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
```

```
               65                  70                  75                  80
           Phe Asn Gly Gly Ala Pro Asn Cys Ile Pro Cys Lys Glu Thr Cys Glu
                            85                  90                  95

Asn Val Asp Cys Gly Pro Gly Lys Lys Cys Arg Met Asn Lys Lys Asn
                           100                 105                 110

Lys Pro Arg Cys Val Cys Ala Pro Asp Cys Ser Asn Ile Thr Trp Lys
                           115                 120                 125

Gly Pro Val Cys Gly Leu Asp Gly Lys Thr Tyr Arg Asn Glu Cys Ala
                           130                 135                 140

Leu Leu Lys Ala Arg Cys Lys Glu Gln Pro Glu Leu Glu Val Gln Tyr
           145                 150                 155                 160

Gln Gly Arg Cys Lys Lys Thr Cys Arg Asp Val Phe Cys Pro Gly Ser
                           165                 170                 175

Ser Thr Cys Val Val Asp Gln Thr Asn Asn Ala Tyr Cys Val Thr Cys
                           180                 185                 190

Asn Arg Ile Cys Pro Glu Pro Ala Ser Ser Glu Gln Tyr Leu Cys Gly
                           195                 200                 205

Asn Asp Gly Val Thr Tyr Ser Ser Ala Cys His Leu Arg Lys Ala Thr
                           210                 215                 220

Cys Leu Leu Gly Arg Ser Ile Gly Leu Ala Tyr Glu Gly Lys Cys Ile
           225                 230                 235                 240

Lys Ala Lys Ser Cys Glu Asp Ile Gln Cys Thr Gly Gly Lys Lys Cys
                           245                 250                 255

Leu Trp Asp Phe Lys Val Gly Arg Gly Arg Cys Ser Leu Cys Asp Glu
                           260                 265                 270

Leu Cys Pro Asp Ser Lys Ser Asp Glu Pro Val Cys Ala Ser Asp Asn
                           275                 280                 285

Ala Thr Tyr Ala Ser Glu Cys Ala Met Lys Glu Ala Ala Cys Ser Ser
                           290                 295                 300

Gly Val Leu Leu Glu Val Lys His Ser Gly Ser Cys Asn Ser Ile Ser
           305                 310                 315                 320

Glu Asp Thr Glu Glu Glu Glu Asp Glu Asp Gln Asp Tyr Ser Phe
                           325                 330                 335

Pro Ile Ser Ser Ile Leu Glu Trp
                           340

<210> SEQ ID NO 27
<211> LENGTH: 317
<212> TYPE: PRT
<213> ORGANISM: Homo sapiens

<400> SEQUENCE: 27

Met Val Arg Ala Arg His Gln Pro Gly Gly Leu Cys Leu Leu Leu
           1               5                   10                  15

Leu Leu Cys Gln Phe Met Glu Asp Arg Ser Ala Gln Ala Gly Asn Cys
                           20                  25                  30

Trp Leu Arg Gln Ala Lys Asn Gly Arg Cys Gln Val Leu Tyr Lys Thr
                           35                  40                  45

Glu Leu Ser Lys Glu Glu Cys Cys Ser Thr Gly Arg Leu Ser Thr Ser
                           50                  55                  60

Trp Thr Glu Glu Asp Val Asn Asp Asn Thr Leu Phe Lys Trp Met Ile
           65                  70                  75                  80

Phe Asn Gly Gly Ala Pro Asn Cys Ile Pro Cys Lys Glu Thr Cys Glu
                           85                  90                  95
```

```
Asn Val Asp Cys Gly Pro Gly Lys Lys Cys Arg Met Asn Lys Lys Asn
            100                 105                 110
Lys Pro Arg Cys Val Cys Ala Pro Asp Cys Ser Asn Ile Thr Trp Lys
        115                 120                 125
Gly Pro Val Cys Gly Leu Asp Gly Lys Thr Tyr Arg Asn Glu Cys Ala
        130                 135                 140
Leu Leu Lys Ala Arg Cys Lys Glu Gln Pro Glu Leu Glu Val Gln Tyr
145                 150                 155                 160
Gln Gly Arg Cys Lys Lys Thr Cys Arg Asp Val Phe Cys Pro Gly Ser
                165                 170                 175
Ser Thr Cys Val Val Asp Gln Thr Asn Asn Ala Tyr Cys Val Thr Cys
            180                 185                 190
Asn Arg Ile Cys Pro Glu Pro Ala Ser Ser Glu Gln Tyr Leu Cys Gly
        195                 200                 205
Asn Asp Gly Val Thr Tyr Ser Ser Ala Cys His Leu Arg Lys Ala Thr
        210                 215                 220
Cys Leu Leu Gly Arg Ser Ile Gly Leu Ala Tyr Glu Gly Lys Cys Ile
225                 230                 235                 240
Lys Ala Lys Ser Cys Glu Asp Ile Gln Cys Thr Gly Gly Lys Lys Cys
                245                 250                 255
Leu Trp Asp Phe Lys Val Gly Arg Gly Arg Cys Ser Leu Cys Asp Glu
            260                 265                 270
Leu Cys Pro Asp Ser Lys Ser Asp Glu Pro Val Cys Ala Ser Asp Asn
        275                 280                 285
Ala Thr Tyr Ala Ser Glu Cys Ala Met Lys Glu Ala Ala Cys Ser Ser
        290                 295                 300
Gly Val Leu Leu Glu Val Lys His Ser Gly Ser Cys Asn
305                 310                 315

<210> SEQ ID NO 28
<211> LENGTH: 63
<212> TYPE: PRT
<213> ORGANISM: Homo sapiens

<400> SEQUENCE: 28

Gly Asn Cys Trp Leu Arg Gln Ala Lys Asn Gly Arg Cys Gln Val Leu
1               5                   10                  15
Tyr Lys Thr Glu Leu Ser Lys Glu Glu Cys Cys Ser Thr Gly Arg Leu
                20                  25                  30
Ser Thr Ser Trp Thr Glu Glu Asp Val Asn Asp Asn Thr Leu Phe Lys
            35                  40                  45
Trp Met Ile Phe Asn Gly Gly Ala Pro Asn Cys Ile Pro Cys Lys
        50                  55                  60

<210> SEQ ID NO 29
<211> LENGTH: 25
<212> TYPE: PRT
<213> ORGANISM: Homo sapiens

<400> SEQUENCE: 29

Glu Thr Cys Glu Asn Val Asp Cys Gly Pro Gly Lys Lys Cys Arg Met
1               5                   10                  15
Asn Lys Lys Asn Lys Pro Arg Cys Val
                20                  25

<210> SEQ ID NO 30
<211> LENGTH: 26
```

```
<212> TYPE: PRT
<213> ORGANISM: Homo sapiens

<400> SEQUENCE: 30

Lys Thr Cys Arg Asp Val Phe Cys Pro Gly Ser Ser Thr Cys Val Val
1               5                   10                  15

Asp Gln Thr Asn Asn Ala Tyr Cys Val Thr
            20                  25

<210> SEQ ID NO 31
<211> LENGTH: 263
<212> TYPE: PRT
<213> ORGANISM: Homo sapiens

<400> SEQUENCE: 31

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
            260

<210> SEQ ID NO 32
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 32

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 33
<211> LENGTH: 21
<212> TYPE: PRT
<213> ORGANISM: Apis sp.

<400> SEQUENCE: 33

Met Lys Phe Leu Val Asn Val Ala Leu Val Phe Met Val Val Tyr Ile
1               5                   10                  15
```

```
Ser Tyr Ile Tyr Ala
            20

<210> SEQ ID NO 34
<211> LENGTH: 22
<212> TYPE: PRT
<213> ORGANISM: Unknown
<220> FEATURE:
<223> OTHER INFORMATION: Description of Unknown:
      Tissue plasminogen activator peptide

<400> SEQUENCE: 34

Met Asp Ala Met Lys Arg Gly Leu Cys Cys Val Leu Leu Leu Cys Gly
1               5                   10                  15

Ala Val Phe Val Ser Pro
            20

<210> SEQ ID NO 35
<211> LENGTH: 20
<212> TYPE: PRT
<213> ORGANISM: Unknown
<220> FEATURE:
<223> OTHER INFORMATION: Description of Unknown:
      Native peptide

<400> SEQUENCE: 35

Met Gly Ala Ala Ala Lys Leu Ala Phe Ala Val Phe Leu Ile Ser Cys
1               5                   10                  15

Ser Ser Gly Ala
            20

<210> SEQ ID NO 36
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
```

```
              165                 170                 175
Arg Thr Pro Glu Val Thr Cys Val Val Asp Val Ser His Glu Asp
        180                 185                 190
Pro Glu Val Lys Phe Asn Trp Tyr Val Asp Gly Val Glu Val His Asn
            195                 200                 205
Ala Lys Thr Lys Pro Arg Glu Glu Gln Tyr Asn Ser Thr Tyr Arg Val
        210                 215                 220
Val Ser Val Leu Thr Val Leu His Gln Asp Trp Leu Asn Gly Lys Glu
225                 230                 235                 240
Tyr Lys Cys Lys Val Ser Asn Lys Ala Leu Pro Val Pro Ile Glu Lys
                245                 250                 255
Thr Ile Ser Lys Ala Lys Gly Gln Pro Arg Glu Pro Gln Val Tyr Thr
            260                 265                 270
Leu Pro Pro Ser Arg Glu Glu Met Thr Lys Asn Gln Val Ser Leu Thr
        275                 280                 285
Cys Leu Val Lys Gly Phe Tyr Pro Ser Asp Ile Ala Val Glu Trp Glu
    290                 295                 300
Ser Asn Gly Gln Pro Glu Asn Asn Tyr Lys Thr Thr Pro Pro Val Leu
305                 310                 315                 320
Asp Ser Asp Gly Ser Phe Phe Leu Tyr Ser Lys Leu Thr Val Asp Lys
                325                 330                 335
Ser Arg Trp Gln Gln Gly Asn Val Phe Ser Cys Ser Val Met His Glu
            340                 345                 350
Ala Leu His Asn His Tyr Thr Gln Lys Ser Leu Ser Leu Ser Pro Gly
        355                 360                 365
Lys

<210> SEQ ID NO 37
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg gtgttgaacc gtgttatggt gacaaagata     180
aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa agttttctta     360
ttttccggag atggaagtca cacagcccac ttcaaatcca gttacaccta gccacccac     420 cggtggtgga actcacacat gcccaccgtg cccagcacct gaactcctgg ggggaccgtc     480
agtcttcctc ttccccccaa aacccaagga caccctcatg atctcccgga cccctgaggt     540
cacatgcgtg gtggtggacg tgagccacga agaccctgag gtcaagttca actggtacgt     600
ggacggcgtg gaggtgcata atgccaagac aaagccgcgg gaggagcagt acaacagcac     660
gtaccgtgtg gtcagcgtcc tcaccgtcct gcaccaggac tggctgaatg gcaaggagta     720
caagtgcaag gtctccaaca aagccctccc agtcccatc gagaaaacca tctccaaagc     780
caaagggcag ccccgagaac cacaggtgta caccctgccc ccatcccggg aggagatgac     840
```

```
caagaaccag gtcagcctga cctgcctggt caaaggcttc tatcccagcg acatcgccgt    900
ggagtgggag agcaatgggc agccggagaa caactacaag accacgcctc ccgtgctgga    960
ctccgacggc tccttcttcc tctatagcaa gctcaccgtg gacaagagca ggtggcagca   1020
ggggaacgtc ttctcatgct ccgtgatgca tgaggctctg cacaaccact acacgcagaa   1080
gagcctctcc ctgtctccgg gtaaatgaga attc                               1114
```

```
<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Leu Gly Arg Ser Glu Thr Gln Glu
1               5

<210> SEQ ID NO 39
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
    195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240
```

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 40
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
        210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp

```
                    260                 265                 270
Ile Ala Val Glu Trp Glu Ser Asn Gly Gln Pro Glu Asn Asn Tyr Lys
                275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 41
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270
```

```
Pro Pro Ser Arg Glu Glu Met Thr Lys Asn Gln Val Ser Leu Thr Cys
        275                 280                 285
Leu Val Lys Gly Phe Tyr Pro Ser Asp Ile Ala Val Glu Trp Glu Ser
        290                 295                 300
Asn Gly Gln Pro Glu Asn Asn Tyr Lys Thr Thr Pro Pro Val Leu Asp
305                 310                 315                 320
Ser Asp Gly Ser Phe Phe Leu Tyr Ser Lys Leu Thr Val Asp Lys Ser
                325                 330                 335
Arg Trp Gln Gln Gly Asn Val Phe Ser Cys Ser Val Met His Glu Ala
            340                 345                 350
Leu His Asn His Tyr Thr Gln Lys Ser Leu Ser Leu Ser Pro Gly Lys
        355                 360                 365
```

<210> SEQ ID NO 42
<211> LENGTH: 1107
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42

```
atggatgcaa tgaagagagg ctctgctgt gtgctgctgc tgtgtggagc agtcttcgtt      60
tcgcccggcg cctctgggcg tggggaggct gagacacggg agtgcatcta ctacaacgcc    120
aactgggagc tggagcgcac caaccagagc ggcctggagc gctgcgaagg cgagcaggac    180
aagcggctgc actgctacgc ctcctggcgc aacagctctg caccatcga gctcgtgaag    240
aagggctgct ggctagatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc accccccgac agcccccacc    420
ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gtccccatcg agaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Arg Gly Glu Ala Glu

<210> SEQ ID NO 44
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340
```

```
<210> SEQ ID NO 45
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 46
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175
```

```
Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 47
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct gggacgatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc accccccgac agcccccacc     420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gtccccatcg agaaaaccat ctccaaagcc     780
aaagggcagc ccgagaacc acaggtgtac accctgcccc catcccggga ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctggac     960
```

-continued

```
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaatga                                        1107
```

<210> SEQ ID NO 48
<211> LENGTH: 141
<212> TYPE: PRT
<213> ORGANISM: Homo sapiens

<400> SEQUENCE: 48

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Ala Gly Asp Gln Gly Ser
        115                 120                 125

Gly Ala Leu Trp Leu Cys Leu Glu Gly Pro Ala His Glu
    130                 135                 140
```

<210> SEQ ID NO 49
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Ala Gly Asp Gln Gly Ser
        115                 120                 125

Gly Ala Leu Trp Leu Cys Leu Glu Gly Pro Ala His Glu
    130                 135                 140
```

<210> SEQ ID NO 50
<211> LENGTH: 370
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu Thr Gly Gly
    130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365
```

Gly Lys
    370

<210> SEQ ID NO 51
<211> LENGTH: 116
<212> TYPE: PRT
<213> ORGANISM: Homo sapiens

<400> SEQUENCE: 51

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115

<210> SEQ ID NO 52
<211> LENGTH: 150
<212> TYPE: PRT
<213> ORGANISM: Rattus sp.

<400> SEQUENCE: 52

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 53
<211> LENGTH: 150
<212> TYPE: PRT
<213> ORGANISM: Sus scrofa

<400> SEQUENCE: 53

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 54
<211> LENGTH: 150
<212> TYPE: PRT
<213> ORGANISM: Mus musculus

<400> SEQUENCE: 54

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 55
<211> LENGTH: 150
<212> TYPE: PRT
<213> ORGANISM: Homo sapiens

<400> SEQUENCE: 55

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 56
<211> LENGTH: 150
<212> TYPE: PRT
<213> ORGANISM: Bos taurus

<400> SEQUENCE: 56

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Arg Asp Lys Arg Leu His Cys Tyr Ala Ser Trp Arg
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150

<210> SEQ ID NO 57
<211> LENGTH: 150
<212> TYPE: PRT
<213> ORGANISM: Xenopus sp.

<400> SEQUENCE: 57

Met Gly Ala Ser Val Ala Leu Thr Phe Leu Leu Leu Ala Thr Phe
1               5                   10                  15
```

```
Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
            35                  40                  45

Arg Leu Val Glu Gly Lys Lys Asp Lys Arg Leu His Cys Tyr Ala Ser
        50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Gly Asn Tyr Cys Asn
                100                 105                 110

Lys Lys Phe Thr His Leu Pro Glu Val Glu Thr Phe Asp Pro Lys Pro
            115                 120                 125

Gln Pro Ser Ala Ser Val Leu Asn Ile Leu Ile Tyr Ser Leu Leu Pro
        130                 135                 140

Ile Val Gly Leu Ser Met
145                 150

<210> SEQ ID NO 58
<211> LENGTH: 150
<212> TYPE: PRT
<213> ORGANISM: Homo sapiens

<400> SEQUENCE: 58

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
        50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
                100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
        130                 135                 140

Val Pro Leu Met Leu Ile
145                 150

<210> SEQ ID NO 59
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (8)..(8)
<223> OTHER INFORMATION: Thr, Ala or not present
<220> FEATURE:
<221> NAME/KEY: MOD_RES
```

```
<222> LOCATION: (121)..(121)
<223> OTHER INFORMATION: Pro, Ala, Val or Met

<400> SEQUENCE: 59

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150

<210> SEQ ID NO 60
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tcatttaccc ggggacaggg agaggctctt ctgcgtgtag tggttgtgca gagcctcatg     60
catcacggag catgagaaga cgttcccctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
cacctgtggt tctcggggct gccctttggc tttggagatg gttttctcga tgggggctgg    360
gagggctttg ttggagacct tgcacttgta ctccttgcca ttcagccagt cctggtgcag    420
gacggtgagg acgctgacca cacgtacgt gctgttgtac tgctcctccc gcggctttgt     480
cttggcatta tgcacctcca cgccgtccac gtaccagttg aacttgacct cagggtcttc    540
gtggctcacg tccaccacca cgcatgtgac ctcaggggtc cgggagatca tgagggtgtc    600
cttgggtttt gggggaaga ggaagactga cgtcccccc aggagttcag gtgctgggca     660
cggtgggcat gtgtgagttc caccaccggt ggggctgtc gggggtggct cgtacgtgac     720
ttccggggcc ccagcctctg gcaaatgagt gaagcgctcg ttgcagaagt tgccttcaca    780
gcagcagaag tacacctggg ggttctcctc agtggccaca cactcctgcc tatcgtagca    840
gttgaagtca tcatcccagc agcccttctt cacgagctcg atggtgccag agctgttgcg    900
ccaggaggcg tagcagtgca gccgcttgtc ctgctcgcct tcgcagcgct ccaggccgct    960
ctggttggtg cgctccagct cccagttggc gttgtagtag atgcactccc gtgtctcagc   1020
```

```
ctccccacgc ccagaggcgc cgggcgaaac gaagactgct ccacacagca gcagcacaca    1080
gcagagccct ctcttcattg catccat                                        1107
```

<210> SEQ ID NO 61
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335
```

```
Ser Cys Ser Val Met His Glu Ala Leu His Asn His Tyr Thr Gln Lys
        340                 345                 350
Ser Leu Ser Leu Ser Pro Gly Lys
        355                 360
```

<210> SEQ ID NO 62
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (76)..(396)

<400> SEQUENCE: 62

```
atggatgcaa tgaagagagg gctctgctgt gtgctgctgc tgtgtggagc agtcttcgtt        60
tcgcccggcg ccgct gag aca cgg gag tgc atc tac tac aac gcc aac tgg       111
              Glu Thr Arg Glu Cys Ile Tyr Tyr Asn Ala Asn Trp
                1               5                   10 gag ctg gag cgc acc aac cag agc ggc ctg gag cgc tgc gaa ggc gag       159
Glu Leu Glu Arg Thr Asn Gln Ser Gly Leu Glu Arg Cys Glu Gly Glu
        15                  20                  25 cag gac aag cgg ctg cac tgc tac gcc tcc tgg cgc aac agc tct ggc       207
Gln Asp Lys Arg Leu His Cys Tyr Ala Ser Trp Arg Asn Ser Ser Gly
    30                  35                  40 acc atc gag ctc gtg aag aag ggc tgc tgg gac gat gac ttc aac tgc       255
Thr Ile Glu Leu Val Lys Lys Gly Cys Trp Asp Asp Asp Phe Asn Cys
45                  50                  55                  60 tac gat agg cag gag tgt gtg gcc act gag gag aac ccc cag gtg tac       303
Tyr Asp Arg Gln Glu Cys Val Ala Thr Glu Glu Asn Pro Gln Val Tyr
                65                  70                  75 ttc tgc tgc tgt gaa ggc aac ttc tgc aac gag cgc ttc act cat ttg       351
Phe Cys Cys Cys Glu Gly Asn Phe Cys Asn Glu Arg Phe Thr His Leu
            80                  85                  90 cca gag gct ggg ggc ccg gaa gtc acg tac gag cca ccc ccg aca           396
Pro Glu Ala Gly Gly Pro Glu Val Thr Tyr Glu Pro Pro Pro Thr
        95                  100                 105 ggtggtggaa ctcacacatg cccaccgtgc ccagcacctg aactcctggg gggaccgtca    456
gtcttcctct tccccccaaa acccaaggac accctcatga tctcccggac ccctgaggtc    516
acatgcgtgg tggtggacgt gagccacgaa gaccctgagg tcaagttcaa ctggtacgtg    576
gacggcgtgg aggtgcataa tgccaagaca aagccgcggg aggagcagta caacagcacg    636
taccgtgtgg tcagcgtcct caccgtcctg caccaggact ggctgaatgg caaggagtac    696
aagtgcaagg tctccaacaa agccctccca gcccccatcg agaaaaccat ctccaaagcc    756
aaagggcagc cccgagaacc acaggtgtac accctgcccc catcccggga ggagatgacc    816
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag   1056
agcctctccc tgtccccggg taaatga                                       1083
```

<210> SEQ ID NO 63
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
tcatttaccc ggggacaggg agaggctctt ctgcgtgtag tggttgtgca gagcctcatg      60
catcacggag catgagaaga cgttccctg ctgccacctg ctcttgtcca cggtgagctt     120
gctatagagg aagaaggagc cgtcggagtc cagcacggga ggcgtggtct tgtagttgtt     180
ctccggctgc ccattgctct cccactccac ggcgatgtcg ctgggataga agcctttgac     240
caggcaggtc aggctgacct ggttcttggt catctcctcc cgggatgggg gcagggtgta     300
cacctgtggt tctcggggct gcccctttggc tttggagatg gttttctcga tgggggctgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cggagatca tgaggtgtc      600
cttgggtttt gggggaaga ggaagactga cggtcccccc aggagttcag gtgctgggca     660
cggtgggcat gtgtgagttc caccacctgt cggggtggc tcgtacgtga cttccgggcc     720
cccagcctct ggcaaatgag tgaagcgctc gttgcagaag ttgccttcac agcagcagaa    780
gtacacctgg gggttctcct cagtggccac acactcctgc ctatcgtagc agttgaagtc    840
atcgtcccag cagcccttct tcacgagctc gatggtgcca gagctgttgc gccaggaggc    900
gtagcagtgc agccgcttgt cctgctcgcc ttcgcagcgc tccaggccgc tctggttggt    960
gcgctccagc tcccagttgg cgttgtagta gatgcactcc cgtgtctcag cggcgccggg   1020
cgaaacgaag actgctccac acagcagcag cacacagcag agccctctct tcattgcatc   1080
cat                                                                 1083
```

<210> SEQ ID NO 64
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125
```

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr
            100                 105

<210> SEQ ID NO 66
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<220> FEATURE:
<221> NAME/KEY: CDS
<222> LOCATION: (76)..(396)

<400> SEQUENCE: 66

```
atggatgcaa tgaagagagg gctctgctgt gtgctgctgc tgtgtggagc agtcttcgtt      60
tcgcccggcg ccgcc gaa acc cgc gaa tgt att tat tac aat gct aat tgg     111
                Glu Thr Arg Glu Cys Ile Tyr Tyr Asn Ala Asn Trp
                  1               5                  10 gaa ctc gaa cgg acg aac caa tcc ggg ctc gaa cgg tgt gag ggg gaa     159
Glu Leu Glu Arg Thr Asn Gln Ser Gly Leu Glu Arg Cys Glu Gly Glu
             15                  20                  25 cag gat aaa cgc ctc cat tgc tat gcg tcg tgg agg aac tcc tcc ggg     207
Gln Asp Lys Arg Leu His Cys Tyr Ala Ser Trp Arg Asn Ser Ser Gly
         30                  35                  40 acg att gaa ctg gtc aag aaa ggg tgc tgg gac gac gat ttc aat tgt     255
Thr Ile Glu Leu Val Lys Lys Gly Cys Trp Asp Asp Asp Phe Asn Cys
 45                  50                  55                  60 tat gac cgc cag gaa tgt gtc gcg acc gaa gag aat ccg cag gtc tat     303
Tyr Asp Arg Gln Glu Cys Val Ala Thr Glu Glu Asn Pro Gln Val Tyr
                 65                  70                  75 ttc tgt tgt tgc gag ggg aat ttc tgt aat gaa cgg ttt acc cac ctc     351
Phe Cys Cys Cys Glu Gly Asn Phe Cys Asn Glu Arg Phe Thr His Leu
             80                  85                  90 ccc gaa gcc ggc ggg ccc gag gtg acc tat gaa ccc ccg ccc acc         396
Pro Glu Ala Gly Gly Pro Glu Val Thr Tyr Glu Pro Pro Pro Thr
         95                  100                 105 ggtggtggaa ctcacacatg cccaccgtgc ccagcacctg aactcctggg ggaccgtca    456
gtcttcctct tccccccaaa acccaaggac accctcatga tctcccggac ccctgaggtc    516
acatgcgtgg tggtggacgt gagccacgaa gaccctgagg tcaagttcaa ctggtacgtg    576
gacggcgtgg aggtgcataa tgccaagaca aagccgcggg aggagcagta caacagcacg    636
taccgtgtgt cagcgtcct caccgtcctg caccaggact ggctgaatgg caaggagtac    696
aagtgcaagg tctccaacaa agccctccca gcccccatcg agaaaaccat ctccaaagcc    756
aaagggcagc cccgagaacc acaggtgtac accctgcccc catcccggga ggagatgacc    816
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag   1056
agcctctccc tgtccccggg taaatga                                       1083
```

<210> SEQ ID NO 67
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
tcatttaccc ggggacaggg agaggctctt ctgcgtgtag tggttgtgca gagcctcatg     60
catcacggag catgagaaga cgttcccctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
```

```
caggcaggtc aggctgacct ggttcttggt catctcctcc cgggatgggg gcagggtgta    300
cacctgtggt tctcggggct gccctttggc tttggagatg gttttctcga tgggggctgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cgggagatca tgagggtgtc    600
cttgggtttt ggggggaaga ggaagactga cgtccccccc aggagttcag gtgctgggca    660
cggtgggcat gtgtgagttc caccaccggt gggcggggt tcataggtca cctcgggccc    720
gccggcttcg gggaggtggg taaaccgttc attacagaaa ttcccctcgc aacaacagaa    780
atagacctgc ggattctctt cggtcgcgac acattcctgg cggtcataac aattgaaatc    840
gtcgtcccag caccctttct tgaccagttc aatcgtcccg gaggagttcc tccacgacgc    900
atagcaatgg aggcgtttat cctgttcccc ctcacaccgt tcgagcccgg attggttcgt    960
ccgttcgagt tcccaattag cattgtaata aatacattcg cgggtttcgg cggcgccggg   1020
cgaaacgaag actgctccac acagcagcag cacacagcag agccctctct tcattgcatc   1080
cat                                                                 1083

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gaaacccgcg aatgtattta ttacaatgct aattgggaac tcgaacggac gaaccaatcc     60
gggctcgaac ggtgtgaggg ggaacaggat aaacgcctcc attgctatgc gtcgtggagg    120
aactcctccg ggacgattga actggtcaag aaagggtgct gggacgacga tttcaattgt    180
tatgaccgcc aggaatgtgt cgcgaccgaa gagaatccgc aggtctattt ctgttgttgc    240 gagggaatt tctgtaatga acggtttacc cacctccccg aagccggcgg gcccgaggtg    300
acctatgaac ccccgcccac c                                             321

<210> SEQ ID NO 69
<211> LENGTH: 115
<212> TYPE: PRT
<213> ORGANISM: Homo sapiens

<400> SEQUENCE: 69

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95
```

-continued

```
Phe Pro Glu Met Glu Val Thr Gln Pro Thr Ser Asn Pro Val Thr Pro
            100                 105                 110

Lys Pro Pro
        115

<210> SEQ ID NO 70
<211> LENGTH: 115
<212> TYPE: PRT
<213> ORGANISM: Ovis aries

<400> SEQUENCE: 70

Ile Leu Gly Arg Ser Glu Thr Gln Glu Cys Ile Phe Tyr Asn Ala Asn
1               5                   10                  15

Trp Glu Arg Asp Arg Thr Asn Arg Thr Gly Val Glu Ser Cys Tyr Gly
            20                  25                  30

Asp Lys Asp Lys Arg Arg His Cys Phe Ala Thr Trp Lys Asn Ile Ser
        35                  40                  45

Gly Ser Ile Asp Ile Val Lys Gln Gly Cys Trp Leu Asp Asp Ile Asn
    50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 71
<211> LENGTH: 115
<212> TYPE: PRT
<213> ORGANISM: Condylura cristata

<400> SEQUENCE: 71

Ile Leu Gly Arg Ser Glu Thr Gln Glu Cys Leu Phe Phe Asn Ala Asn
1               5                   10                  15

Trp Glu Arg Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Ala Pro
        115

<210> SEQ ID NO 72
<211> LENGTH: 115
<212> TYPE: PRT
<213> ORGANISM: Mus musculus

<400> SEQUENCE: 72

Ile Leu Gly Arg Ser Glu Thr Gln Glu Cys Leu Phe Phe Asn Ala Asn
```

```
                1               5                   10                  15
Trp Glu Arg Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
                35                  40                  45

Gly Ser Ile Glu Ile Val Lys Gln Gly Cys Trp Leu Asp Asp Ile Asn
                50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Lys Phe Ser Tyr
                    85                  90                  95

Phe Pro Glu Met Glu Val Thr Gln Pro Thr Ser Asn Pro Val Thr Pro
                100                 105                 110

Lys Pro Pro
        115

<210> SEQ ID NO 73
<211> LENGTH: 115
<212> TYPE: PRT
<213> ORGANISM: Gallus gallus

<400> SEQUENCE: 73

Ile Leu Gly Arg Ser Glu Thr Gln Glu Cys Ile Tyr Tyr Asn Ala Asn
1               5                   10                  15

Trp Glu Lys Asp Lys Thr Asn Arg Ser Gly Ile Glu Pro Cys Tyr Gly
                20                  25                  30

Asp Lys Asp Lys Arg Arg His Cys Phe Ala Thr Trp Lys Asn Ile Ser
                35                  40                  45

Gly Ser Ile Glu Ile Val Lys Gln Gly Cys Trp Leu Asp Asp Ile Asn
                50                  55                  60

Cys Tyr Asp Arg Asn Asp Cys Ile Glu Lys Lys Asp Ser Pro Glu Val
65                  70                  75                  80

Phe Phe Cys Cys Cys Glu Gly Asn Met Cys Asn Glu Arg Phe Phe Tyr
                    85                  90                  95

Phe Pro Glu Met Glu Val Thr Gln Pro Thr Ser Asn Pro Val Thr Pro
                100                 105                 110

Lys Pro Pro
        115

<210> SEQ ID NO 74
<211> LENGTH: 115
<212> TYPE: PRT
<213> ORGANISM: Bos taurus

<400> SEQUENCE: 74

Ile Leu Gly Arg Ser Glu Thr Gln Glu Cys Ile Phe Tyr Asn Ala Asn
1               5                   10                  15

Trp Glu Arg Asp Arg Thr Asn Arg Thr Gly Val Glu Ser Cys Tyr Gly
                20                  25                  30

Asp Lys Asp Lys Arg Arg His Cys Phe Ala Thr Trp Lys Asn Ile Ser
                35                  40                  45

Gly Ser Ile Glu Ile Val Lys Gln Gly Cys Trp Leu Asp Asp Ile Asn
                50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
```

```
                    85                  90                  95

Phe Pro Glu Met Glu Val Thr Gln Pro Thr Ser Asn Pro Val Thr Pro
                100                 105                 110

Lys Pro Pro
        115

<210> SEQ ID NO 75
<211> LENGTH: 115
<212> TYPE: PRT
<213> ORGANISM: Tyto alba

<400> SEQUENCE: 75

Ile Leu Gly Arg Ser Glu Thr Gln Glu Cys Ile Tyr Tyr Asn Ala Asn
1               5                   10                  15

Trp Glu Lys Asp Lys Thr Asn Arg Ser Gly Ile Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Asn Asp Cys Ile Glu Lys Lys Asp Ser Pro Glu Val
65                  70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 76
<211> LENGTH: 115
<212> TYPE: PRT
<213> ORGANISM: Myotis davidii

<400> SEQUENCE: 76

Ile Leu Gly Arg Ser Glu Thr Gln Glu Cys Ile Phe Tyr Asn Ala Asn
1               5                   10                  15

Trp Glu Arg Asp Lys Thr Asn Arg Thr Gly Val Glu Leu Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 77
<211> LENGTH: 20
<212> TYPE: PRT
<213> ORGANISM: Unknown
<220> FEATURE:
<223> OTHER INFORMATION: Description of Unknown:
```

Native peptide

<400> SEQUENCE: 77

Met Gly Ala Ala Ala Lys Leu Ala Phe Ala Val Phe Leu Ile Ser Cys
1               5                   10                  15

Ser Ser Gly Ala
            20

<210> SEQ ID NO 78
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu 305               310               315               320

His Asn His Tyr Thr Gln Lys Ser Leu Ser Leu Ser Pro Gly Lys
            325               330               335

<210> SEQ ID NO 79
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
50                  55                  60

Arg Asn Ser Ser Gly Thr Ile Glu Leu Val Lys Lys Gly Cys Trp Leu
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
        340                 345                 350

Ser Leu Ser Leu Ser Pro Gly Lys
        355                 360

<210> SEQ ID NO 80
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 80

```
atggatgcaa tgaagagagg gctctgctgt gtgctgctgc tgtgtggagc agtcttcgtt      60
tcgcccggcg cc gct gag aca cgg gag tgc atc tac tac aac gcc aac tgg    111
              Ala Glu Thr Arg Glu Cys Ile Tyr Tyr Asn Ala Asn Trp
               1               5                  10 gag ctg gag cgc acc aac cag agc ggc ctg gag cgc tgc gaa ggc gag    159
Glu Leu Glu Arg Thr Asn Gln Ser Gly Leu Glu Arg Cys Glu Gly Glu
 15                  20                  25 cag gac aag cgg ctg cac tgc tac gcc tcc tgg cgc aac agc tct ggc    207
Gln Asp Lys Arg Leu His Cys Tyr Ala Ser Trp Arg Asn Ser Ser Gly
 30                  35                  40                  45 acc atc gag ctc gtg aag aag ggc tgc tgg cta gat gac ttc aac tgc    255
Thr Ile Glu Leu Val Lys Lys Gly Cys Trp Leu Asp Asp Phe Asn Cys
                 50                  55                  60 tac gat agg cag gag tgt gtg gcc act gag gag aac ccc cag gtg tac    303
Tyr Asp Arg Gln Glu Cys Val Ala Thr Glu Glu Asn Pro Gln Val Tyr
             65                  70                  75 ttc tgc tgc tgt gaa ggc aac ttc tgc aac gag cgc ttc act cat ttg    351
Phe Cys Cys Cys Glu Gly Asn Phe Cys Asn Glu Arg Phe Thr His Leu
         80                  85                  90 cca gag gct ggg ggc ccg gaa gtc acg tac gag cca ccc ccg aca       396
Pro Glu Ala Gly Gly Pro Glu Val Thr Tyr Glu Pro Pro Pro Thr
     95                 100                 105 ggtggtggaa ctcacacatg cccaccgtgc ccagcacctg aactcctggg ggaccgtca    456 gtcttcctct ccccccaaaa cccaaggac acccctcatga tctcccggac ccctgaggtc    516
acatgcgtgg tggtggacgt gagccacgaa gaccctgagg tcaagttcaa ctggtacgtg    576
gacggcgtgg aggtgcataa tgccaagaca aagccgcggg aggagcagta caacagcacg    636
taccgtgtgg tcagcgtcct caccgtcctg caccaggact ggctgaatgg caaggagtac    696
aagtgcaagg tctccaacaa agccctccca gcccccatcg agaaaaccat ctccaaagcc    756
aaagggcagc ccgagaacc acaggtgtac accctgcccc catcccggga ggagatgacc    816
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag   1056
agcctctccc tgtccccggg taaatga                                       1083
```

<210> SEQ ID NO 81
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
tcatttaccc ggggacaggg agaggctctt ctgcgtgtag tggttgtgca gagcctcatg      60
catcacggag catgagaaga cgttccctg ctgccacctg ctcttgtcca cggtgagctt     120
gctatagagg aagaaggagc cgtcggagtc cagcacggga ggcgtggtct tgtagttgtt     180
ctccggctgc ccattgctct cccactccac ggcgatgtcg ctgggataga agcctttgac     240
caggcaggtc aggctgacct ggttcttggt catctcctcc cgggatgggg gcagggtgta     300
cacctgtggt tctcggggct gccctttggc tttggagatg gttttctcga tggggctgg     360
gagggctttg ttggagacct tgcacttgta ctccttgcca ttcagccagt cctggtgcag     420
gacggtgagg acgctgacca cacggtacgt gctgttgtac tgctcctccc gcggctttgt     480
cttggcatta tgcacctcca cgccgtccac gtaccagttg aacttgacct cagggtcttc     540
gtggctcacg tccaccacca cgcatgtgac ctcaggggtc cggagatca tgagggtgtc     600
cttgggtttt ggggggaaga ggaagactga cggtcccccc aggagttcag gtgctgggca     660
cggtgggcat gtgtgagttc caccacctgt cggggggtggc tcgtacgtga cttccgggcc     720
cccagcctct ggcaaatgag tgaagcgctc gttgcagaag ttgccttcac agcagcagaa     780
gtacacctgg gggttctcct cagtggccac acactcctgc ctatcgtagc agttgaagtc     840
atctagccag cagcccttct tcacgagctc gatggtgcca gagctgttgc gccaggaggc     900
gtagcagtgc agccgcttgt cctgctcgcc ttcgcagcgc tccaggccgc tctggttggt     960
gcgctccagc tcccagttgg cgttgtagta gatgcactcc cgtgtctcag cggcgccggg    1020
cgaaacgaag actgctccac acagcagcag cacacagcag agccctctct tcattgcatc    1080
cat                                                                  1083
```

<210> SEQ ID NO 82
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 82

```
atggatgcaa tgaagagagg gctctgctgt gtgctgctgc tgtgtggagc agtcttcgtt      60
tcgcccggcg cc gcc gaa acc cgc gaa tgt att tat tac aat gct aat tgg     111
               Ala Glu Thr Arg Glu Cys Ile Tyr Tyr Asn Ala Asn Trp
               1               5                  10 gaa ctc gaa cgg acg aac caa tcc ggg ctc gaa cgg tgt gag ggg gaa        159
Glu Leu Glu Arg Thr Asn Gln Ser Gly Leu Glu Arg Cys Glu Gly Glu
 15                  20                  25 cag gat aaa cgc ctc cat tgc tat gcg tcg tgg agg aac tcc tcc ggg        207
Gln Asp Lys Arg Leu His Cys Tyr Ala Ser Trp Arg Asn Ser Ser Gly
 30                  35                  40                  45 acg att gaa ctg gtc aag aaa ggg tgc tgg ctg gac gat ttc aat tgt        255
Thr Ile Glu Leu Val Lys Lys Gly Cys Trp Leu Asp Asp Phe Asn Cys
                 50                  55                  60 tat gac cgc cag gaa tgt gtc gcg acc gaa gag aat ccg cag gtc tat        303
Tyr Asp Arg Gln Glu Cys Val Ala Thr Glu Glu Asn Pro Gln Val Tyr
             65                  70                  75
```

```
ttc tgt tgt tgc gag ggg aat ttc tgt aat gaa cgg ttt acc cac ctc    351
Phe Cys Cys Cys Glu Gly Asn Phe Cys Asn Glu Arg Phe Thr His Leu
         80                  85                  90 ccc gaa gcc ggc ggg ccc gag gtg acc tat gaa ccc ccg ccc acc        396
Pro Glu Ala Gly Gly Pro Glu Val Thr Tyr Glu Pro Pro Pro Thr
 95                 100                 105 ggtggtggaa ctcacacatg cccaccgtgc ccagcacctg aactcctggg gggaccgtca    456
gtcttcctct tcccccaaa acccaaggac accctcatga tctcccggac ccctgaggtc     516
acatgcgtgg tggtggacgt gagccacgaa gaccctgagg tcaagttcaa ctggtacgtg    576
gacggcgtga aggtgcataa tgccaagaca aagccgcggg aggagcagta caacagcacg    636
taccgtgtgg tcagcgtcct caccgtcctg caccaggact ggctgaatgg caaggagtac    696
aagtgcaagg tctccaacaa agccctccca gcccccatcg agaaaaccat ctccaaagcc    756
aaagggcagc ccgagaacc acaggtgtac accctgcccc catcccggga ggagatgacc     816
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag   1056
agcctctccc tgtccccggg taaatga                                       1083

<210> SEQ ID NO 83
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
tacctacgtt acttctctcc cgagacgaca cacgacgacg acacacctcg tcagaagcaa     60
agcgggccgc ggcggctttg ggcgcttaca taataatgt tacgattaac ccttgagctt    120
gcctgcttgg ttaggcccga gcttgccaca ctccccttg tcctatttgc ggaggtaacg    180
atacgcagca cctccttgag gaggccctgc taacttgacc agttctttcc cacgaccgac    240
ctgctaaagt taacaatact gcggtcctt acacagcgct ggcttctctt aggcgtccag    300
ataaagacaa caacgctccc cttaaagaca ttacttgcca aatgggtgga ggggcttcgg    360
ccgcccgggc tccactggat acttgggggc gggtggccac caccttgagt gtgtacgggt    420
ggcacgggtc gtggacttga ggacccccct ggcagtcaga aggagaaggg gggttttggg    480
ttcctgtggg agtactagag ggcctgggga ctccagtgta cgcaccacca cctgcactcg    540
gtgcttctgg gactccagtt caagttgacc atgcacctgc cgcacctcca cgtattacgg    600
ttctgtttcg gcgccctcct cgtcatgttg tcgtgcatgg cacaccagtc gcaggagtgg    660
caggacgtgg tcctgaccga cttaccgttc ctcatgttca cgttccagag gttgtttcgg    720
gagggtcggg ggtagctctt ttggtagagg tttcggtttc ccgtcggggc tcttggtgtc    780
cacatgtggg acggggtag ggccctcctc tactggttct tggtccagtc ggactggacg     840
gaccagtttc cgaagatagg gtcgctgtag cggcacctca ccctctcgtt accgtcggc    900
ctcttgttga tgttctggtg cggagggcac gacctgaggc tgccgaggaa gaagagata    960
tcgttcgagt ggcacctgtt ctcgtccacc gtcgtccct tgcagaagag tacgaggcac   1020
tacgtactcc gagacgtgtt ggtgatgtgc gtcttctcgg agagggacag gggcccattt   1080
``` act 1083

<210> SEQ ID NO 84
<211> LENGTH: 413
<212> TYPE: PRT
<213> ORGANISM: Homo sapiens

<400> SEQUENCE: 84

| Met | Glu | Phe | Pro | Gly | Leu | Gly | Ser | Leu | Gly | Thr | Ser | Glu | Pro | Leu | Pro |
|---|---|---|---|---|---|---|---|---|---|---|---|---|---|---|---|
| 1 | | | | 5 | | | | | 10 | | | | | 15 | |

Gln Phe Val Asp Pro Ala Leu Val Ser Ser Thr Pro Glu Ser Gly Val
            20                  25                  30

Phe Phe Pro Ser Gly Pro Glu Gly Leu Asp Ala Ala Ser Ser Thr
        35                  40                  45

Ala Pro Ser Thr Ala Thr Ala Ala Ala Ala Leu Ala Tyr Tyr Arg
50                  55                  60

Asp Ala Glu Ala Tyr Arg His Ser Pro Val Phe Gln Val Tyr Pro Leu
65                  70                  75                  80

Leu Asn Cys Met Glu Gly Ile Pro Gly Gly Ser Pro Tyr Ala Gly Trp
                85                  90                  95

Ala Tyr Gly Lys Thr Gly Leu Tyr Pro Ala Ser Thr Val Cys Pro Thr
                100                 105                 110

Arg Glu Asp Ser Pro Pro Gln Ala Val Glu Asp Leu Asp Gly Lys Gly
                115                 120                 125

Ser Thr Ser Phe Leu Glu Thr Leu Lys Thr Glu Arg Leu Ser Pro Asp
        130                 135                 140

Leu Leu Thr Leu Gly Pro Ala Leu Pro Ser Ser Leu Pro Val Pro Asn
145                 150                 155                 160

Ser Ala Tyr Gly Gly Pro Asp Phe Ser Ser Thr Phe Phe Ser Pro Thr
                165                 170                 175

Gly Ser Pro Leu Asn Ser Ala Ala Tyr Ser Ser Pro Lys Leu Arg Gly
                180                 185                 190

Thr Leu Pro Leu Pro Pro Cys Glu Ala Arg Glu Cys Val Asn Cys Gly
                195                 200                 205

Ala Thr Ala Thr Pro Leu Trp Arg Arg Asp Arg Thr Gly His Tyr Leu
        210                 215                 220

Cys Asn Ala Cys Gly Leu Tyr His Lys Met Asn Gly Gln Asn Arg Pro
225                 230                 235                 240

Leu Ile Arg Pro Lys Lys Arg Leu Ile Val Ser Lys Arg Ala Gly Thr
                245                 250                 255

Gln Cys Thr Asn Cys Gln Thr Thr Thr Thr Thr Leu Trp Arg Arg Asn
                260                 265                 270

Ala Ser Gly Asp Pro Val Cys Asn Ala Cys Gly Leu Tyr Tyr Lys Leu
        275                 280                 285

His Gln Val Asn Arg Pro Leu Thr Met Arg Lys Asp Gly Ile Gln Thr
        290                 295                 300

Arg Asn Arg Lys Ala Ser Gly Lys Gly Lys Lys Lys Arg Gly Ser Ser
305                 310                 315                 320

Leu Gly Gly Thr Gly Ala Ala Glu Gly Pro Ala Gly Gly Phe Met Val
                325                 330                 335

Val Ala Gly Gly Ser Gly Ser Gly Asn Cys Gly Glu Val Ala Ser Gly
            340                 345                 350

Leu Thr Leu Gly Pro Pro Gly Thr Ala His Leu Tyr Gln Gly Leu Gly
        355                 360                 365

```
Pro Val Val Leu Ser Gly Pro Val Ser His Leu Met Pro Phe Pro Gly
    370                 375                 380

Pro Leu Leu Gly Ser Pro Thr Gly Ser Phe Pro Thr Gly Pro Met Pro
385                 390                 395                 400

Pro Thr Thr Ser Thr Thr Val Val Ala Pro Leu Ser Ser
                405                 410

<210> SEQ ID NO 85
<211> LENGTH: 373
<212> TYPE: PRT
<213> ORGANISM: Homo sapiens

<400> SEQUENCE: 85

Met Ser Pro Cys Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
50                  55                  60

Tyr Cys Pro Cys Ser Ile His Pro Asp Ser Gly Phe Pro Leu Pro Pro
65                  70                  75                  80

Pro Pro Tyr Glu Leu Pro Ala Ser Thr Ser His Val Pro Asp Pro Pro
                85                  90                  95

Tyr Ser Tyr Gly Asn Met Ala Ile Pro Val Ser Lys Pro Leu Ser Leu
            100                 105                 110

Ser Gly Leu Leu Ser Glu Pro Leu Gln Asp Pro Leu Ala Leu Leu Asp
        115                 120                 125

Ile Gly Leu Pro Ala Gly Pro Pro Lys Pro Gln Glu Asp Pro Glu Ser
130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Ser Glu Tyr Val Glu Met Tyr
                165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
        195                 200                 205

Ser Gly Pro Val Arg Ala Lys Pro Thr Ala Arg Gly Glu Ala Gly Ser
    210                 215                 220

Arg Asp Glu Arg Arg Ala Leu Ala Met Lys Ile Pro Phe Pro Thr Asp
225                 230                 235                 240

Lys Ile Val Asn Leu Pro Val Asp Asp Phe Asn Glu Leu Leu Ala Arg
                245                 250                 255

Tyr Pro Leu Thr Glu Ser Gln Leu Ala Leu Val Arg Asp Ile Arg Arg
            260                 265                 270

Arg Gly Lys Asn Lys Val Ala Ala Gln Asn Cys Arg Lys Arg Lys Leu
        275                 280                 285

Glu Thr Ile Val Gln Leu Glu Arg Glu Leu Glu Arg Leu Thr Asn Glu
    290                 295                 300

Arg Glu Arg Leu Leu Arg Ala Arg Gly Glu Ala Asp Arg Thr Leu Glu
305                 310                 315                 320

Val Met Arg Gln Gln Leu Thr Glu Leu Tyr Arg Asp Ile Phe Gln His
```

-continued

```
                325                 330                 335
Leu Arg Asp Glu Ser Gly Asn Ser Tyr Ser Pro Glu Glu Tyr Ala Leu
                340                 345                 350

Gln Gln Ala Ala Asp Gly Thr Ile Phe Leu Val Pro Arg Gly Thr Lys
                355                 360                 365

Met Glu Ala Thr Asp
        370

<210> SEQ ID NO 86
<211> LENGTH: 529
<212> TYPE: PRT
<213> ORGANISM: Homo sapiens

<400> SEQUENCE: 86

Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
                20                  25                  30

Ala Leu Ile Cys Trp Ser Pro Ser Gly Asn Ser Phe His Val Phe Asp
                35                  40                  45

Gln Gly Gln Phe Ala Lys Glu Val Leu Pro Lys Tyr Phe Lys His Asn
        50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
                100                 105                 110

Glu Asn Ile Lys Arg Lys Val Thr Ser Val Ser Thr Leu Lys Ser Glu
                115                 120                 125

Asp Ile Lys Ile Arg Gln Asp Ser Val Thr Lys Leu Leu Thr Asp Val
        130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
                180                 185                 190

Leu Ile Ser Leu Val Gln Ser Asn Arg Ile Leu Gly Val Lys Arg Lys
                195                 200                 205

Ile Pro Leu Met Leu Asn Asp Ser Gly Ser Ala His Ser Met Pro Lys
        210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
                245                 250                 255

Ala Val Ala Ser Ser Gly Pro Ile Ile Ser Asp Ile Thr Glu Leu Ala
                260                 265                 270

Pro Ala Ser Pro Met Ala Ser Pro Gly Gly Ser Ile Asp Glu Arg Pro
                275                 280                 285

Leu Ser Ser Ser Pro Leu Val Arg Val Lys Glu Glu Pro Pro Ser Pro
        290                 295                 300

Pro Gln Ser Pro Arg Val Glu Glu Ala Ser Pro Gly Arg Pro Ser Ser
305                 310                 315                 320
```

Val Asp Thr Leu Leu Ser Pro Thr Ala Leu Ile Asp Ser Ile Leu Arg
            325                 330                 335

Glu Ser Glu Pro Ala Pro Ala Ser Val Thr Ala Leu Thr Asp Ala Arg
            340                 345                 350

Gly His Thr Asp Thr Glu Gly Arg Pro Pro Ser Pro Pro Pro Thr Ser
            355                 360                 365

Thr Pro Glu Lys Cys Leu Ser Val Ala Cys Leu Asp Lys Asn Glu Leu
            370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
            405                 410                 415

Leu Phe Ser Pro Ser Val Thr Val Pro Asp Met Ser Leu Pro Asp Leu
            420                 425                 430

Asp Ser Ser Leu Ala Ser Ile Gln Glu Leu Leu Ser Pro Gln Glu Pro
            435                 440                 445

Pro Arg Pro Pro Glu Ala Glu Asn Ser Ser Pro Asp Ser Gly Lys Gln
            450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
            485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
            515                 520                 525

Ser

<210> SEQ ID NO 87
<211> LENGTH: 840
<212> TYPE: PRT
<213> ORGANISM: Homo sapiens

<400> SEQUENCE: 87

Met Ser Val Val Gly Ile Asp Leu Gly Phe Gln Ser Cys Tyr Val Ala
1               5                   10                  15

Val Ala Arg Ala Gly Gly Ile Glu Thr Ile Ala Asn Glu Tyr Ser Asp
            20                  25                  30

Arg Cys Thr Pro Ala Cys Ile Ser Phe Gly Pro Lys Asn Arg Ser Ile
            35                  40                  45

Gly Ala Ala Ala Lys Ser Gln Val Ile Ser Asn Ala Lys Asn Thr Val
            50                  55                  60

Gln Gly Phe Lys Arg Phe His Gly Arg Ala Phe Ser Asp Pro Phe Val
65                  70                  75                  80

Glu Ala Glu Lys Ser Asn Leu Ala Tyr Asp Ile Val Gln Leu Pro Thr
            85                  90                  95

Gly Leu Thr Gly Ile Lys Val Thr Tyr Met Glu Glu Glu Arg Asn Phe
            100                 105                 110

Thr Thr Glu Gln Val Thr Ala Met Leu Leu Ser Lys Leu Lys Glu Thr
            115                 120                 125

Ala Glu Ser Val Leu Lys Lys Pro Val Val Asp Cys Val Val Ser Val
            130                 135                 140

Pro Cys Phe Tyr Thr Asp Ala Glu Arg Arg Ser Val Met Asp Ala Thr
145                 150                 155                 160

-continued

Gln Ile Ala Gly Leu Asn Cys Leu Arg Leu Met Asn Glu Thr Thr Ala
165                     170                     175

Val Ala Leu Ala Tyr Gly Ile Tyr Lys Gln Asp Leu Pro Ala Leu Glu
        180                     185                     190

Glu Lys Pro Arg Asn Val Val Phe Val Asp Met Gly His Ser Ala Tyr
            195                     200                     205

Gln Val Ser Val Cys Ala Phe Asn Arg Gly Lys Leu Lys Val Leu Ala
        210                     215                     220

Thr Ala Phe Asp Thr Thr Leu Gly Gly Arg Lys Phe Asp Glu Val Leu
225                     230                     235                     240

Val Asn His Phe Cys Glu Glu Phe Gly Lys Lys Tyr Lys Leu Asp Ile
                245                     250                     255

Lys Ser Lys Ile Arg Ala Leu Leu Arg Leu Ser Gln Glu Cys Glu Lys
            260                     265                     270

Leu Lys Lys Leu Met Ser Ala Asn Ala Ser Asp Leu Pro Leu Ser Ile
        275                     280                     285

Glu Cys Phe Met Asn Asp Val Asp Val Ser Gly Thr Met Asn Arg Gly
    290                     295                     300

Lys Phe Leu Glu Met Cys Asn Asp Leu Leu Ala Arg Val Glu Pro Pro
305                     310                     315                     320

Leu Arg Ser Val Leu Glu Gln Thr Lys Leu Lys Lys Glu Asp Ile Tyr
                325                     330                     335

Ala Val Glu Ile Val Gly Gly Ala Thr Arg Ile Pro Ala Val Lys Glu
            340                     345                     350

Lys Ile Ser Lys Phe Phe Gly Lys Glu Leu Ser Thr Thr Leu Asn Ala
        355                     360                     365

Asp Glu Ala Val Thr Arg Gly Cys Ala Leu Gln Cys Ala Ile Leu Ser
370                     375                     380

Pro Ala Phe Lys Val Arg Glu Phe Ser Ile Thr Asp Val Val Pro Tyr
385                     390                     395                     400

Pro Ile Ser Leu Arg Trp Asn Ser Pro Ala Glu Glu Gly Ser Ser Asp
                405                     410                     415

Cys Glu Val Phe Ser Lys Asn His Ala Ala Pro Phe Ser Lys Val Leu
            420                     425                     430

Thr Phe Tyr Arg Lys Glu Pro Phe Thr Leu Glu Ala Tyr Tyr Ser Ser
        435                     440                     445

Pro Gln Asp Leu Pro Tyr Pro Asp Pro Ala Ile Ala Gln Phe Ser Val
    450                     455                     460

Gln Lys Val Thr Pro Gln Ser Asp Gly Ser Ser Ser Lys Val Lys Val
465                     470                     475                     480

Lys Val Arg Val Asn Val His Gly Ile Phe Ser Val Ser Ser Ala Ser
                485                     490                     495

Leu Val Glu Val His Lys Ser Glu Glu Asn Glu Glu Pro Met Glu Thr
            500                     505                     510

Asp Gln Asn Ala Lys Glu Glu Lys Met Gln Val Asp Gln Glu Glu
        515                     520                     525

Pro His Val Glu Glu Gln Gln Gln Thr Pro Ala Glu Asn Lys Ala
    530                     535                     540

Glu Ser Glu Glu Met Glu Thr Ser Gln Ala Gly Ser Lys Asp Lys Lys
545                     550                     555                     560

Met Asp Gln Pro Pro Gln Ala Lys Lys Ala Lys Val Lys Thr Ser Thr
                565                     570                     575

Val Asp Leu Pro Ile Glu Asn Gln Leu Leu Trp Gln Ile Asp Arg Glu

```
            580                 585                 590
Met Leu Asn Leu Tyr Ile Glu Asn Glu Gly Lys Met Ile Met Gln Asp
        595                 600                 605

Lys Leu Glu Lys Glu Arg Asn Asp Ala Lys Asn Ala Val Glu Glu Tyr
    610                 615                 620

Val Tyr Glu Met Arg Asp Lys Leu Ser Gly Glu Tyr Glu Lys Phe Val
625                 630                 635                 640

Ser Glu Asp Asp Arg Asn Ser Phe Thr Leu Lys Leu Glu Asp Thr Glu
                645                 650                 655

Asn Trp Leu Tyr Glu Asp Gly Glu Asp Gln Pro Lys Gln Val Tyr Val
            660                 665                 670

Asp Lys Leu Ala Glu Leu Lys Asn Leu Gly Gln Pro Ile Lys Ile Arg
        675                 680                 685

Phe Gln Glu Ser Glu Glu Arg Pro Lys Leu Phe Glu Glu Leu Gly Lys
    690                 695                 700

Gln Ile Gln Gln Tyr Met Lys Ile Ile Ser Ser Phe Lys Asn Lys Glu
705                 710                 715                 720

Asp Gln Tyr Asp His Leu Asp Ala Ala Asp Met Thr Lys Val Glu Lys
                725                 730                 735

Ser Thr Asn Glu Ala Met Glu Trp Met Asn Asn Lys Leu Asn Leu Gln
            740                 745                 750

Asn Lys Gln Ser Leu Thr Met Asp Pro Val Val Lys Ser Lys Glu Ile
        755                 760                 765

Glu Ala Lys Ile Lys Glu Leu Thr Ser Thr Cys Ser Pro Ile Ile Ser
    770                 775                 780

Lys Pro Lys Pro Lys Val Glu Pro Pro Lys Glu Gln Lys Asn Ala
785                 790                 795                 800

Glu Gln Asn Gly Pro Val Asp Gly Gln Gly Asp Asn Pro Gly Pro Gln
                805                 810                 815

Ala Ala Glu Gln Gly Thr Asp Thr Ala Val Pro Ser Asp Ser Asp Lys
            820                 825                 830

Lys Leu Pro Glu Met Asp Ile Asp
        835                 840

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 88

His His His His His His
1               5

<210> SEQ ID NO 89
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Glu Thr Arg Glu Cys Ile Tyr Tyr Asn Ala Asn Trp Glu Leu Glu
1               5                   10                  15

Arg Thr Asn Gln Ser Gly Leu Glu Arg Cys Glu Gly Glu Gln Asp Lys
```

```
                    20                  25                  30
Arg Leu His Cys Tyr Ala Ser Trp Arg Asn Ser Ser Gly Thr Ile Glu
            35                  40                  45

Leu Val Lys Lys Gly Cys Trp Leu Asp Asp Phe Asn Cys Tyr Asp Arg
        50                  55                  60

Gln Glu Cys Val Ala Thr Glu Glu Asn Pro Gln Val Tyr Phe Cys Cys
65                      70                  75                  80

Cys Glu Gly Asn Phe Cys Asn Glu Arg Phe Thr His Leu Pro Glu Ala
                85                  90                  95

Gly Gly Pro Glu Val Thr Tyr Glu Pro Pro Thr
            100                 105

<210> SEQ ID NO 90
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
atggatgcaa tgaagagagg gctctgctgt gtgctgctgc tgtgtggagc agtcttcgtt        60
tcgcccggcg cctctgggcg tggggaggct gagacacggg agtgcatcta ctacaacgcc       120
aactgggagc tggagcgcac caaccagagc ggcctggagc gctgcgaagg cgagcaggac       180
aagcggctgc actgctacgc ctcctggcgc aacagctctg gcaccatcga gctcgtgaag       240
aagggctgct gggatgatga cttcaactgc tacgataggc aggagtgtgt ggccactgag       300
gagaaccccc aggtgtactt ctgctgctgt gaaggcaact tctgcaacga gcgcttcact       360
catttgccag aggctggggg cccggaagtc acgtacgagc cacccccgac agcccccacc       420
ggtggtggaa ctcacacatg cccaccgtgc ccagcacctg aactcctggg gggaccgtca       480
gtcttcctct tccccccaaa acccaaggac accctcatga tctcccggac ccctgaggtc       540
acatgcgtgg tggtggacgt gagccacgaa gaccctgagg tcaagttcaa ctggtacgtg       600
gacggcgtgg aggtgcataa tgccaagaca aagccgcggg aggagcagta caacagcacg       660
taccgtgtgg tcagcgtcct caccgtcctg caccaggact ggctgaatgg caaggagtac       720
aagtgcaagg tctccaacaa agccctccca gcccccatcg agaaaaccat ctccaaagcc       780
aaagggcagc ccgagaacc acaggtgtac accctgcccc catcccggga ggagatgacc       840
aagaaccagg tcagcctgac ctgcctggtc aaaggcttct atcccagcga catcgccgtg       900
gagtgggaga gcaatgggca gccggagaac aactacaaga ccacgcctcc cgtgctggac       960
tccgacggct ccttcttcct ctatagcaag ctcaccgtgg acaagagcag gtggcagcag      1020
gggaacgtct tctcatgctc cgtgatgcat gaggctctgc acaaccacta cacgcagaag      1080
agcctctccc tgtccccggg taaatga                                          1107
```